(12) United States Patent
Sakamoto

(10) Patent No.: US 12,391,668 B2
(45) Date of Patent: Aug. 19, 2025

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventor: Naoya Sakamoto, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 666 days.

(21) Appl. No.: 16/270,108

(22) Filed: Feb. 7, 2019

(65) Prior Publication Data

US 2019/0296247 A1 Sep. 26, 2019

(30) Foreign Application Priority Data

Mar. 22, 2018 (KR) .................. 10-2018-0033427

(51) Int. Cl.
| | | |
|---|---|---|
| H01L 51/00 | (2006.01) | |
| C07D 401/14 | (2006.01) | |
| C07D 413/14 | (2006.01) | |
| C07D 417/14 | (2006.01) | |
| C07D 491/10 | (2006.01) | |
| C07F 7/08 | (2006.01) | |
| C09K 11/06 | (2006.01) | |
| H10K 85/60 | (2023.01) | |
| H10K 50/11 | (2023.01) | |
| H10K 50/15 | (2023.01) | |
| H10K 50/16 | (2023.01) | |
| H10K 50/17 | (2023.01) | |
| H10K 50/81 | (2023.01) | |
| H10K 50/82 | (2023.01) | |
| H10K 71/00 | (2023.01) | |
| H10K 71/16 | (2023.01) | |
| H10K 71/60 | (2023.01) | |
| H10K 101/20 | (2023.01) | |
| H10K 102/00 | (2023.01) | |
| H10K 102/10 | (2023.01) | |

(52) U.S. Cl.
CPC ......... *C07D 401/14* (2013.01); *C07D 413/14* (2013.01); *C07D 417/14* (2013.01); *C07D 491/10* (2013.01); *C07F 7/0814* (2013.01); *C07F 7/0816* (2013.01); *C09K 11/06* (2013.01); *H10K 85/654* (2023.02); *H10K 85/6572* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/81* (2023.02); *H10K 50/82* (2023.02); *H10K 71/00* (2023.02); *H10K 71/164* (2023.02); *H10K 71/60* (2023.02); *H10K 2101/20* (2023.02); *H10K 2102/00* (2023.02); *H10K 2102/103* (2023.02); *H10K 2102/351* (2023.02)

(58) Field of Classification Search
CPC ............. H10K 85/6572; H10K 85/654; C07D 401/14; C07D 413/14; C07D 417/14; C07D 491/10; C07F 7/0814; C07F 7/0816; C09K 11/06
See application file for complete search history.

(56) References Cited

U.S. PATENT DOCUMENTS

| | | |
|---|---|---|
| 9,761,811 B2 | 9/2017 | Suda |
| 9,899,609 B2 | 2/2018 | Ren et al. |
| 10,062,853 B2 | 8/2018 | Jung et al. |
| 10,665,792 B2 | 5/2020 | Bergmann et al. |
| 11,069,860 B2 * | 7/2021 | Aguilera-Iparraguirre ................. C07D 487/04 |
| 11,597,719 B2 * | 3/2023 | Arjona Esteban ..... C09K 11/06 |
| 2007/0059552 A1 * | 3/2007 | Takeda ................ H01L 51/0087 428/690 |
| 2011/0306922 A1 | 12/2011 | Khan et al. |
| 2016/0013423 A1 | 1/2016 | Huh et al. |
| 2016/0380209 A1 * | 12/2016 | Kim ..................... C07D 209/86 548/440 |
| 2017/0186973 A1 * | 6/2017 | Ren ..................... C07D 209/86 |
| 2018/0026202 A1 | 1/2018 | Danz et al. |
| 2018/0212158 A1 * | 7/2018 | Aspuru-Guzik ..... C07D 519/00 |
| 2018/0215711 A1 | 8/2018 | Lee et al. |
| 2019/0058130 A1 * | 2/2019 | Aguilera-Iparraguirre ................. H10K 85/6572 |

(Continued)

FOREIGN PATENT DOCUMENTS

| | | | |
|---|---|---|---|
| CN | 105254555 A | | 1/2016 |
| DE | 102017112965 | * | 6/2017 |

(Continued)

OTHER PUBLICATIONS

EP3290411 machine translation from Google Patents downloaded Apr. 22, 2022.*

(Continued)

*Primary Examiner* — Alexander R Pagano
(74) *Attorney, Agent, or Firm* — Womble Bond Dickinson (US) LLP

(57) ABSTRACT

An organic electroluminescence device includes a first electrode, a hole transport region disposed on the first electrode, an emission layer disposed on the hole transport region, an electron transport region disposed on the emission layer, and a second electrode disposed on the electron transport region, wherein the emission layer includes a polycyclic compound containing two electron donors and one electron acceptor, and the electron acceptor includes a benzonitrile part and a pyridine part, thereby showing high emission efficiency.

19 Claims, 2 Drawing Sheets

(56) References Cited

U.S. PATENT DOCUMENTS

| | | | |
|---|---|---|---|
| 2020/0062734 A1* | 2/2020 | Arjona Esteban | ............................ H10K 85/6572 |
| 2023/0422613 A1* | 12/2023 | Kwon | ..................... C09K 11/06 |

FOREIGN PATENT DOCUMENTS

| | | | | |
|---|---|---|---|---|
| DE | 102017130249 | * | 12/2017 | |
| EP | 2 966 146 A1 | | 1/2016 | |
| EP | 3 190 164 A1 | | 7/2017 | |
| EP | 3290411 | * | 8/2017 | ........... C07D 401/10 |
| EP | 3 263 569 A1 | | 1/2018 | |
| JP | 4552382 B2 | | 9/2010 | |
| JP | 2016-17078 A | | 2/2016 | |
| JP | 2017-197482 A | | 11/2017 | |
| JP | 6326251 B2 | | 5/2018 | |
| KR | 10-2015-0033700 A | | 4/2015 | |
| KR | 10-2016-0006629 A | | 1/2016 | |
| KR | 10-2017-0088822 A | | 8/2017 | |
| KR | 10-1769764 B1 | | 8/2017 | |
| KR | 10-2017-0139339 A | | 12/2017 | |
| KR | 10-2018-0022616 A | | 3/2018 | |
| WO | WO 2014/002629 A1 | | 1/2014 | |
| WO | WO 2015/170882 A1 | | 11/2015 | |
| WO | WO 2016/116517 A1 | | 7/2016 | |
| WO | WO 2016/178463 A1 | | 11/2016 | |
| WO | WO-2018229053 A1 | * | 12/2018 | ........... C07D 401/14 |
| WO | WO-2019115446 A1 | * | 6/2019 | ........... C07D 213/60 |

OTHER PUBLICATIONS

CAS Abstract and Indexed Compounds, J. Aguilera-Iparraguirre et al. US 2019/0058130 (2019) (Year: 2019).*

Extended European Search Report for corresponding European Application No. 19161700.0, dated May 27, 2019, 8 pages.

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2018-0033427, filed on Mar. 22, 2018, the entire content of which is hereby incorporated by reference.

BACKGROUND

1. Field

The present disclosure herein relates to an organic electroluminescence device and a polycyclic compound utilized in the organic electroluminescence device.

2. Description of the Related Art

Recently, the development of an organic electroluminescence display device as an image display device is being actively conducted. Different from a liquid crystal display device, the organic electroluminescence display device is a so-called self-luminescent display device in which holes and electrons injected from a first electrode and a second electrode recombine in an emission layer, and a light emission material including an organic compound in the emission layer emits light to attain display (e.g., an image).

In the application of an organic electroluminescence device to a display device, the decrease of the driving voltage, and the increase of the light-emitting efficiency and the life (e.g., lifespan) of the organic electroluminescence device are required, and materials for an organic electroluminescence device that can stably attain (e.g., satisfy) the requirements are being continuously developed.

Particularly, recently, in order to accomplish an organic electroluminescence device with high efficiency, techniques on phosphorescence emission (which utilizes energy in a triplet state) or delayed fluorescence emission (which utilizes the generating phenomenon of singlet excitons by the collision of triplet excitons (triplet-triplet annihilation, TTA)) are being developed, and development on a material for thermally activated delayed fluorescence (TADF) utilizing delayed fluorescence phenomenon is being conducted.

SUMMARY

Aspects according to one or more embodiments of the present disclosure are directed toward an organic electroluminescence device having long lifespan and high efficiency, and a polycyclic compound utilized therein.

Aspects according to one or more embodiments of the present disclosure are directed toward an organic electroluminescence device including a material for emitting thermally activated delayed fluorescence, and a polycyclic compound utilized as a material for emitting thermally activated delayed fluorescence.

According to an embodiment of the inventive concept, an organic electroluminescence device includes a first electrode, a hole transport region on the first electrode, an emission layer on the hole transport region, an electron transport region on the emission layer, and a second electrode on the electron transport region, wherein the emission layer includes a polycyclic compound containing two electron donors (e.g., two electron donor groups) and one electron acceptor (e.g., one electron acceptor group), and the electron acceptor includes a benzonitrile part (e.g., a benzonitrile group) and a pyridine part (e.g., a pyridine group).

In an embodiment, the emission layer may be configured to emit delayed fluorescence.

In an embodiment, the emission layer may include a host and a dopant, and the dopant may be the polycyclic compound.

In an embodiment, the emission layer may be a thermally activated delayed fluorescence emission layer configured to emit blue light.

In an embodiment, the polycyclic compound may be represented by the following Formula 1:

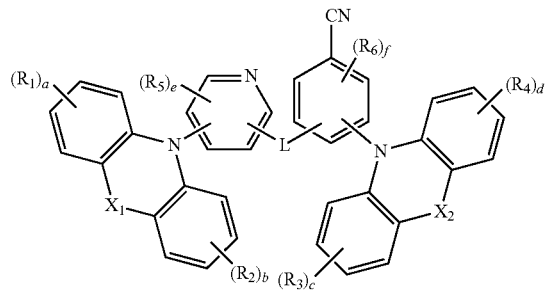

Formula 1

In Formula 1, $X_1$ and $X_2$ are each independently a direct linkage, $CR_7R_8$, $SiR_9R_{10}$, O, or S; L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring; $R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, $R_1$ to $R_4$ may be each optionally independently combined with an adjacent group to form a ring; a, b, c and d are each independently an integer of 0 to 4; $R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, $R_5$ to $R_{14}$ may be each optionally independently combined with an adjacent group to form a ring; and e and f are each independently an integer of 0 to 3.

In an embodiment, Formula 1 may be represented by one of the following Formula 1-1 to Formula 1-3:

Formula 1-1
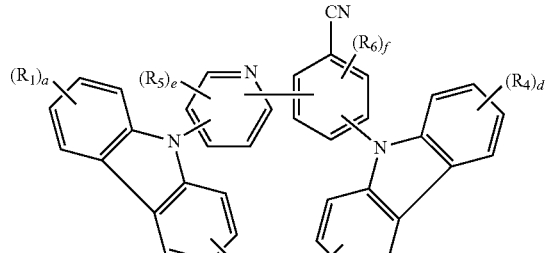

Formula 1-2
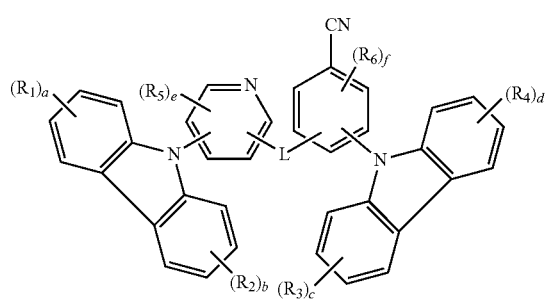

Formula 1-3
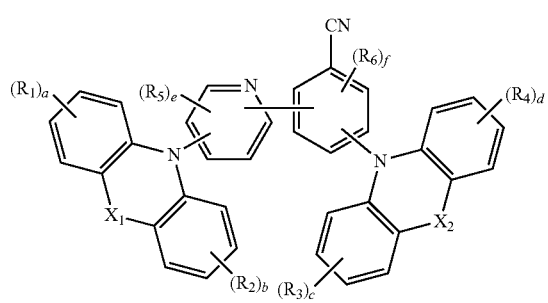

In Formula 1-1 to Formula 1-3, $X_1$ and $X_2$, L, $R_1$ to $R_6$, and a to f are the same as respectively defined in association with Formula 1.

In an embodiment, $X_1$ and $X_2$ of Formula 1 may be the same.

In an embodiment, $R_5$ and $R_6$ of Formula 1 may be each independently represented by one of the following Formula 2-1 to Formula 2-4:

Formula 2-1
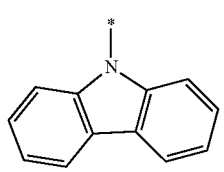

-continued

Formula 2-2
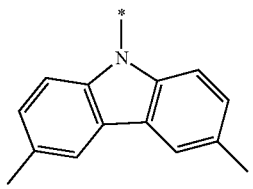

Formula 2-3
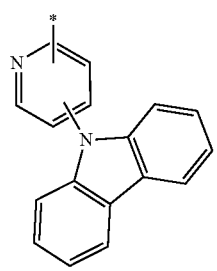

Formula 2-4
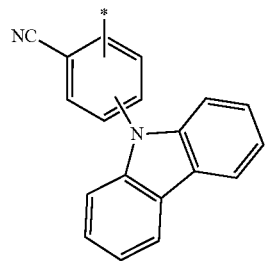

In an embodiment, $R_1$ to $R_4$ of Formula 1 may be each independently represented by one of the following Formula 3-1 to Formula 3-3:

Formula 3-1
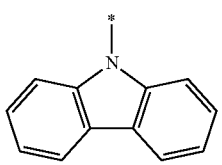

Formula 3-2
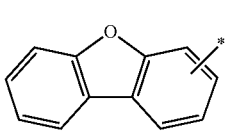

Formula 3-3
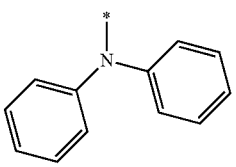

In an embodiment of the inventive concept, an organic electroluminescence device includes a first electrode, a hole transport region on the first electrode, an emission layer on the hole transport region, an electron transport region on the emission layer, and a second electrode on the electron transport region, wherein the emission layer includes the polycyclic compound represented by Formula 1 above.

In an embodiment of the inventive concept, a polycyclic compound is represented by Formula 1 above.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
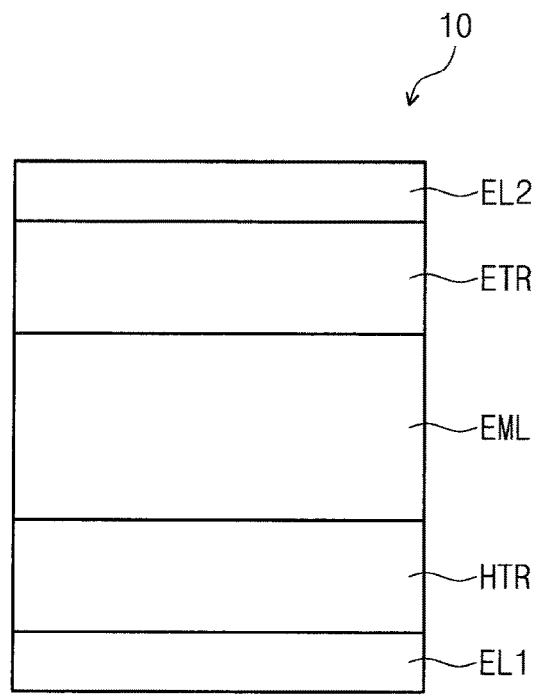
FIG. 1 is a cross-sectional view schematically illustrating an organic electroluminescence device according to an embodiment of the inventive concept.

The inventive concept may have various modifications and may be embodied in different forms, and example embodiments will be explained in more detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout. In the drawings, the dimensions of structures may be exaggerated for clarity of illustration. It will be understood that, although the terms "first," "second," etc., may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc., is referred to as being "on" another part, it can be "directly on" the other part, or intervening layers may also be present.

In the description, -* represents a connecting position.

In the description, the term "unsubstituted" corresponds to an unsubstituted functional group and the term "substituted" corresponds to a functional group substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocyclic group. In addition, each of the substituents may be substituted or unsubstituted. For example, a biphenyl group may be interpreted as an aryl group or a phenyl group substituted with a phenyl group.

In the description, the terms "forming a ring via the combination with an adjacent group" may refer to forming a substituted or unsubstituted hydrocarbon ring, or a substituted or unsubstituted heterocycle (e.g., heterocyclic ring) via the combination with an adjacent group. The hydrocarbon ring may include an aliphatic hydrocarbon ring and/or an aromatic hydrocarbon ring. The heterocycle may include an aliphatic heterocycle and/or an aromatic heterocycle. The hydrocarbon ring and the heterocycle may be monocyclic or polycyclic. In addition, the ring formed via the combination with an adjacent group may be combined with another ring to form a spiro structure.

In the description, the terms "an adjacent group" may refer to a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen atom may be a fluorine atom, a chlorine atom, a bromine atom and/or an iodine atom.

In the description, the alkyl (e.g., the alkyl group) may be a linear, branched or cyclic group. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without being limited thereto.

In the description, the term "aryl group" refers to an optional functional group or substituent derived from an aromatic hydrocarbon ring. The aryl group may be a monocyclic aryl group or a polycyclic aryl group. The carbon number for forming a ring in the aryl group may be, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without being limited thereto.

In the description, the heteroaryl (e.g., the heteroaryl group) may be a heteroaryl including at least one of O, N, P, Si and S as a heteroatom. The carbon number for forming a ring of the heteroaryl may be 2 to 30, or 2 to 20. The heteroaryl may be monocyclic heteroaryl or polycyclic heteroaryl. Examples of the polycyclic heteroaryl may have a dicyclic or tricyclic structure. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuran, etc., without being limited thereto.

In the description, the silyl group may include an alkyl silyl group and/or an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, an embodiment of the inventive concept is not limited thereto.

In the description, the carbon number of the amine group is not specifically limited, but may be 1 to 30. The amine group may include an alkyl amine group and/or an aryl amine group. Examples of the amine group include a methylamine group, a dimethylamine group, a phenylamine group, a naphthylamine group, a 9-methyl-anthracenylamine group, a triphenylamine group, etc., without being limited thereto.

In the description, the explanation on the aryl group may be applied to the arylene group except that the arylene group is a divalent group.

In the description, the explanation on the heteroaryl group may be applied to the heteroarylene group except that the heteroarylene group is a divalent group.

Hereinafter, the organic electroluminescence device according to an embodiment of the inventive concept will be explained with reference to FIGS. 1 to 3.

Figure 2:
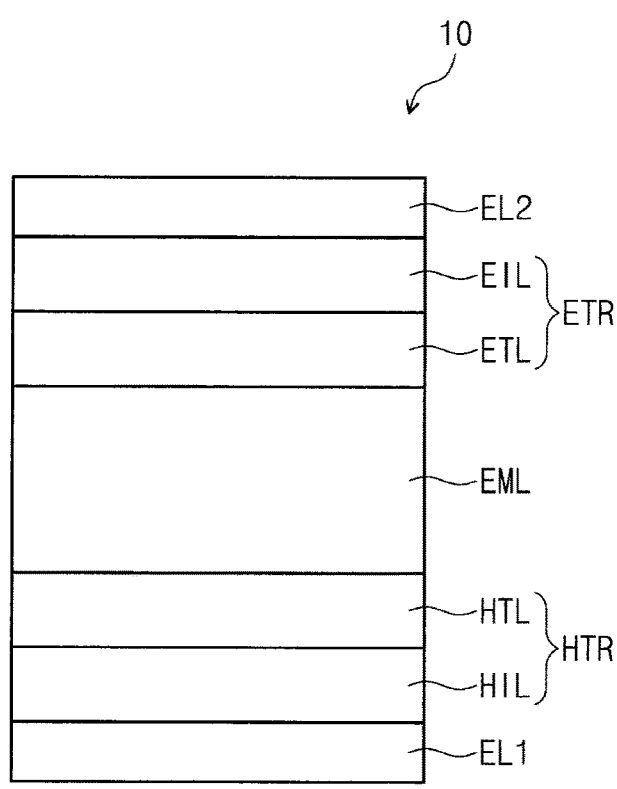
FIG. 2 is a cross-sectional view schematically illustrating an organic electroluminescence device according to an embodiment of the inventive concept.
Figure 3:
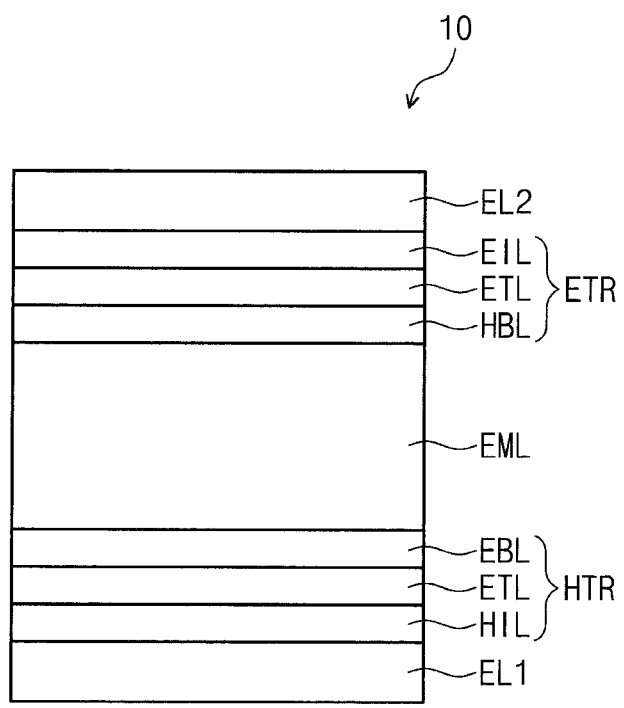
FIG. 3 is a cross-sectional view schematically illustrating an organic electroluminescence device according to an embodiment of the inventive concept.

Referring to FIGS. 1 to 3, an organic electroluminescence device 10 according to an embodiment may include a first electrode EL1, a hole transport region HTR, an emission layer EML, an electron transport region ETR and a second electrode EL2, laminated one by one (e.g., in the stated order).

The first electrode EL1 and the second electrode EL2 are oppositely disposed from each other, and a plurality of organic layers may be disposed between the first electrode EL1 and the second electrode EL2. The plurality of the organic layers may include a hole transport region HTR, an emission layer EML, and an electron transport region ETR. The organic electroluminescence device 10 of an embodiment may include the polycyclic compound of an embodiment in the emission layer EML.

When compared with FIG. 1, FIG. 2 shows the cross-sectional view of an organic electroluminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of an organic electroluminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL.

In the organic electroluminescence devices 10 of exemplary embodiments shown in FIGS. 1 to 3, the polycyclic compound of an embodiment, including two electron donors (e.g., two electron donors groups) and one electron acceptor (e.g., one electron acceptor group) may be included in at least one organic layer among the plurality of organic layers.

In the polycyclic compound of an embodiment, the electron acceptor may include a benzonitrile part (e.g., a benzonitrile group) and a pyridine part (e.g., a pyridine group). For example, the polycyclic compound of an embodiment may have an electron donor-electron acceptor-electron donor (D-A-D) structure.

The organic electroluminescence device 10 of an embodiment may include a polycyclic compound including two electron donors and one electron acceptor in an emission layer EML. In the polycyclic compound, the electron acceptor may include a benzonitrile part and a pyridine part.

In the organic electroluminescence devices 10 of an embodiment, the first electrode EL1 has conductivity. The first electrode EL1 may be formed utilizing a metal alloy or a conductive compound. The first electrode EL1 may be an anode.

The first electrode EL1 may be a transmissive electrode, a transflective electrode, or a reflective electrode. If the first electrode EL1 is the transmissive electrode, the first electrode EL1 may be formed utilizing a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or a transflective layer formed utilizing the above materials, and a transmissive conductive layer formed utilizing ITO, IZO, ZnO, or ITZO. For example, the first electrode EL1 may include a plurality of layers, such as ITO/Ag/ITO.

The hole transport region HTR is provided on the first electrode EL1. The hole transport region HTR may include at least one of a hole injection layer HIL, a hole transport layer HTL, a hole buffer layer, or an electron blocking layer EBL.

The hole transport region HTR may have a single layer formed utilizing a single material, a single layer formed utilizing a plurality of different materials, or have a multi-layer structure including a plurality of layers formed utilizing a plurality of different materials.

For example, the hole transport region HTR may have the structure of a single layer such as a hole injection layer HIL, or a hole transport layer HTL, and may have a structure of a single layer formed utilizing a hole injection material and a hole transport material. Alternatively, the hole transport region HTR may have a structure of a single layer formed utilizing a plurality of different materials, or a multilayer structure laminated (e.g., stacked) from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without being limited thereto.

The hole transport region HTR may be formed utilizing various suitable methods, such as a vacuum deposition method, a spin coating method, a cast method, a Langmuir-Blodgett (LB) method, an inkjet printing method, a laser printing method, and a laser induced thermal imaging (LITI) method.

The hole injection layer HIL of the organic electroluminescence device 10 of an embodiment may include a suitable (e.g., a known) hole injection material. For example, the hole injection layer HIL may include triphenylamine-containing polyetherketone (TPAPEK), 4-isopropyl-4'-methyl-diphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4"-tris(3-methyl phenyl phenylamino)triphenylamine (m-MTDATA), N,N'-di(1-naphthyl)-N,N'-diphenylbenzidine (NPB), N,N'-bis(1-naphthyl)-N,N'-diphenyl-4,4'-diamine (α-NPD), 4,4',4"-tris (N,N-diphenylamino)triphenylamine (TDATA), 4,4',4"-tris (N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or dipyrazino[2,3-f:2',3'-h]quinoxaline-2,3,6,7,10,11-hexacarbonitrile (HAT-CN). However, an embodiment of the inventive concept is not limited thereto.

The hole transport layer HTL of the organic electroluminescence device 10 of an embodiment may include a suitable (e.g., a known) hole transport material. For example, the hole transport layer HTL may include 1,1-bis[(di-4-trileamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphtyl)-N,N'-diphenylbenzidine (NPB), N,N'-bis(1-naphthyl)-N,N'-diphenyl-4,4'-diamine (α-NPD), etc. However, an embodiment of the inventive concept is not limited thereto.

Meanwhile, the hole transport region HTR may further include an electron blocking layer EBL, and the electron blocking layer EBL may be disposed between a hole transport layer HTL and an emission layer EML. The electron blocking layer EBL may play the role of preventing or substantially preventing electron injection from an electron transport region ETR to a hole transport region HTR.

The electron blocking layer EBL may include a common material (e.g., a known material) in the art. The electron blocking layer EBL may include, for example, carbazole derivatives (such as N-phenylcarbazole, and polyvinyl carbazole), fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, etc. In addition, as described above, the electron blocking layer EBL may include the polycyclic compound according to an embodiment of the inventive concept.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to improve conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without being limited thereto. For example, non-limiting examples of the p-dopant may include quinone derivatives (such as tetracyanoquinodimethane (TCNQ) and 2,3,5,6-tetrafluoro-tetracyanoquinodimethane (F4-TCNQ)), and metal oxides (such as tungsten oxide and molybdenum oxide), without being limited thereto.

As described above, the hole transport region HTR may further include at least one of a hole buffer layer or an electron blocking layer EBL in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be utilized as materials included in the hole buffer layer.

The emission layer EML is provided on the hole transport region HTR. The emission layer EML may have a thickness of, for example, about 100 Å to about 600 Å. The emission layer EML may have a single layer formed utilizing a single material, a single layer formed utilizing a plurality of different materials, or have a multilayer structure having a plurality of layers formed utilizing a plurality of different materials.

The emission layer EML may emit one of red light, green light, blue light, white light, yellow light, and cyan light. The emission layer EML may include a fluorescence emitting material or a phosphorescence emitting material.

In an embodiment, the emission layer EML includes a polycyclic compound containing two electron donors and one electron acceptor, and the electron acceptor includes a benzonitrile part and a pyridine part.

In an embodiment, the emission layer EML may be a fluorescence emission layer. For example, a portion of the light emitted from the emission layer EML may be attributed to thermally activated delayed fluorescence. In an embodiment, the emission layer EML may include a light-emitting component that emits thermally activated delayed fluorescence. In an embodiment, the emission layer EML may be an emission layer emitting thermally activated delayed fluorescence that emits blue light. Light-emitting component emitting thermally activated delayed fluorescence may be a material having excellent electron accepting and electron donating properties and smooth charge transfer (CT) in a molecule.

In an embodiment, the emission layer EML may include a polycyclic compound containing two electron donors and one electron acceptor. In addition, in an embodiment, the emission layer EML may include a host and a dopant, and the dopant may include a polycyclic compound containing two electron donors and one electron acceptor.

The polycyclic compound may, for example, have a structure represented by the following Formula 1:

Formula 1

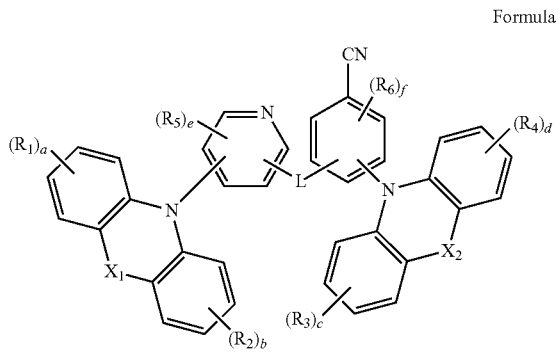

In Formula 1, $X_1$ and $X_2$ are each independently a direct linkage, $CR_7R_8$, $SiR_9R_{10}$, O, or S; and L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring.

In Formula 1, $R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or combined with an adjacent group to form a ring; and a, b, c and d are each independently an integer of 0 to 4.

If each of a to d is an integer of 2 or more, a plurality of $R_1$, $R_2$, $R_3$ and $R_4$ may be respectively the same or different from each other. For example, when a, b, c or d is an integer of 2 or more, a plurality of $R_1$, $R_2$, $R_3$ or $R_4$ may be the same or different from each other.

In Formula 1, $R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or combined with an adjacent group to form a ring; and e and f are each independently an integer of 0 to 3.

If each of e and f is an integer of 2 or more, a plurality of $R_5$ and $R_6$ may be respectively the same or different from each other. For example, when e or f is an integer of 2 or more, a plurality of $R_5$ or $R_6$ may be the same or different from each other.

e and f may each be 0. For example, if e is 0, a pyridine group in the polycyclic compound represented by Formula 1 may be an unsubstituted pyridylene group.

According to an embodiment, in the polycyclic compound represented by Formula 1,

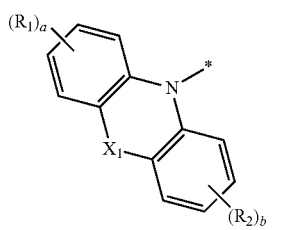

and

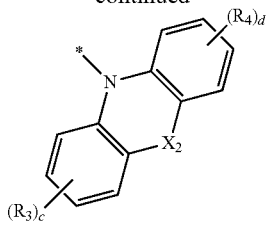

parts may be electron donors, and

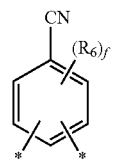

corresponding to a benzonitrile part and

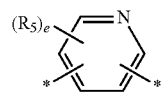

corresponding to a pyridine part may be electron acceptors. However, an embodiment of the inventive concept is not limited thereto.

In Formula 1, if L (which corresponds to a linker) is a direct linkage, the benzonitrile part and the pyridine part of the electron donor are directly bonded, and if L (which corresponds to a linker) is CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring, the benzonitrile part and the pyridine part of the electron acceptor are bonded via L.

The electron donor of Formula 1 does not include a cyano group. If the electron donor includes a cyano group, the absolute value (ΔEst) of the difference between a singlet energy level (S1) and a triplet energy level (T1), which will be explained later, becomes relatively large, and is not applicable as a material for emitting thermally activated delayed fluorescence.

In an embodiment, Formula 1 may be represented by one of the following Formula 1-1 to Formula 1-3:

Formula 1-1

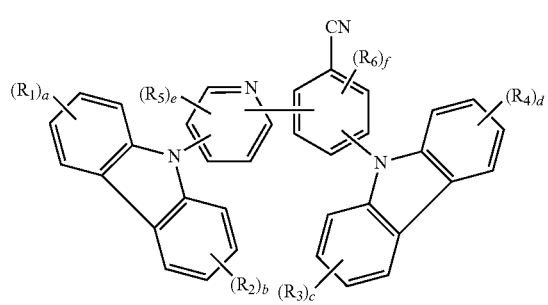

-continued

Formula 1-2

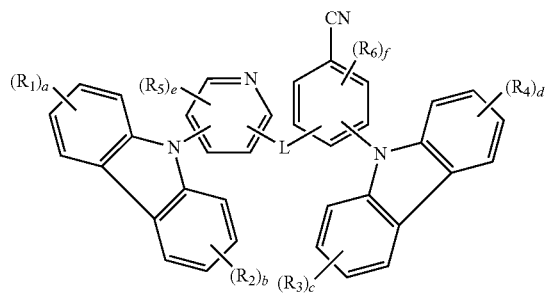

Formula 1-3

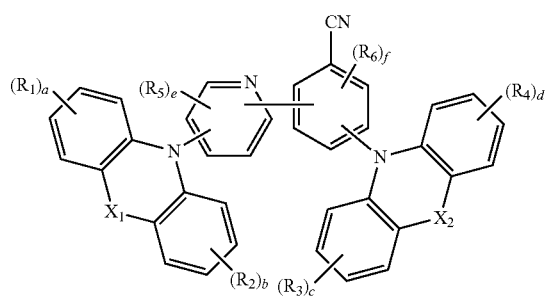

In Formula 1-1 to Formula 1-3, $X_1$ and $X_2$, L, $R_1$ to $R_6$, and a to f are the same as respectively defined in association with Formula 1. Formula 1-1 represents a case where $X_1$, $X_2$ and L are direct linkages, Formula 1-2 represents a case where $X_1$ and $X_2$ are direct linkages, and Formula 1-3 represents a case where L is a direct linkage.

In an embodiment, $X_1$ and $X_2$ of Formula 1 may be the same. For example, if $X_1$ is a direct linkage, $X_2$ is also a direct linkage, and if $X_1$ is $C(CH_3)_2$, $X_2$ is also $C(CH_3)_2$.

In an embodiment, $R_5$ and $R_6$ of Formula 1 may be each independently one of the following Formula 2-1 to Formula 2-4:

Formula 2-1

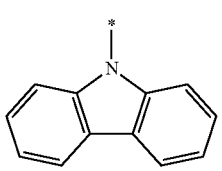

Formula 2-2

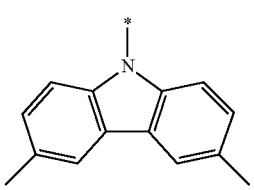

Formula 2-3

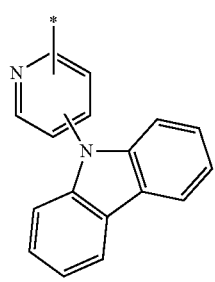

-continued

Formula 2-4

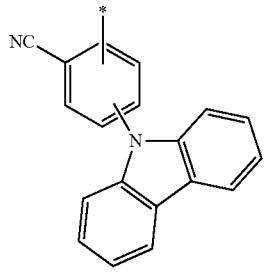

That is, $R_5$ and $R_6$ are each independently a substituted or unsubstituted carbazole group, a substituted pyridyl group, or a substituted benzonitrile group. In an embodiment, $R_5$ and $R_6$ are each independently an unsubstituted carbazole group, a carbazole group substituted with an alkyl group, a pyridyl group substituted with a carbazole group, or a benzonitrile group substituted with a carbazole group.

In Formula 1, $R_1$ to $R_4$ are each independently a hydrogen atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring.

In $R_1$ to $R_4$ of Formula 1, a cyano group is excluded from "substituted or unsubstituted" substituents. Particularly, the substituents in $R_1$ to $R_4$ may be each independently a hydrogen atom, a fluorine atom, a methyl group, an unsubstituted aryl group having 6 to 30 carbon atoms for forming a ring, or an unsubstituted heteroaryl group having 2 to 30 carbon atoms for forming a ring.

In an embodiment, $R_1$ to $R_4$ of Formula 1 may be each independently represented by one of the following Formula 3-1 to Formula 3-3:

Formula 3-1

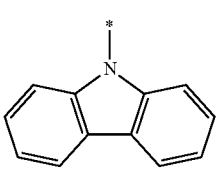

Formula 3-2

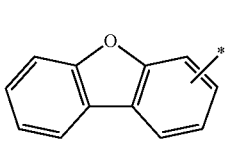

Formula 3-3

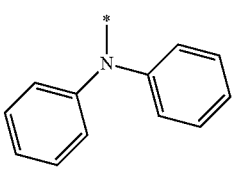

In an embodiment, L of Formula 1 may be represented by one of the following Formulae 4-1 and 4-2:

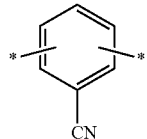

Formula 4-1

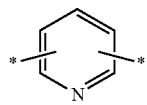

Formula 4-2

According to an embodiment, the polycyclic compound represented by Formula 1 may be a material for emitting delayed fluorescence. The polycyclic compound of an embodiment may be a material for emitting thermally activated delayed fluorescence.

According to an embodiment, the polycyclic compound represented by Formula 1 may have an absolute value (ΔEst) of the difference between a singlet energy level (S1) and a triplet energy level (T1) of about 0.2 eV or less. For example, S1-T1≤0.2 eV may be satisfied.

For example, the polycyclic compound represented by Formula 1 has a small difference between a singlet energy level (S1) and a triplet energy level (T1) and may be utilized as a material for emitting thermally activated delayed fluorescence. In an embodiment, the polycyclic compound represented by Formula 1 may be utilized as a material for emitting thermally activated delayed fluorescence, which emits blue light. However, an embodiment of the inventive concept is not limited thereto. The polycyclic compound of an embodiment may be a material for emitting thermally activated delayed fluorescence, which emits red light.

According to an embodiment, the polycyclic compound represented by Formula 1 may be any one among the compounds represented in the following Compound Group 1:

Compound Group 1

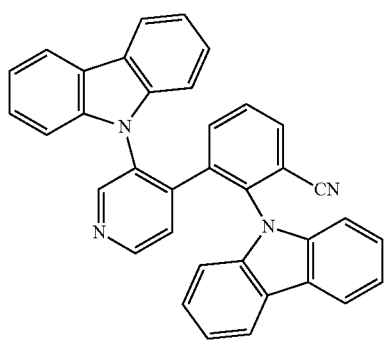

1

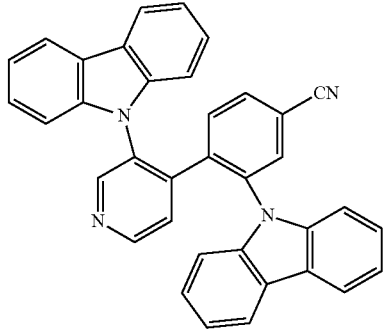

2

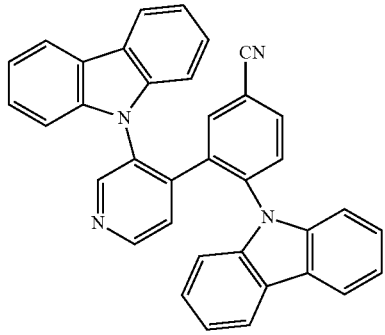

3

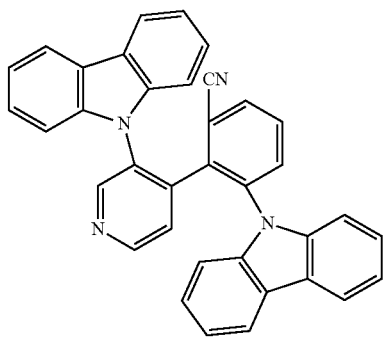

4

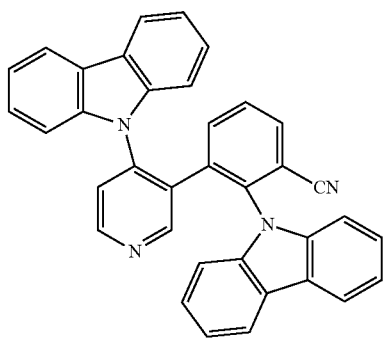

5

-continued
6
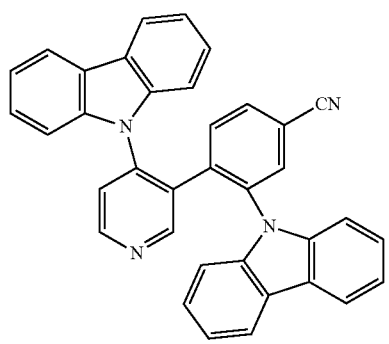
7
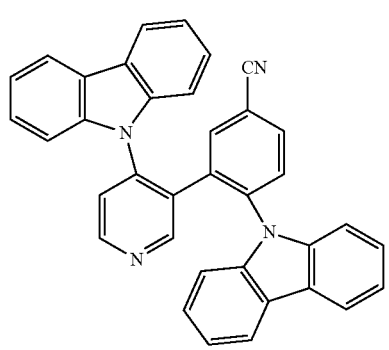
8
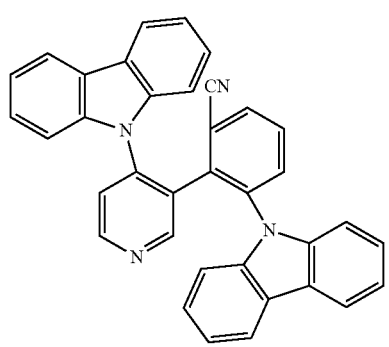
9
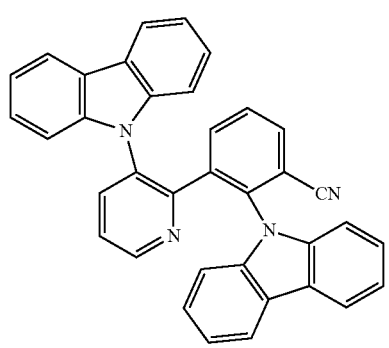
-continued
10
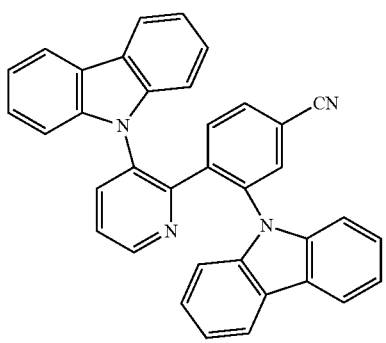
11
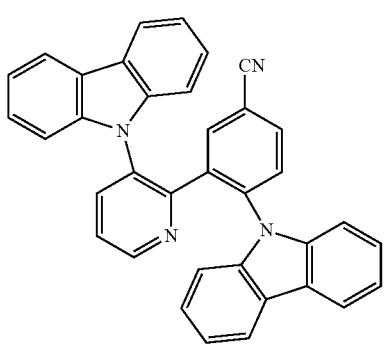
12
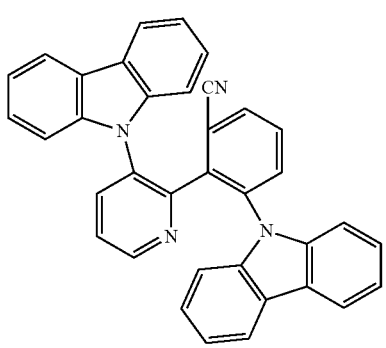
13
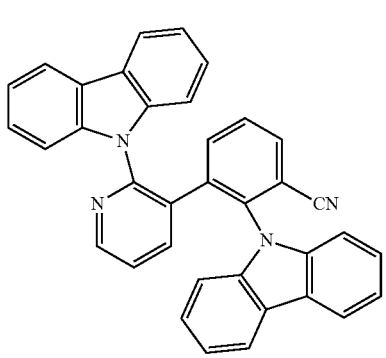

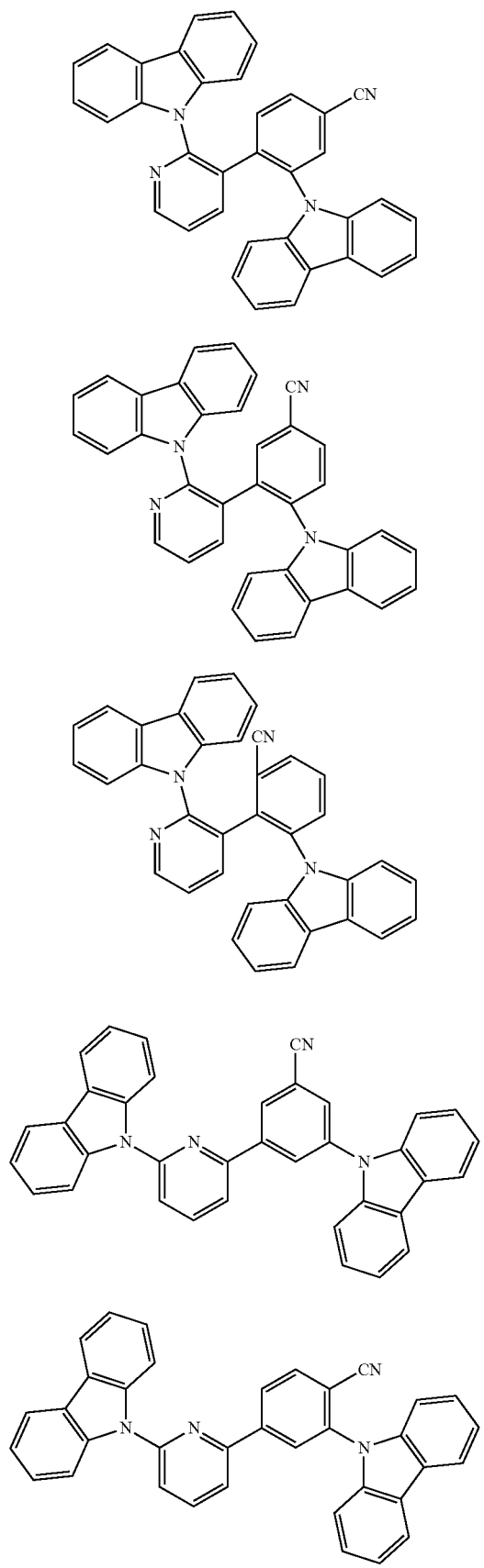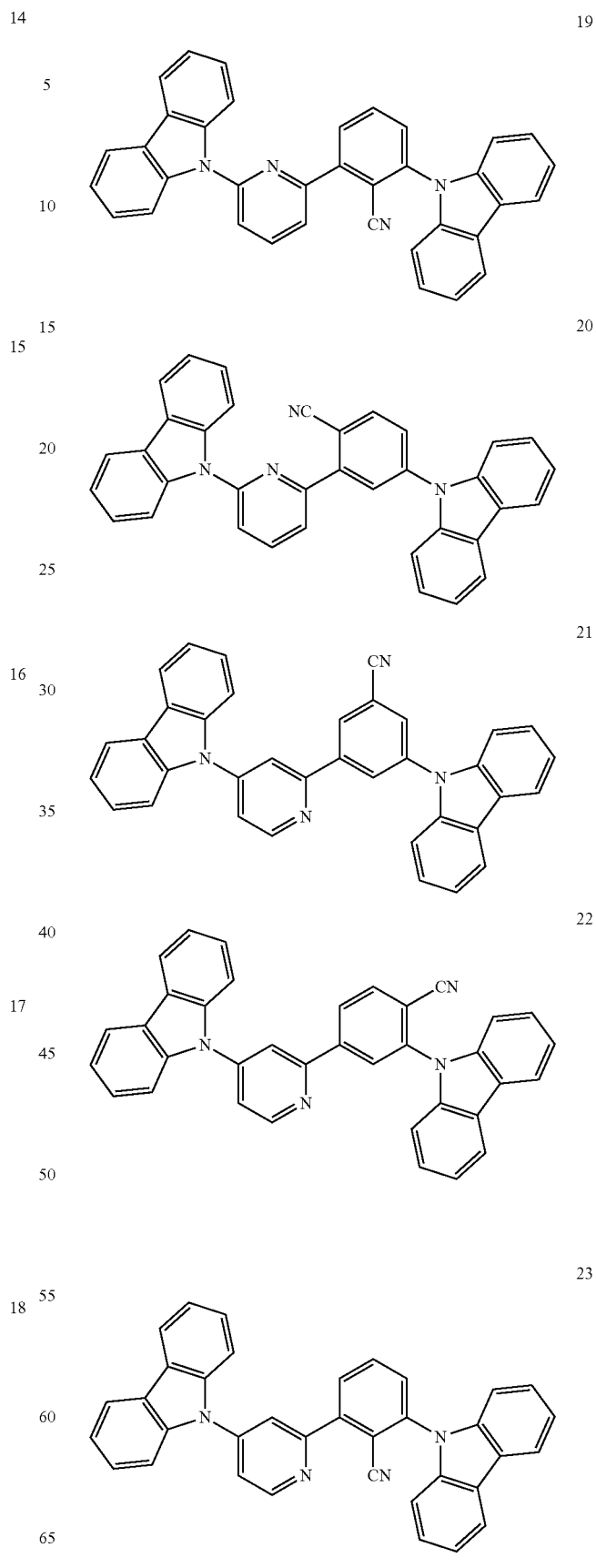

24
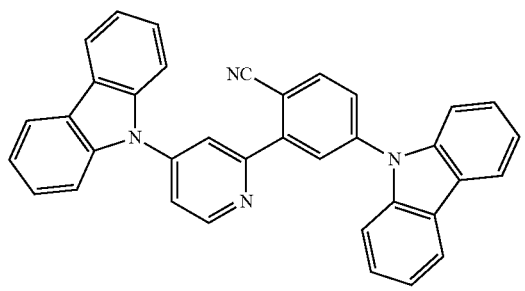
25
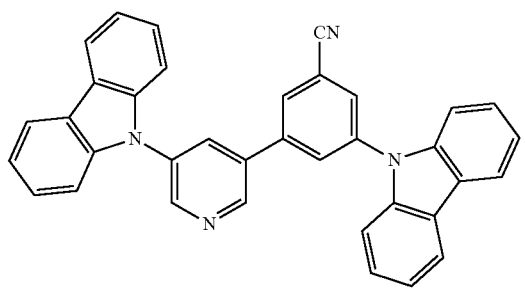
26
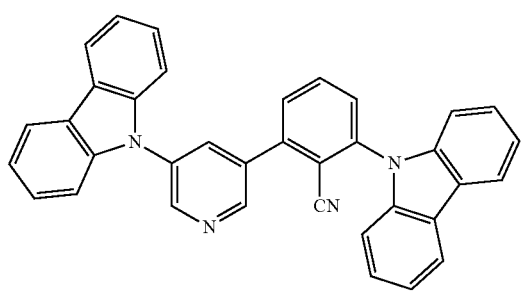
27
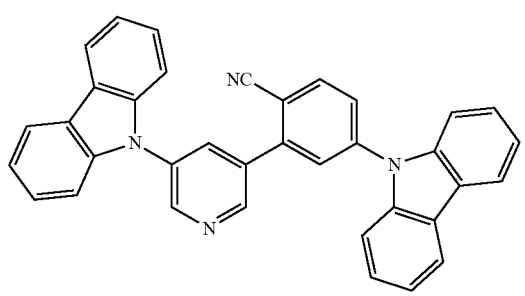
28
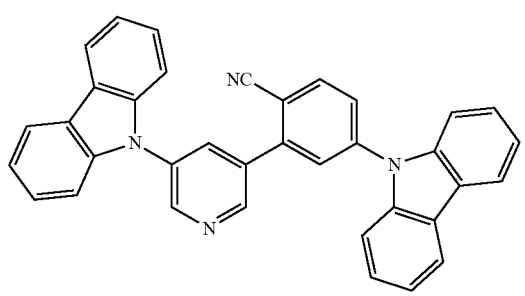
29
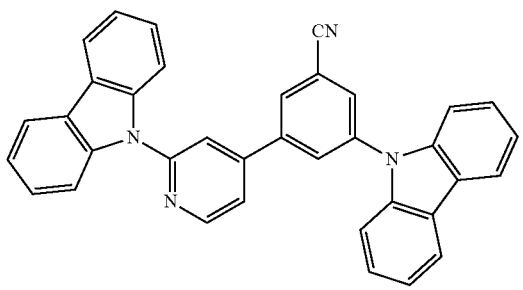
30
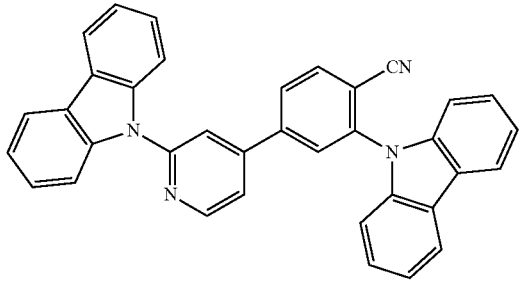
31
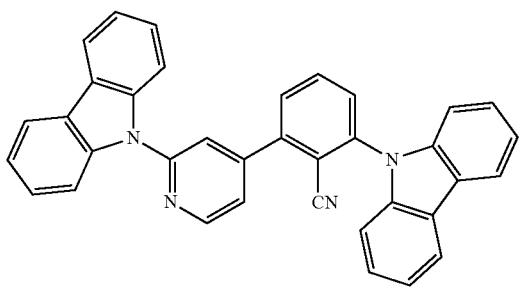
32
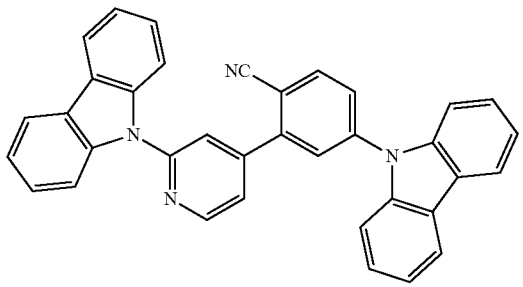

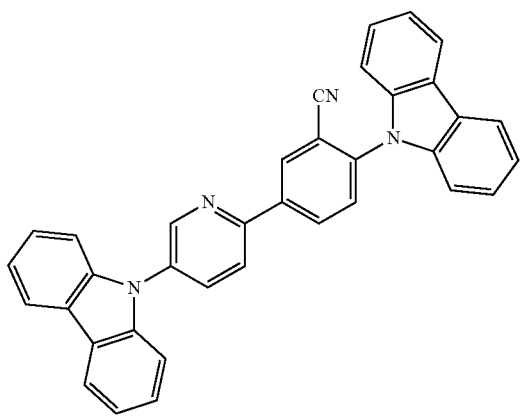
33
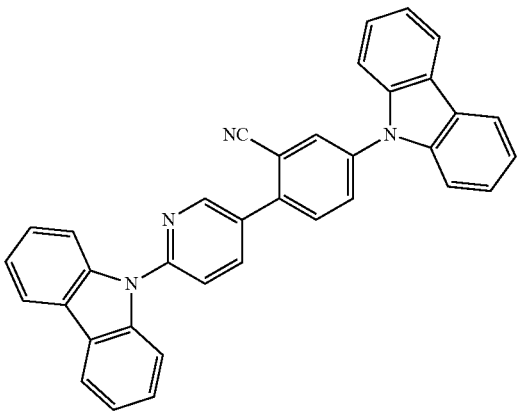
36
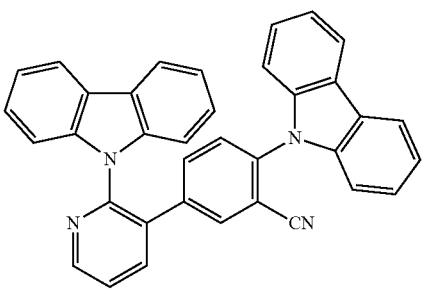
37
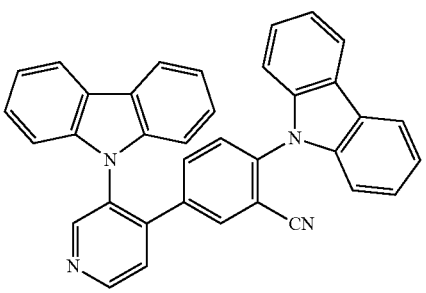
38
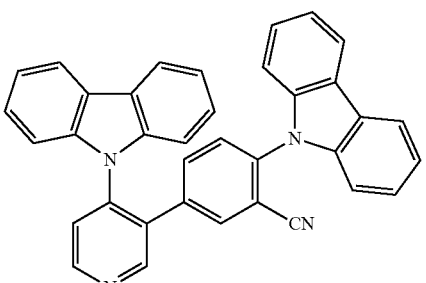
39
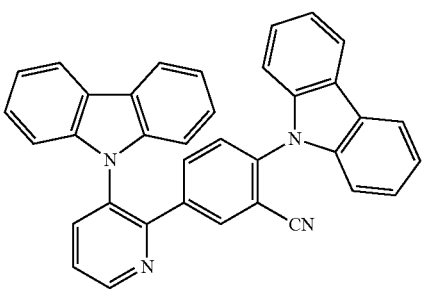
40
34
35

41
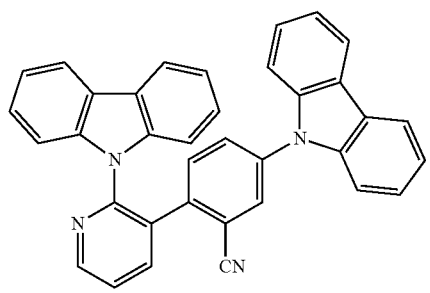
42
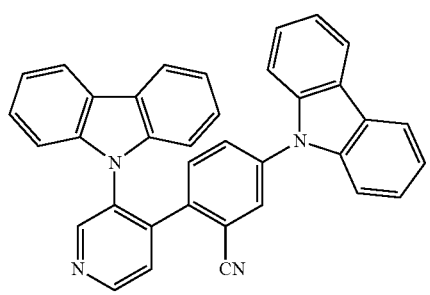
43
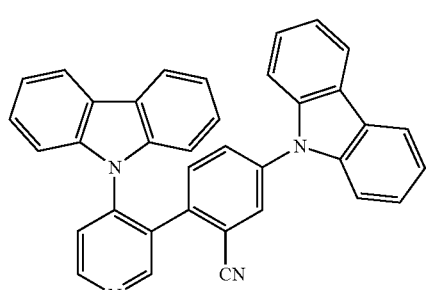
44
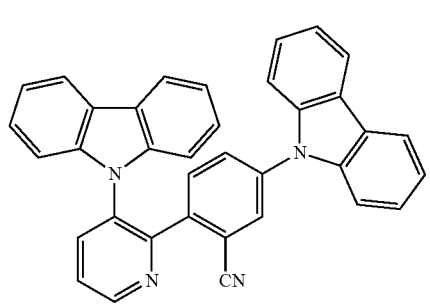
45
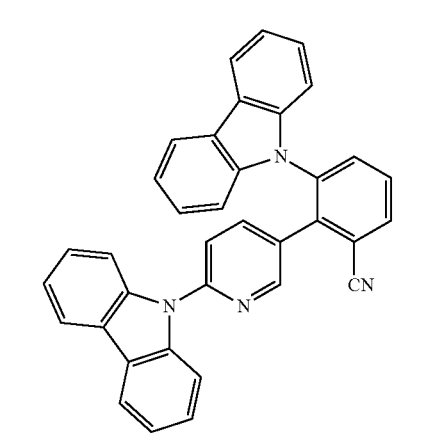
46
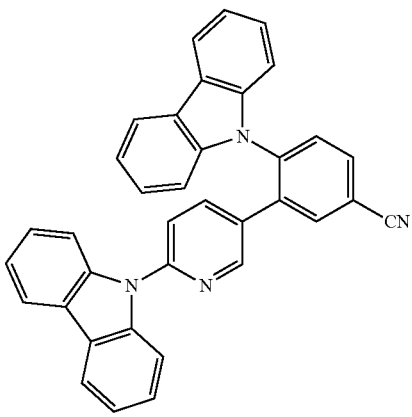
47
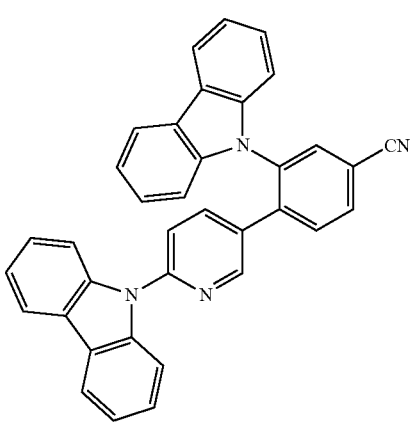
48
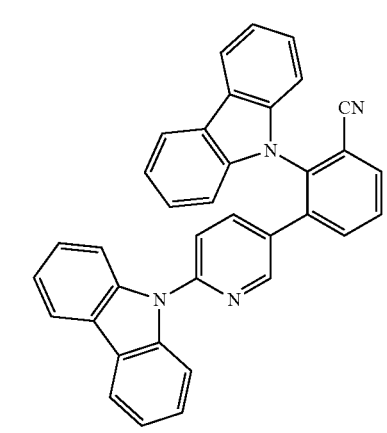

49
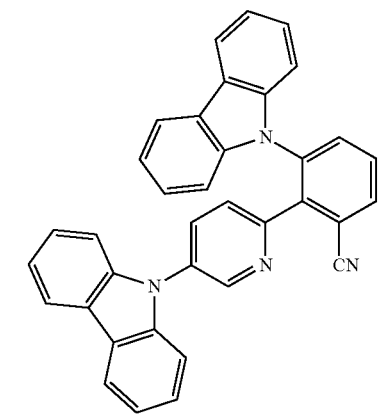
50
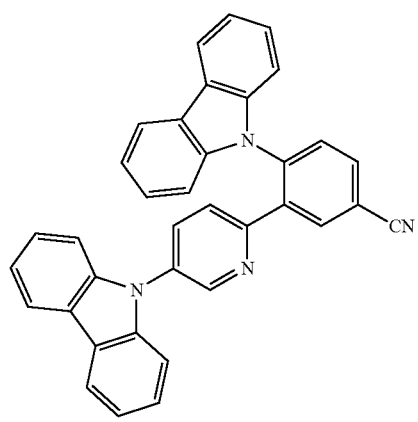
51
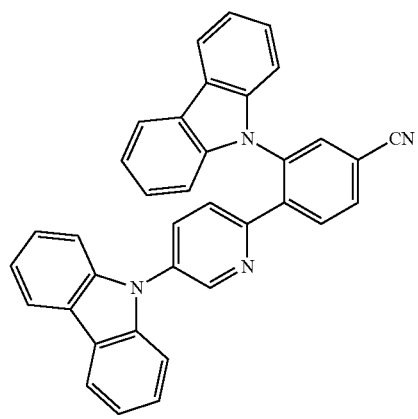
52
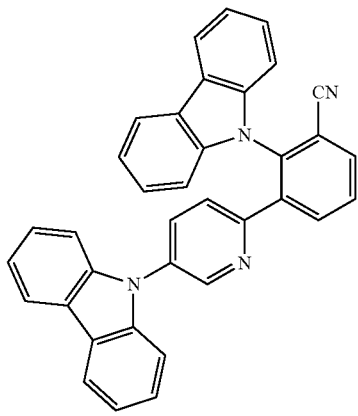
53
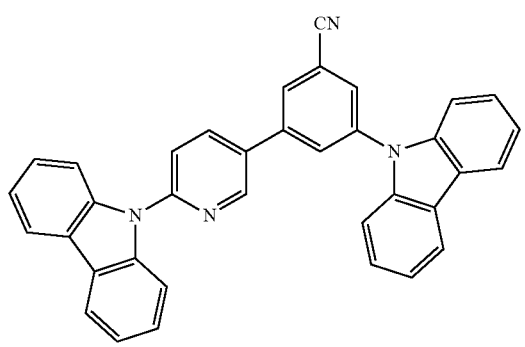
54
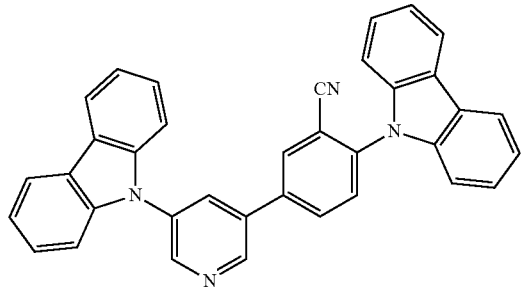
55

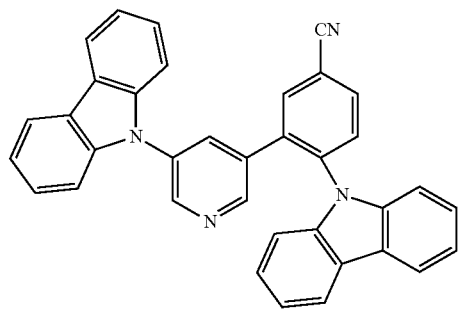
56
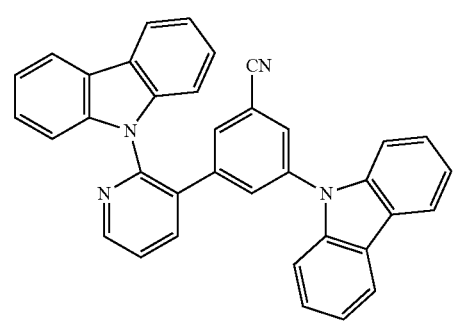
57
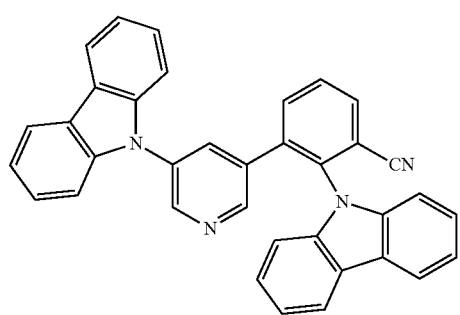
58
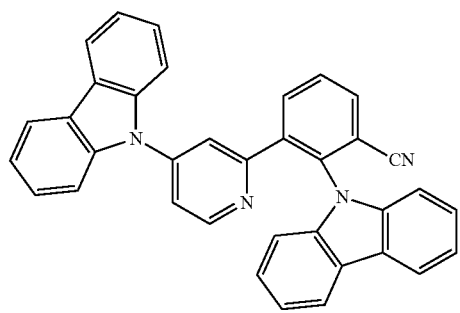
59
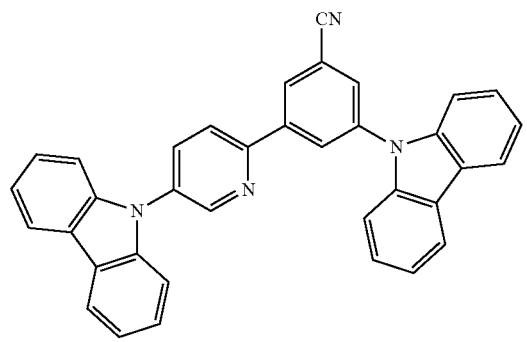
60
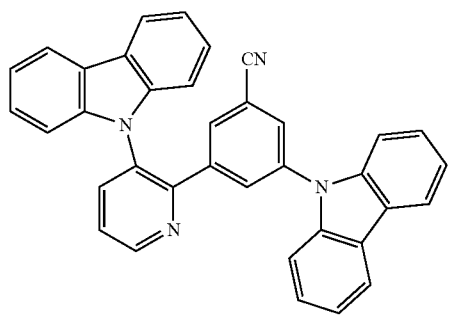
61
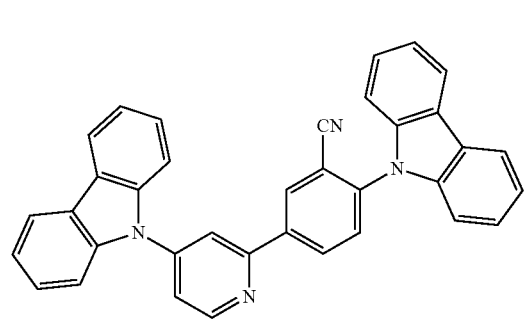
62
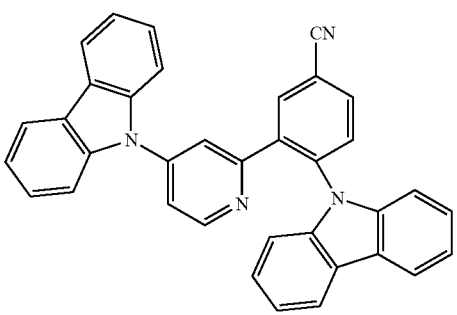
63
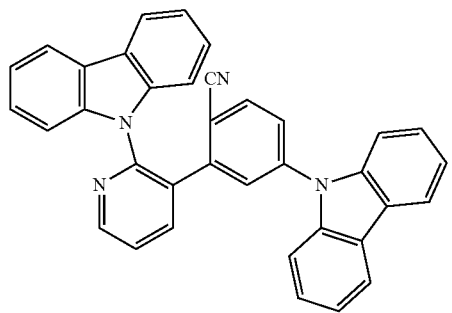
64
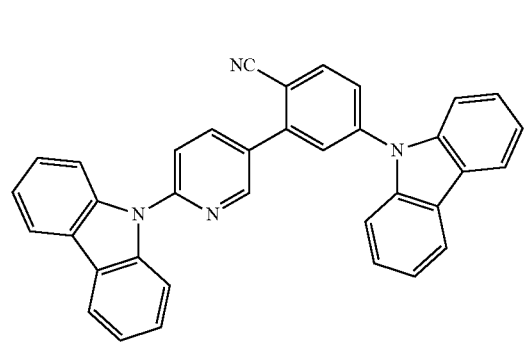
65

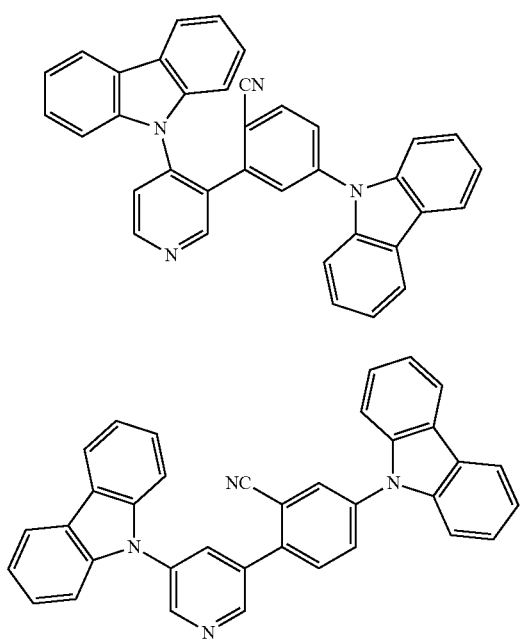
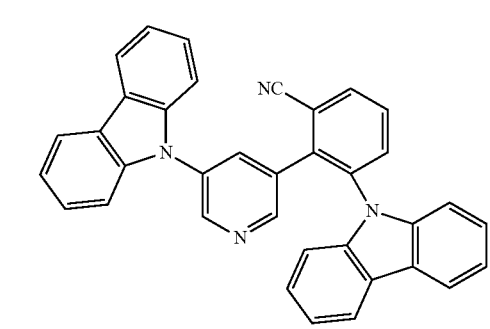
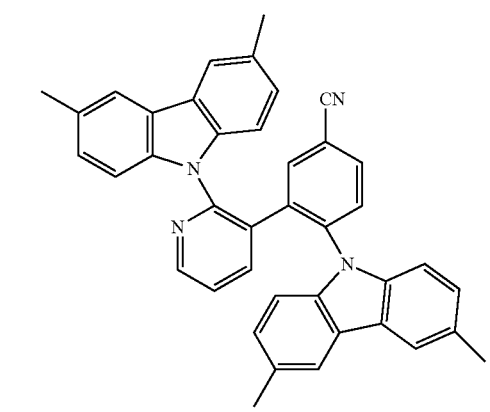
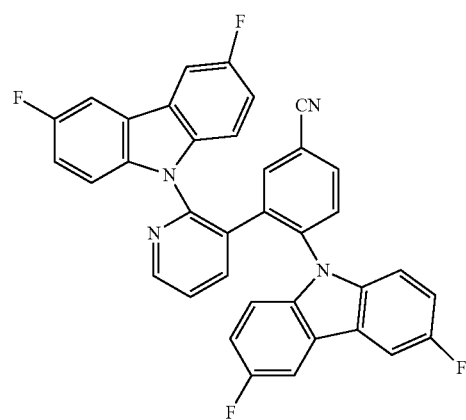
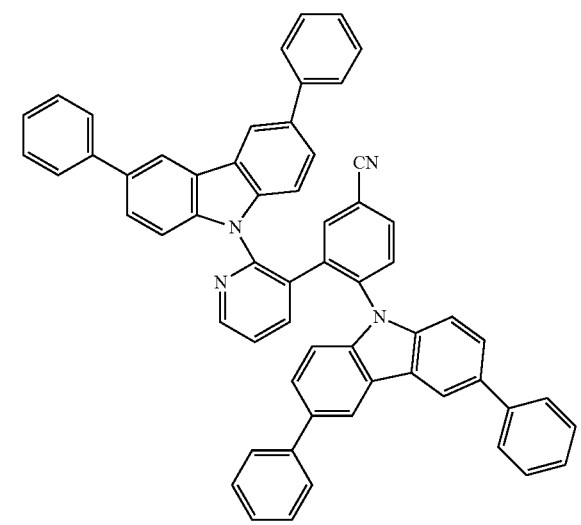

73
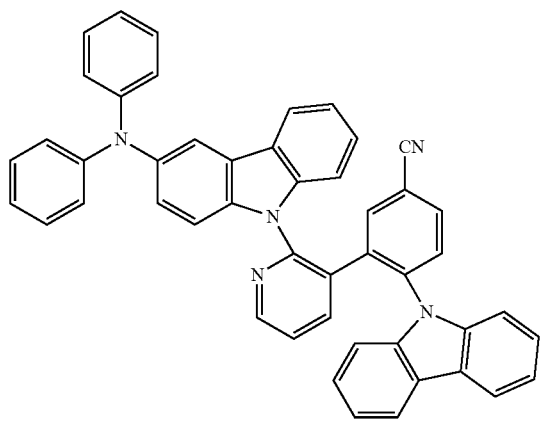
74
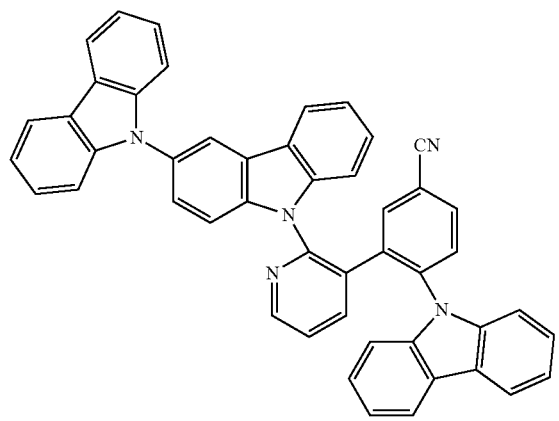
75
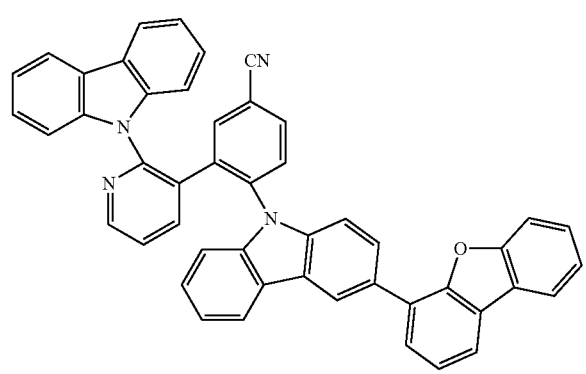
76
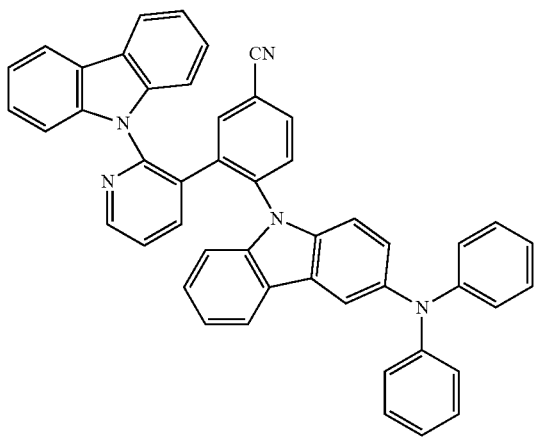
77
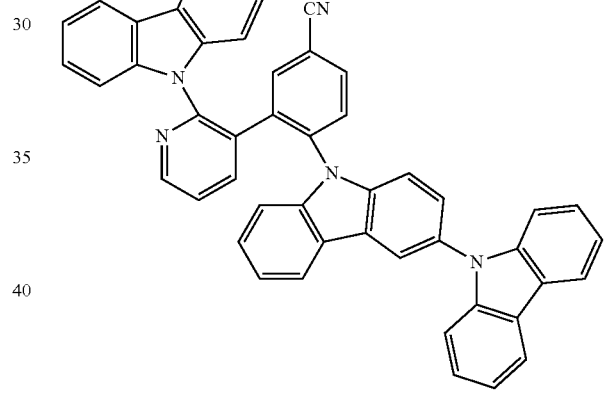
78
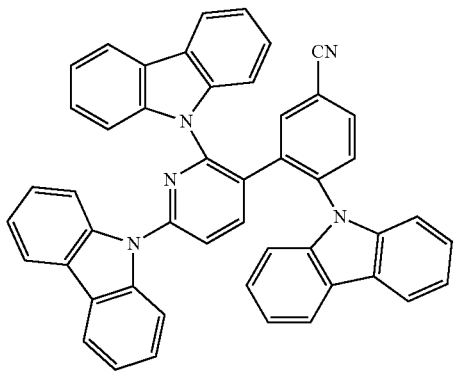

79
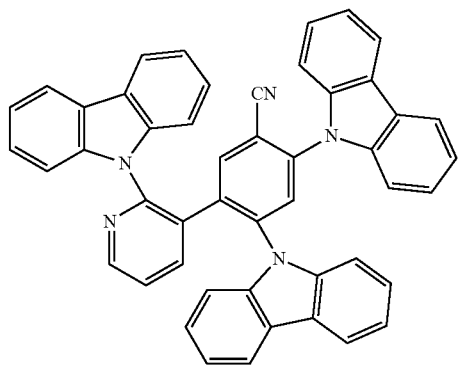
80
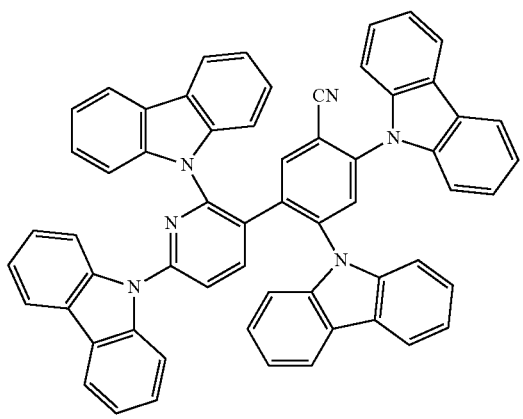
81
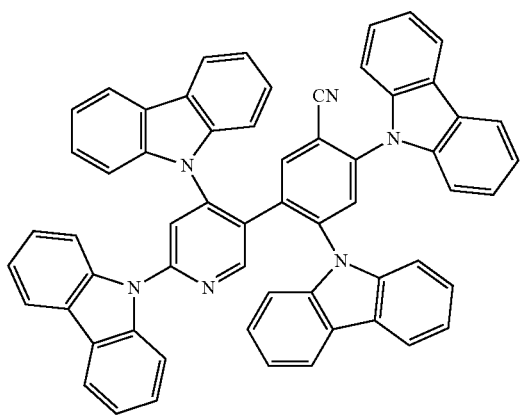
82
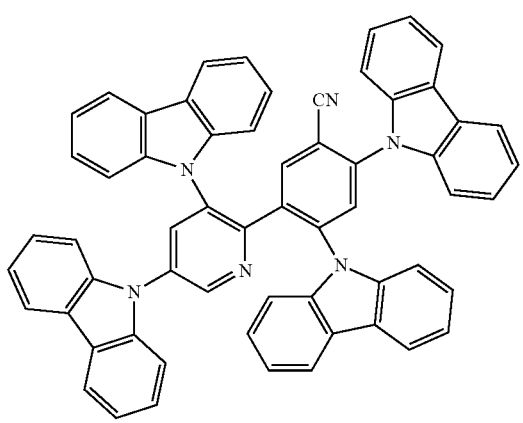
83
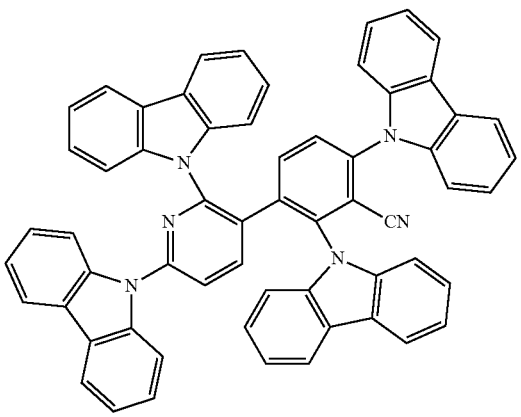
84
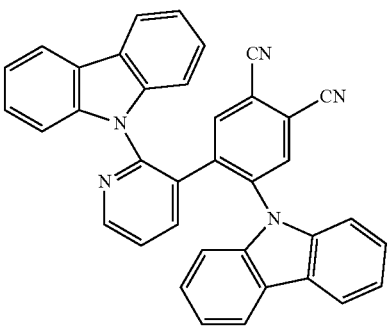
85
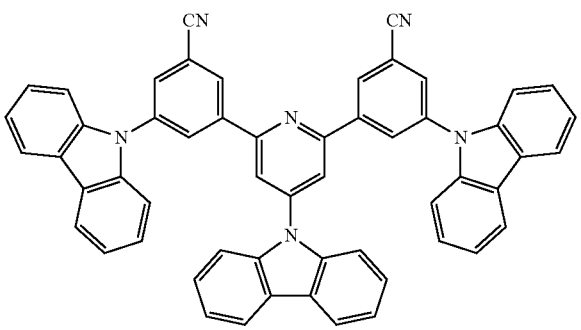
86
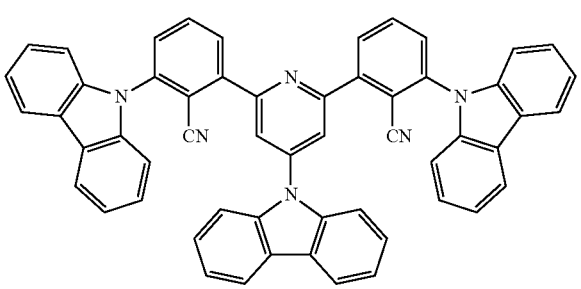

87
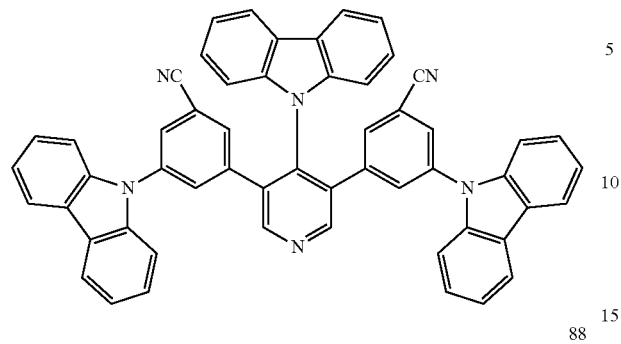
88
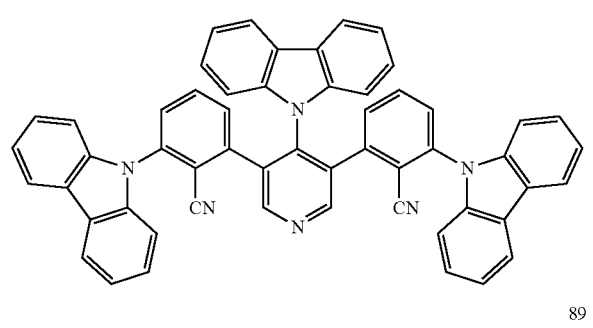
89
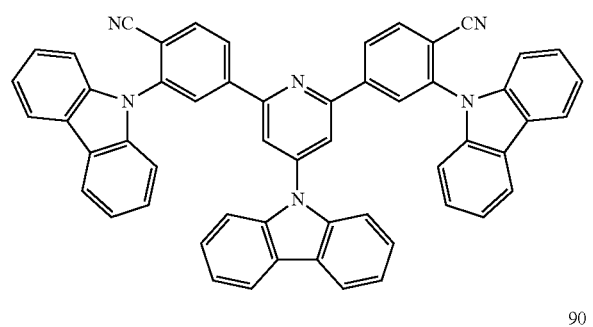
90
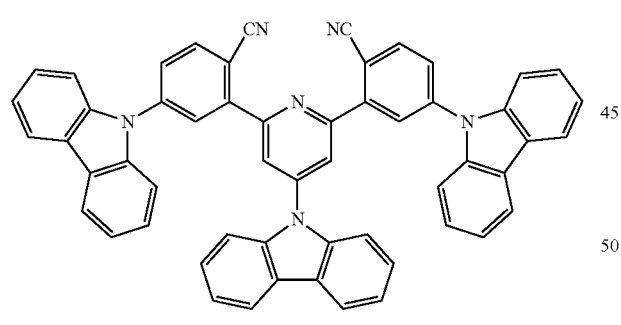
91
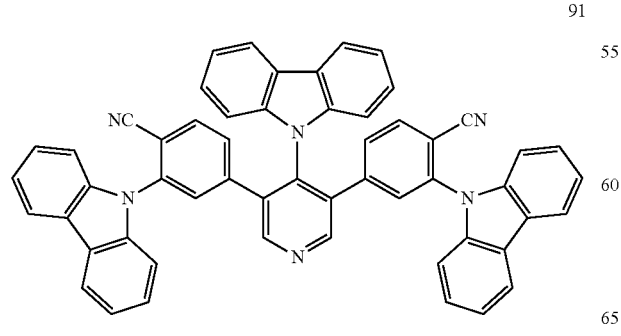
92
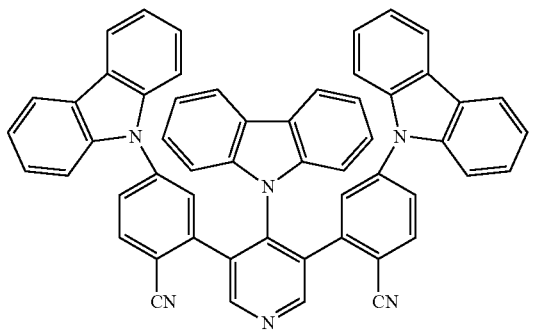
93
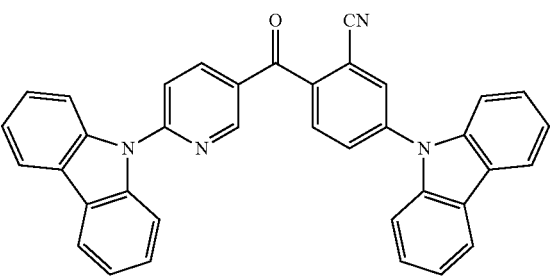
94
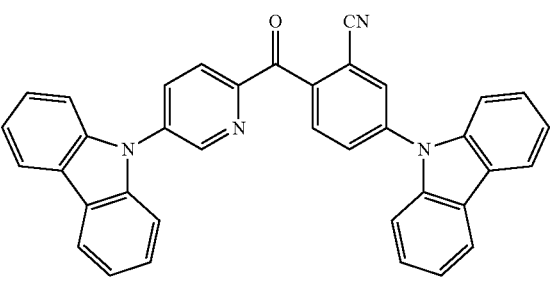
95
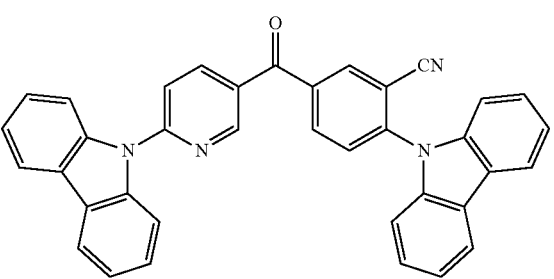
96
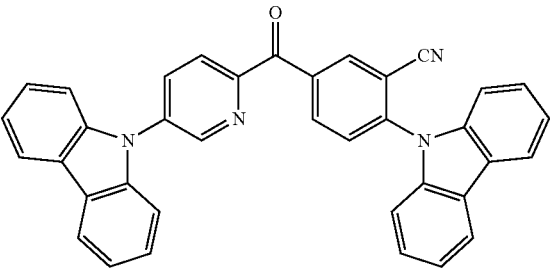

97
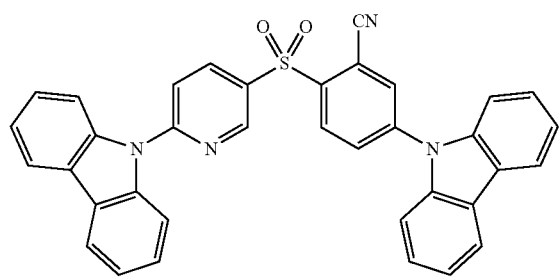
98
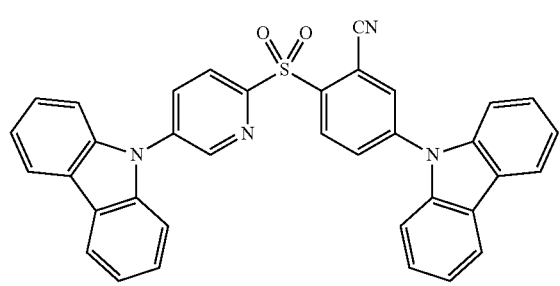
99
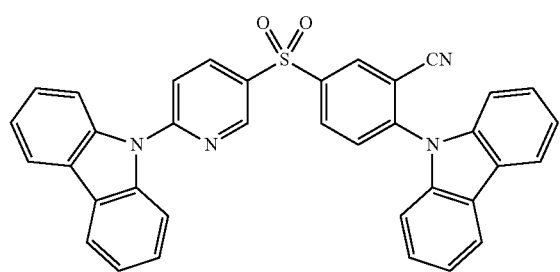
100
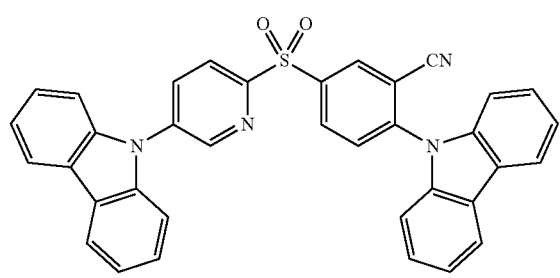
101
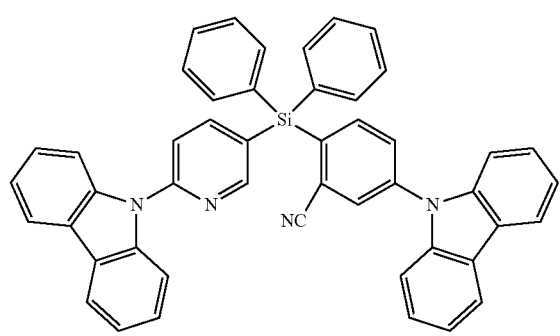
102
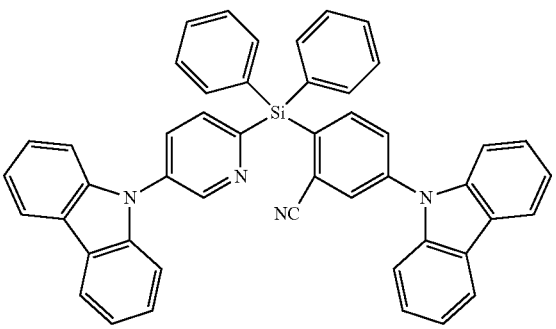
103
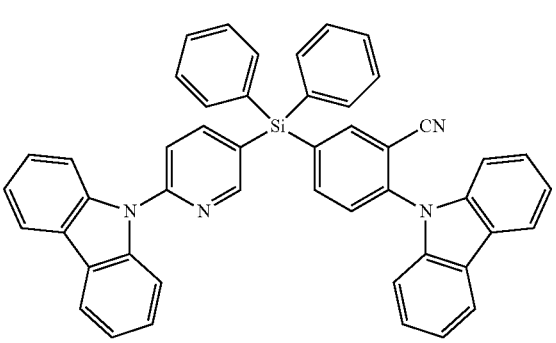
104
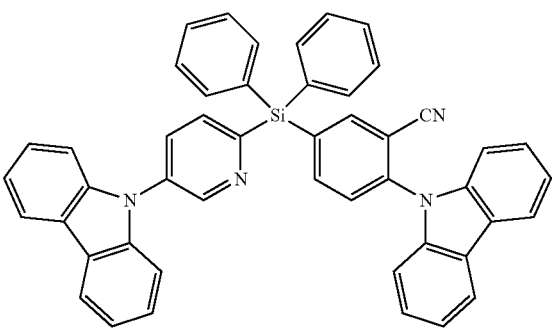
105
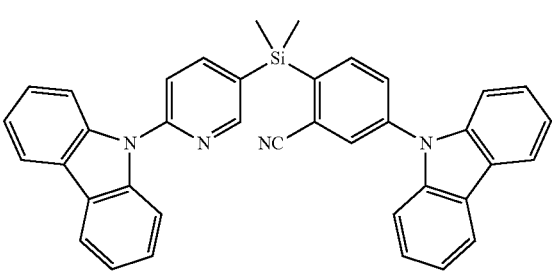
106

-continued
107
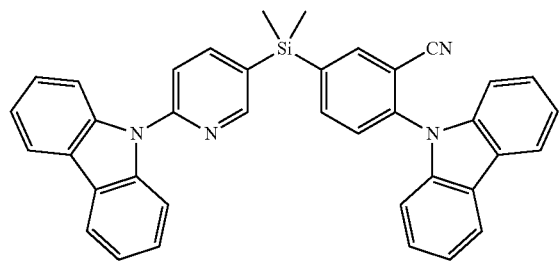
108
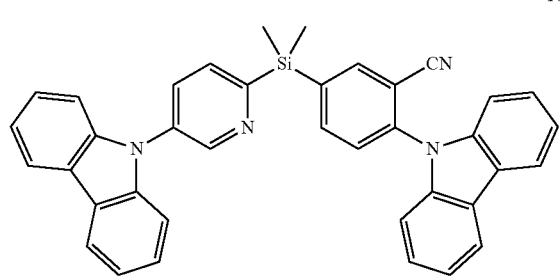
109
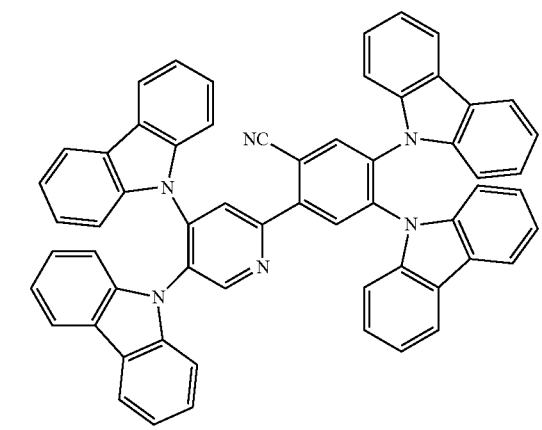
110
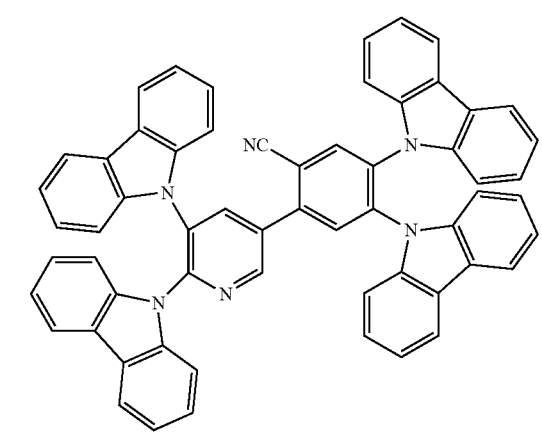
-continued
111
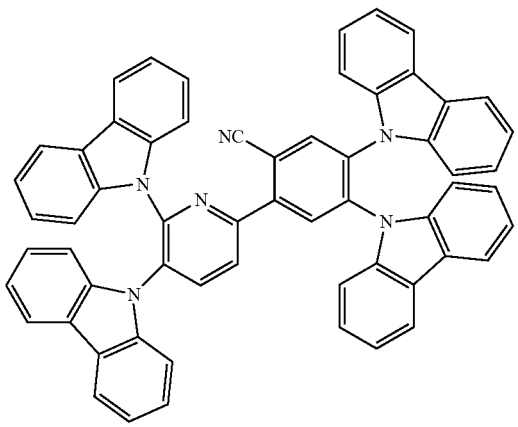
112
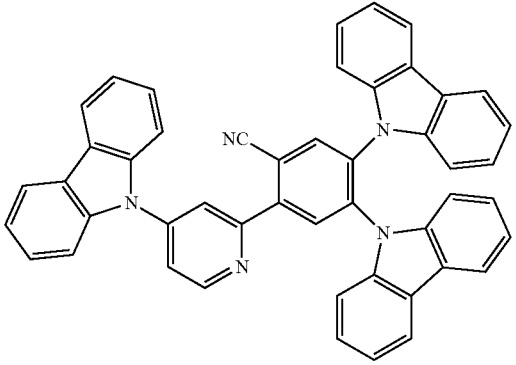
113
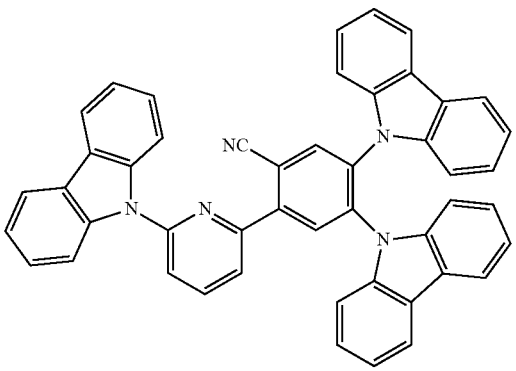
114
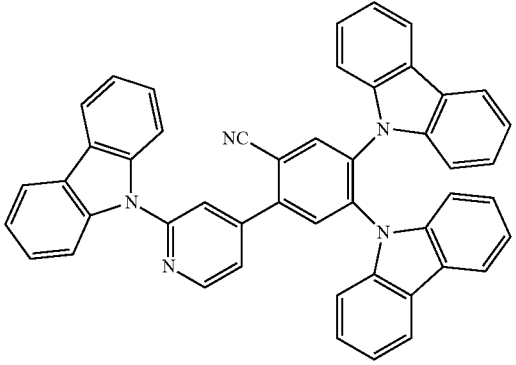

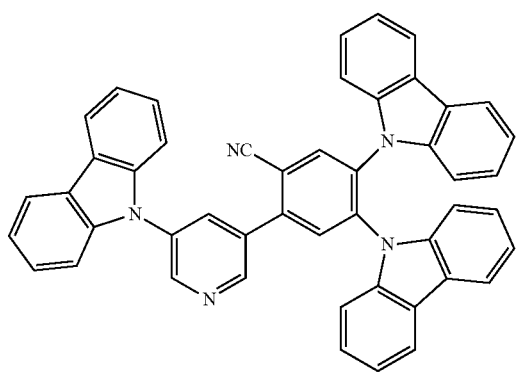
115
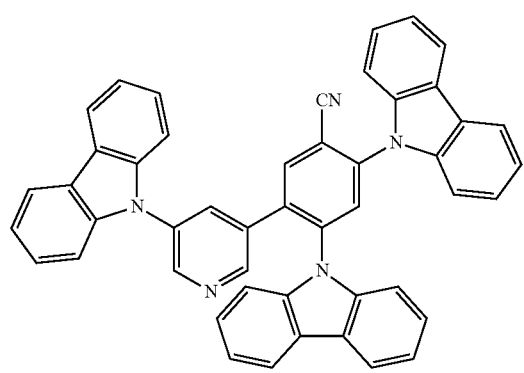
116
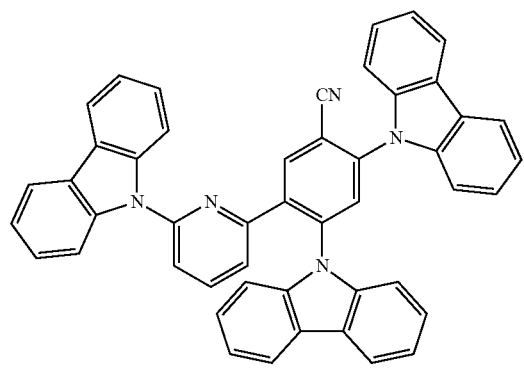
117
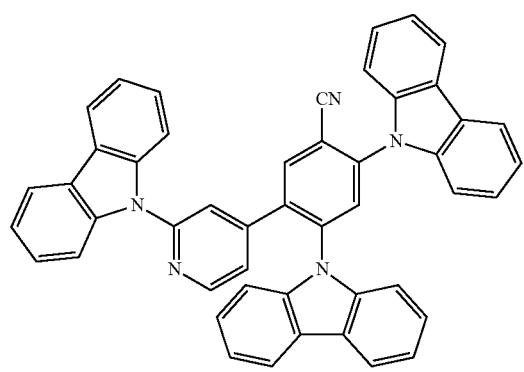
118
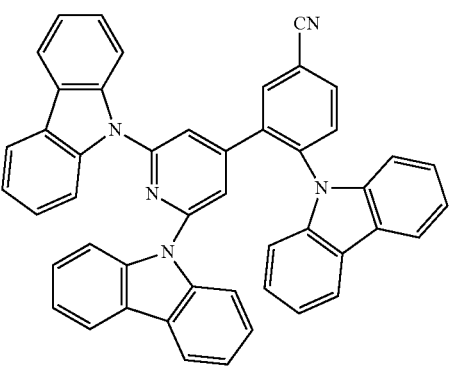
119
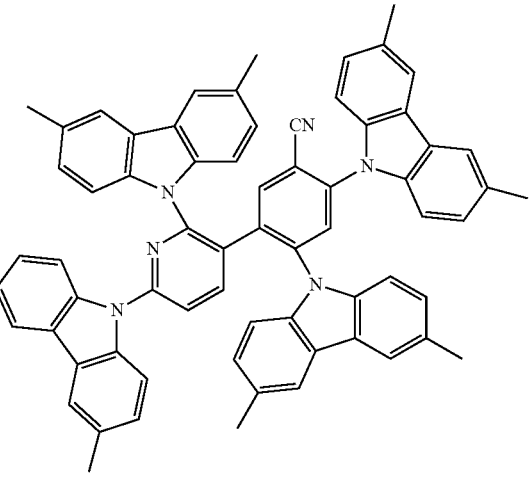
120
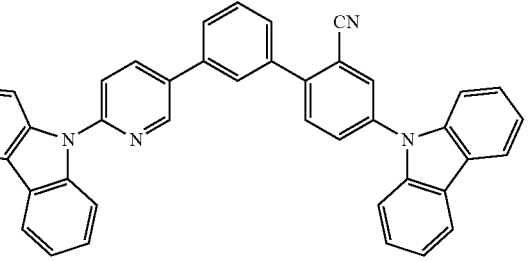
121
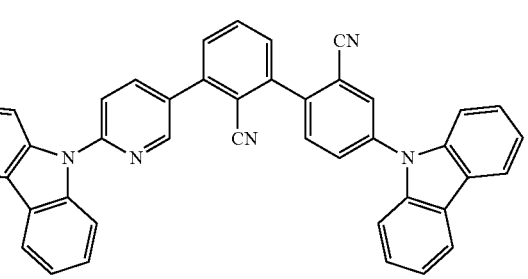
122

123
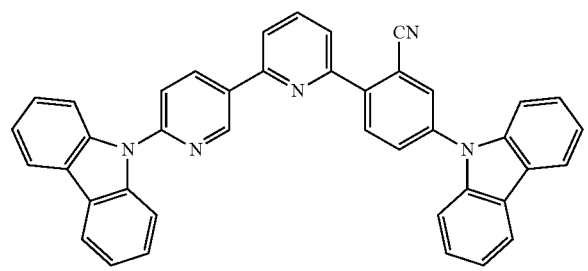
124
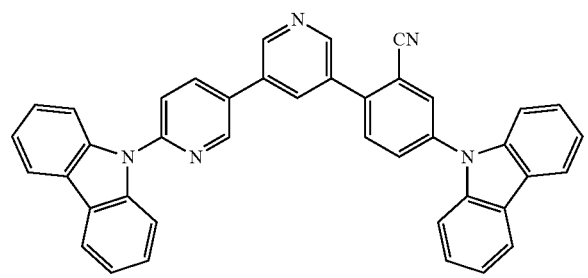
125
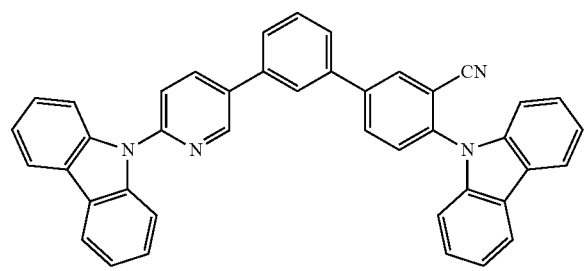
126
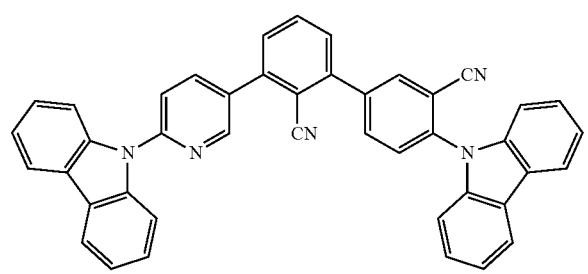
127
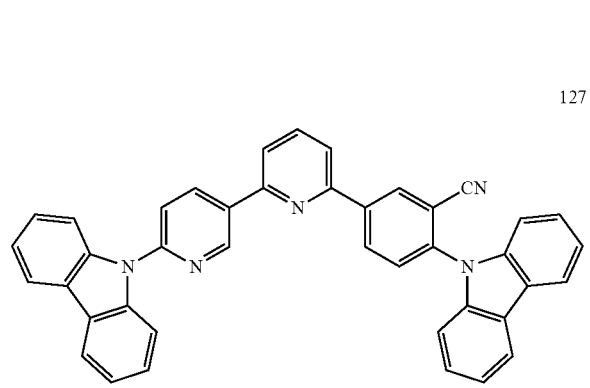
128
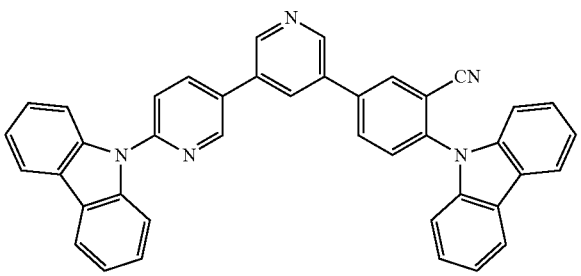
129
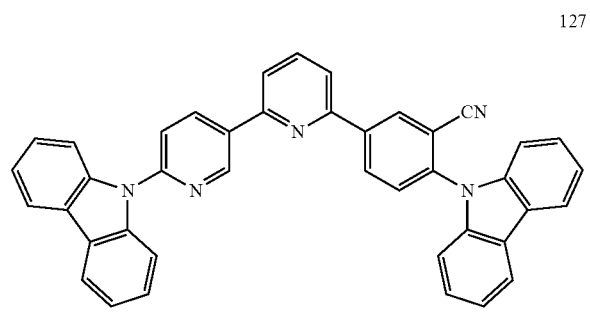
130
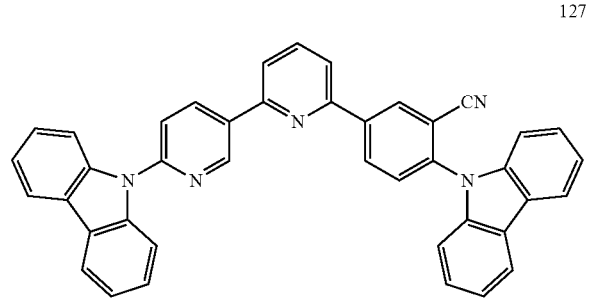
131
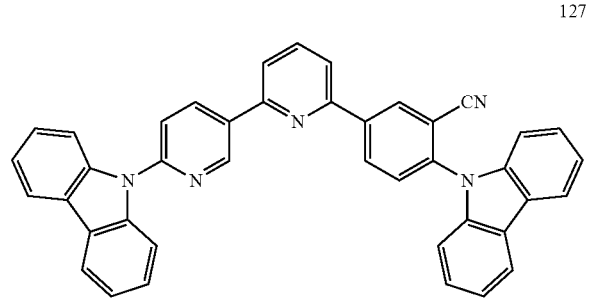
132
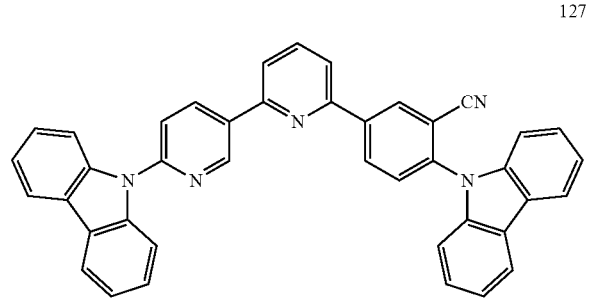

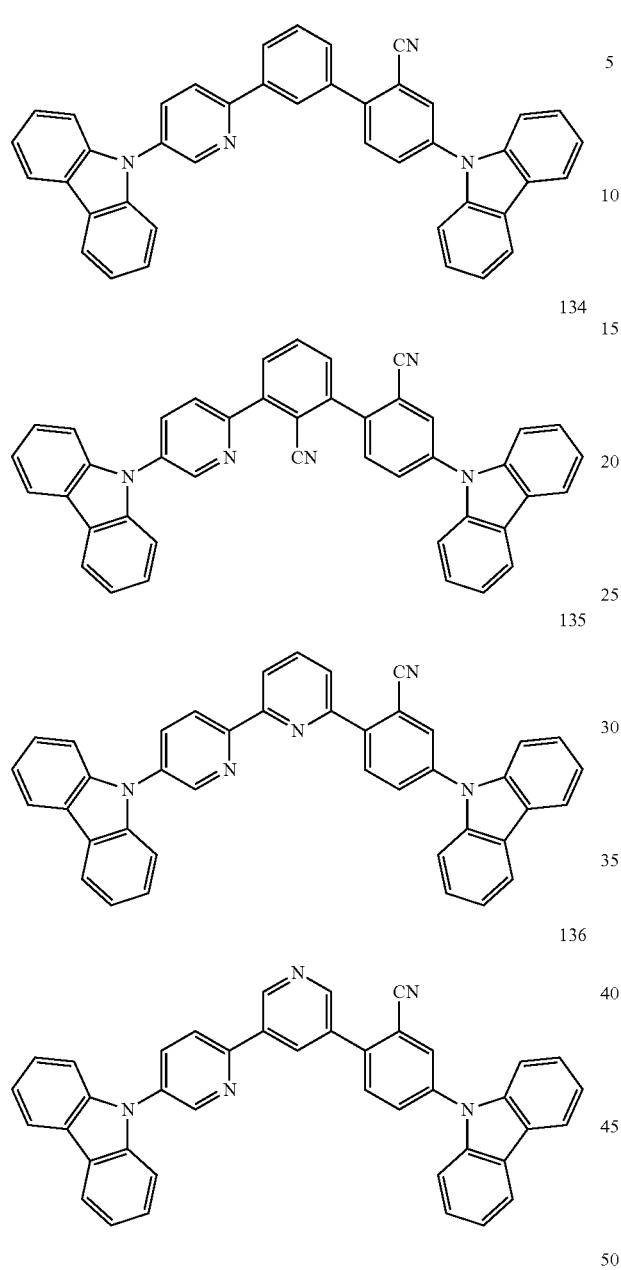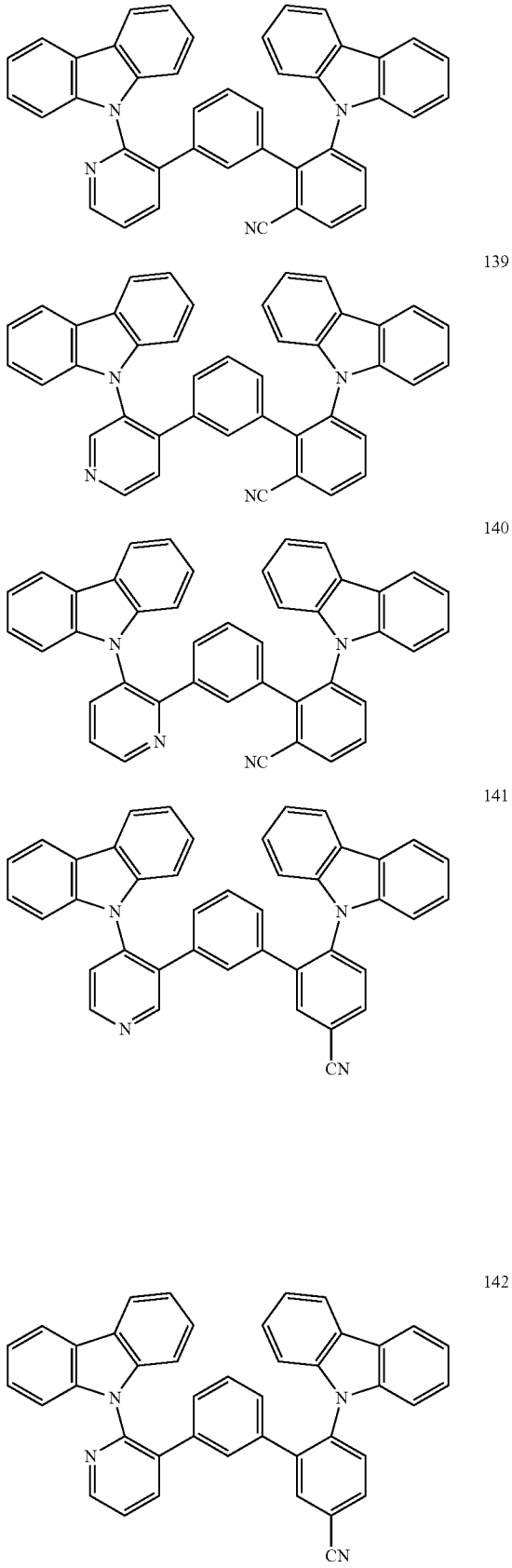

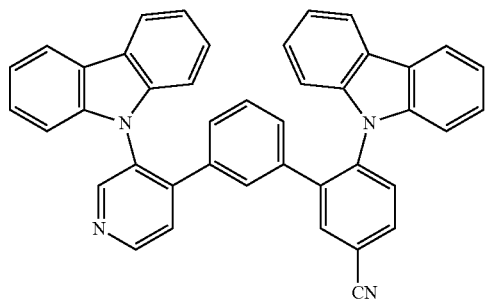
143
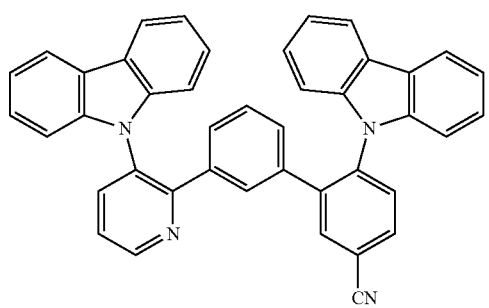
144
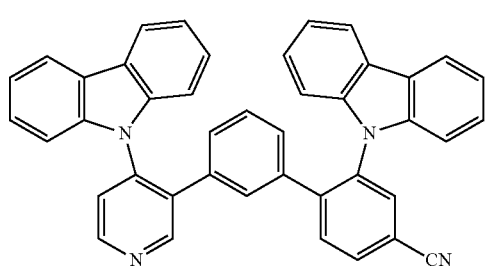
145
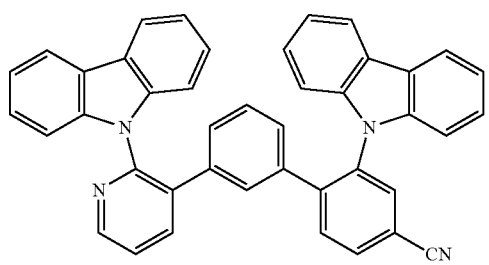
146
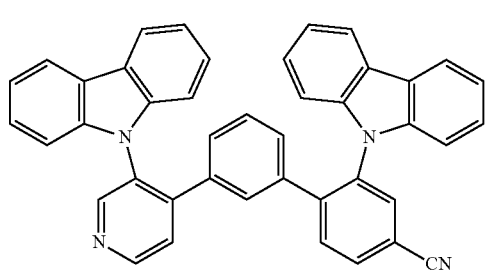
147
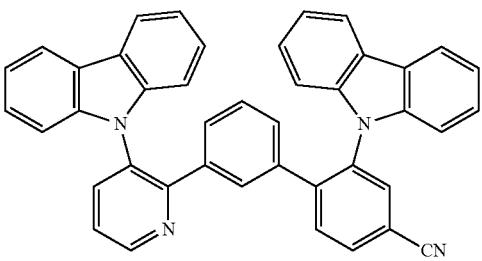
148
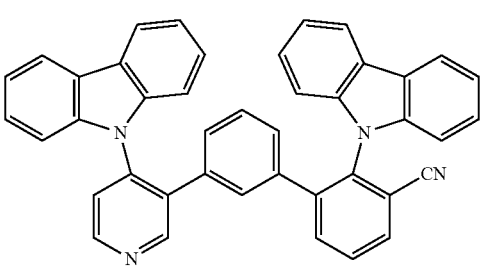
149
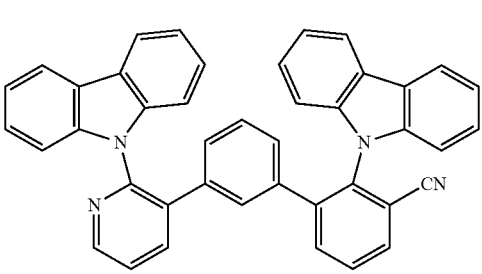
150
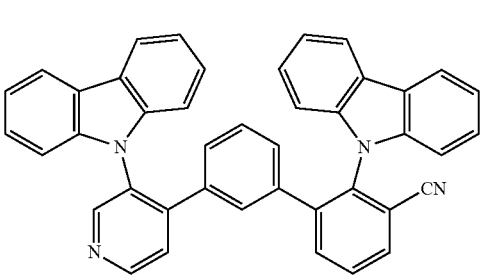
151
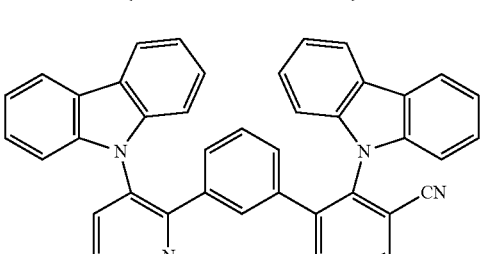
152
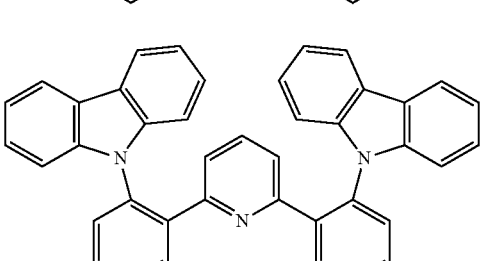
153

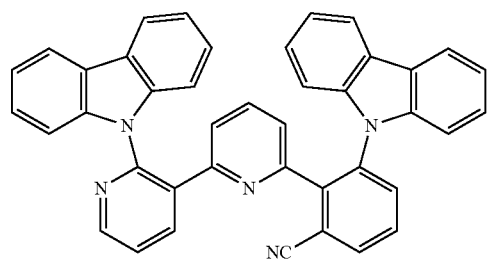
154
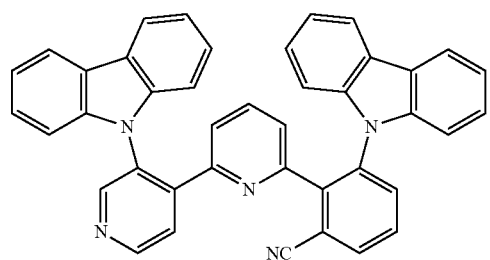
155
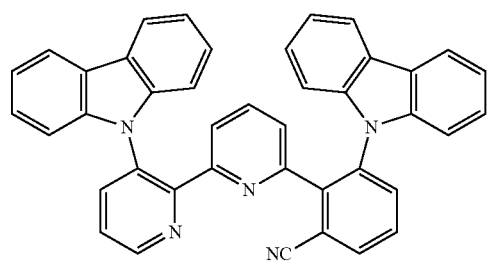
156
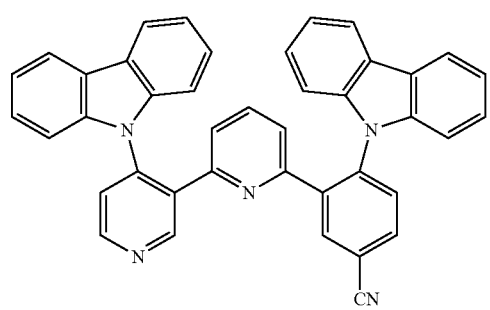
157
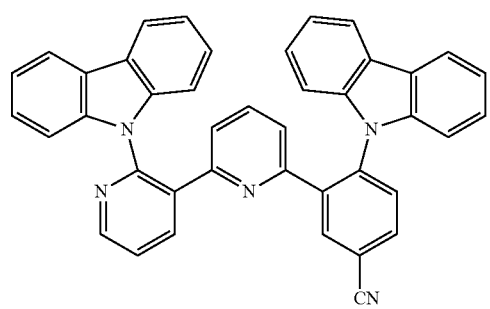
158
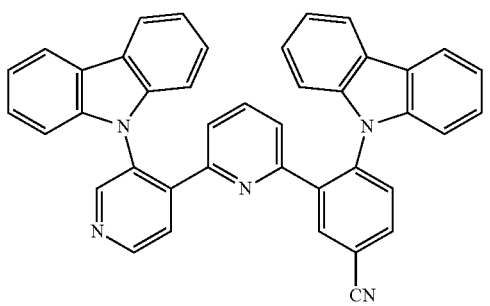
159
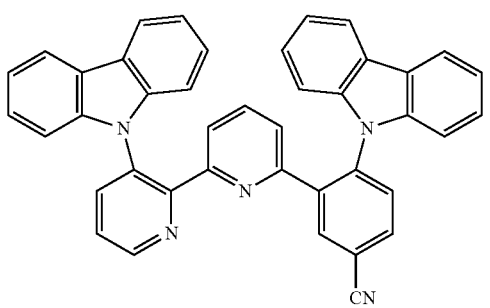
160
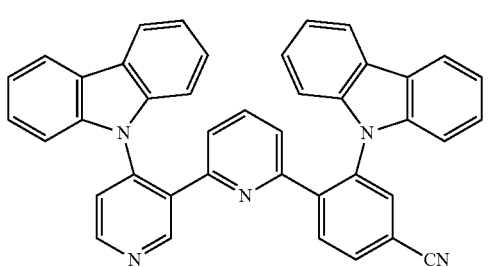
161
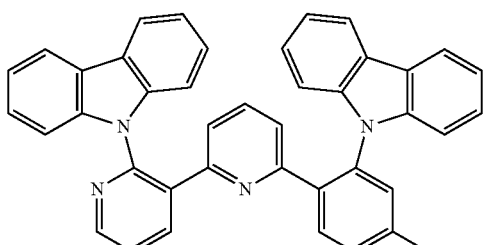
162
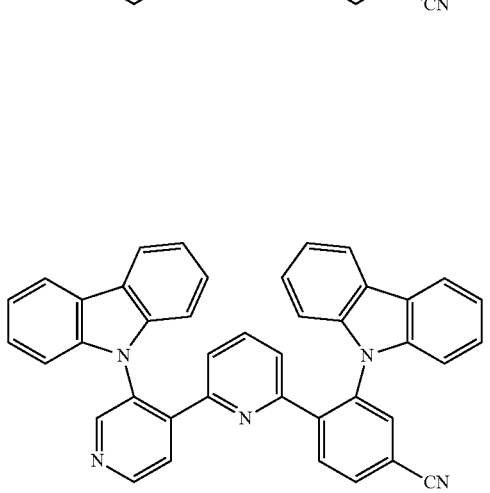
163

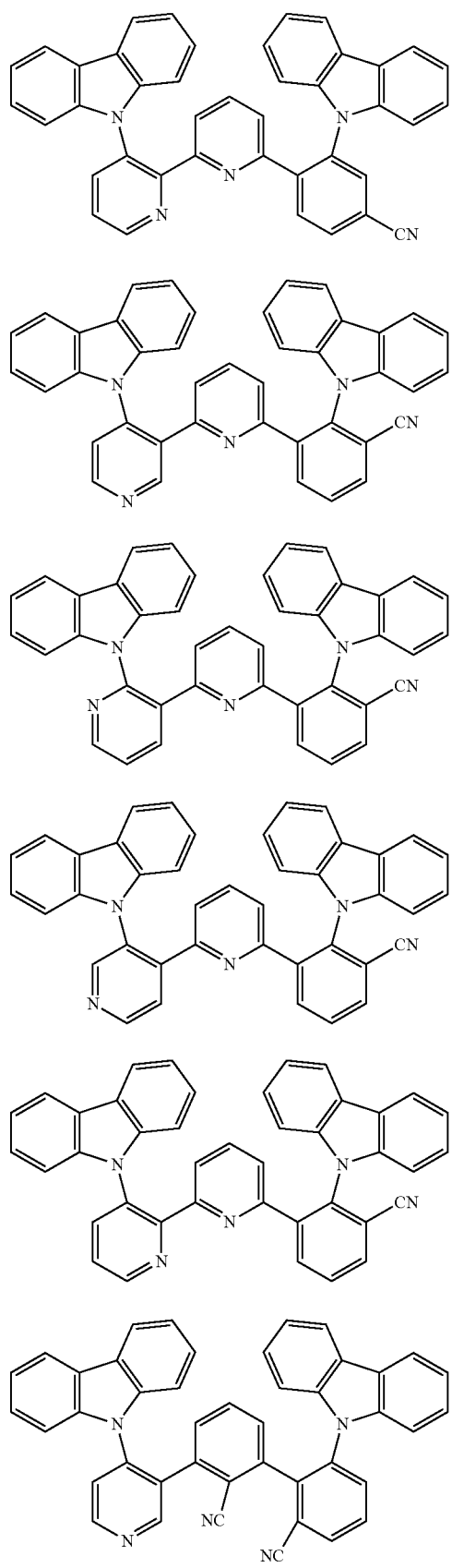
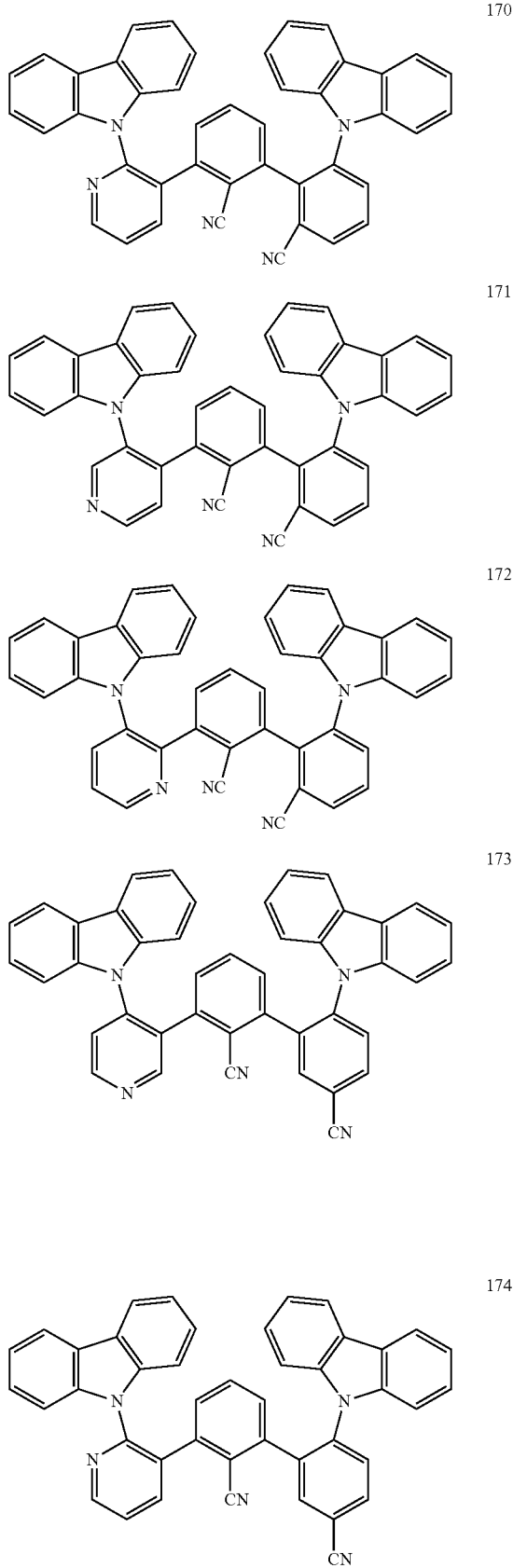

-continued
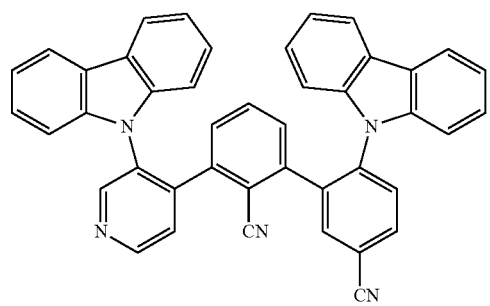
175
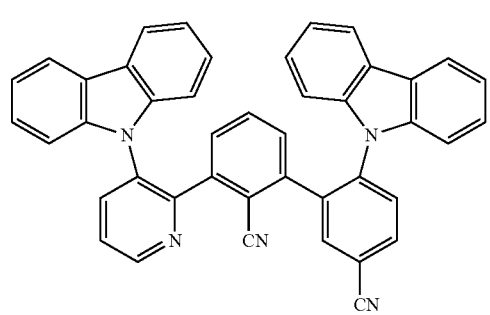
176
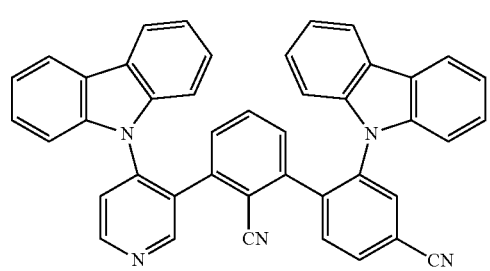
177
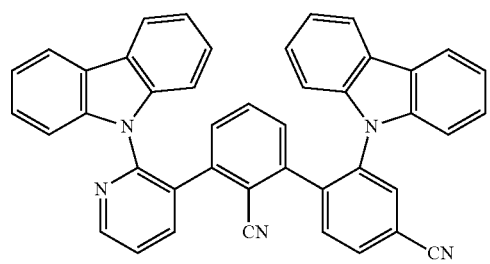
178
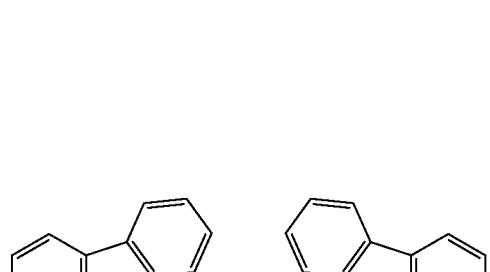
179
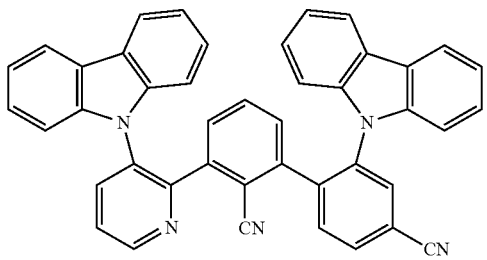
180
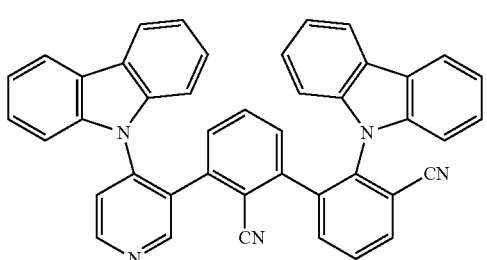
181
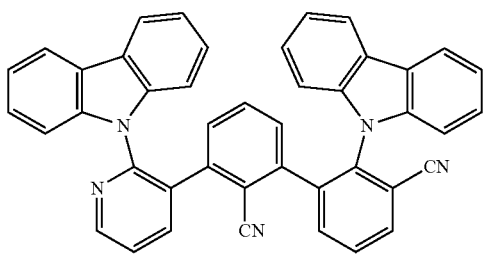
182
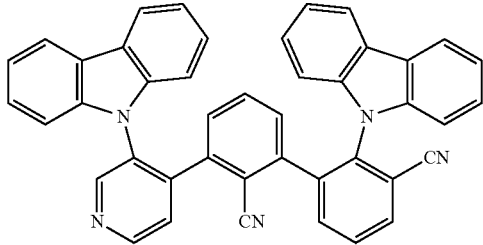
183
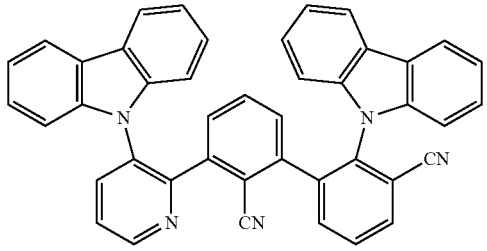
184
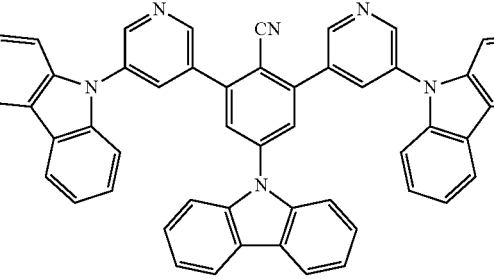
185

186
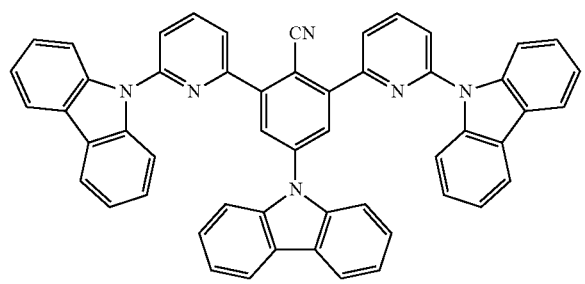
187
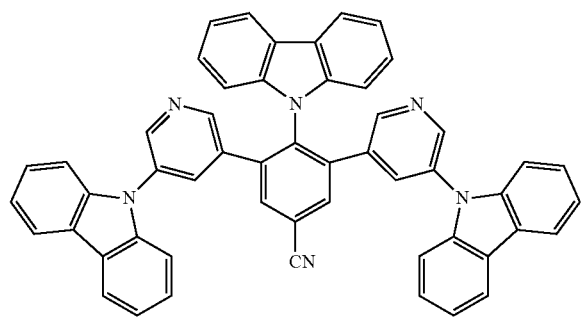
188
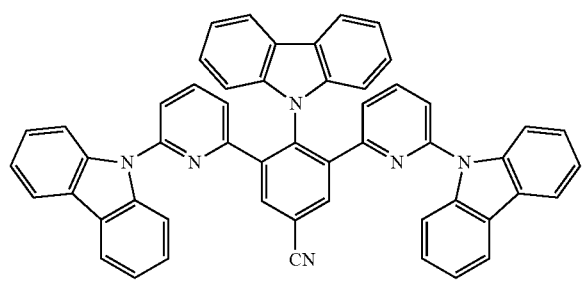
189
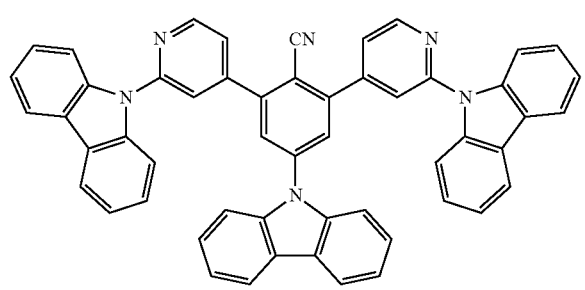
190
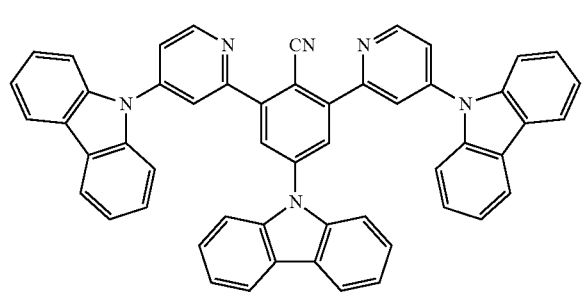
191
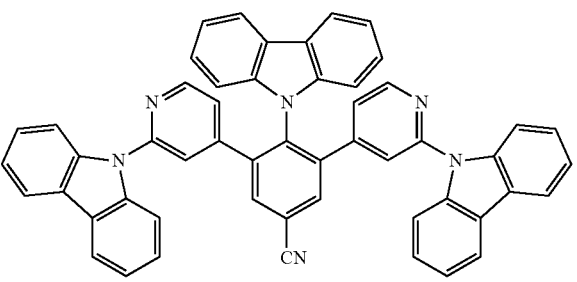
192
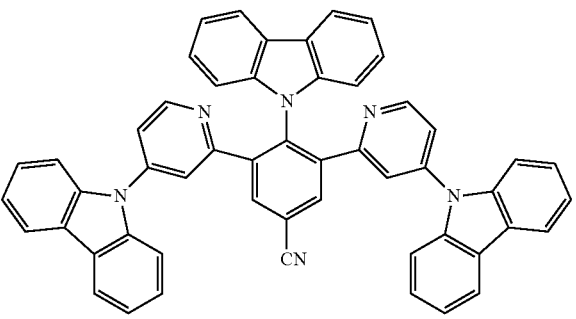
193
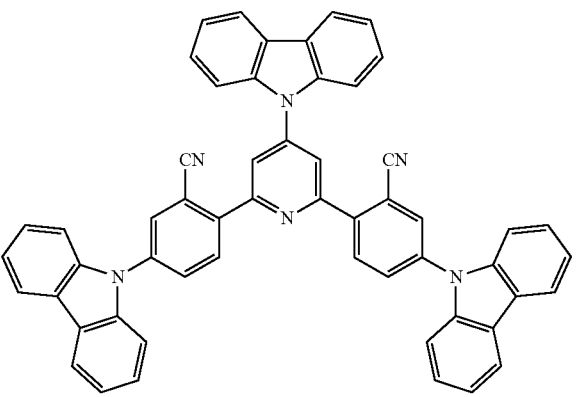
194
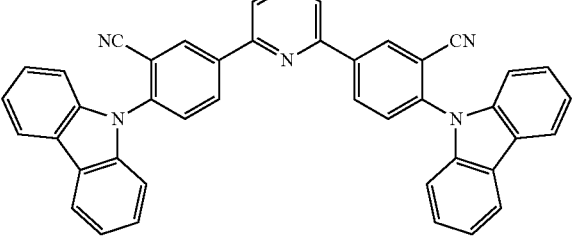

195
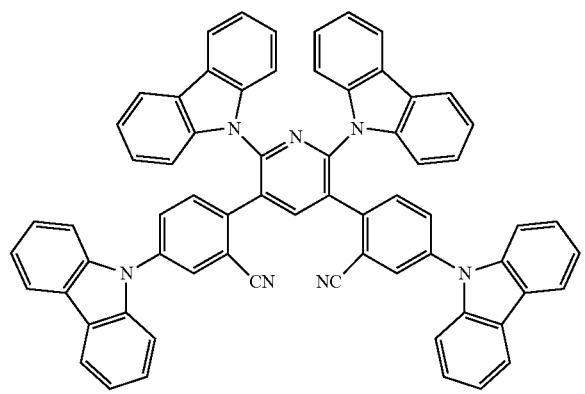
196
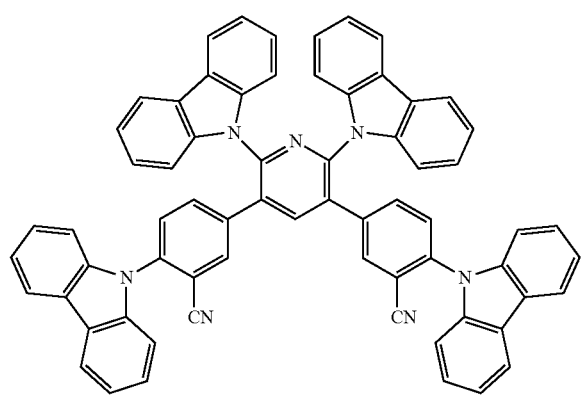
197
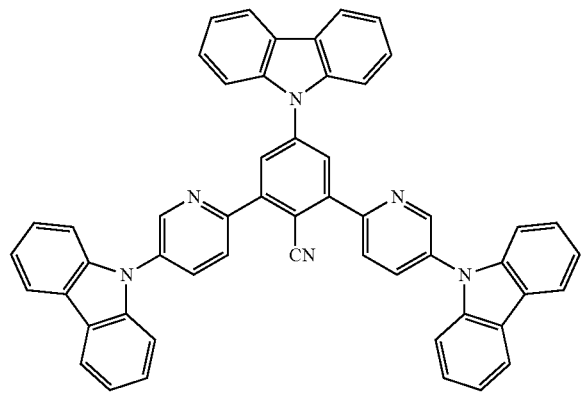
198
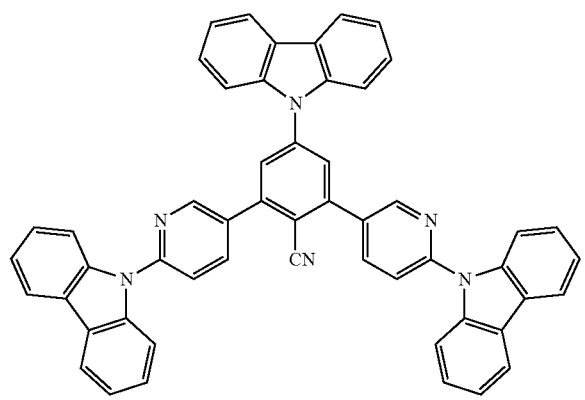
199
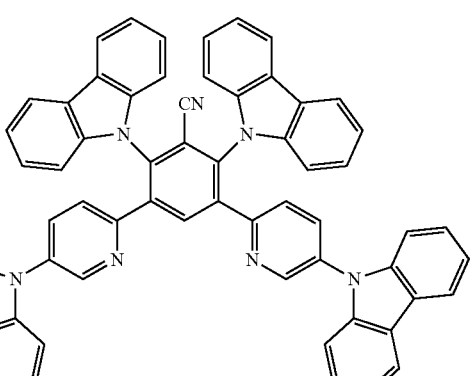
200
201
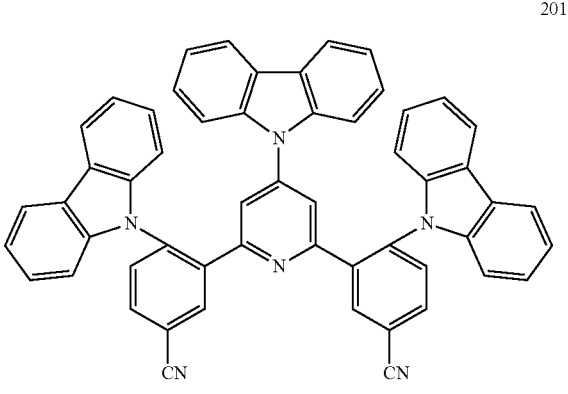
202
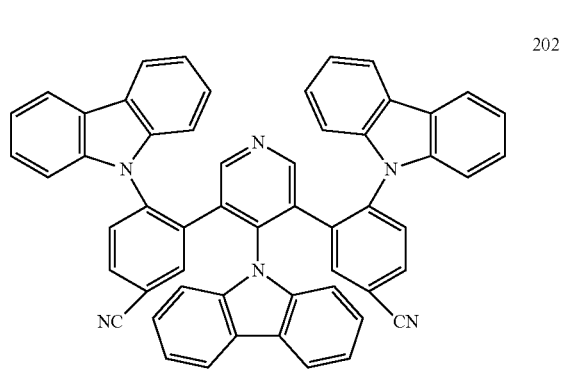

-continued
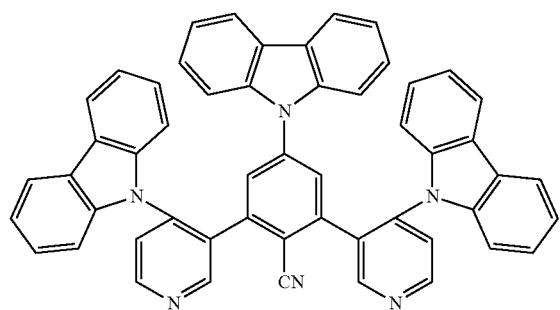
203
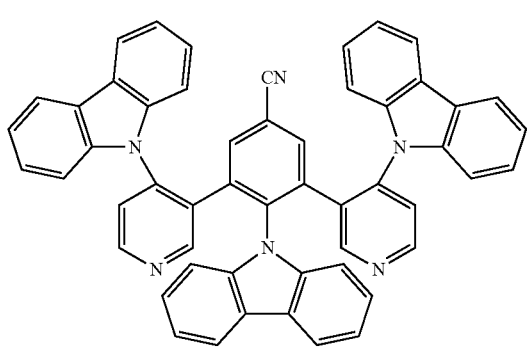
204
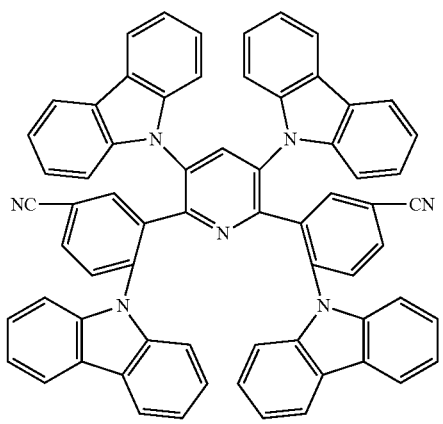
205
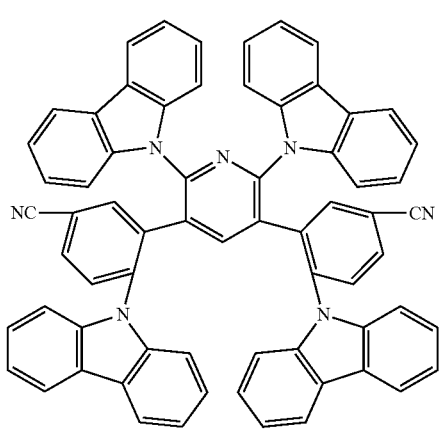
206
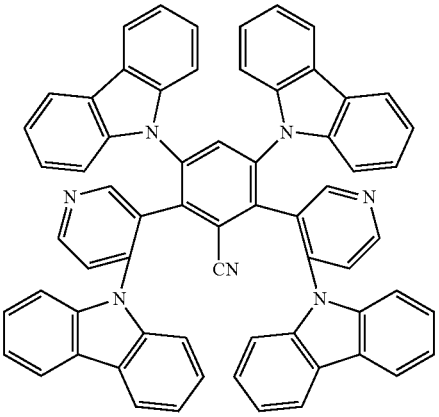
207
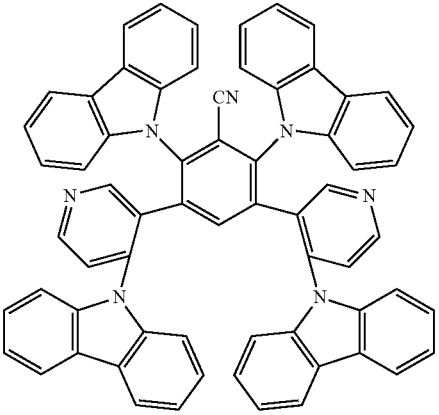
208
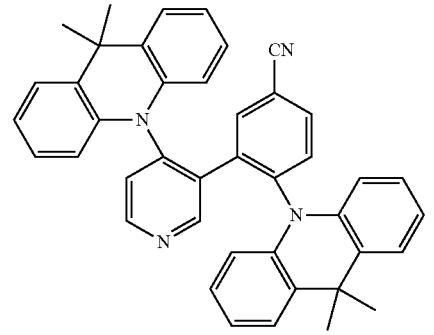
209
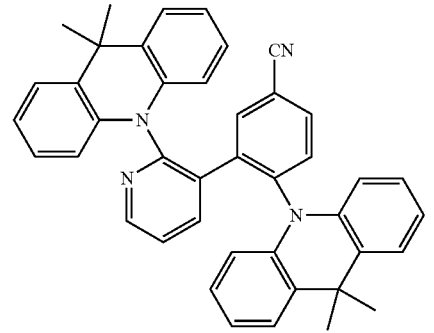
210

-continued
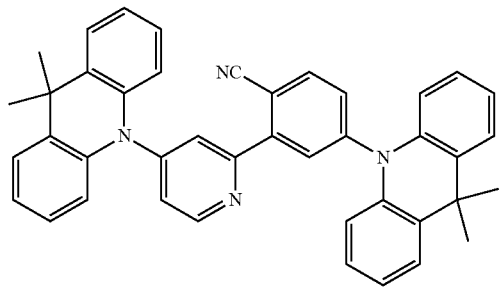
211
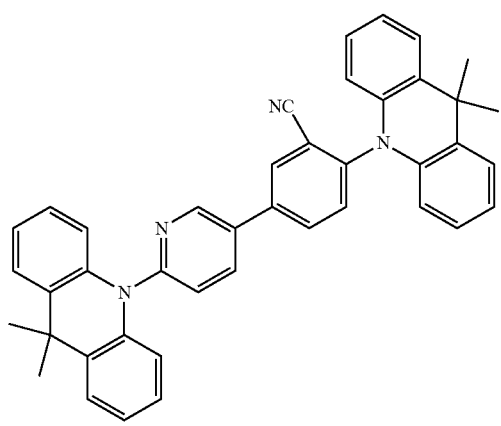
212
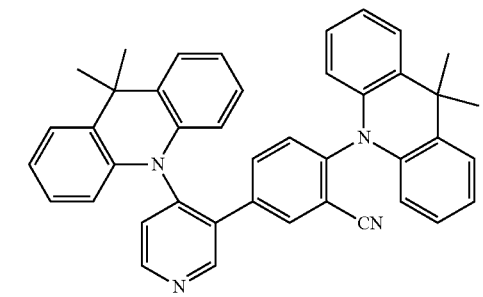
213
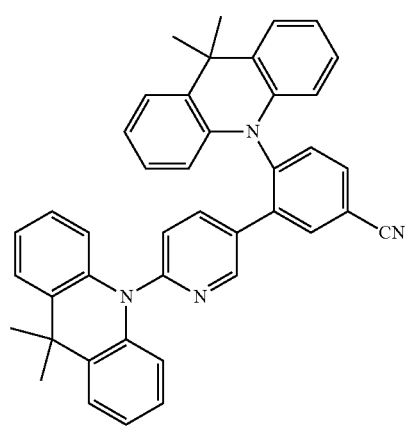
214
-continued
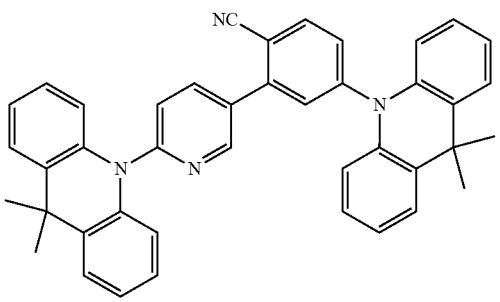
215
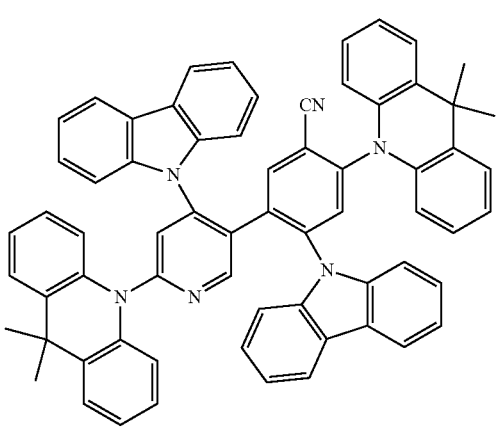
216
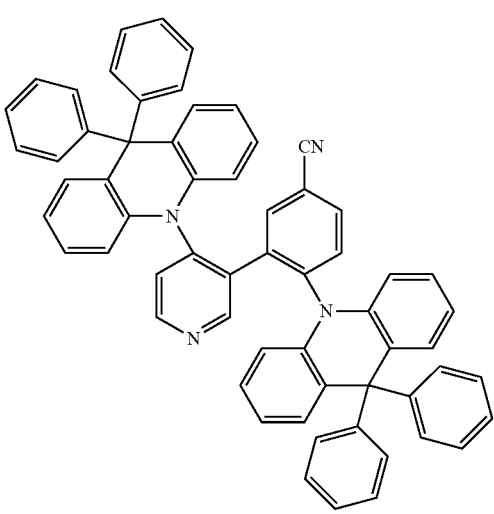
217

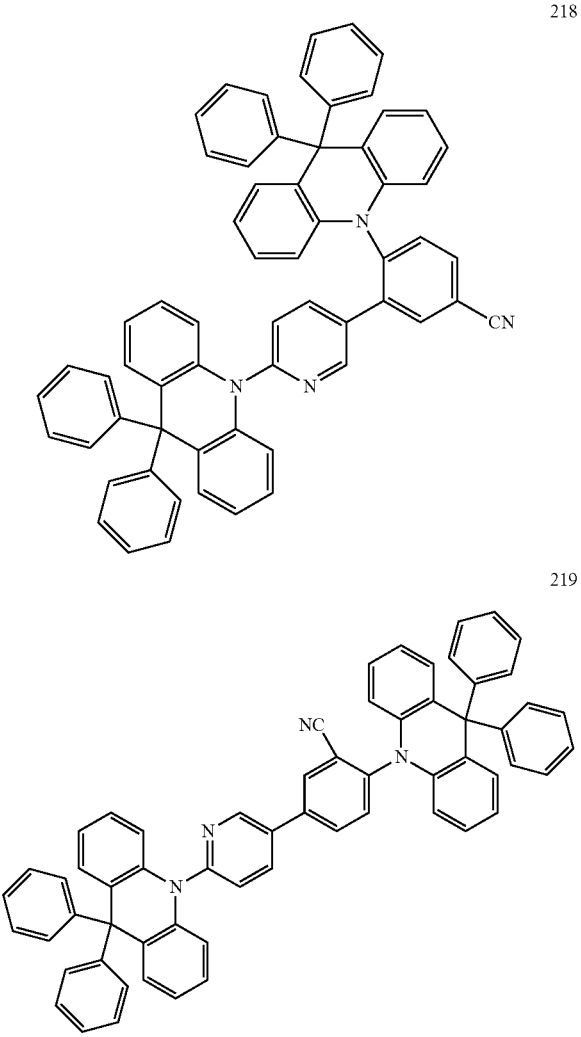
218
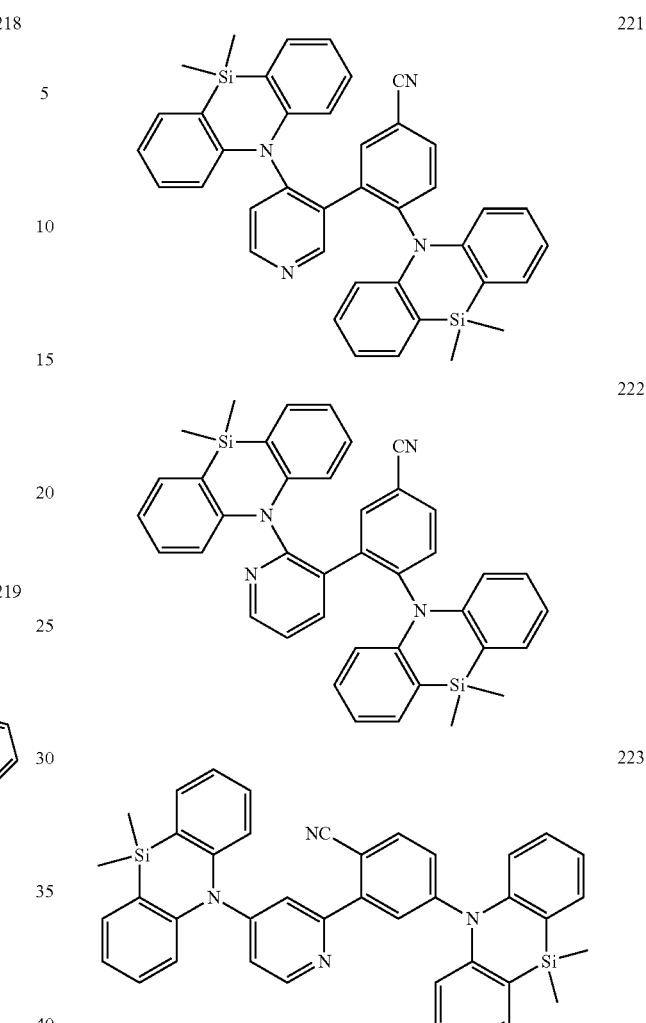
221
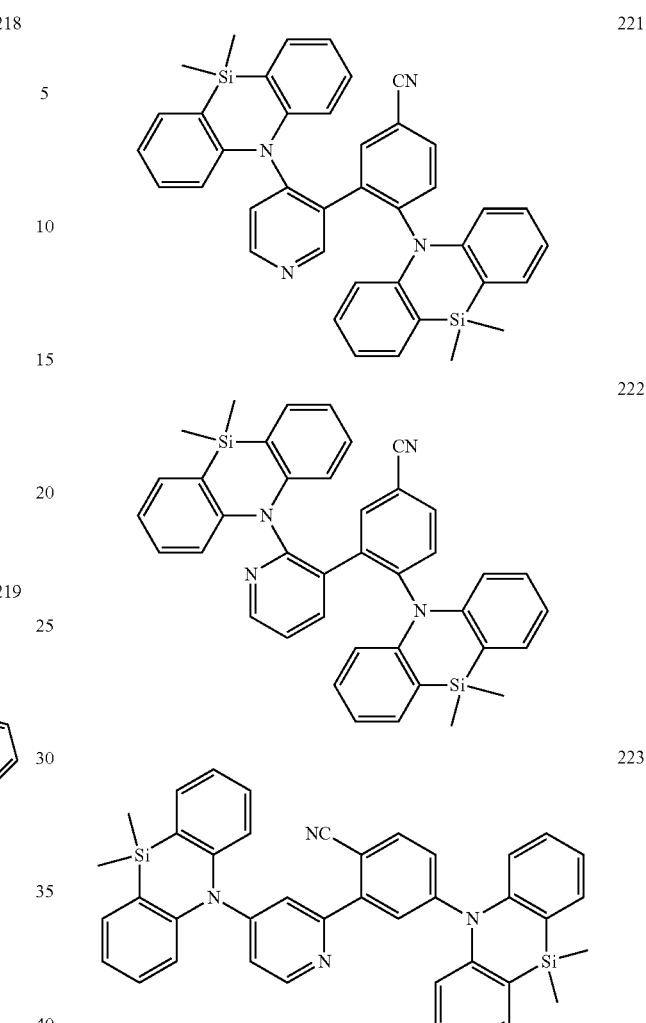
222
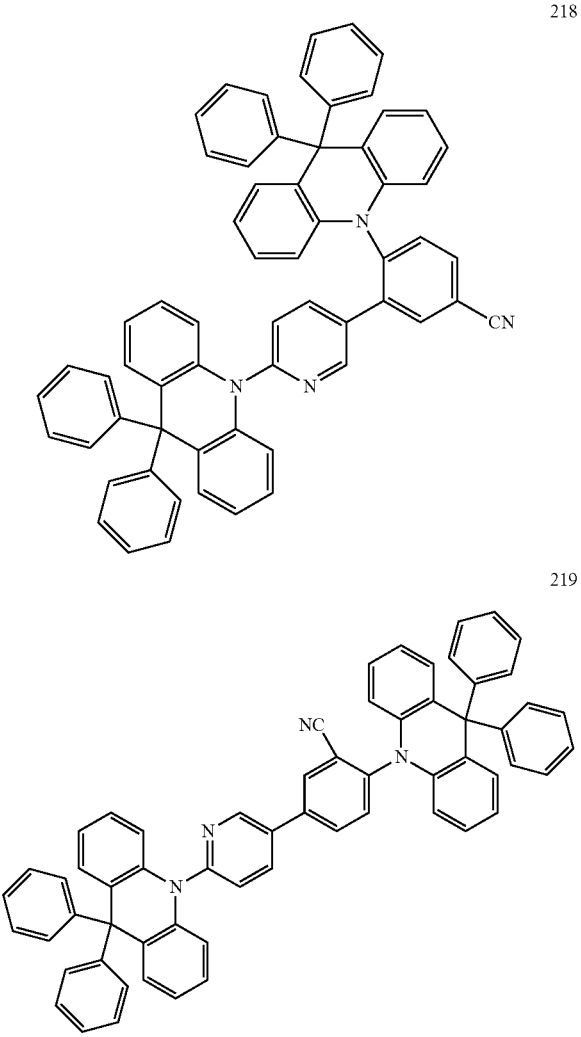
219
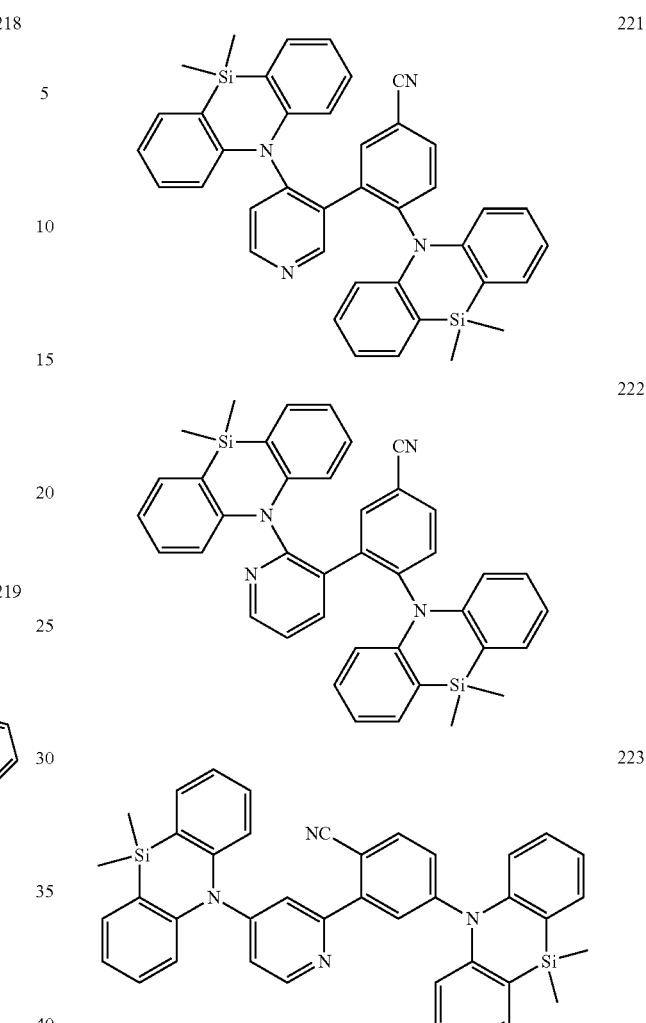
223
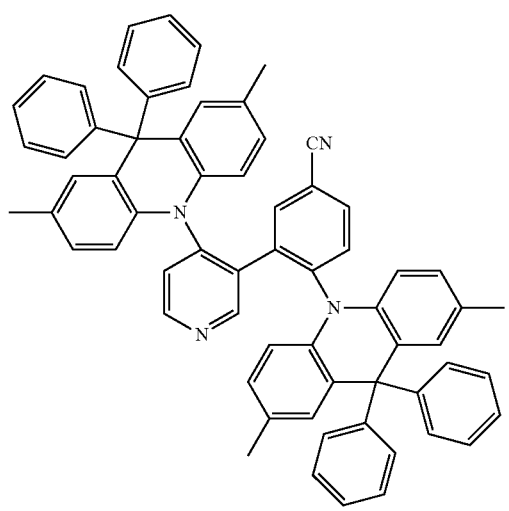
220
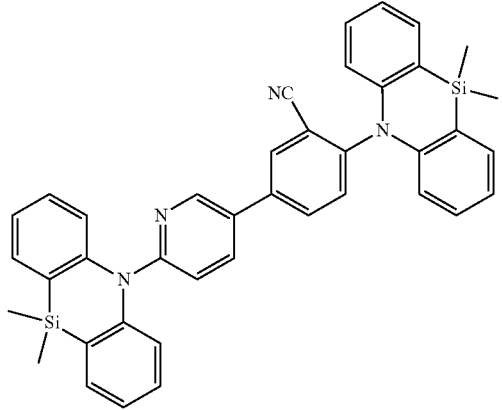
224

225
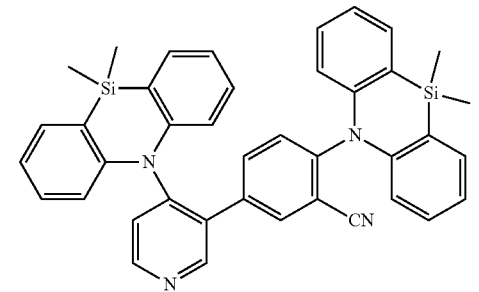
226
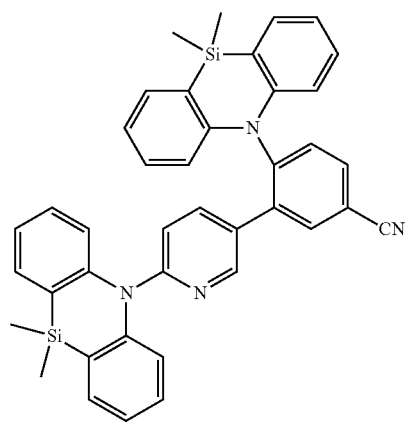
227
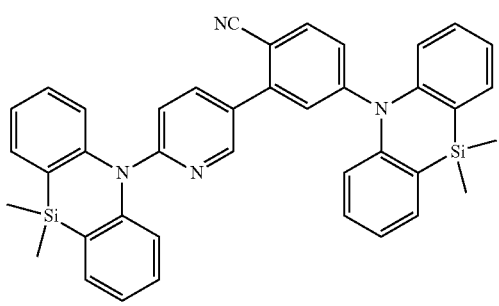
228
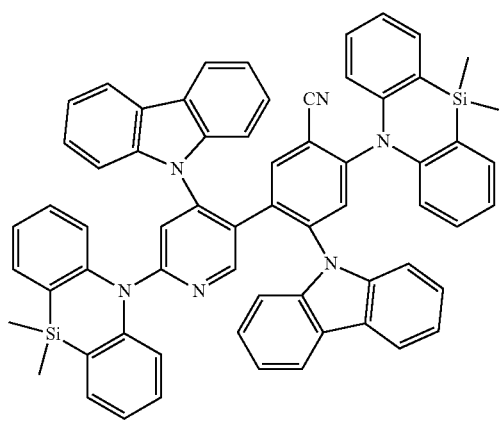
229
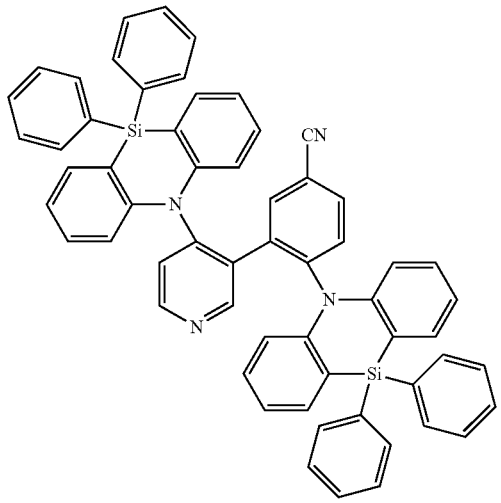
230
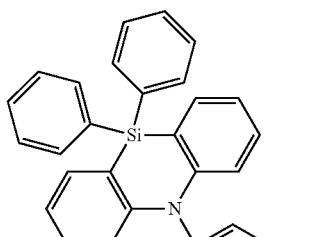
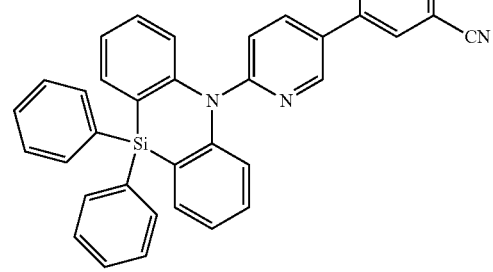
231
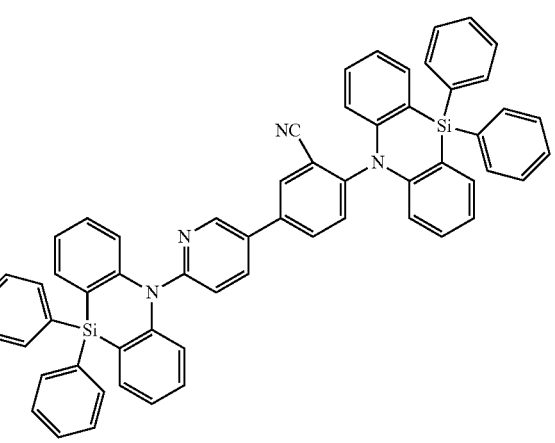

232
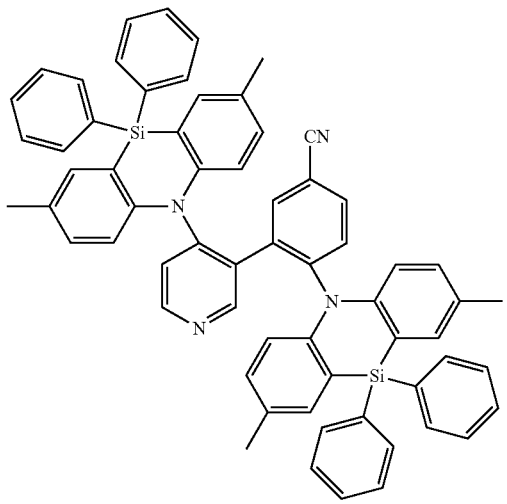
233
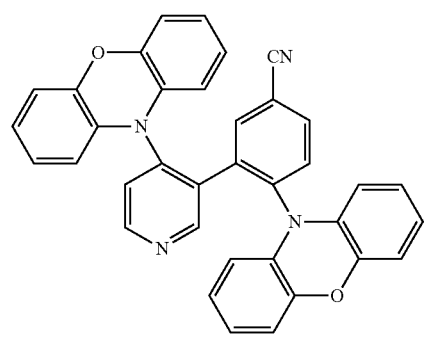
234
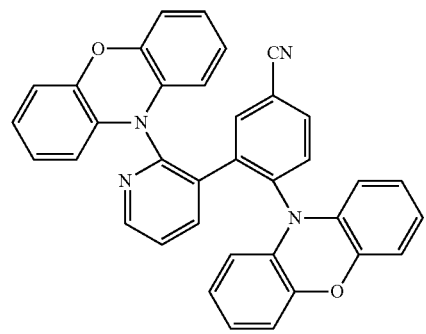
235
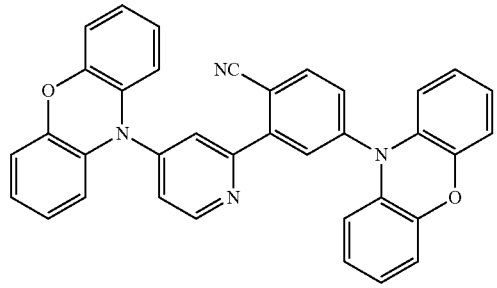
236
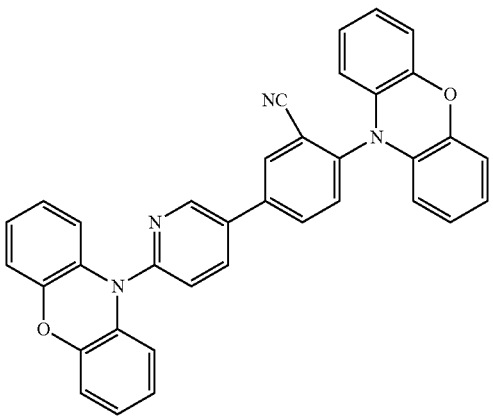
237
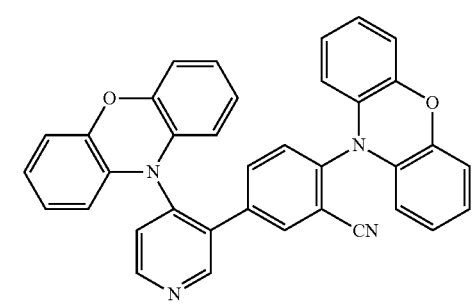
238
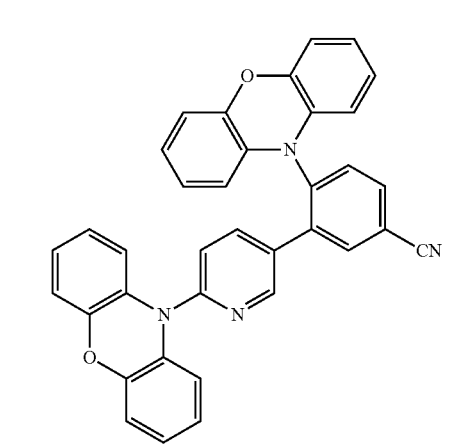
239
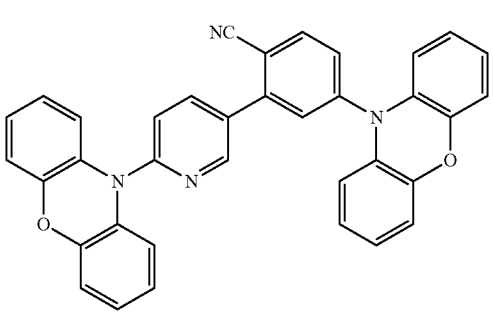

-continued
240
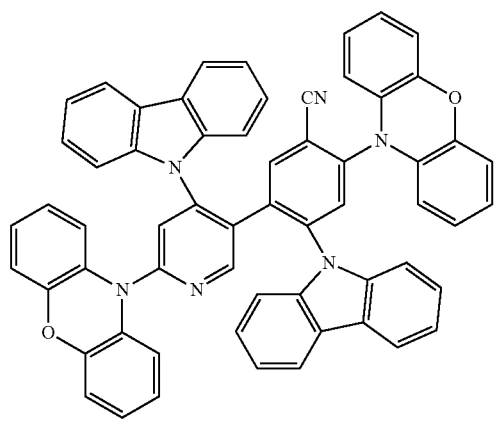
241
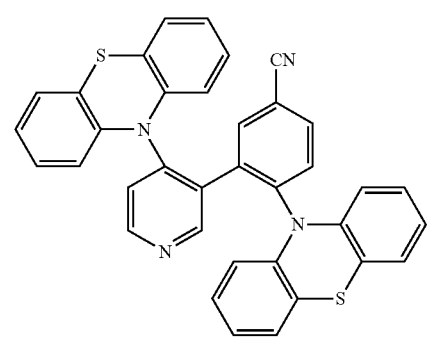
242
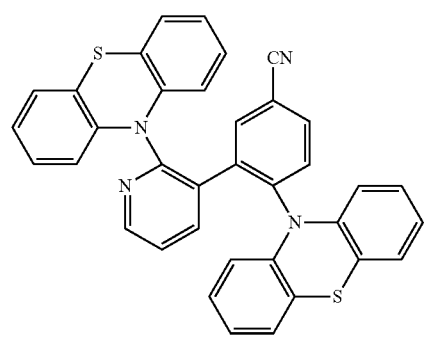
243
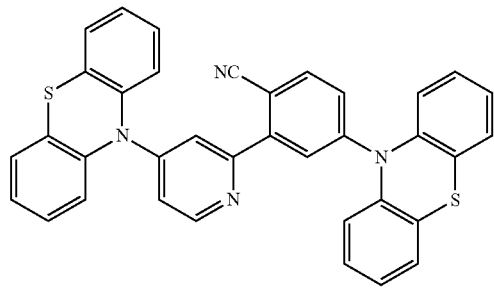
-continued
244
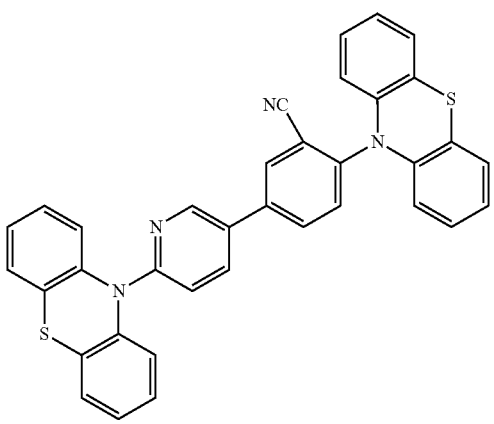
245
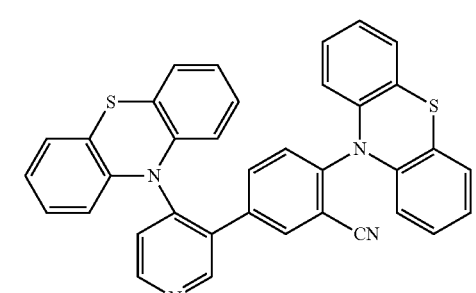
246
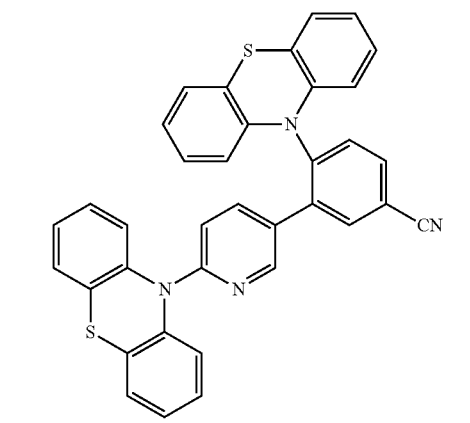
247
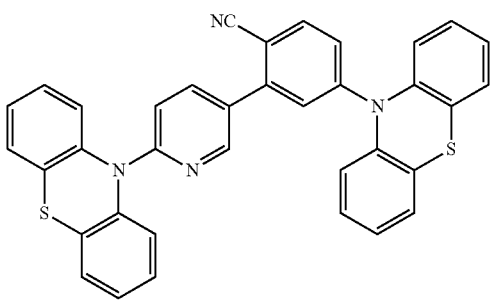

248
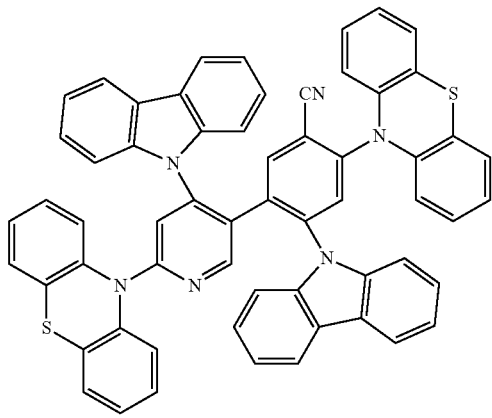
249
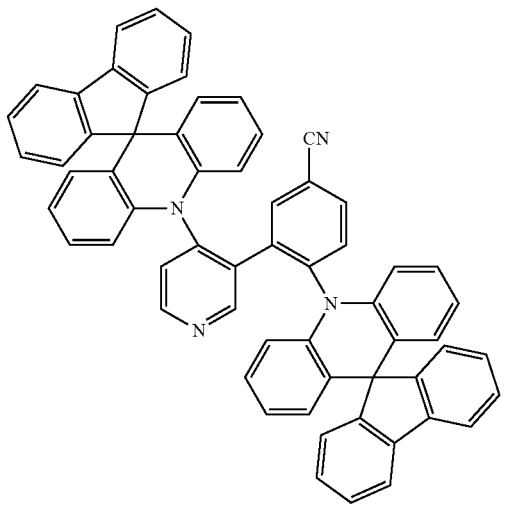
250
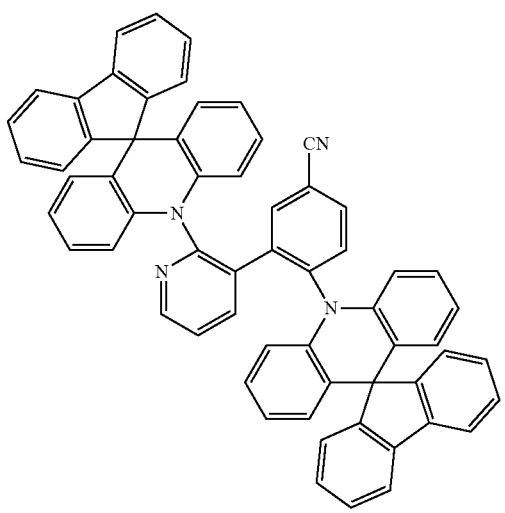
251
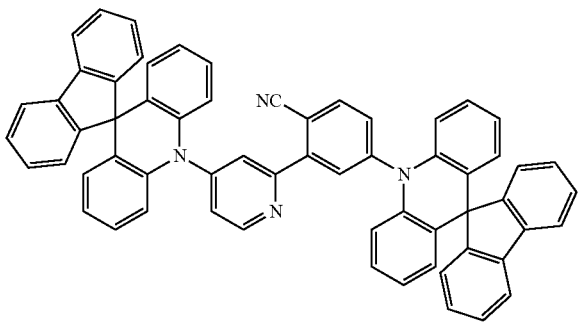
252
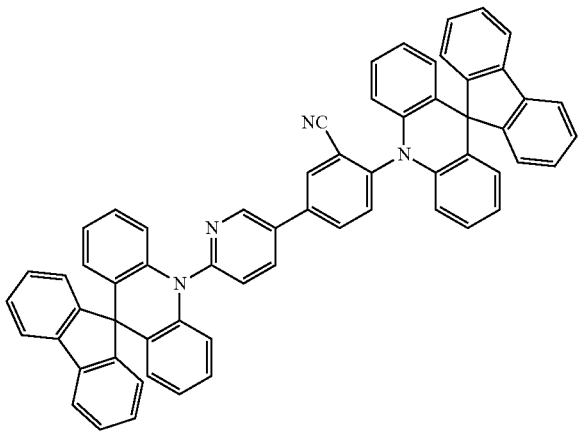
253
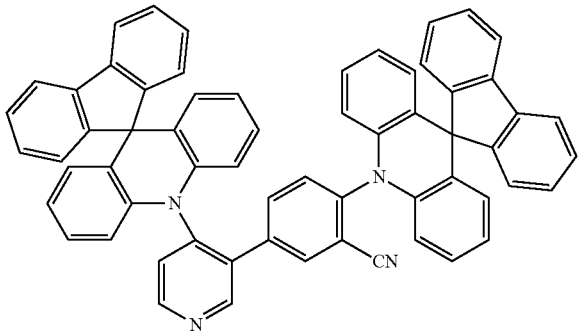

-continued
254
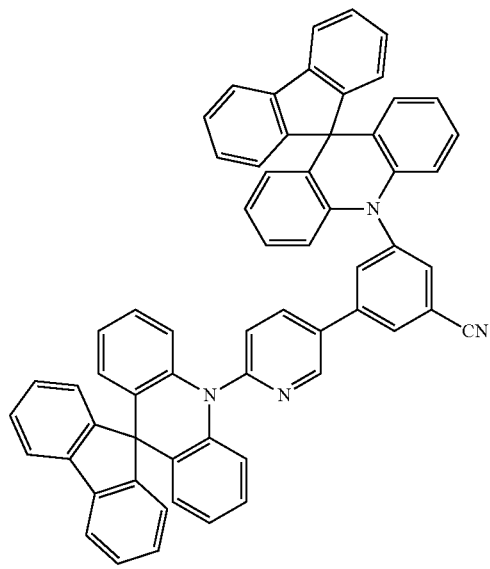
255
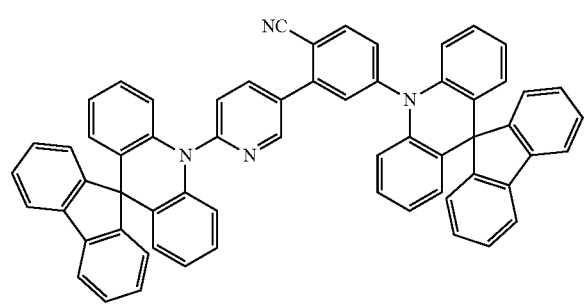
256
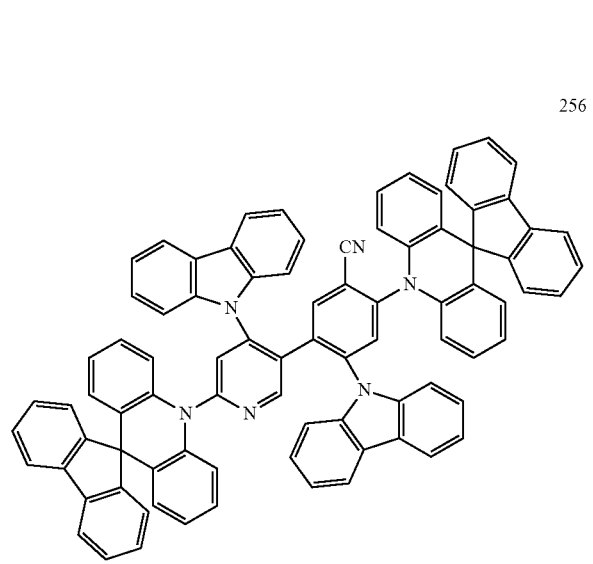
-continued
257
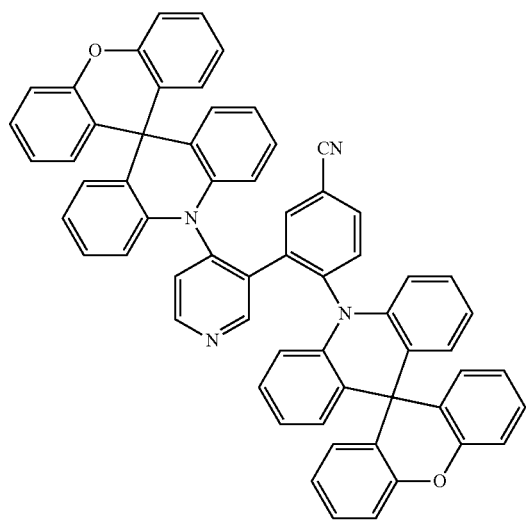
258
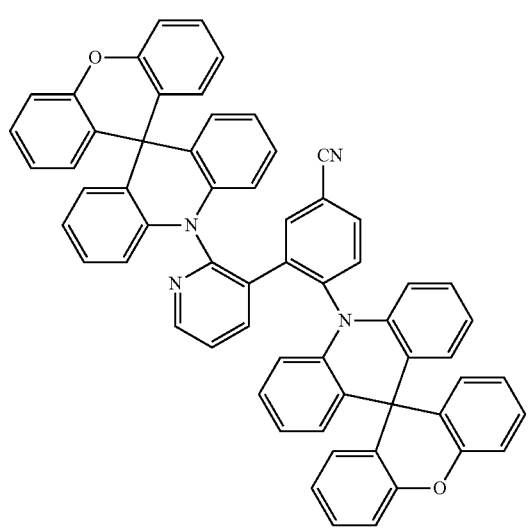
259
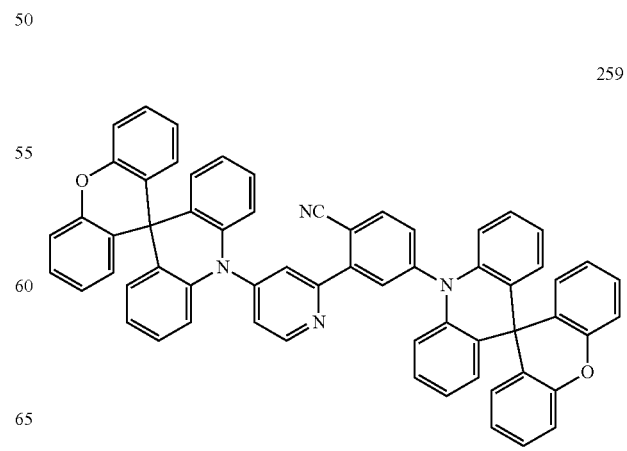

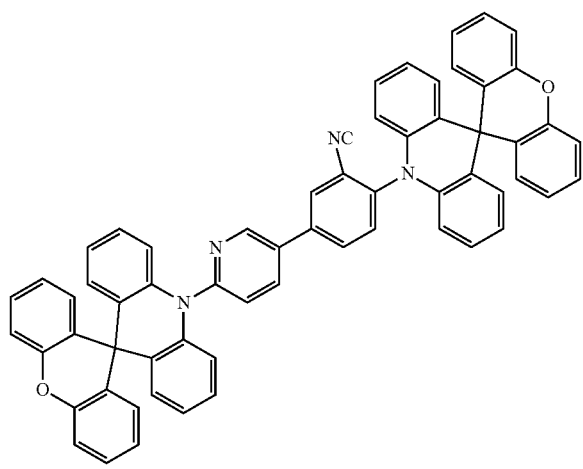

260

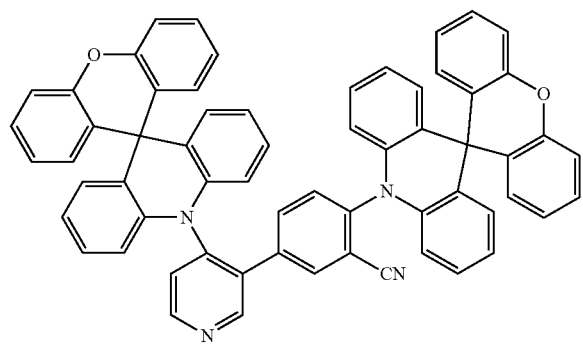

261

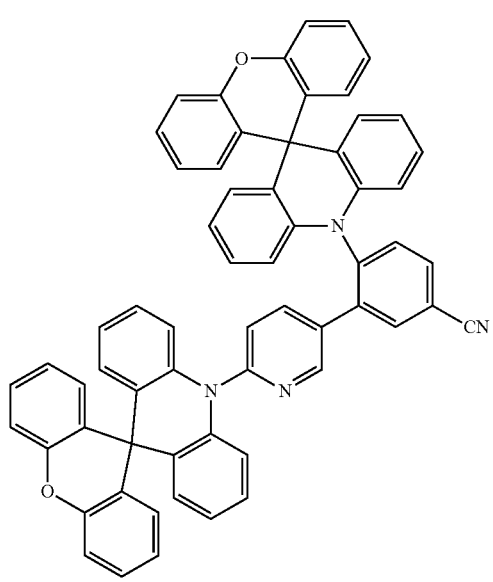

262

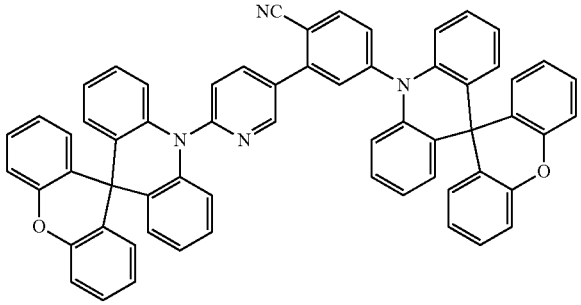

263

264

The polycyclic compound represented by Formula 1 may be utilized in an organic electroluminescence device 10 of an embodiment to improve the efficiency and life of the organic electroluminescence device. For example, the polycyclic compound represented by Formula 1 may be utilized in an emission layer EML of an organic electroluminescence device 10 of an embodiment and may improve the emission efficiency and life of the organic electroluminescence device.

In addition, the polycyclic compound of an embodiment includes two electron donors and one electron acceptor in one compound unit, in which the two electron donors each does not include a cyano group and the electron acceptor includes a benzonitrile part and a pyridine part. Accordingly, the difference between singlet energy and triplet energy is minimized or reduced and a triplet energy level is increased, and thus, the polycyclic compound may be utilized as a material for emitting blue light, which emits thermally activated delayed fluorescence. In addition, because the polycyclic compound has excellent electron accepting and electron donating properties, charge transfer (CT) in a molecule is smooth, and the compound may be utilized as a material for emitting thermally activated delayed fluorescence.

In an embodiment, the emission layer EML includes a host and a dopant, and the host may be a host for emitting delayed fluorescence and the dopant may be a dopant for emitting delayed fluorescence. According to an embodiment, the polycyclic compound represented by Formula 1 may be included as a dopant material of an emission layer EML. For example, according to an embodiment, the polycyclic compound represented by Formula 1 may be utilized as a TADF dopant.

Meanwhile, in an embodiment, the emission layer EML may include a suitable (e.g., a known) host material. For example, in an embodiment, the emission layer EML may include, as a host material, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl) anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino) phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc. However, an embodiment of the inventive concept is not limited thereto. Any suitable (e.g., known) host materials for emitting delayed fluorescence other than the suggested host materials may be included.

In the organic electroluminescence device 10 of an embodiment, the emission layer EML may further include a suitable (e.g., a known) dopant material. In an embodiment, the emission layer EML may include, as a dopant, styryl derivatives (for example, 1,4-bis[2-(3-N-ethylcarbazoryl) vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

Referring to FIGS. 1 to 3 again, in the organic electroluminescence device 10 of an embodiment, the electron transport region ETR is provided on the emission layer EML. The electron transport region ETR may include at least one of an electron blocking layer, an electron transport layer ETL or an electron injection layer EIL. However, an embodiment of the inventive concept is not limited thereto.

The electron transport region ETR may have a single layer formed utilizing a single material, a single layer formed utilizing a plurality of different materials, or a multilayer structure having a plurality of layers formed utilizing a plurality of different materials.

For example, the electron transport region ETR may have a single layer structure of an electron injection layer EIL or an electron transport layer ETL, or a single layer structure formed utilizing an electron injection material and an electron transport material. Further, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL, without being limited thereto. The thickness of the electron transport region ETR may be, for example, from about 100 Å to about 1,500 Å.

The electron transport region ETR may be formed utilizing various suitable methods, such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl) anthracene (ADN), or a mixture thereof, without being limited thereto.

If the electron transport region ETR includes the electron transport layer ETL, the thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, for example, LiF, lithium quinolate (LiQ), $Li_2O$, BaO, NaCl, CsF, a metal in lanthanoides (such as Yb), or a metal halide (such as RbCl, RbI and KI). However, an embodiment of the inventive concept is not limited thereto. The electron injection layer EIL may also be formed utilizing a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, or metal stearates.

If the electron transport region ETR includes the electron injection layer EIL, the thickness of the electron injection layer EIL may be from about 1 Å to about 100 Å, or from about 3 Å to about 90 Å. If the thickness of the electron injection layer EIL satisfies the above described ranges, satisfactory electron injection properties may be obtained without inducing substantial increase of a driving voltage.

The electron transport region ETR may include a hole blocking layer HBL as described above. The hole blocking layer may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

The second electrode EL2 is provided on the electron transport region ETR. The second electrode EL2 has conductivity. The second electrode EL2 may be formed utilizing a metal alloy or a conductive compound. The second electrode EL2 may be a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed utilizing the above-described materials and a transparent conductive layer formed utilizing ITO, IZO, ZnO, ITZO, etc.

Though not shown, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission device, the first electrode EL1 may be a reflective electrode and the second electrode EL2 may be a transmissive electrode or a transflective electrode. If the organic electroluminescence device 10 is a bottom emission device, the first electrode EL1 may be a transmissive electrode or a transflective electrode and the second electrode EL2 may be a reflective electrode.

The organic electroluminescence device of an embodiment of the inventive concept utilizes the polycyclic compound as a material for an emission layer and may have improved light-emitting efficiency and life characteristics.

An embodiment of the inventive concept provides a polycyclic compound represented by the following Formula 1:

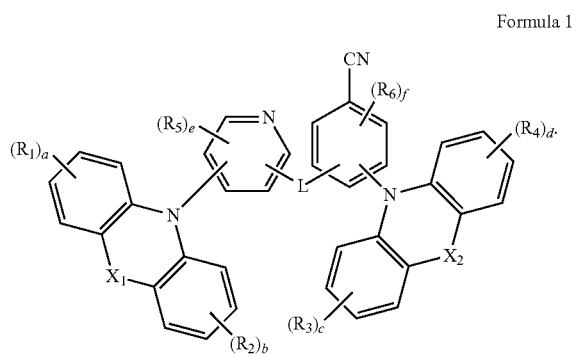

Formula 1

In Formula 1, $X_1$ and $X_2$ are each independently a direct linkage, $CR_7R_8$, $SiR_9R_{10}$, O, or S, and L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring.

In Formula 1, $R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or combined with an adjacent group to form a ring; a, b, c and d are each independently an integer of 0 to 4.

If each of a to d is an integer of 2 or more, a plurality of $R_1$, $R_2$, $R_3$ and $R_4$ may be respectively the same or different from each other.

In Formula 1, $R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, a substituted or unsubstituted heteroaryl group having 2 to 30 carbon atoms for forming a ring, or combined with an adjacent group to form a ring; and e and f are each independently an integer of 0 to 3.

If each of e and f is an integer of 2 or more, a plurality of $R_5$ and $R_6$ may be respectively the same or different from each other.

The same explanation on the polycyclic compound in the organic electroluminescence device of an embodiment may be applied to the polycyclic compound of an embodiment, represented by Formula 1.

The polycyclic compound according to an embodiment may be any one selected from the compounds represented in Compound Group 1 above.

Hereinafter, the inventive concept will be more particularly explained referring to embodiments and comparative embodiments. The following embodiments are only illustrations to assist the understanding of the inventive concept, and the scope of the inventive concept is not limited thereto.

EXAMPLES

1. Synthesis of Polycyclic Compounds

First, the synthetic method of the polycyclic compounds according to exemplary embodiments of the inventive concept will be particularly explained referring to the synthetic methods of Compound 2, Compound 69, Compound 71, Compound 74, Compound 77, Compound 80, Compound 83, Compound 84, Compound 119, Compound 174, and Compound 212. In addition, the synthetic methods of the polycyclic compounds explained below are only embodiments, and the synthetic method of the polycyclic compound according to an embodiment of the inventive concept is not limited thereto.

Synthesis of Compound 2

Compound 2, which is a polycyclic compound according to an embodiment, may be synthesized, for example, by the following Reaction 1:

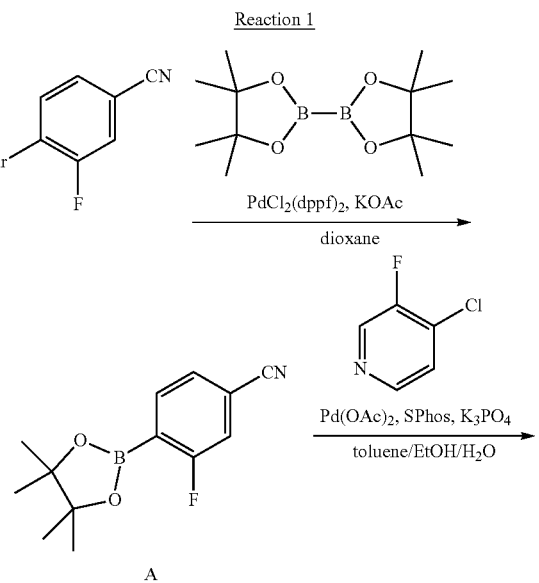

Reaction 1

83

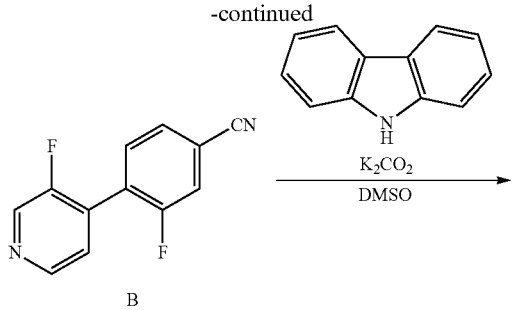

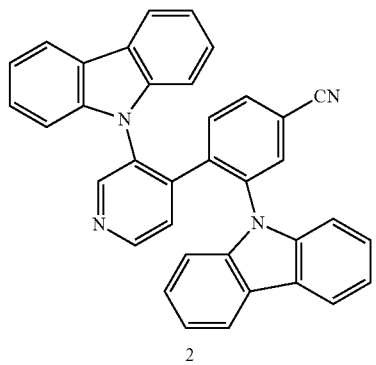

Under an argon atmosphere, to a 500 mL, three-neck flask, 5.00 g of 4-bromo-3-fluorobenzonitrile, 6.35 g of bis(pinacolato)diboron, 2.04 g of a [1,1'-bis(diphenylphos-phino)ferrocene]dichloropalladium(II) dichloromethane adduct, and 4.91 g of potassium acetate were added and dissolved in 130 mL of 1,4-dioxane, followed by stirring at about 90° C. for about 6 hours. After dissipating heat, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 5.25 g (yield 85%) of Intermediate A. The molecular weight of Intermediate A measured by FAB-MS was 247.

Under an argon atmosphere, in a 500 mL, three-neck flask, 5.00 g of Intermediate A, 2.66 g of 4-chloro-3-fluoropyridine, 0.23 g of palladium acetate (Pd(OAc)$_2$), 0.83 g of 2-dicyclohexylphosphino-2',6'-dimethoxybiphenyl (SPhos), and 8.59 g of tripotassium phosphate (K$_3$PO$_4$) were dissolved in 100 mL of a deaerated mixture solvent of toluene/ethanol/water (10:1:2), followed by stirring at about 80° C. for about 10 hours. After cooling in the air, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 3.50 g (yield 80%) of Intermediate B. The molecular weight of Intermediate B measured by FAB-MS was 216.

Under an argon atmosphere, to a 200 mL, three-neck flask, 3.00 g of Intermediate B, 4.64 g of carbazole, and 9.59 g of potassium carbonate (K$_2$CO$_3$) were added and dissolved in 50 ml of anhydrous DMSO, followed by stirring at about 150° C. for about 6 hours. After cooling in the air, 300 ml of water was added to the reaction mixture, followed by stirring. The precipitate thus obtained was recovered by filtering with suction and dissolved in 150 ml of CH$_2$Cl$_2$. The resultant solution was dried with MgSO$_4$, and solvents were removed by distillation under a reduced pressure. The crude product thus obtained was separated by recrystalliza-

84 tion, and 4.82 g (yield 68%) of Compound 2 was obtained as a target product. The molecular weight of the target product measured by FAB-MS was 510. From the result, the target product was identified as Compound 2.

Synthesis of Compound 69

Compound 69, which is a polycyclic compound according to an embodiment may be synthesized, for example, by the following Reaction 2:

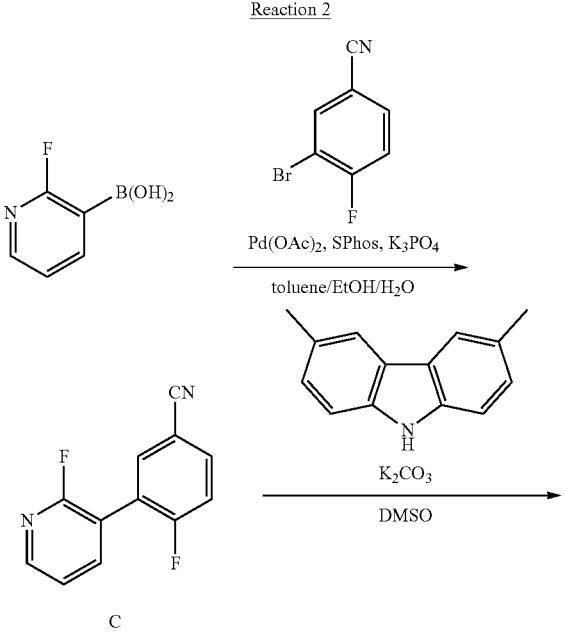

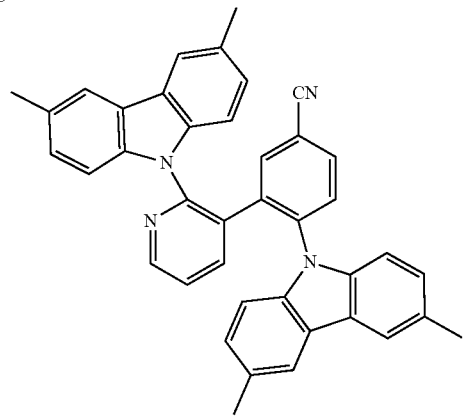

Under an argon atmosphere, to a 500 mL, three-neck flask, 5.00 g of 2-fluoropyridine-3-boronic acid, 7.10 g of 3-bromo-4-fluorobenzonitrile, 0.40 g of Pd(OAc)$_2$, 1.46 g of SPhos, and 15.06 g of K$_3$PO$_4$ were dissolved in 180 ml of a deaerated mixture solvent of toluene/ethanol/water (10:1:2), followed by stirring at about 80° C. for about 10 hours. After finishing the reaction, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 5.98 g (yield 78%) of Intermediate C. The molecular weight of Intermediate C measured by FAB-MS was 216.

Under an argon atmosphere, to a 200 mL, three-neck flask, 3.00 g of Intermediate C, 5.42 g of dimethylcarbazole, and 9.59 g of $K_2CO_3$ were added and dissolved in 50 ml of anhydrous DMSO, followed by stirring at about 150° C. for about 6 hours. After cooling in the air, 300 ml of water was added to the reaction mixture, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 6.29 g (yield 80%) of Compound 69 was obtained as a target product. The molecular weight of the target product measured by FAB-MS was 566. From the result, the target product was identified as Compound 69.

Synthesis of Compound 71

Compound 71, which is a polycyclic compound according to an embodiment may be synthesized, for example, by the following Reaction 3:

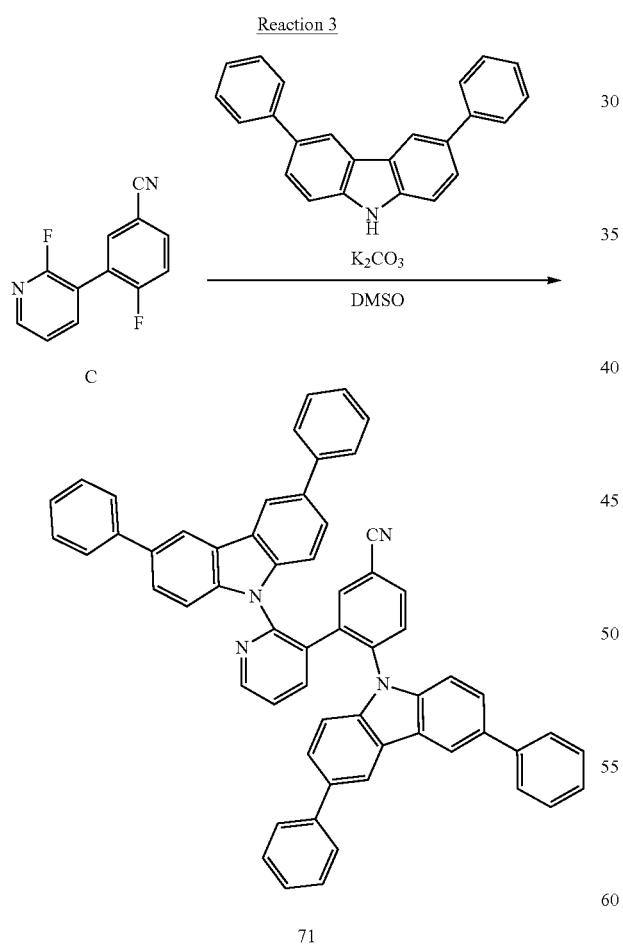

Under an argon atmosphere, to a 200 ml, three-neck flask, 3.00 g of Intermediate C, 8.86 g of 3,6-diphenylcarbazole, and 9.59 g of $K_2CO_3$ were added and dissolved in 50 ml of anhydrous DMSO, followed by stirring at about 150° C. for about 6 hours. After cooling in the air, 300 ml of water was added to the reaction mixture, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 8.14 g (yield 72%) of Compound 71 was obtained as a target product. The molecular weight of the target product measured by FAB-MS was 814. From the result, the target product was identified as Compound 71.

Synthesis of Compound 74

Compound 74, which is a polycyclic compound according to an embodiment may be synthesized, for example, by the following Reaction 4:

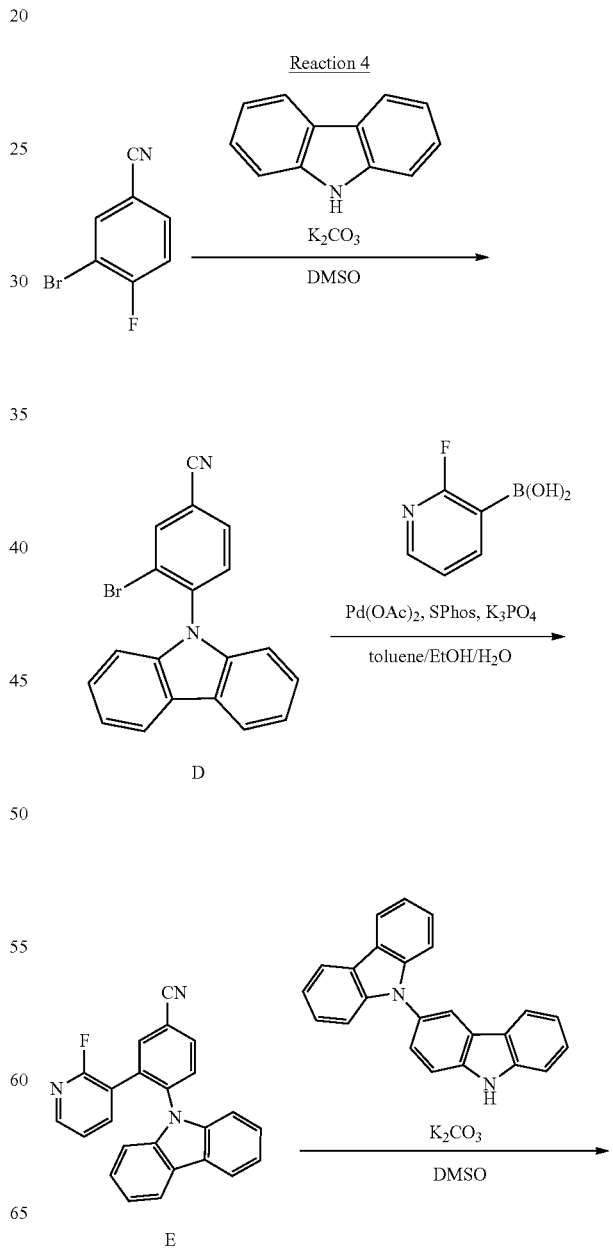

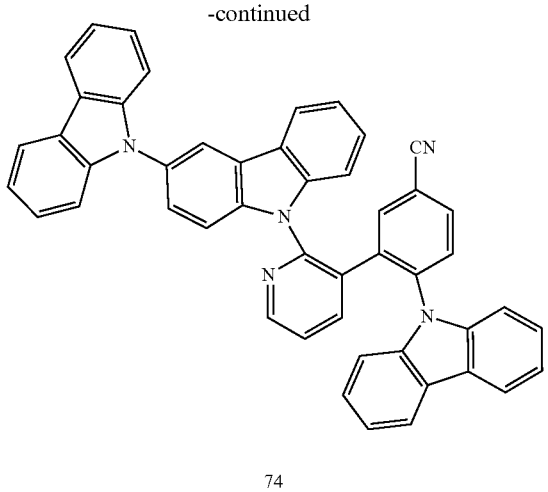

74

Under an argon atmosphere, to a 200 ml, three-neck flask, 5.00 g of 3-bromo-4-fluorobenzonitrile, 4.18 g of carbazole and 5.18 g of $K_2CO_3$ were added and dissolved in 50 ml of anhydrous DMSO, followed by stirring at about 110° C. for about 8 hours. After cooling in the air, 300 ml of water was added to the reaction solution, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 6.08 g (yield 70%) of Intermediate D was obtained. The molecular weight of Intermediate D measured by FAB-MS was 347.

Under an argon atmosphere, in a 500 ml, three-neck flask, 6.00 g of Intermediate D, 2.44 g of (2-fluoropyridine-3-yl) boronic acid, 0.19 g of $Pd(OAc)_2$, 0.71 g of SPhos, and 7.34 g of $K_3PO_4$ were dissolved in 100 ml of a deaerated mixture solvent of toluene/ethanol/water (10:1:2), followed by stirring at about 80° C. for about 16 hours. After finishing the reaction, water was added, and extraction with $CH_2Cl_2$ was conducted. An organic layer was separated and dried with $MgSO_4$, and solvents were removed by distillation under a reduced pressure. The crude product thus obtained was separated by silica gel column chromatography to obtain 3.08 g (yield 49%) of Intermediate E. The molecular weight of Intermediate E measured by FAB-MS was 363.

Under an argon atmosphere, to a 200 ml, three-neck flask, 3.00 g of Intermediate E, 2.74 g of 3,9'-bicarbazole, and 2.28 g of $K_2CO_3$ were added and dissolved in 30 ml of anhydrous DMSO, followed by stirring at about 150° C. for about 6 hours. After cooling in the air, 300 ml of water was added to the reaction mixture, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 3.07 g (yield 55%) of Compound 74 was obtained as a target product. The molecular weight of the target product measured by FAB-MS was 675. From the result, the target product was identified as Compound 74.

Synthesis of Compound 77

Compound 77, which is a polycyclic compound according to an embodiment may be synthesized, for example, by the following Reaction 5:

Reaction 5

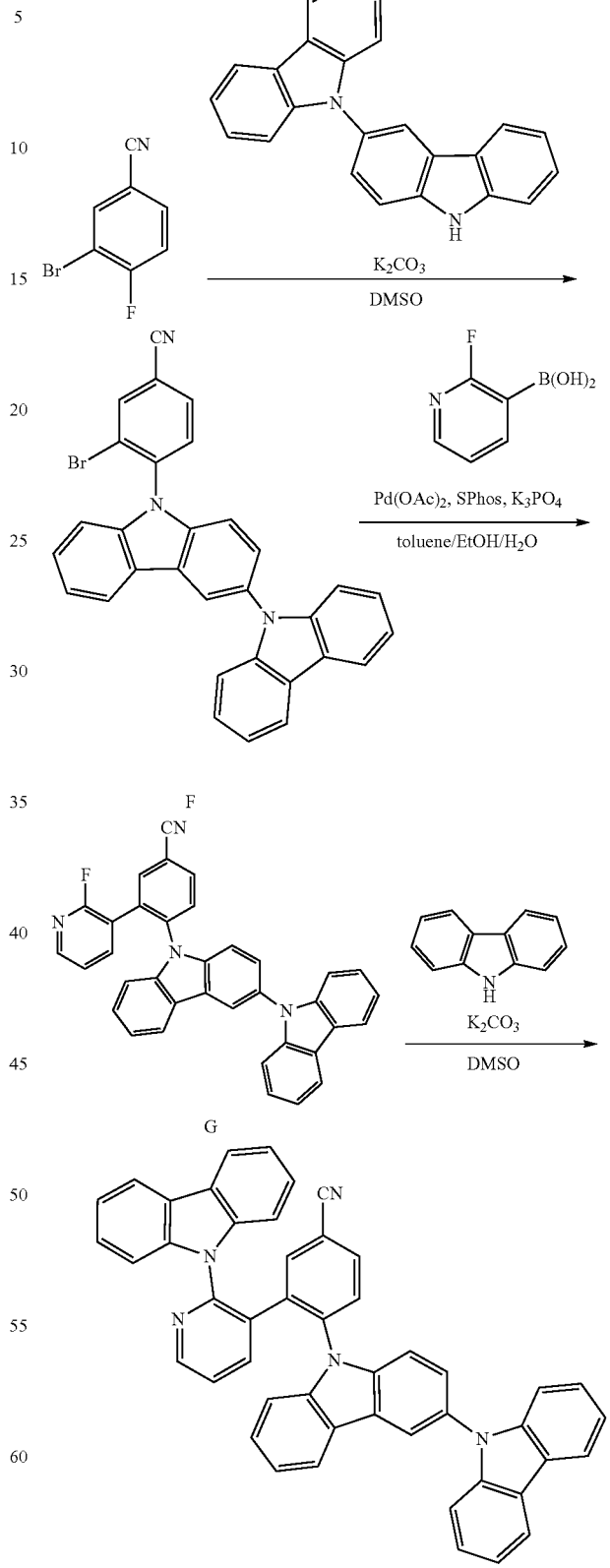

Under an argon atmosphere, to a 200 ml, three-neck flask, 5.00 g of 3-bromo-4-fluorobenzonitrile, 8.31 g of 3,9'-bicarbazole and 6.91 g of $K_2CO_3$ were added and dissolved in 50 ml of anhydrous DMSO, followed by stirring at about 110° C. for about 8 hours. After cooling in the air, 300 ml of water was added to the reaction solution, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 7.56 g (yield 59%) of Intermediate F was obtained. The molecular weight of Intermediate F measured by FAB-MS was 512.

Under an argon atmosphere, in a 500 ml, three-neck flask, 7.00 g of Intermediate F, 1.93 g of (2-fluoropyridine-3-yl) boronic acid, 0.15 g of $Pd(OAc)_2$, 0.56 g of SPhos, and 5.80 g of $K_3PO_4$ were dissolved in 100 ml of a deaerated mixture solvent of toluene/ethanol/water (10:1:2), followed by stirring at about 80° C. for about 16 hours. After finishing the reaction, water was added, and extraction with $CH_2Cl_2$ was conducted. An organic layer was separated and dried with $MgSO_4$, and solvents were removed by distillation under a reduced pressure. The crude product thus obtained was separated by silica gel column chromatography to obtain 3.03 g (yield 42%) of Intermediate G. The molecular weight of Intermediate G measured by FAB-MS was 528.

Under an argon atmosphere, to a 200 ml, three-neck flask, 3.00 g of Intermediate G, 0.95 g of carbazole, and 1.56 g of $K_2CO_3$ were added and dissolved in 30 ml of anhydrous DMSO, followed by stirring at about 150° C. for about 6 hours. After cooling in the air, 300 ml of water was added to the reaction mixture, followed by stirring. The precipitate thus obtained was recovered by filtering with suction and dissolved in 150 ml of $CH_2Cl_2$. The resultant solution was dried with $MgSO_4$, and solvents were removed by distillation under a reduced pressure. The crude product thus obtained was separated by recrystallization, and 2.15 g (yield 56%) of Compound 77 was obtained as a target product. The molecular weight of the target product measured by FAB-MS was 675. From the result, the target product was identified as Compound 77.

Synthesis of Compound 80

Compound 80, which is a polycyclic compound according to an embodiment may be synthesized, for example, by the following Reaction 6:

Reaction 6

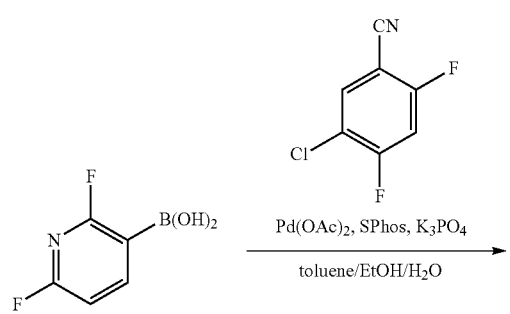

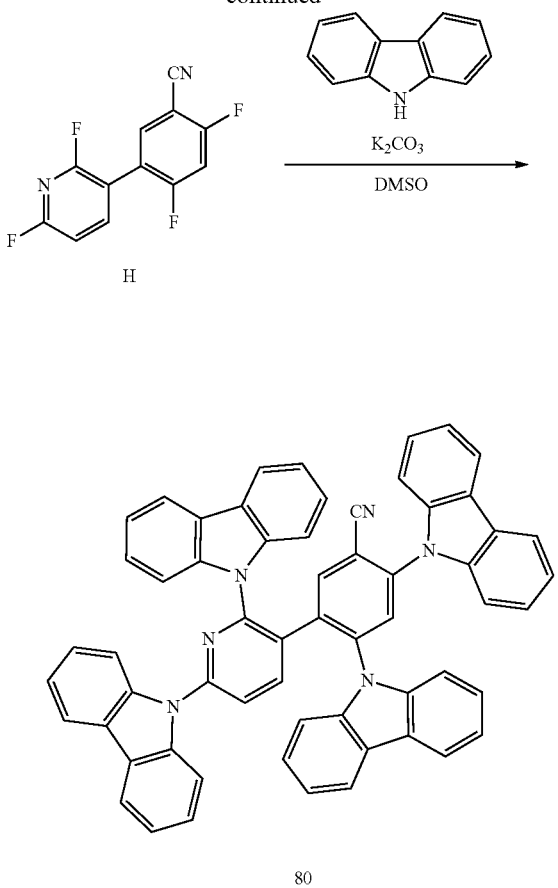

80

Under an argon atmosphere, in a 500 ml, three-neck flask, 5.00 g of 2,6-difluoro-3-pyridineboronic acid, 5.46 g of 5-chloro-2,4-difluorobenzonitrile, 0.35 g of $Pd(OAc)_2$, 1.29 g of SPhos, and 13.36 g of $K_3PO_4$ were dissolved in 160 ml of a deaerated mixture solvent of toluene/ethanol/water (10:1:2), followed by stirring at about 80° C. for about 12 hours. After finishing the reaction, water was added, and extraction with $CH_2Cl_2$ was conducted. An organic layer was separated and dried with $MgSO_4$, and solvents were removed by distillation under a reduced pressure. The crude product thus obtained was separated by silica gel column chromatography to obtain 5.71 g (yield 72%) of Intermediate H. The molecular weight of Intermediate H measured by FAB-MS was 252.

Under an argon atmosphere, to a 200 ml, three-neck flask, 3.00 g of Intermediate H, 7.96 g of carbazole, and 16.44 g of $K_2CO_3$ were added and dissolved in 80 ml of anhydrous DMSO, followed by stirring at about 150° C. for about 8 hours. After cooling in the air, 500 ml of water was added to the reaction mixture, followed by stirring. The precipitate thus obtained was recovered by filtering with suction and dissolved in 200 ml of $CH_2Cl_2$. The resultant solution was dried with $MgSO_4$, and solvents were removed by distillation under a reduced pressure. The crude product thus obtained was separated by recrystallization, and 4.80 g (yield 48%) of Compound 80 was obtained as a target product. The molecular weight of the target product measured by FAB-MS was 840. From the result, the target product was identified as Compound 80.

Synthesis of Compound 83

Compound 83, which is a polycyclic compound according to an embodiment may be synthesized, for example, by the following Reaction 7:

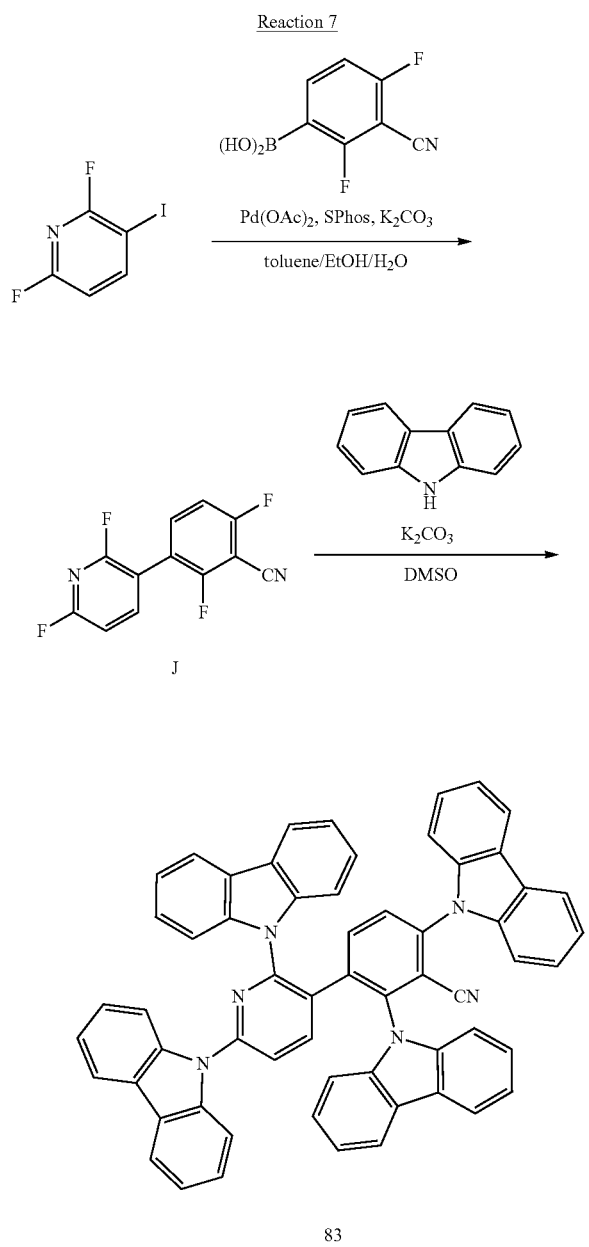

83

Under an argon atmosphere, in a 500 ml, three-neck flask, 5.00 g of 2,6-difluoro-3-iodopyridine, 3.80 g of 3-cyano-2,4-difluorophenylboronic acid, 1.20 g of tetrakis(triphenylphosphine)palladium(O), 0.85 g of SPhos, and 5.74 g of $K_2CO_3$ were dissolved in 100 ml of a deaerated mixture solvent of toluene/ethanol/water (10:1:2), followed by stirring at about 80° C. for about 10 hours. After finishing the reaction, water was added, and extraction with $CH_2Cl_2$ was conducted. An organic layer was separated and dried with $MgSO_4$, and solvents were removed by distillation under a reduced pressure. The crude product thus obtained was separated by silica gel column chromatography to obtain 3.98 g (yield 76%) of Intermediate J. The molecular weight of Intermediate J measured by FAB-MS was 252.

Under an argon atmosphere, to a 200 ml, three-neck flask, 3.00 g of Intermediate J, 7.96 g of carbazole, and 16.44 g of $K_2CO_3$ were added and dissolved in 80 ml of anhydrous DMSO, followed by stirring at about 150° C. for about 8 hours. After cooling in the air, 500 ml of water was added to the reaction mixture, followed by stirring. The precipitate thus obtained was recovered by filtering with suction and dissolved in 200 ml of $CH_2Cl_2$. The resultant solution was dried with $MgSO_4$, and solvents were removed by distillation under a reduced pressure. The crude product thus obtained was separated by recrystallization, and 4.60 g (yield 46%) of Compound 83 was obtained as a target product. The molecular weight of the target product measured by FAB-MS was 840. From the result, the target product was identified as Compound 83.

Synthesis of Compound 84

Compound 84, which is a polycyclic compound according to an embodiment may be synthesized, for example, by the following Reaction 8:

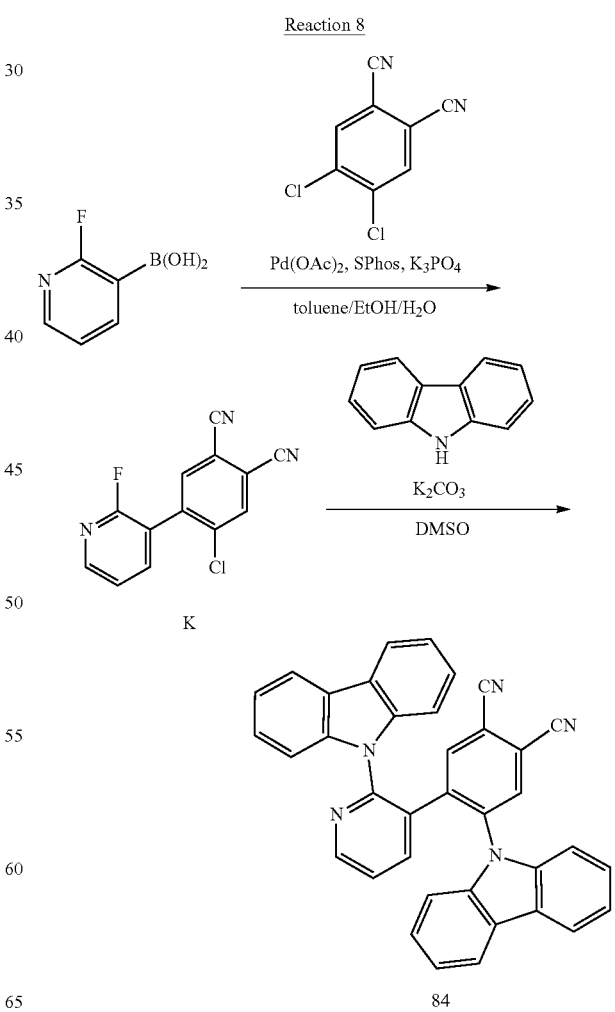

84

Under an argon atmosphere, in a 500 ml, three-neck flask, 5.00 g of (2-fluoropyridin-3-yl)boronic acid, 6.99 g of 4,5-dichlorophthalonitrile, 0.40 g of Pd(OAc)$_2$, 1.47 g of SPhos, and 15.06 g of K$_3$PO$_4$ were dissolved in 180 ml of a deaerated mixture solvent of toluene/ethanol/water (10:1:2), followed by stirring at about 80° C. for about 8 hours. After finishing the reaction, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 4.85 g (yield 53%) of Intermediate K. The molecular weight of Intermediate K measured by FAB-MS was 257.

Under an argon atmosphere, to a 200 ml, three-neck flask, 3.00 g of Intermediate K, 3.89 g of carbazole, and 8.05 g of K$_2$CO$_3$ were added and dissolved in 40 ml of anhydrous DMSO, followed by stirring at about 150° C. for about 8 hours. After cooling in the air, 300 ml of water was added to the reaction mixture, followed by stirring. The precipitate thus obtained was recovered by filtering with suction and dissolved in 150 ml of CH$_2$Cl$_2$. The resultant solution was dried with MgSO$_4$, and solvents were removed by distillation under a reduced pressure. The crude product thus obtained was separated by recrystallization, and 4.37 g (yield 70%) of Compound 84 was obtained as a target product. The molecular weight of the target product measured by FAB-MS was 535. From the result, the target product was identified as Compound 84.

Synthesis of Compound 119

Compound 119, which is a polycyclic compound according to an embodiment may be synthesized, for example, by the following Reaction 9:

Reaction 9

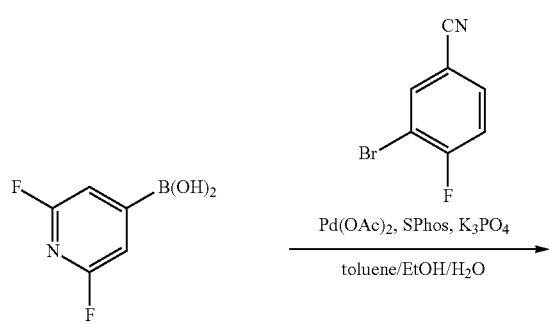

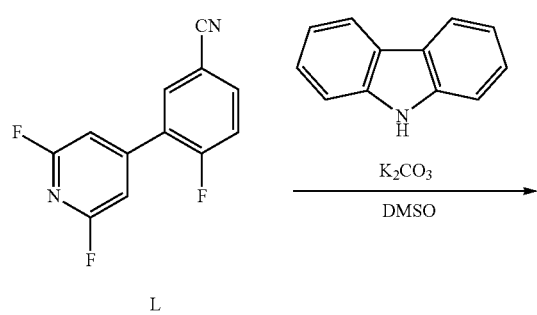

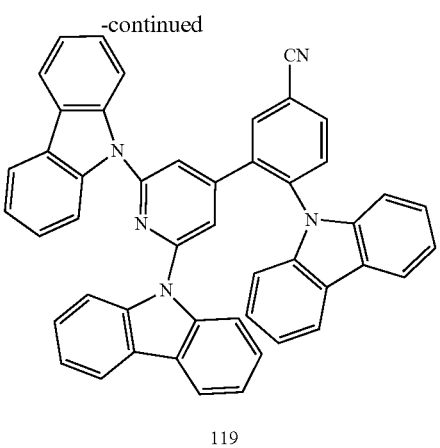

119

Under an argon atmosphere, in a 500 ml, three-neck flask, 5.00 g of (2,6-difluoropyridin-4-yl)boronic acid, 6.29 g of 3-bromo-4-fluorobenzonitrile, 0.35 g of Pd(OAc)$_2$, 1.29 g of SPhos, and 13.36 g of K$_3$PO$_4$ were dissolved in 160 ml of a deaerated mixture solvent of toluene/ethanol/water (10:1:2), followed by stirring at about 80° C. for about 8 hours. After finishing the reaction, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 4.79 g (yield 65%) of Intermediate L. The molecular weight of Intermediate L measured by FAB-MS was 234.

Under an argon atmosphere, to a 200 ml, three-neck flask, 3.00 g of Intermediate L, 6.43 g of carbazole, and 14.16 g of K$_2$CO$_3$ were added and dissolved in 50 ml of anhydrous DMSO, followed by stirring at about 150° C. for about 10 hours. After cooling in the air, 300 ml of water was added to the reaction mixture, followed by stirring. The precipitate thus obtained was recovered by filtering with suction and dissolved in 150 ml of CH$_2$Cl$_2$. The resultant solution was dried with MgSO$_4$, and solvents were removed by distillation under a reduced pressure. The crude product thus obtained was separated by recrystallization, and 6.06 g (yield 70%) of Compound 119 was obtained as a target product. The molecular weight of the target product measured by FAB-MS was 675. From the result, the target product was identified as Compound 119.

Synthesis of Compound 174

Compound 174, which is a polycyclic compound according to an embodiment may be synthesized, for example, by the following Reaction 10:

Reaction 10

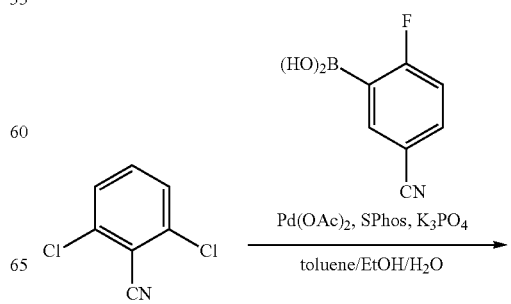

-continued

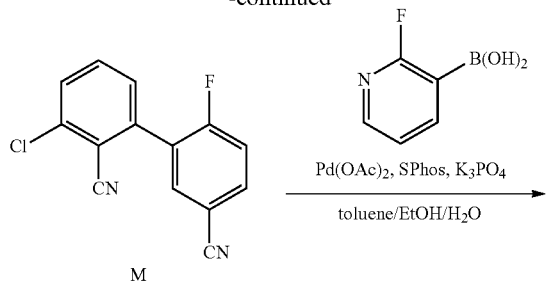

M

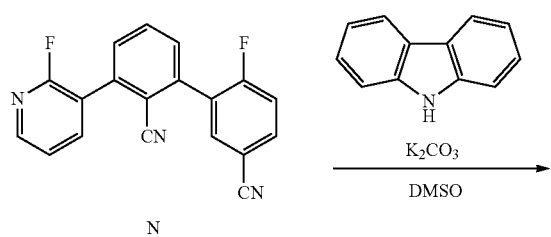

N

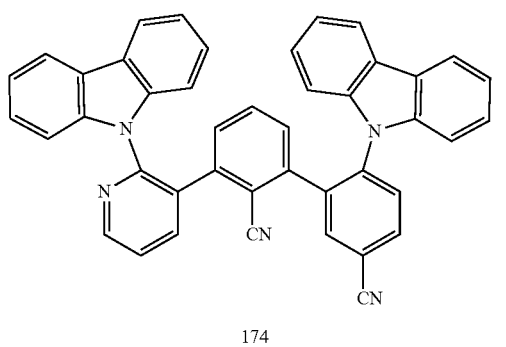

174

Under an argon atmosphere, to a 1 L, three-neck flask, 10.00 g of 2,6-dichlorobenzonitrile, 4.79 g of 5-cyano-2-fluorophenylboronic acid, 0.32 g of Pd(OAc)$_2$, 1.19 g of SPhos, and 12.34 g of K$_3$PO$_4$ were dissolved in 290 ml of a deaerated mixture solvent of toluene/ethanol/water (10:1:2), followed by stirring at about 80° C. for about 8 hours. After finishing the reaction, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 5.07 g (yield 68%) of Intermediate M. The molecular weight of Intermediate M measured by FAB-MS was 256.

Under an argon atmosphere, to a 500 ml, three-neck flask, 5.00 g of Intermediate M, 2.75 g of (2-fluoropyridin-3-yl) boronic acid, 0.22 g of Pd(OAc)$_2$, 0.80 g of SPhos, and 8.27 g of K$_3$PO$_4$ were dissolved in 100 ml of a deaerated mixture solvent of toluene/ethanol/water (10:1:2), followed by stirring at about 80° C. for about 8 hours. After finishing the reaction, water was added, and extraction with CH$_2$Cl$_2$ was conducted. An organic layer was separated and dried with MgSO$_4$, and solvents were removed by distillation under a reduced pressure. The crude product thus obtained was separated by silica gel column chromatography to obtain 3.96 g (yield 64%) of Intermediate N. The molecular weight of Intermediate N measured by FAB-MS was 317.

Under an argon atmosphere, to a 200 ml, three-neck flask, 3.00 g of Intermediate N, 3.16 g of carbazole, and 6.53 g of K$_2$CO$_3$ were added and dissolved in 40 ml of anhydrous DMSO, followed by stirring at about 1500° C. for about 8 hours. After cooling in the air, 300 ml of water was added to the reaction mixture, followed by stirring. The precipitate thus obtained was recovered by filtering with suction and dissolved in 150 ml of CH$_2$Cl$_2$. The resultant solution was dried with MgSO$_4$, and solvents were removed by distillation under a reduced pressure. The crude product thus obtained was separated by recrystallization, and 3.87 g (yield 67%) of Compound 174 was obtained as a target product. The molecular weight of the target product measured by FAB-MS was 611. From the result, the target product was identified as Compound 174.

Synthesis of Compound 212

Compound 212, which is a polycyclic compound according to an embodiment may be synthesized, for example, by the following Reaction 11:

Reaction 11

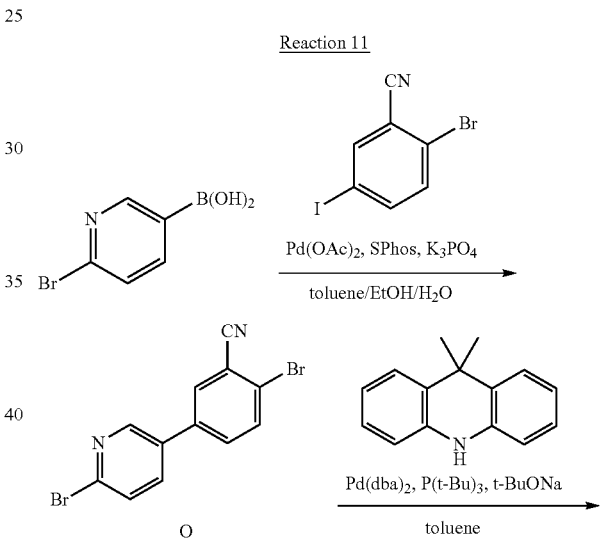

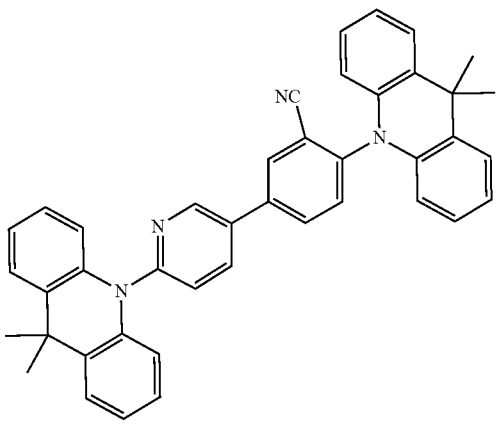

212

Under an argon atmosphere, to a 500 ml, three-neck flask, 5.00 g of (6-bromopyridin-3-yl)boronic acid, 7.63 g of 2-bromo-5-iodobenzonitrile, 0.28 g of $Pd(OAc)_2$, 1.02 g of SPhos, and 10.52 g of $K_3PO_4$ were dissolved in 120 ml of a deaerated mixture solvent of toluene/ethanol/water (10:1:2), followed by stirring at about 80° C. for about 12 hours. After finishing the reaction, water was added, and extraction with $CH_2Cl_2$ was conducted. An organic layer was separated and dried with $MgSO_4$, and solvents were removed by distillation under a reduced pressure. The crude product thus obtained was separated by silica gel column chromatography to obtain 6.20 g (yield 74%) of Intermediate O. The molecular weight of Intermediate O measured by FAB-MS was 338.

Under an argon atmosphere, to a 200 ml, three-neck flask, 3.00 g of Intermediate O, 3.71 g of 9,9-dimethyl-9,10-dihydroacridine, 0.51 g of bis(dibenzylideneacetone)palladium(O), 1.78 ml of tri-tert-butylphosphine (2 M in toluene) and 1.71 g of sodium tert-butoxide were added and dissolved in 50 ml of anhydrous toluene, followed by heating and refluxing for about 8 hours. After finishing the reaction, water was added to the reaction mixture, and extraction with $CH_2Cl_2$ was conducted. An organic layer was separated and dried with $MgSO_4$, and solvents were removed by distillation under a reduced pressure. The crude product thus obtained was separated by recrystallization, and 3.96 g (yield 75%) of Compound 212 was obtained as a target product. The molecular weight of the target product measured by FAB-MS was 594. From the result, the target product was identified as Compound 212.

2. Manufacture and Evaluation of Organic Electroluminescence Device Including a Polycyclic Compound Manufacture of Organic Electroluminescence Devices Organic electroluminescence devices of exemplary embodiments including the polycyclic compounds of exemplary embodiments in an emission layer were manufactured by a method described below. Organic electroluminescence devices of Examples 1 to 11 were manufactured utilizing the polycyclic compounds of Compound 2, Compound 69, Compound 71, Compound 74, Compound 77, Compound 80, Compound 83, Compound 84, Compound 119, Compound 174 and Compound 212 respectively as materials for an emission layer. Compounds utilized in the emission layer in Examples 1 to 11 and Comparative Examples 1 to 5 are shown below in Table

TABLE 1

Example Compounds

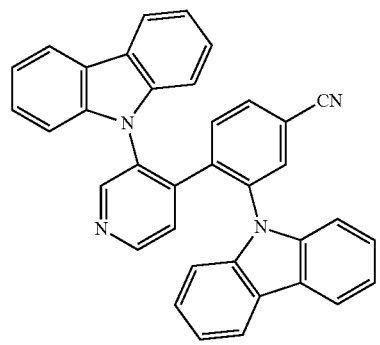 [SMILES: N#Cc1ccc(-c2ccncc2-n2c3ccccc3c3ccccc32)c(-n2c3ccccc3c3ccccc32)c1]

2

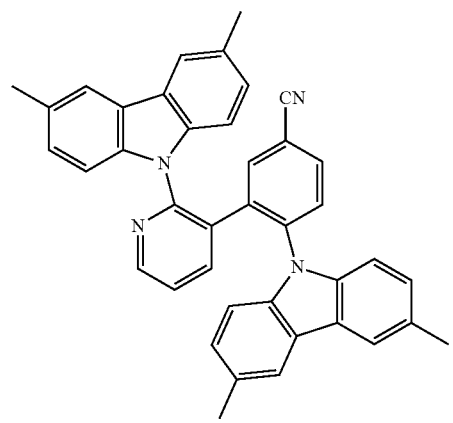

69

TABLE 1-continued
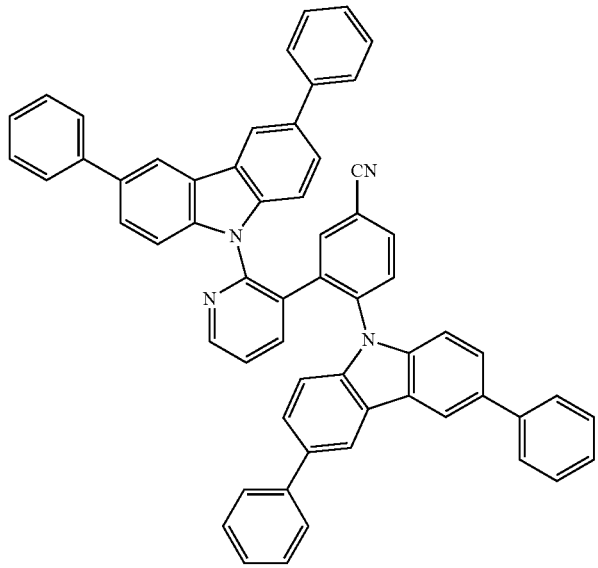 [SMILES: N#Cc1ccc(-n2c3ccc(-c4ccccc4)cc3c3cc(-c4ccccc4)ccc32)c(-c2cccnc2-n2c3ccc(-c4ccccc4)cc3c3cc(-c4ccccc4)ccc32)c1]
71
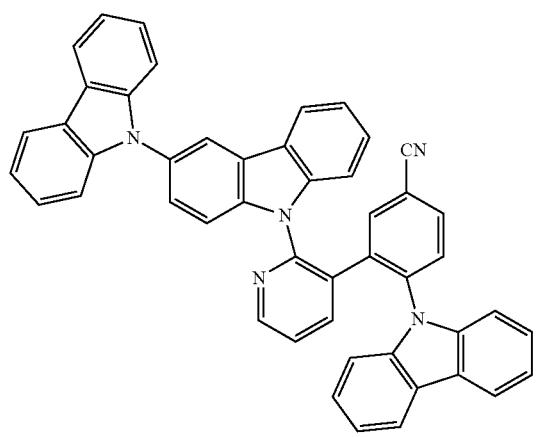 [SMILES: N#Cc1ccc(-n2c3ccccc3c3ccccc32)c(-c2cccnc2-n2c3ccccc3c3cc(-n4c5ccccc5c5ccccc54)ccc32)c1]
74
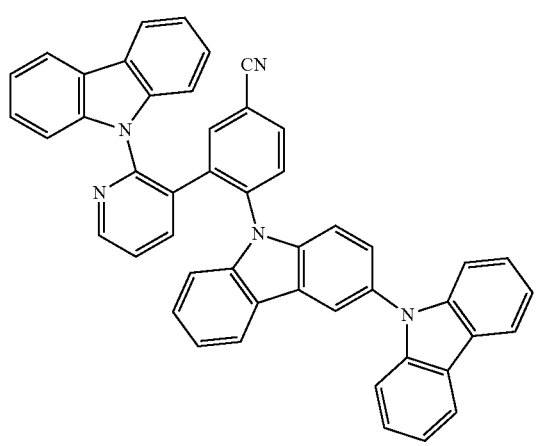 [SMILES: N#Cc1ccc(-n2c3ccccc3c3cc(-n4c5ccccc5c5ccccc54)ccc32)c(-c2cccnc2-n2c3ccccc3c3ccccc32)c1]
77

TABLE 1-continued
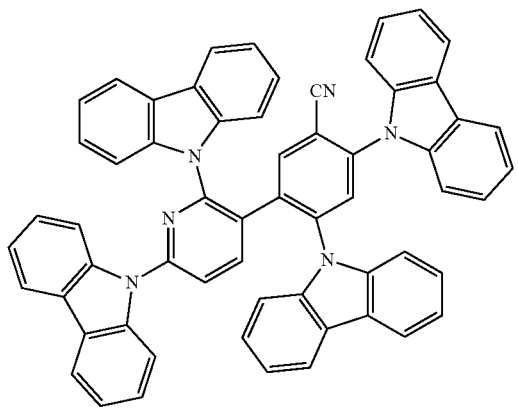 [SMILES: N#Cc1cc(-c2ccc(-n3c4ccccc4c4ccccc43)nc2-n2c3ccccc3c3ccccc32)c(-n2c3ccccc3c3ccccc32)cc1-n1c2ccccc2c2ccccc21]
80
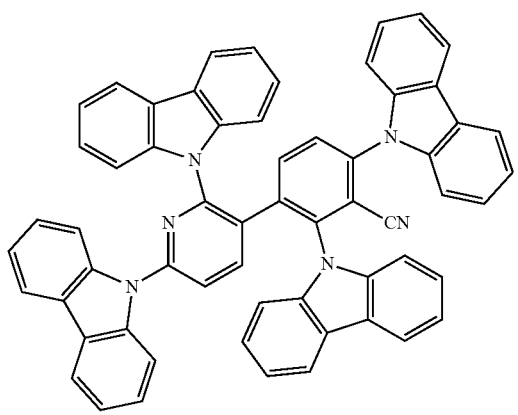 [SMILES: N#Cc1c(-n2c3ccccc3c3ccccc32)ccc(-c2ccc(-n3c4ccccc4c4ccccc43)nc2-n2c3ccccc3c3ccccc32)c1-n1c2ccccc2c2ccccc21]
83
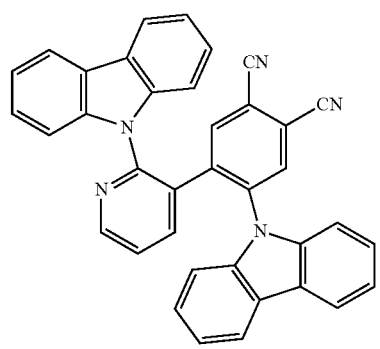 [SMILES: N#Cc1cc(-c2cccnc2-n2c3ccccc3c3ccccc32)c(-n2c3ccccc3c3ccccc32)cc1C#N]
84
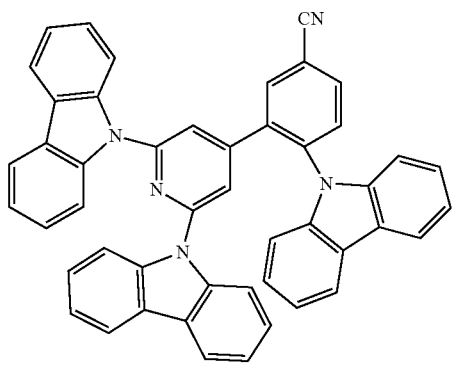 [SMILES: N#Cc1ccc(-n2c3ccccc3c3ccccc32)c(-c2cc(-n3c4ccccc4c4ccccc43)nc(-n3c4ccccc4c4ccccc43)c2)c1]
119

TABLE 1-continued
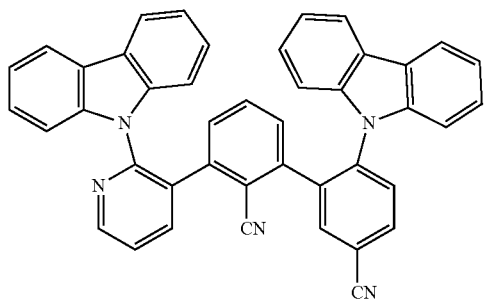 [SMILES: N#Cc1ccc(-n2c3ccccc3c3ccccc32)c(-c2cccc(-c3cccnc3-n3c4ccccc4c4ccccc43)c2C#N)c1]
174
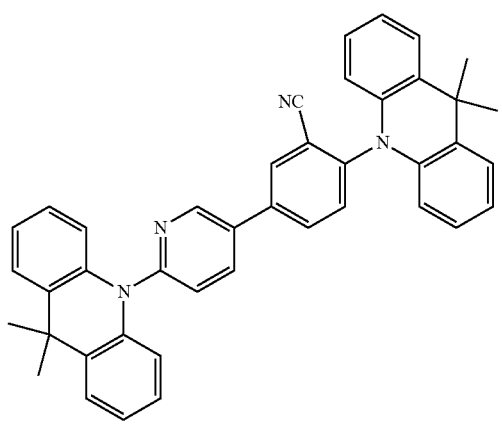
212
Comparative Compounds
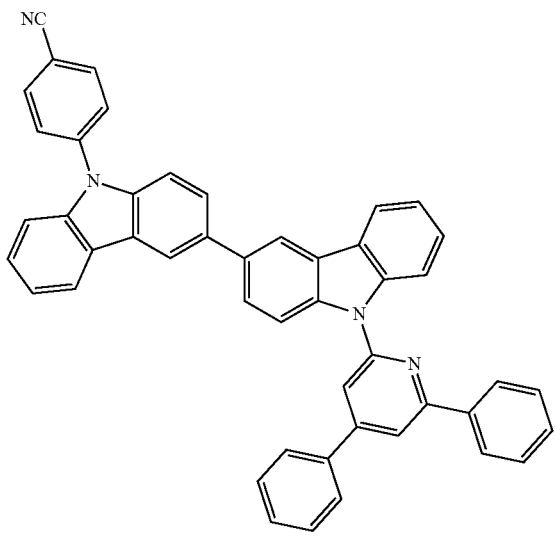 [SMILES: N#Cc1ccc(-n2c3ccccc3c3cc(-c4ccc5c(c4)c4ccccc4n5-c4cc(-c5ccccc5)cc(-c5ccccc5)n4)ccc32)cc1]
X-1
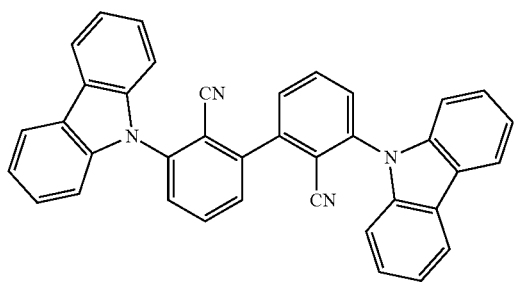 [SMILES: N#Cc1c(-c2cccc(-n3c4ccccc4c4ccccc43)c2C#N)cccc1-n1c2ccccc2c2ccccc21]
X-2

TABLE 1-continued

X-3

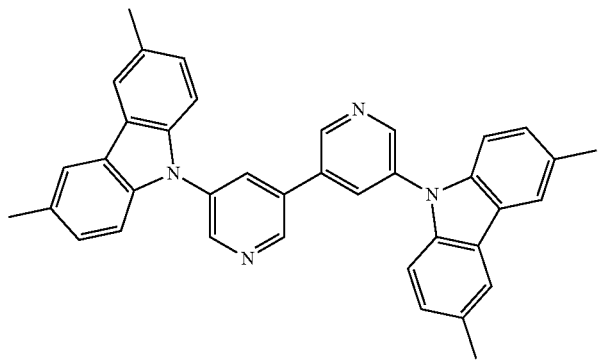

X-4

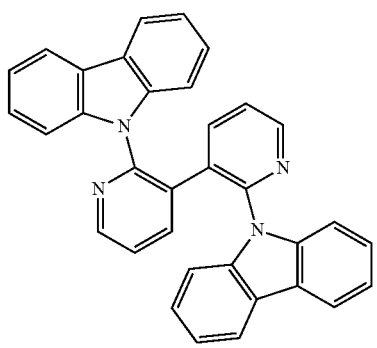 [SMILES: c1cnc(-n2c3ccccc3c3ccccc32)c(-c2cccnc2-n2c3ccccc3c3ccccc32)c1]

X-5

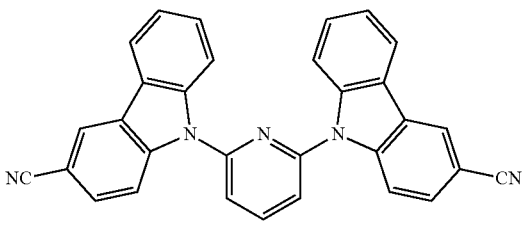 [SMILES: N#Cc1ccc2c(c1)c1ccccc1n2-c1cccc(-n2c3ccccc3c3cc(C#N)ccc32)n1]

The organic electroluminescence devices of the examples and the comparative examples were manufactured by a method described below.

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, α-NPD was deposited to a thickness of about 800 Å, and mCP was deposited to a thickness of about 50 Å to form a hole transport region.

Then, each of the polycyclic compounds of an embodiment and the Comparative Compound, and DPEPO were co-deposited in a ratio of 18:82 to form an emission layer to a thickness of about 200 Å. Then, a layer with a thickness of about 100 Å was formed utilizing DPEPO. That is, in order to form the emission layer by the co-deposition, each of Compounds 2, 69, 71, 74, 77, 80, 83, 84, 119, 174 and 212 was mixed with DPEPO and deposited in Examples 1 to 11, and each of Comparative Compounds X-1, X-2, X-3, X-4 and X-5 was mixed with DPEPO and deposited in Comparative Examples 1 to 5.

On the emission layer, a layer was formed utilizing TPBi to a thickness of about 300 Å, and a layer was formed utilizing LiF to a thickness of about 5 Å to form an electron transport region. Then, a second electrode was formed utilizing aluminum (Al) to a thickness of about 1,000 Å.

In the examples, the hole transport region, the emission layer, the electron transport region and the second electrode were formed by utilizing a vacuum deposition apparatus.

Energy Levels of Each Compound

In Table 2 below, the singlet (S1) energy levels and the triplet (T1) energy levels of Compounds 2, 69, 71, 74, 77, 80, 83, 84, 119, 174 and 212, which are example compounds, and Comparative Compounds X-1, X-2, X-3, X-4 and X-5 are shown. The energy level values in Table 2 were calculated by a non-empirical molecular orbital method. Particularly, the energy level values were calculated by B3LYP/6-31G(d) utilizing Gaussian 09 of Gaussian Co. $\Delta E_{ST}$ represents the difference between a singlet (S1) energy level and a triplet (T1) energy level.

TABLE 2

| Compound | S1 energy level | T1 energy level | $\Delta E_{ST}$ |
|---|---|---|---|
| Compound 2 | 2.96 | 2.87 | 0.09 |
| Compound 69 | 2.96 | 2.81 | 0.15 |
| Compound 71 | 2.85 | 2.72 | 0.13 |
| Compound 74 | 2.82 | 2.80 | 0.02 |
| Compound 77 | 2.95 | 2.83 | 0.12 |
| Compound 80 | 2.97 | 2.80 | 0.17 |
| Compound 83 | 2.96 | 2.85 | 0.11 |
| Compound 84 | 2.55 | 2.47 | 0.08 |

TABLE 2-continued

| Compound | S1 energy level | T1 energy level | $\Delta E_{ST}$ |
|---|---|---|---|
| Compound 119 | 2.99 | 2.81 | 0.18 |
| Compound 174 | 3.08 | 2.99 | 0.09 |
| Compound 212 | 2.45 | 2.44 | 0.01 |
| Comparative Compound X-1 | 3.20 | 2.85 | 0.35 |
| Comparative Compound X-2 | 2.96 | 2.87 | 0.09 |
| Comparative Compound X-3 | 3.28 | 3.07 | 0.21 |
| Comparative Compound X-4 | 3.35 | 3.14 | 0.21 |
| Comparative Compound X-5 | 3.24 | 3.03 | 0.21 |

Compounds 2, 69, 71, 74, 77, 80, 83, 84, 119, 174 and 212, which are example compounds, showed low $\Delta E_{ST}$ values of about 0.2 eV or less. In comparison, Comparative Compounds X-1, and X-3 to X-5 were found to show $\Delta E_{ST}$ values greater than about 0.2 eV.

Evaluation of Properties of Organic Electroluminescence Device

In order to evaluate the properties of the organic electroluminescence devices of the examples and the comparative examples, the maximum emission wavelength (nm) and external quantum yield (%) were measured. The measurement was conducted utilizing a luminous brightness measurement apparatus, C9920-11 of HAMAMATSU Photonics Co.

TABLE 3

| | Emission layer dopant | Maximum emission wavelength (nm) | External quantum yield (%) |
|---|---|---|---|
| Example 1 | Compound 2 | 492 | 10 |
| Example 2 | Compound 69 | 462 | 12 |
| Example 3 | Compound 71 | 460 | 11 |
| Example 4 | Compound 74 | 460 | 13 |
| Example 5 | Compound 77 | 448 | 10 |
| Example 6 | Compound 80 | 458 | 13 |
| Example 7 | Compound 83 | 456 | 14 |
| Example 8 | Compound 84 | 486 | 10 |
| Example 9 | Compound 119 | 455 | 10 |
| Example 10 | Compound 174 | 446 | 8 |
| Example 11 | Compound 212 | 490 | 12 |
| Comparative Example 1 | Comparative Compound X-1 | 445 | 1 |
| Comparative Example 2 | Comparative Compound X-2 | 458 | 4 |
| Comparative Example 3 | Comparative Compound X-3 | 430 | 2 |
| Comparative Example 4 | Comparative Compound X-4 | 428 | 1 |
| Comparative Example 5 | Comparative Compound X-5 | 431 | 2 |

Referring to Table 3, it may be found that the organic electroluminescence devices of Examples 1 to 11, which utilized the polycyclic compounds of exemplary embodiments as dopant materials of an emission layer, showed excellent external quantum efficiency when compared to Comparative Examples 1 to 5. In addition, the organic electroluminescence devices of Examples 1 to 11, which utilized the polycyclic compounds of exemplary embodiments as the dopant materials of an emission layer, and the organic electroluminescence devices of Comparative Examples 1 to 5, which utilized Comparative Compounds X-1 to X-5, were found to have emission wavelength of about 495 nm or less and emit blue light.

Referring to the results of Tables 2 and 3, the Example Compounds had a small $\Delta E_{ST}$ and showed high emission efficiency in a blue emission region at the same time, thus might be utilized as materials for thermally activated delayed fluorescence with high efficiency.

The organic electroluminescence device of an embodiment includes the polycyclic compound of an embodiment in an emission layer and may accomplish deep blue light with relatively short wavelengths and may show high emission efficiency at the same time.

Also, the polycyclic compound of an embodiment has an electron donor-electron acceptor-electron donor (D-A-D) structure, and the electron donor does not include a cyano group but the electron acceptor includes a benzonitrile part and a pyridine part at the same time, and thus, the polycyclic compound shows a low $\Delta E_{ST}$ value and high emission efficiency.

In comparison to the examples, Comparative Compound X-1 had an electron donor-electron donor-electron acceptor (D-D-A) structure, and the electron acceptor included only a pyridine part. Thus, this compound showed a high $\Delta E_{ST}$ value and may not be utilized as a thermally activated delayed fluorescence material. In addition, the organic electroluminescence device of Comparative Example 1 showed low external quantum efficiency than those of the examples.

Comparative Compound X-2, which was utilized in Comparative Example 2, had a low $\Delta E_{ST}$ value, but included only a benzonitrile part in an electron acceptor, and thus, had low electron accepting properties. Accordingly, charge transfer (CT) in a molecule was not smooth and thermally activated delayed fluorescence was not shown. Therefore, the organic electroluminescence device of Comparative Example 2 was found to show low external quantum efficiency.

Comparative Compounds X-3 and X-4, which were utilized in Comparative Examples 3 and 4, showed relatively not high $\Delta E_{ST}$ values but included only a pyridine part in an electron acceptor, and thus, the accepting properties of the electron acceptor was low. Accordingly, charge transfer (CT) in a molecule was not smooth and thermally activated delayed fluorescence was not shown. Therefore, the organic electroluminescence devices of Comparative Examples 3 and 4 were found to show low external quantum efficiency.

In addition, Comparative Compound X-5 utilized in Comparative Example 5 showed a relatively not high $\Delta E_{ST}$ value but included only a pyridine part in an electron acceptor, and thus, the accepting properties of the electron acceptor was low. Because the carbazole group of the electron donor included a cyano group, the donating properties of the electron donor was low and charge transfer (CT) in an molecule was not smooth, and thus, thermally activated delayed fluorescence was not shown. Therefore, the organic electroluminescence device of Comparative Example 5 was found to show low external quantum efficiency.

Referring to Table 3, the organic electroluminescence devices of exemplary embodiments, which utilized the polycyclic compounds of exemplary embodiments as luminescent materials of an emission layer, showed higher emission efficiency than the comparative examples. In addition, with regard to emission wavelengths, it was found that maximum emission wavelength of about 495 nm or less was shown and deep blue color was achieved.

The organic electroluminescence device of an embodiment has an electron donor-electron acceptor-electron donor (D-A-D) structure, which includes two electron donors and one electron acceptor, and utilizes a polycyclic compound including an electron acceptor having a benzonitrile part and a pyridine part as a material for an emission layer. Thus, high emission efficiency in a blue light wavelength region may be achieved.

The organic electroluminescence device according to an embodiment of the inventive concept may attain high efficiency and long life.

The polycyclic compound according to an embodiment of the inventive concept may improve the life and efficiency of an organic electroluminescence device.

Throughout the disclosure, the use of "may" when describing embodiments of the present invention refers to "one or more embodiments of the present invention." Moreover, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112, first paragraph, or 35 U.S.C. § 112(a), and 35 U.S.C. § 132(a).

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed, and equivalents thereof.

What is claimed is:

1. An organic electroluminescence device, comprising:

a first electrode;

a hole transport region on the first electrode;

an emission layer on the hole transport region;

an electron transport region on the emission layer; and a second electrode on the electron transport region, wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof, and wherein the emission layer comprises a polycyclic compound represented by following Formula 1:

Formula 1

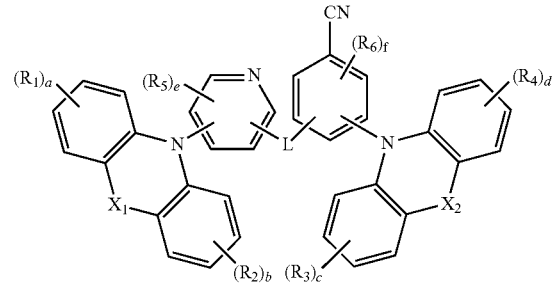

wherein in Formula 1, $X_1$ and $X_2$ are each independently a direct linkage, $CR_7R_8$, $SiR_9R_{10}$, O, or S, L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring, $R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;

$R_1$ to $R_4$ are each optionally independently combined with an adjacent group to form a ring, a, b, c and d are each independently an integer of 0 to 4, $R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;

$R_5$ to $R_{14}$ are each optionally independently combined with an adjacent group to form a ring, and e and f are each independently an integer of 0 to 3, wherein when L is a direct linkage, then:

1) the pyridine group of Formula 1 is at an ortho or a meta position to the cyano group of the benzonitrile group of Formula 1, e and f are each 3, at least one $R_5$ or $R_6$ is a substituted or unsubstituted carbazole group, a substituted pyridyl group, or a substituted benzonitrile group and a rest of $R_5$ and Re are each a hydrogen atom, and the benzonitrile group of Formula 1 is at a meta position to the $X_1$ containing group of Formula 1; or 2) the pyridine group of Formula 1 is at an ortho or a meta position to the cyano group of the benzonitrile group of Formula 1, and $X_1$ and/or $X_2$ is $CR_7R_8$, in which $R_7$ and $R_8$ are combined to form a 9H-xanthenyl or 9H-fluorenyl ring.

2. The organic electroluminescence device of claim 1, wherein the polycyclic compound represented by Formula 1 is represented by one of following Formula 1-1 to Formula 1-3:

Formula 1-1

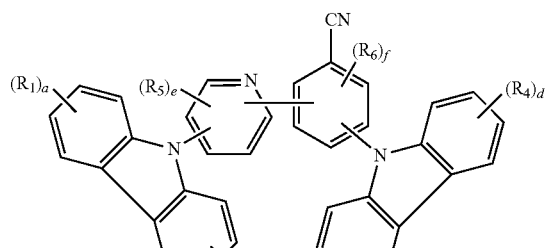

Formula 1-2

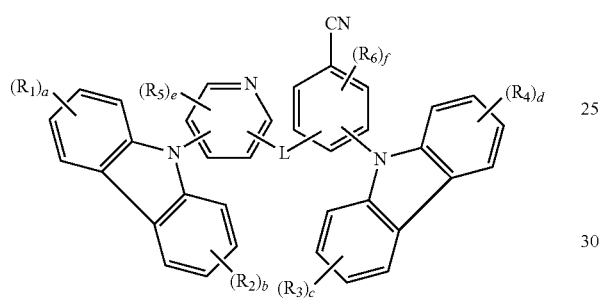

Formula 1-3

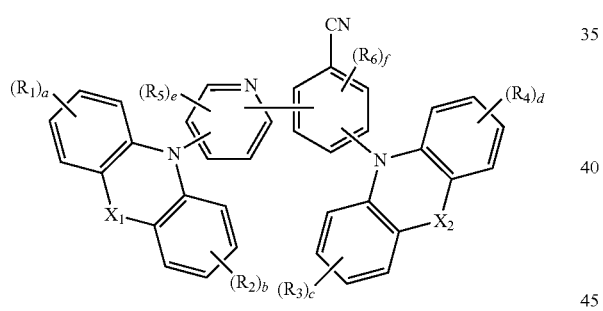

wherein in Formula 1-1 to Formula 1-3, $X_1$ and $X_2$, L, $R_1$ to $R_6$, and a to f are the same as respectively defined in association with Formula 1.

3. The organic electroluminescence device of claim 1, wherein $X_1$ and $X_2$ of Formula 1 are the same.

4. The organic electroluminescence device of claim 1, wherein $R_5$ and $R_6$ of Formula 1 are each independently represented by one of following Formula 2-1 to Formula 2-4:

Formula 2-1

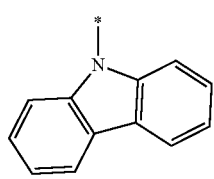

Formula 2-2

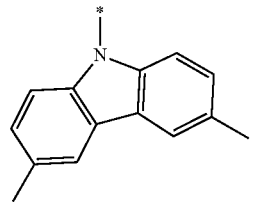

Formula 2-3

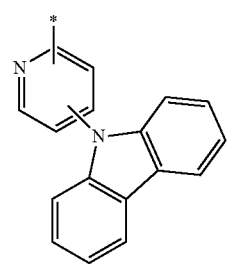

Formula 2-4

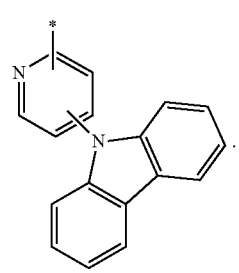

5. The organic electroluminescence device of claim 1, wherein $R_1$ to $R_4$ of Formula 1 are each independently represented by one of following Formula 3-1 to Formula 3-3:

Formula 3-1

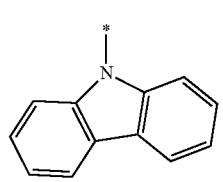

Formula 3-2

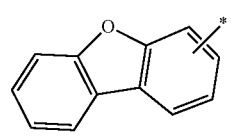

Formula 3-3

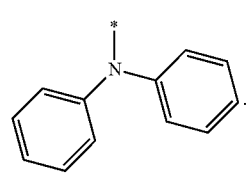

6. The organic electroluminescence device of claim 1, wherein the compound represented by Formula 1 is any one among compounds represented in following Compound Group 1:
[Compound Group 1]
78
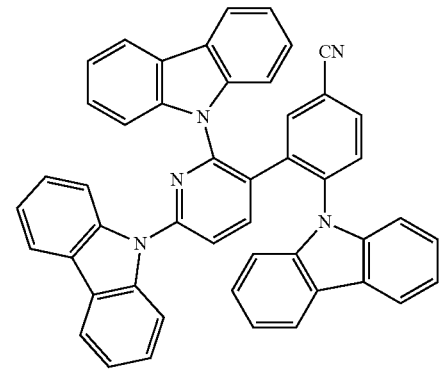
79
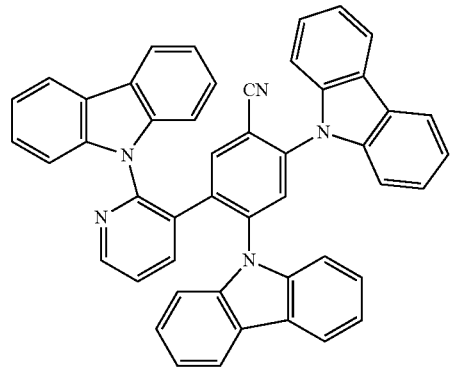
80
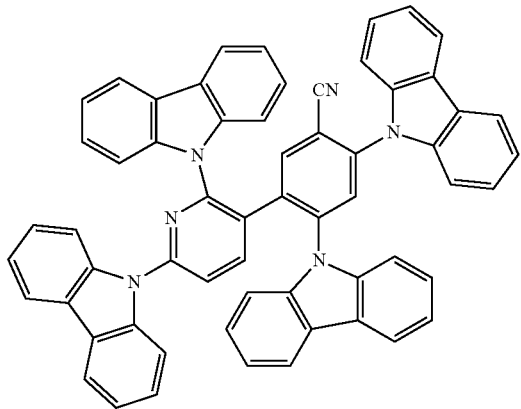
-continued
81
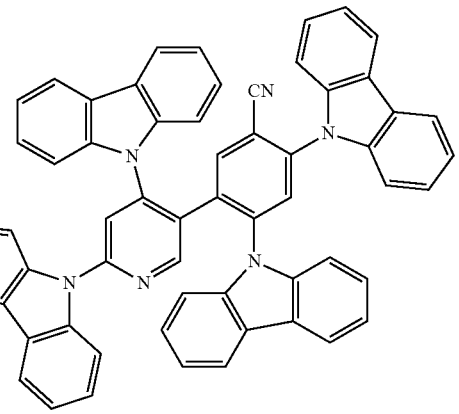
82
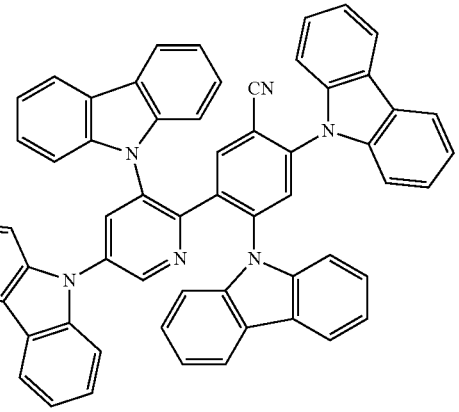
83
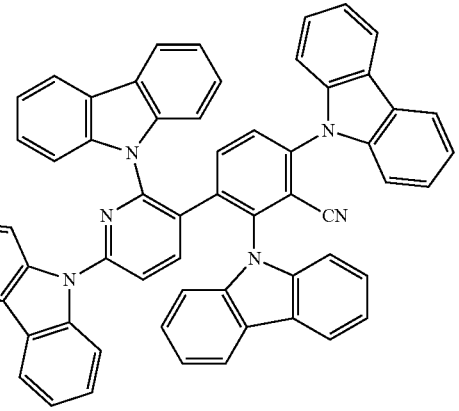
85
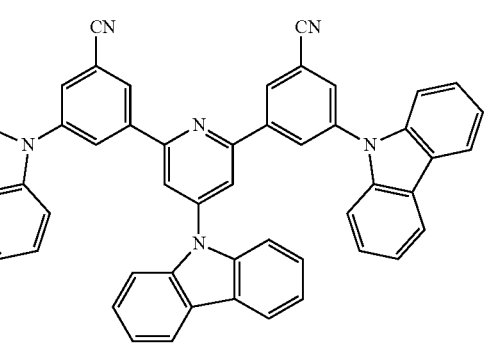

86
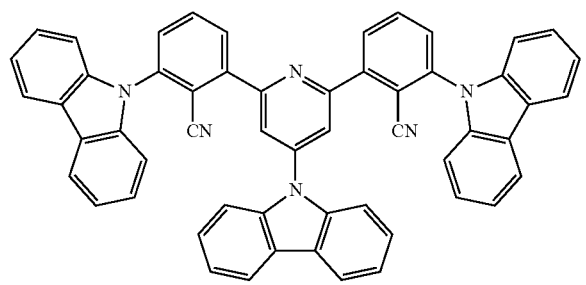
87
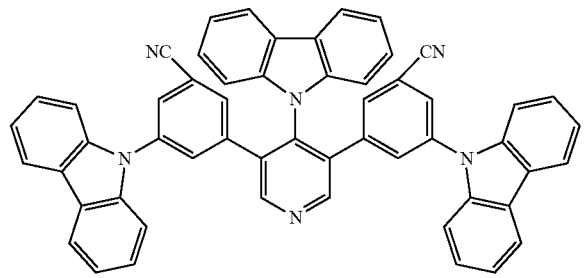
88
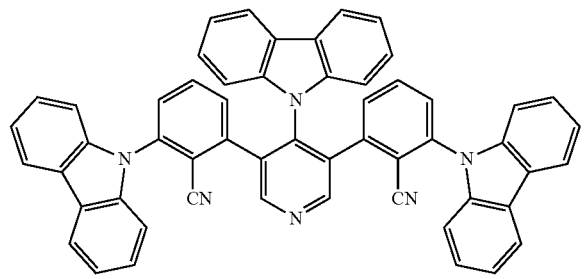
90
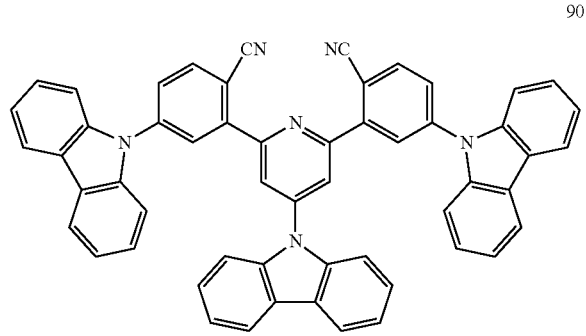
92
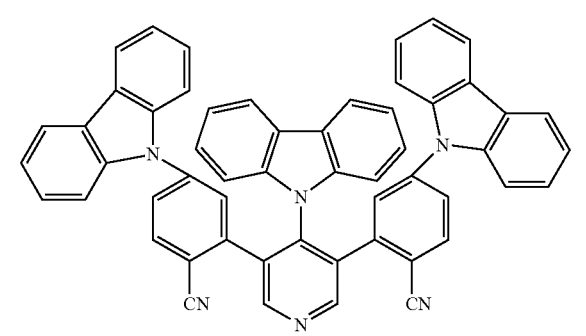
93
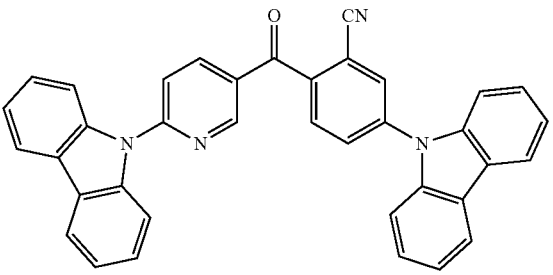
94
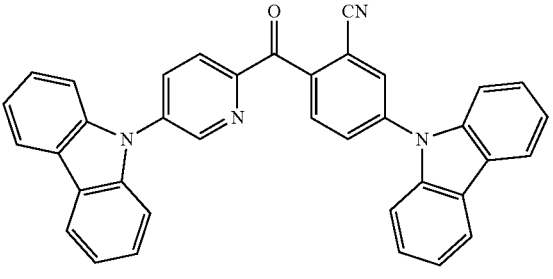
95
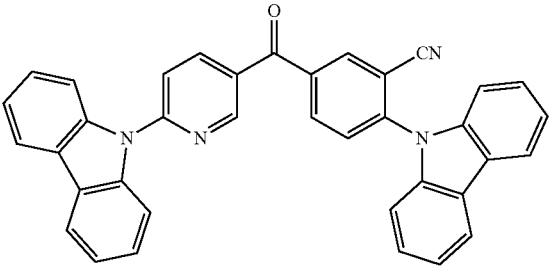
96
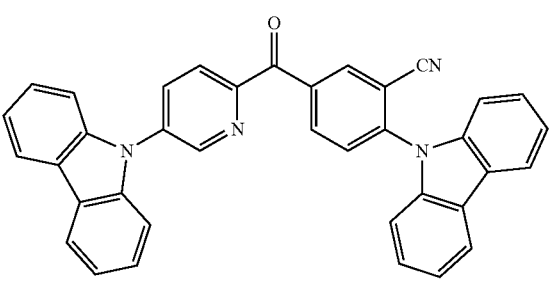
97
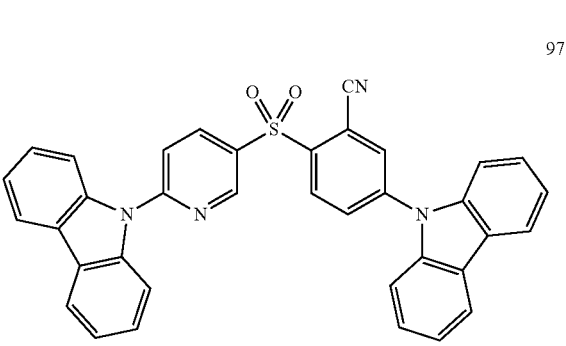

98
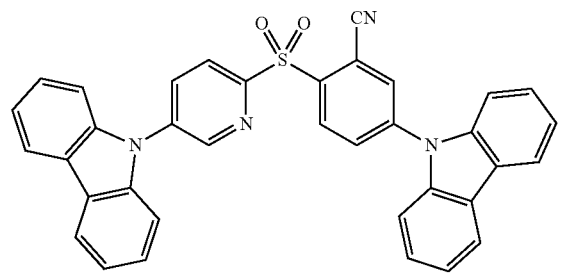
99
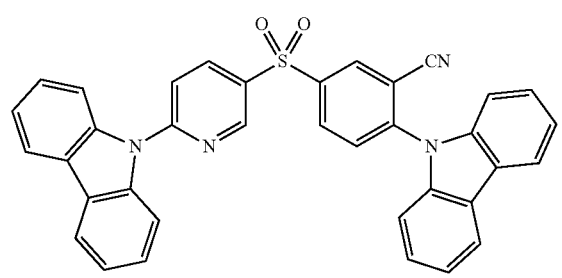
100
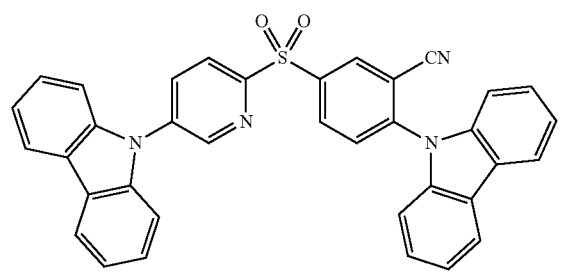
101
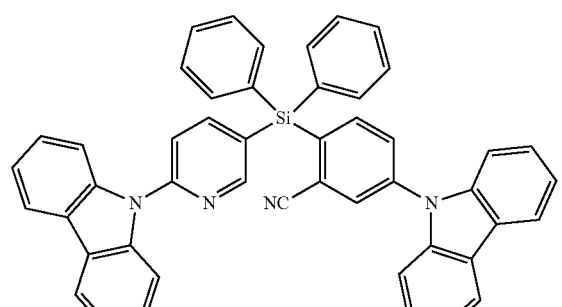
102
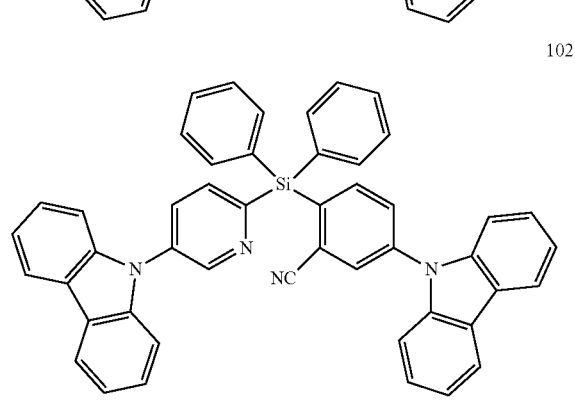
103
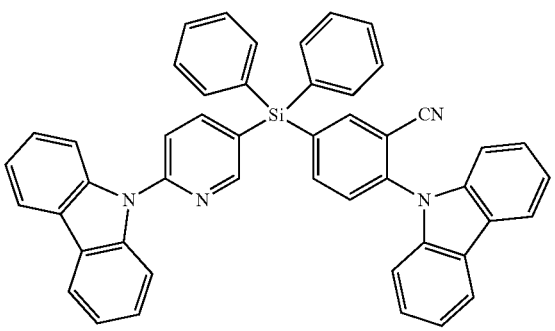
104
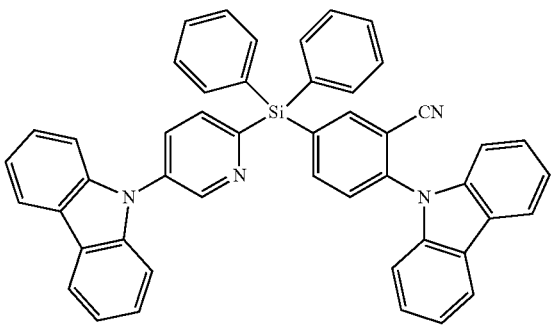
105
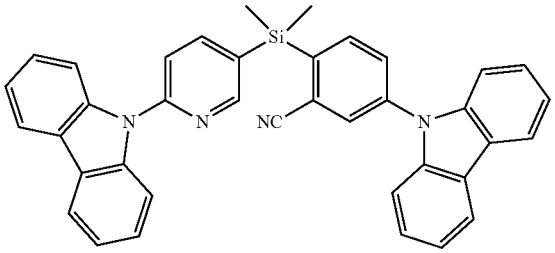
106
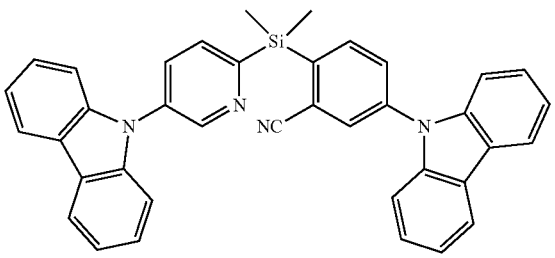
107
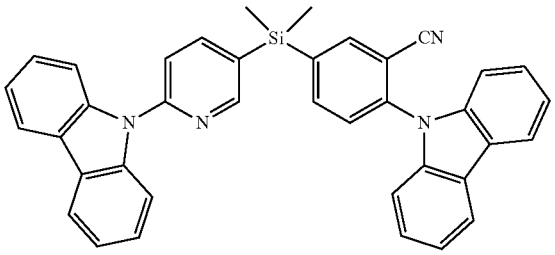

108
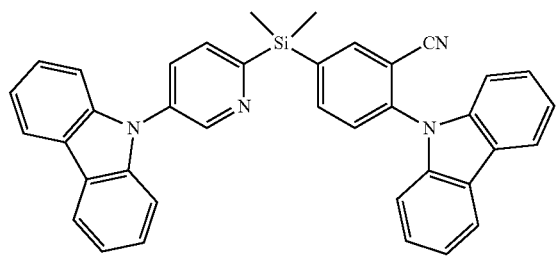
109
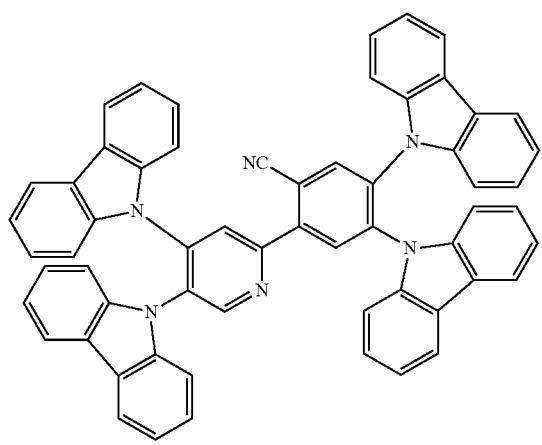
110
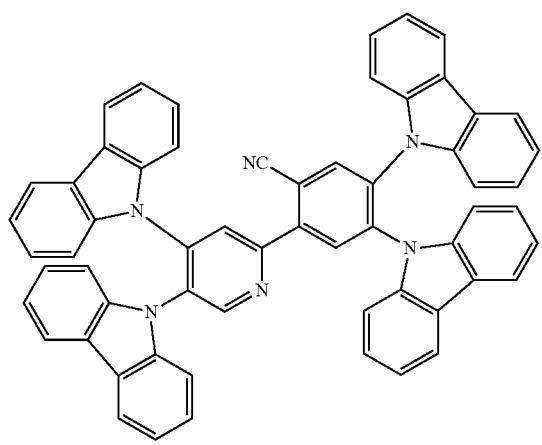
111
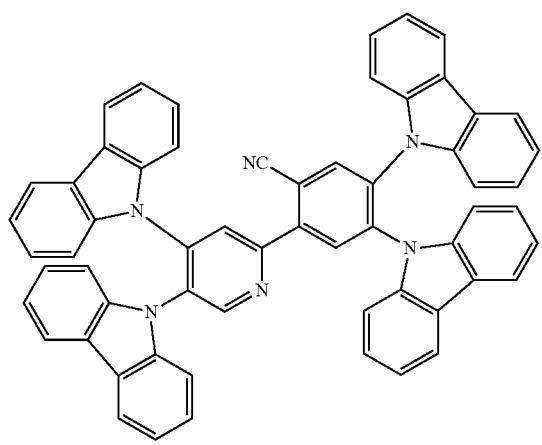
112
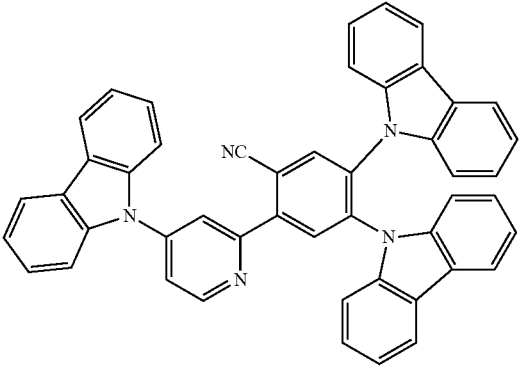
113
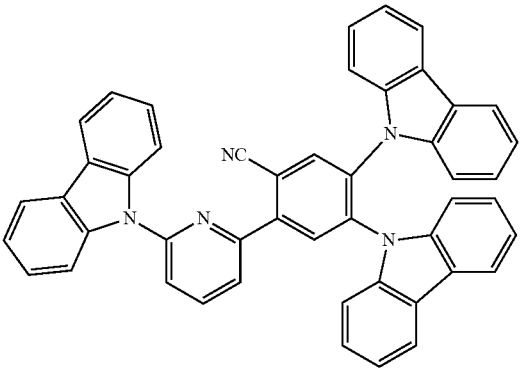
114
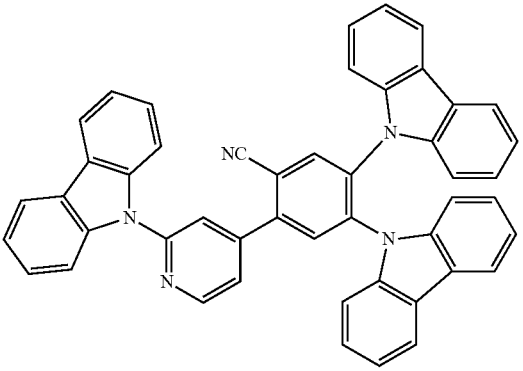
115
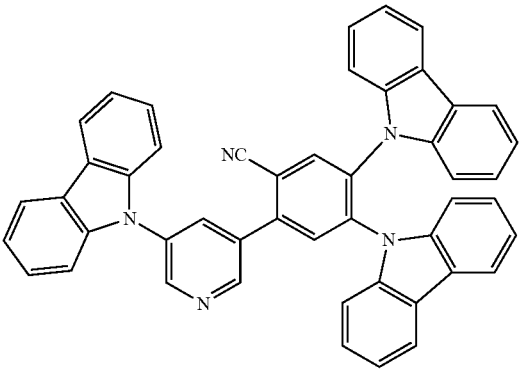

116
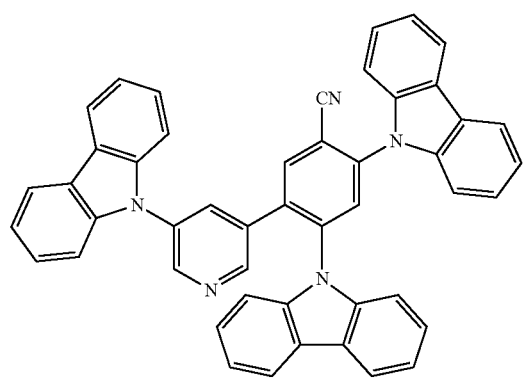
117
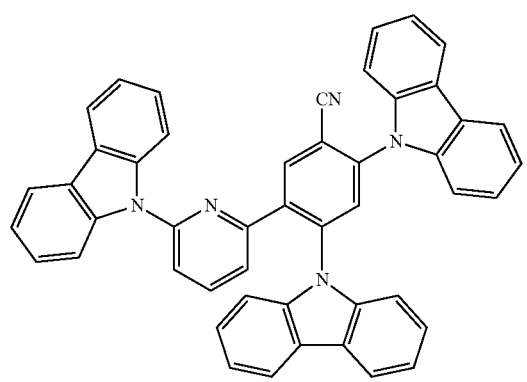
118
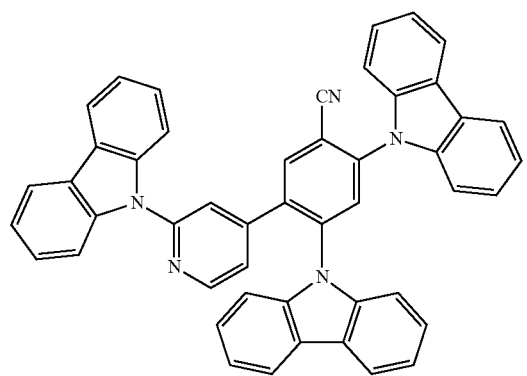
119
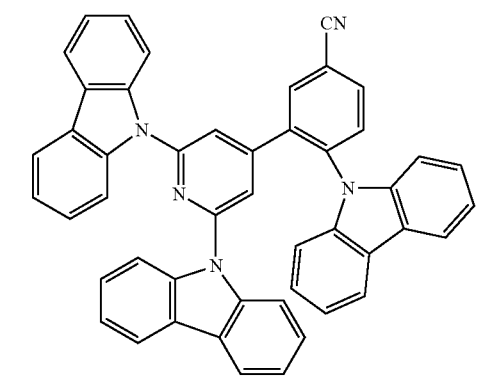
120
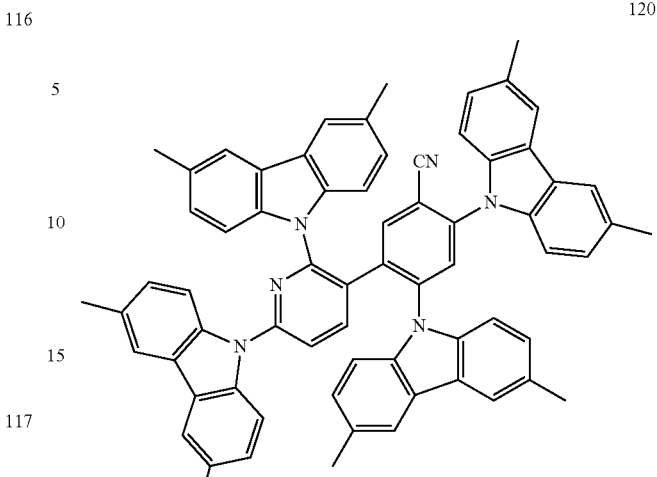
121
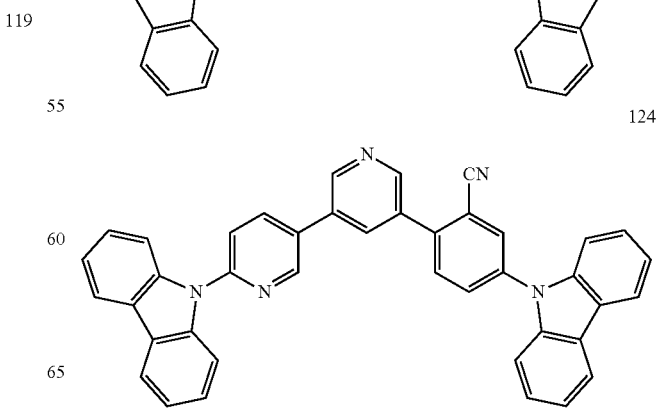
122
123
124

125
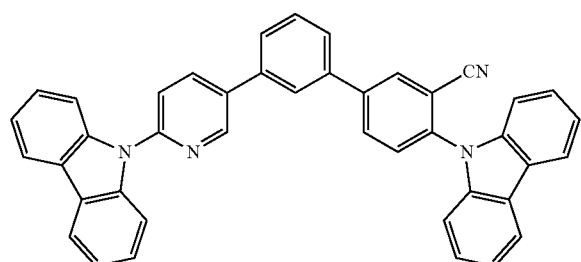
126
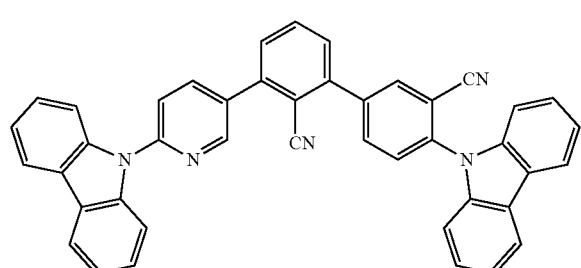
127
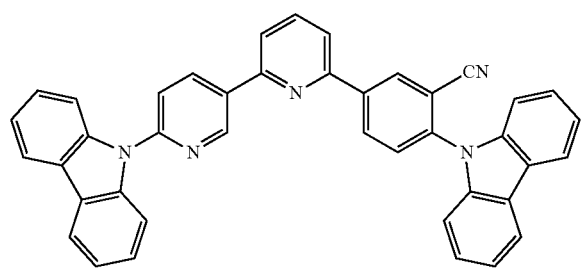
128
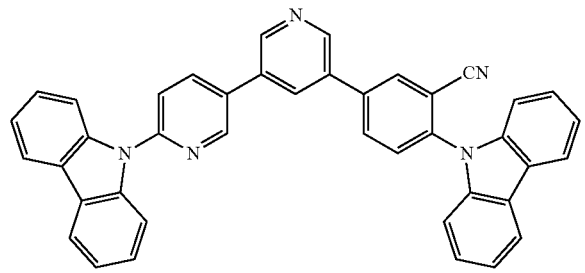
129
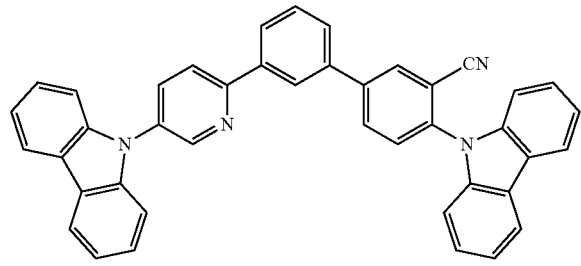
130
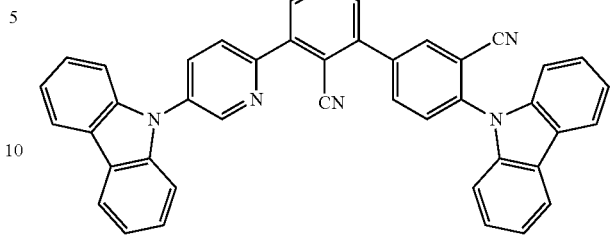
131
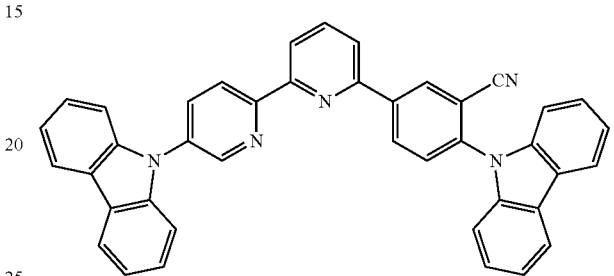
132
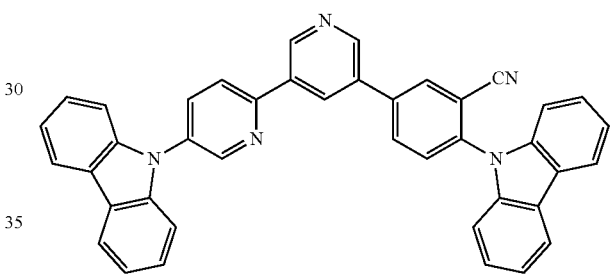
133
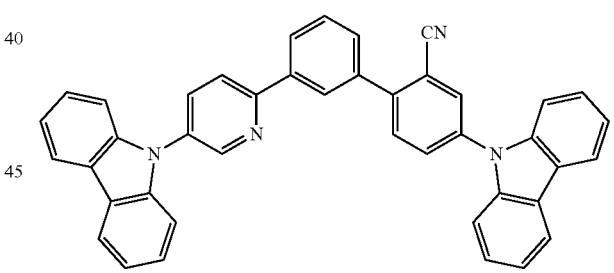
134
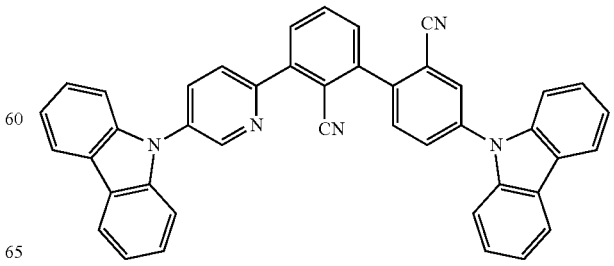

135
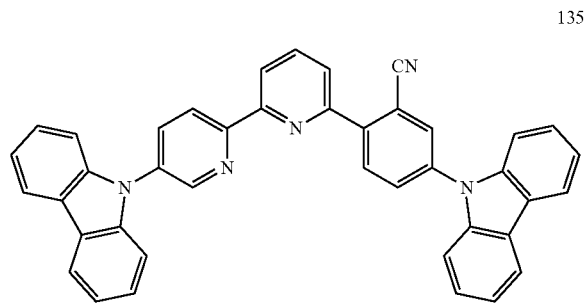
136
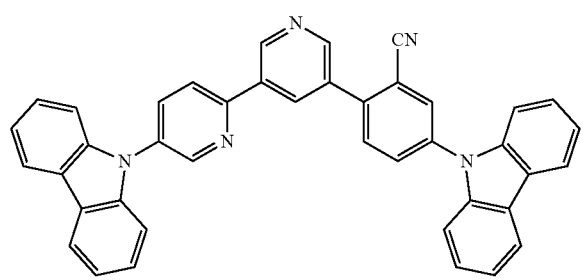
137
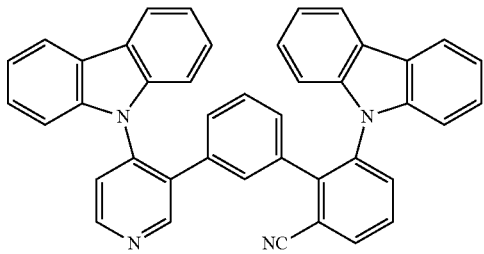
138
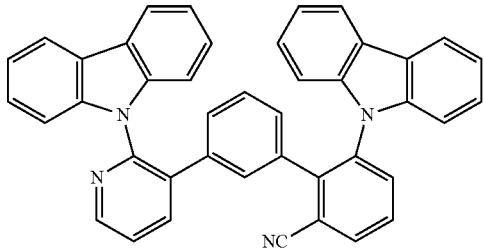
139
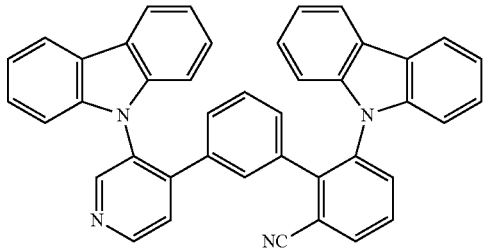
140
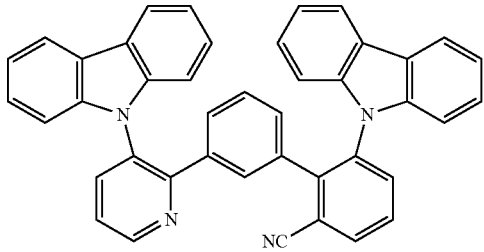
141
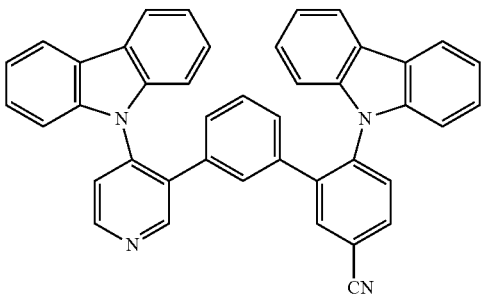
142
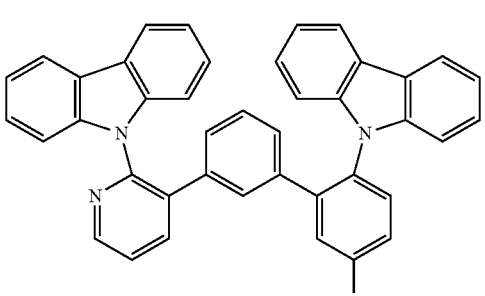
143
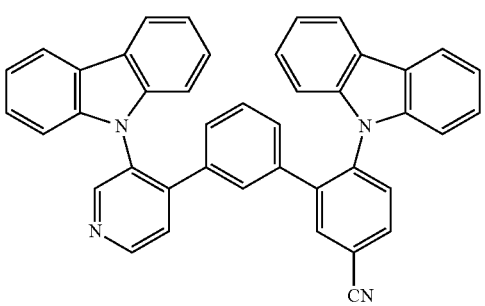
144
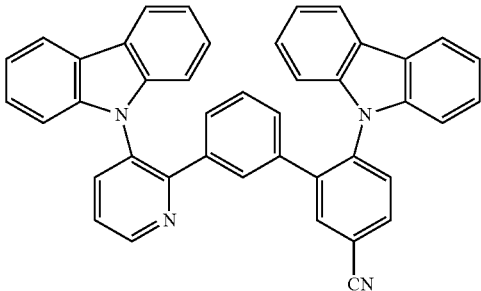
145
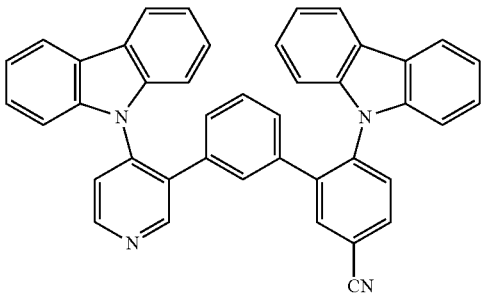

127
-continued
146
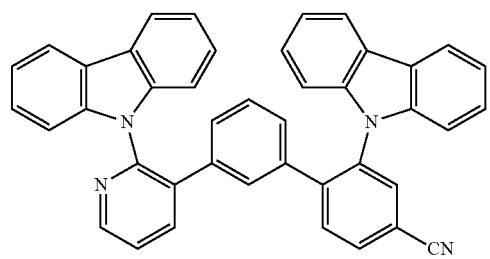
147
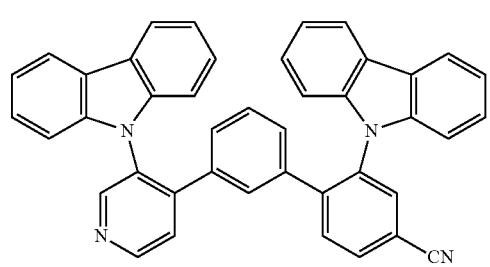
148
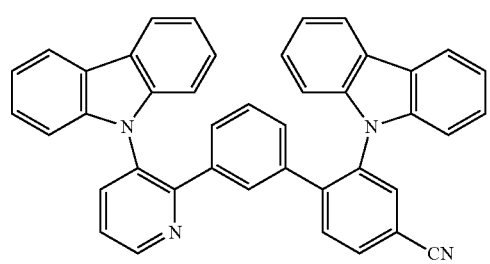
149
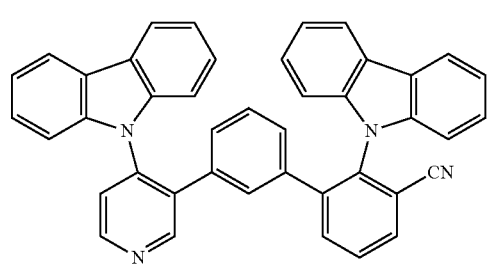
150
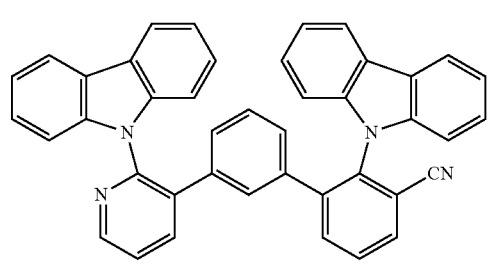
151
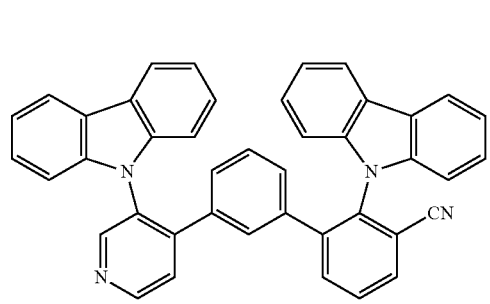
128
-continued
152
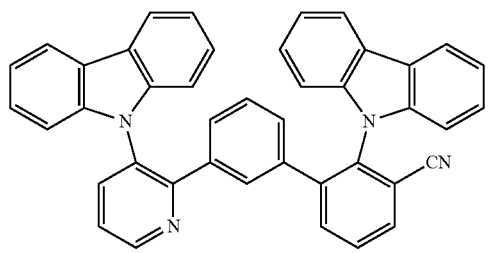
153
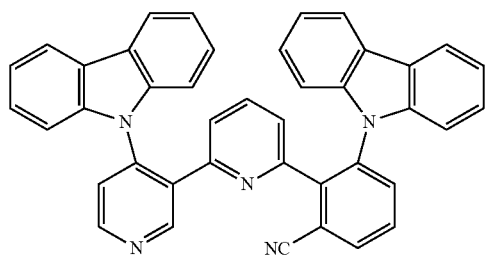
154
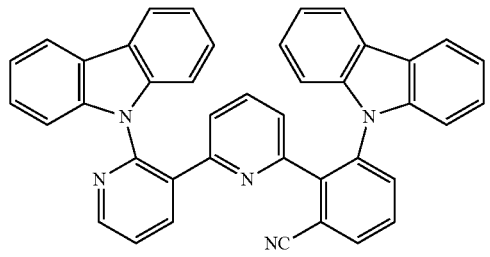
155
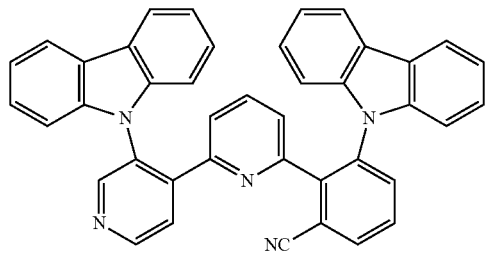
156
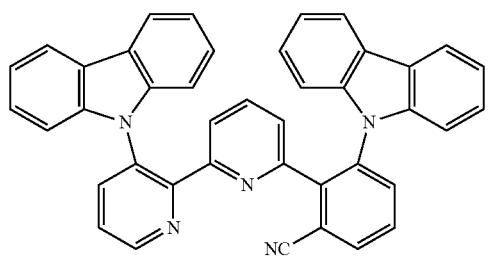
157
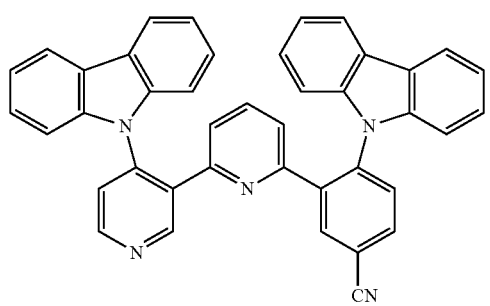

158
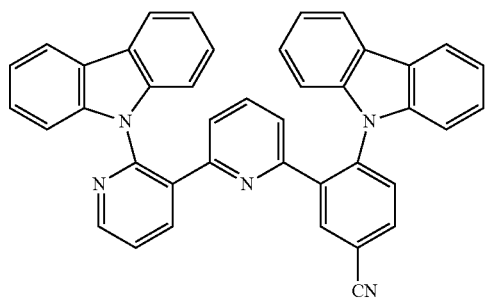
159
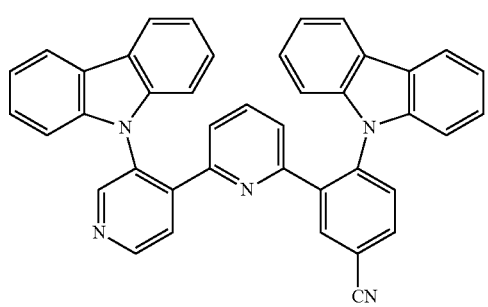
160
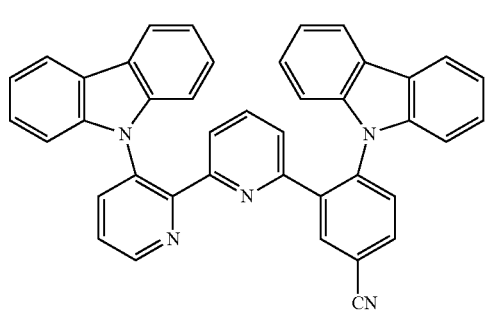
161
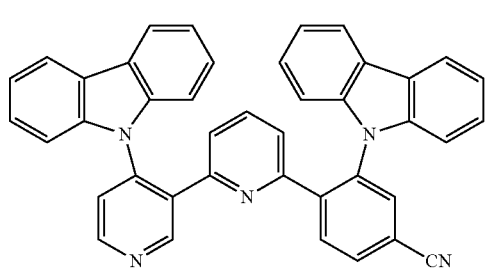
162
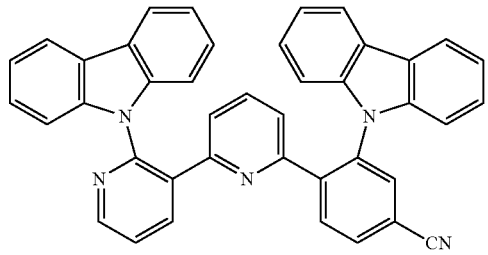
163
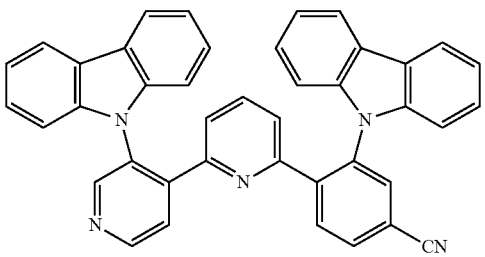
164
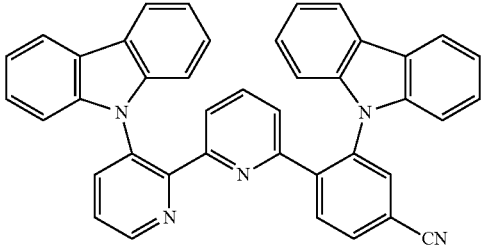
165
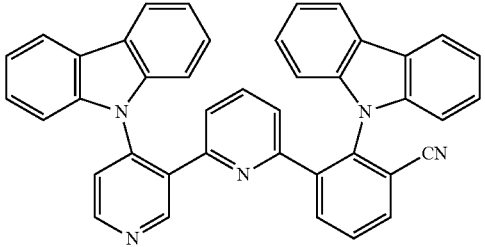
166
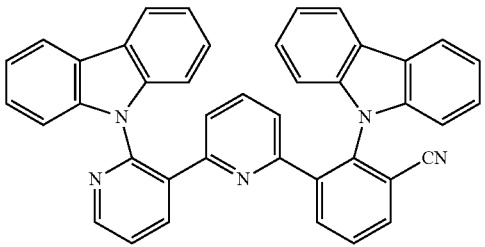
167
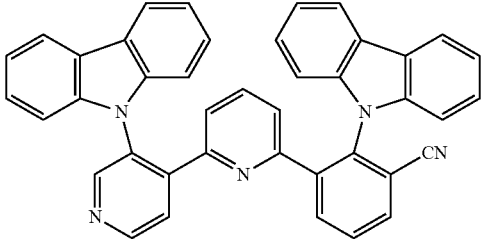
168
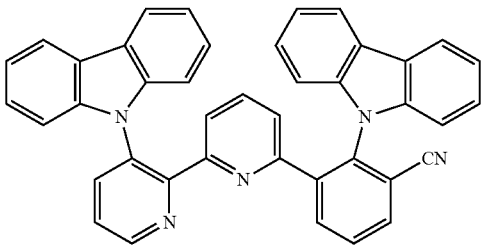

169
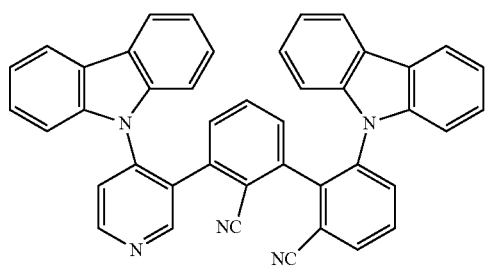
170
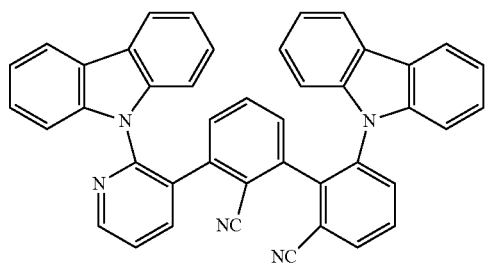
171
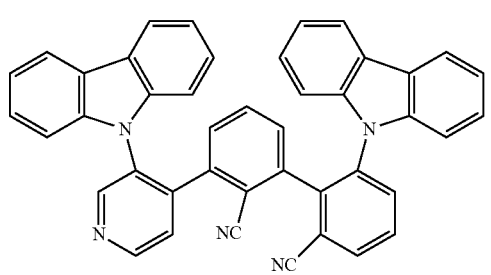
172
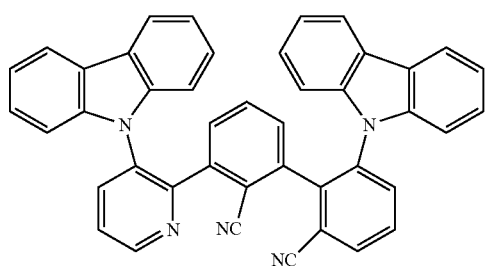
173
174
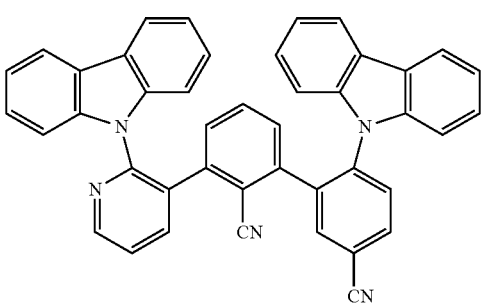
175
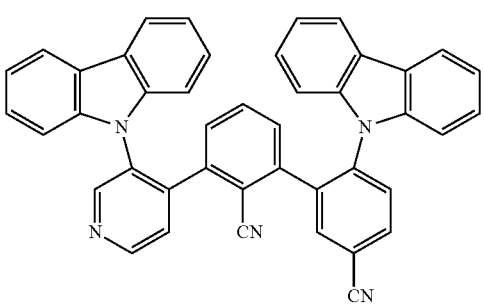
176
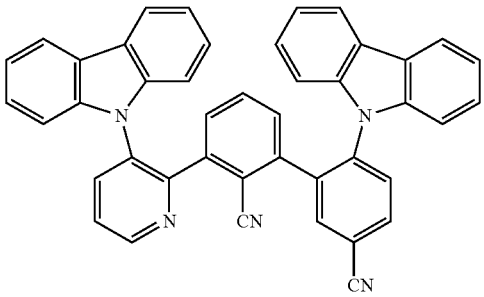
177
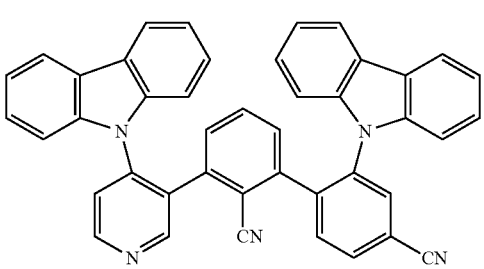
178
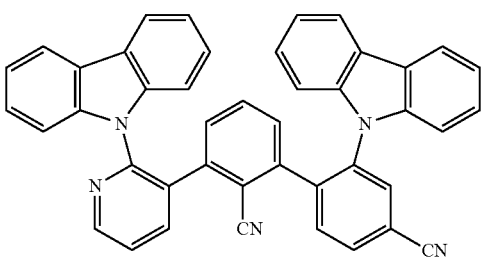

179
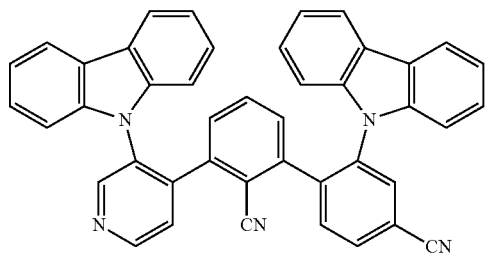
180
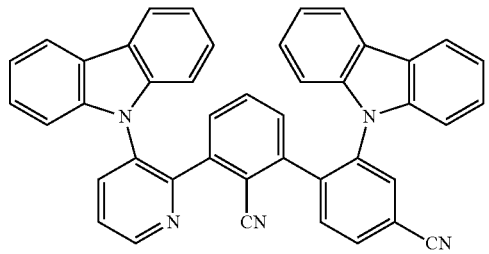
181
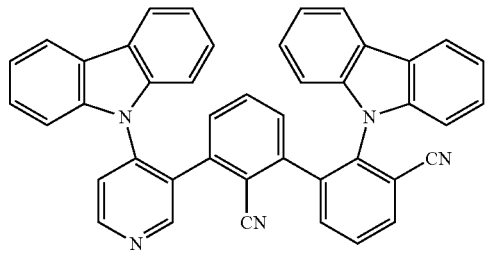
182
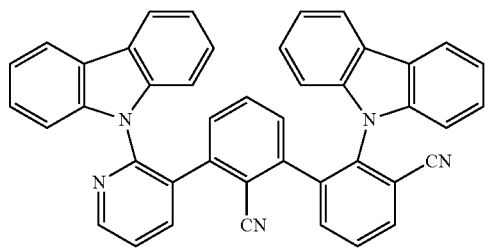
183
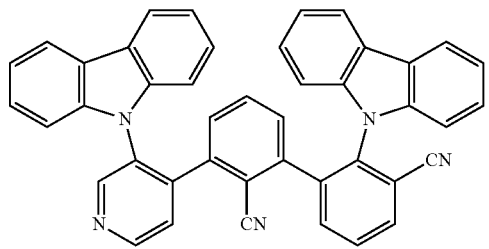
184
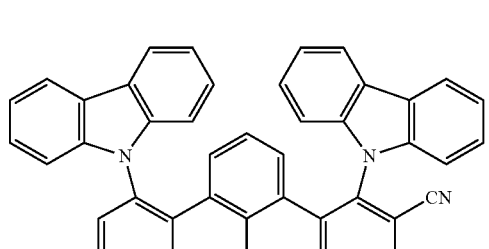
185
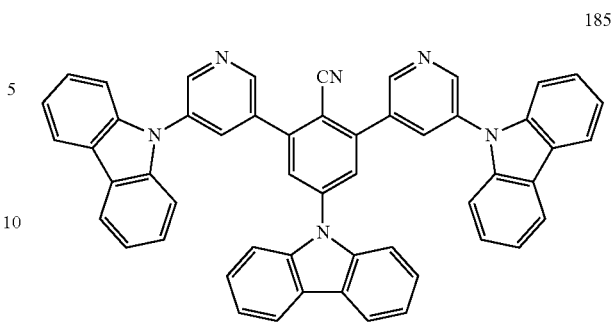
186
187
188
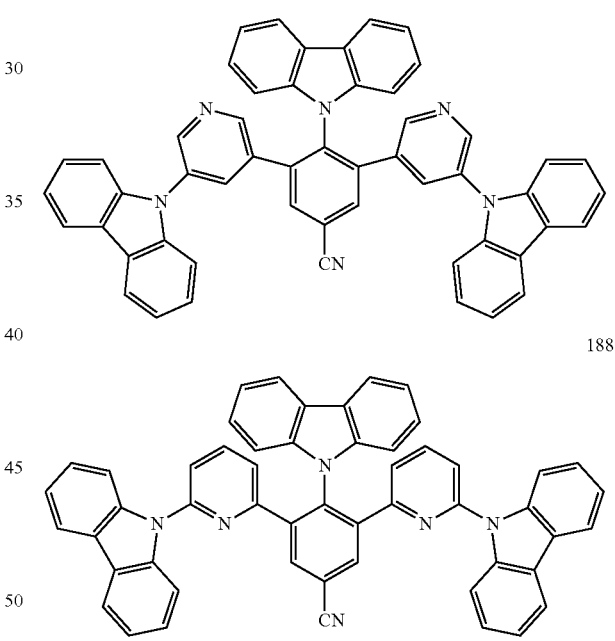
189
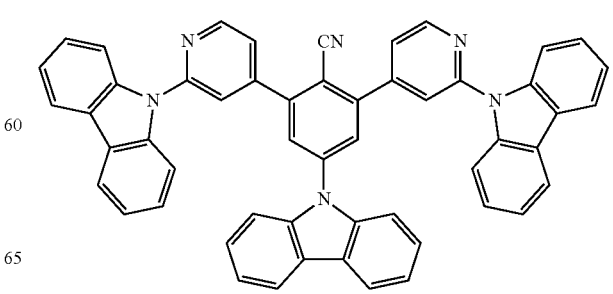

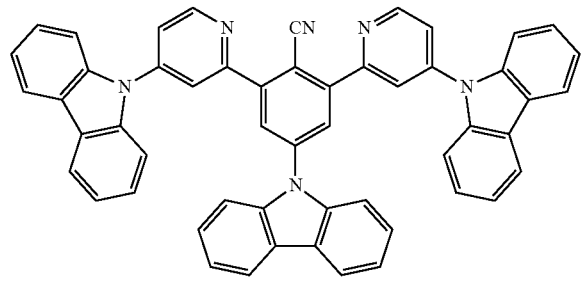
190
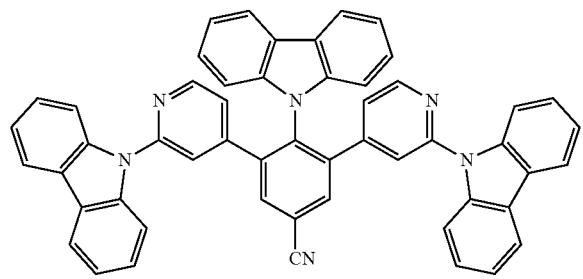
191
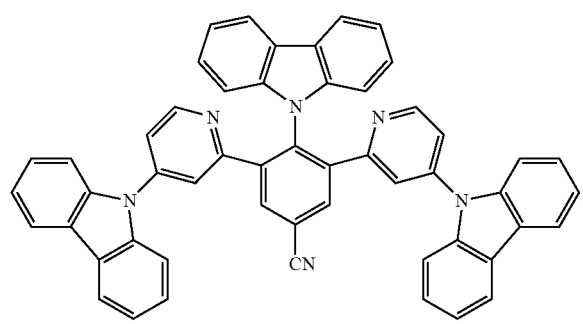
192
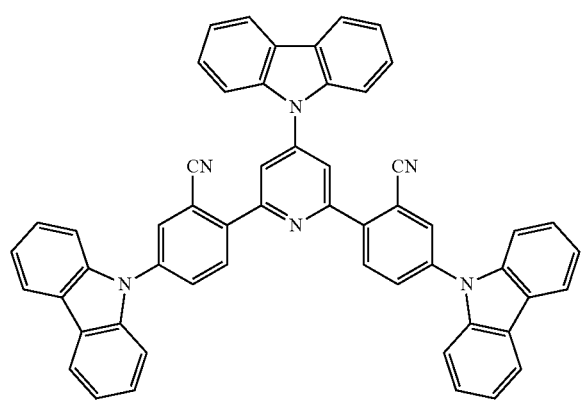
193
194
195
196
197

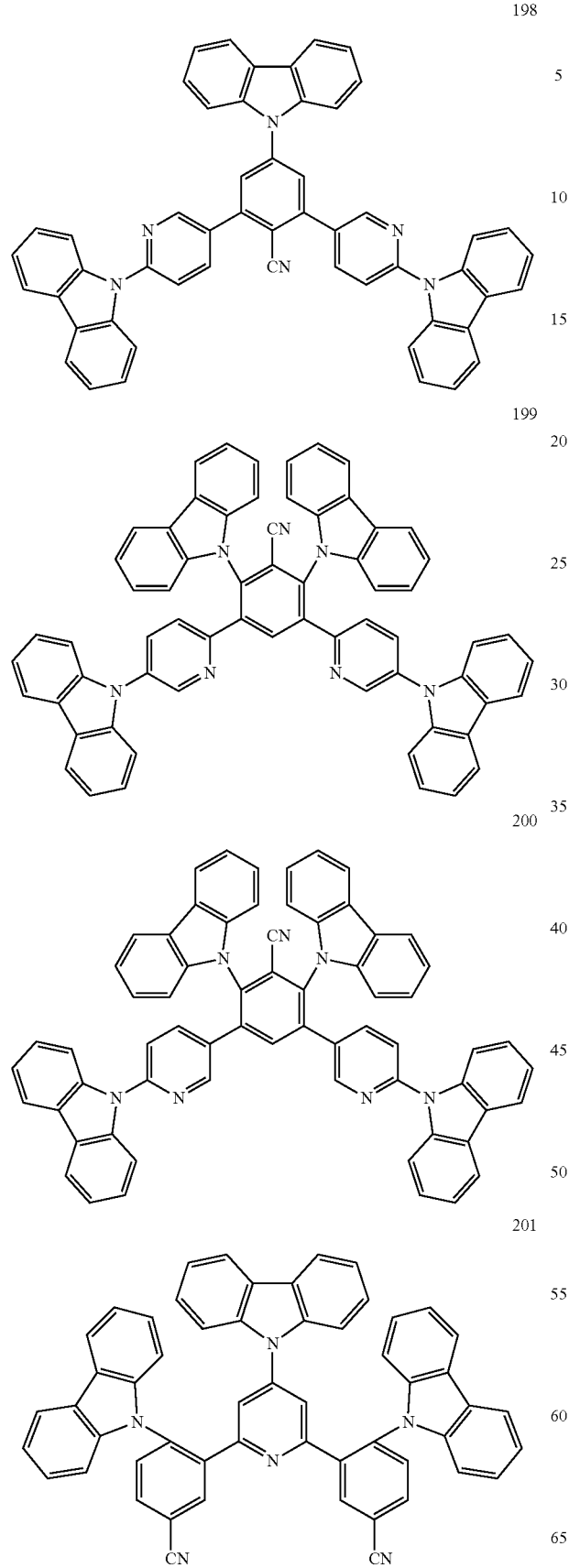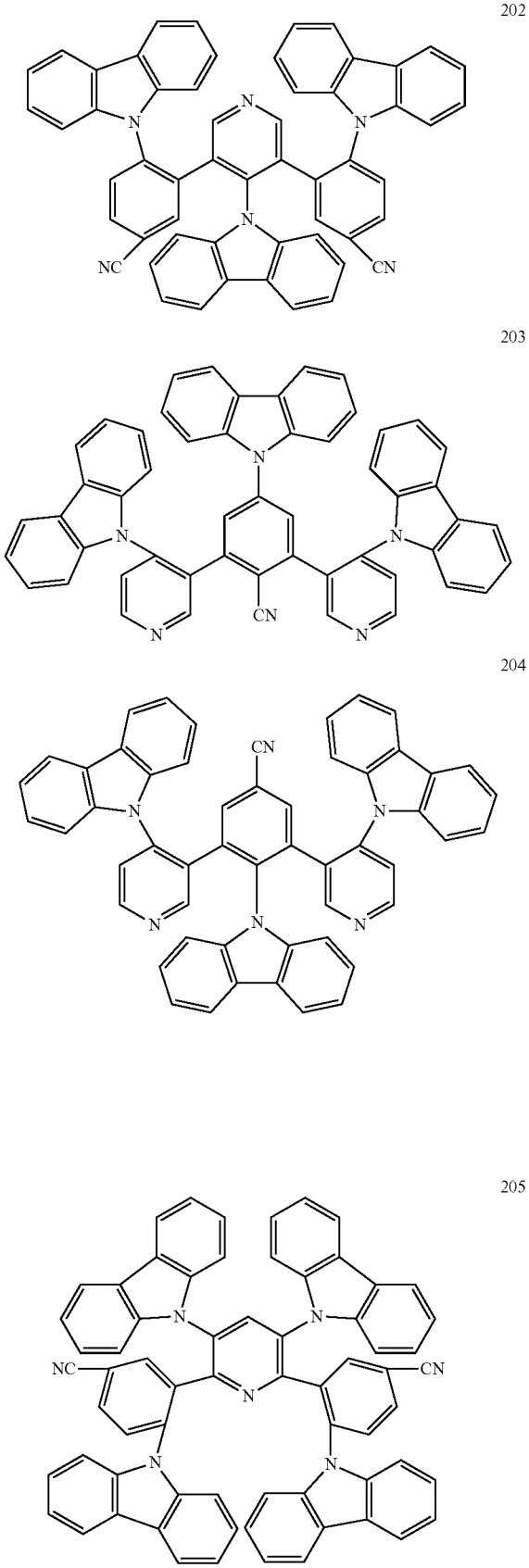

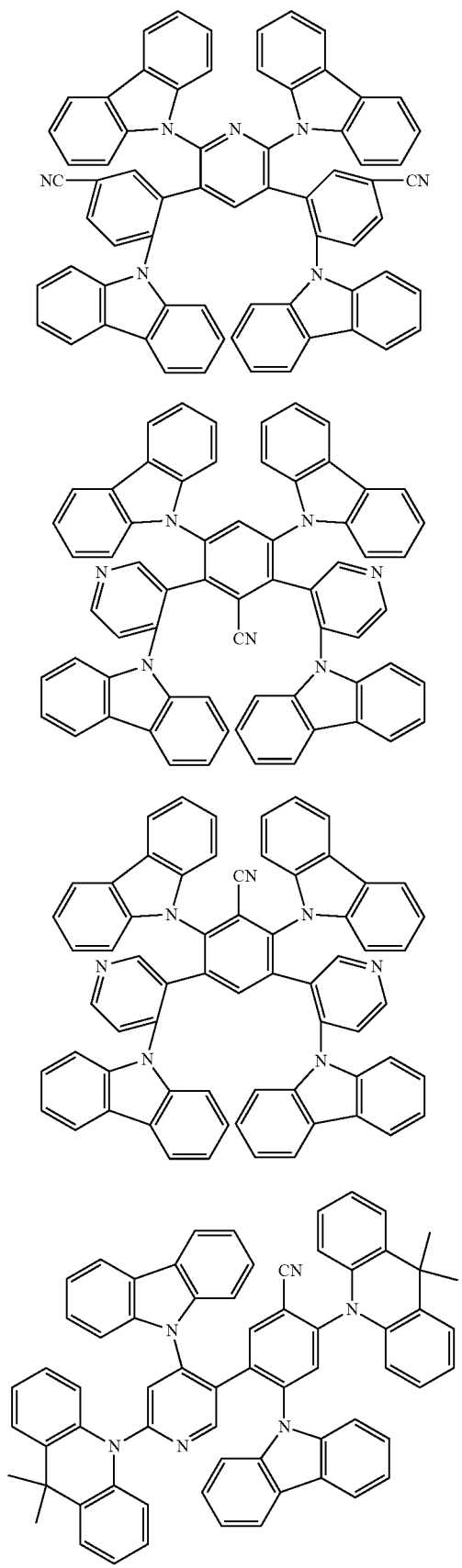
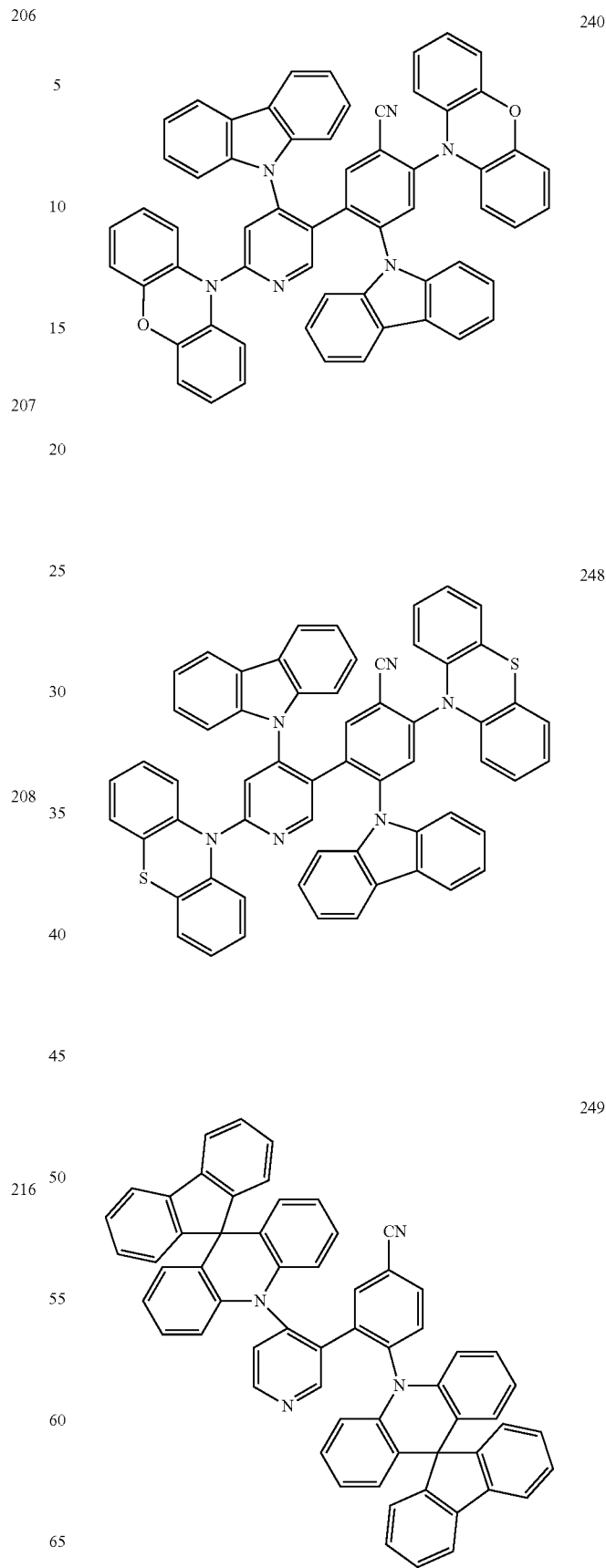

250 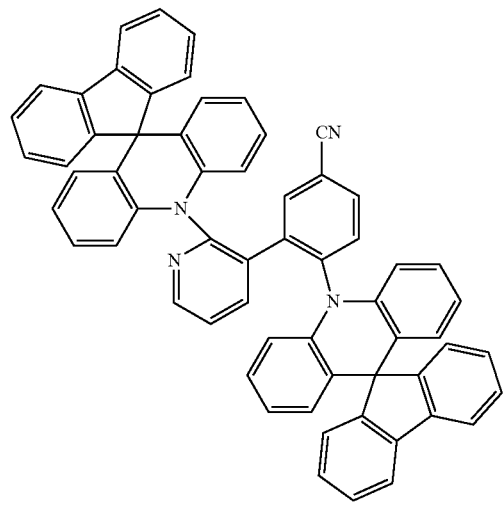
251 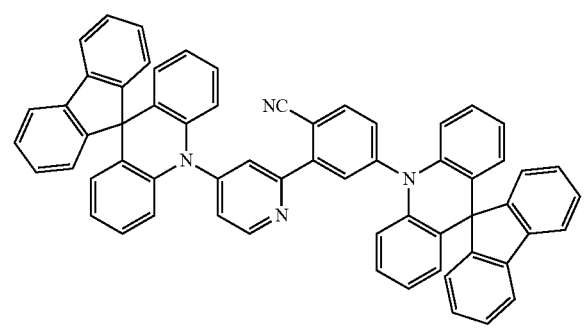
252 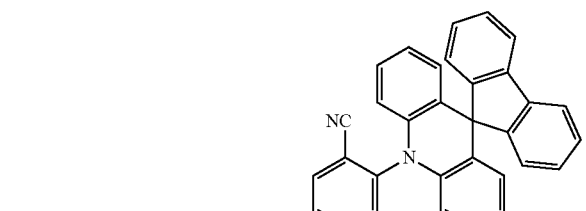
253 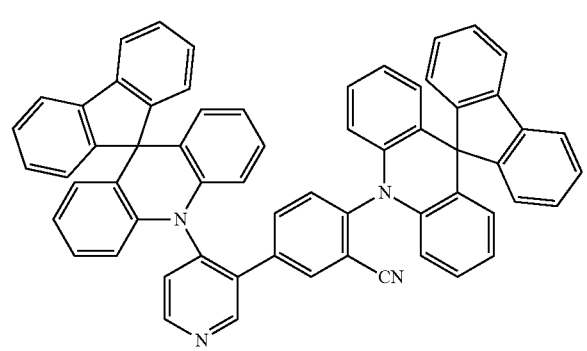
254 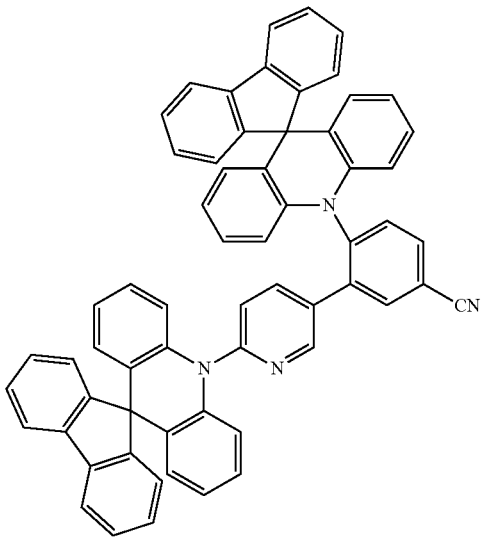
255 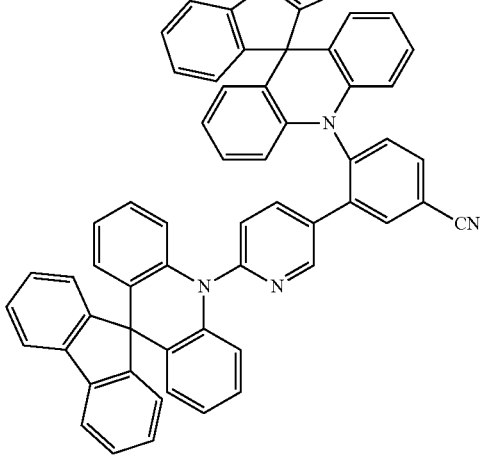
256 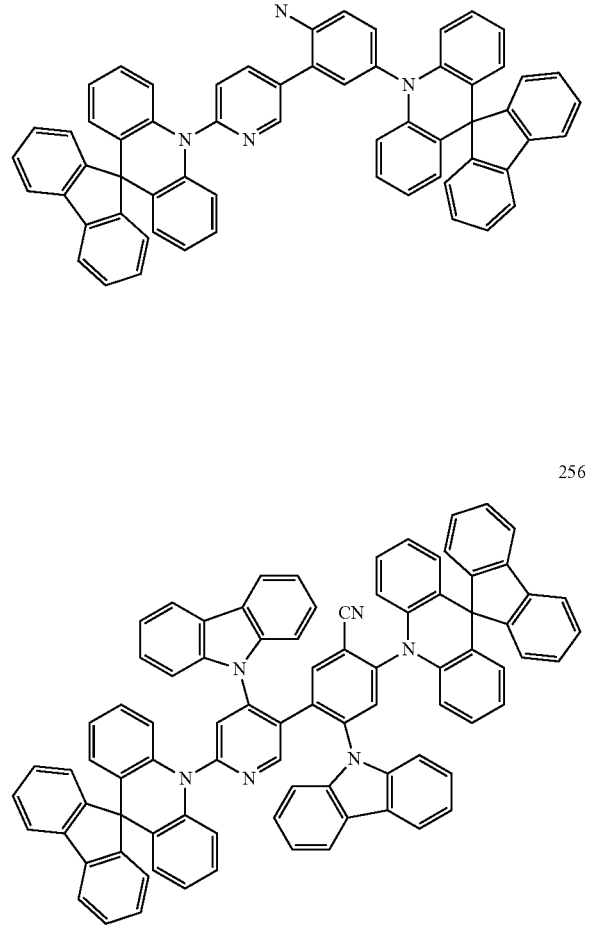

257
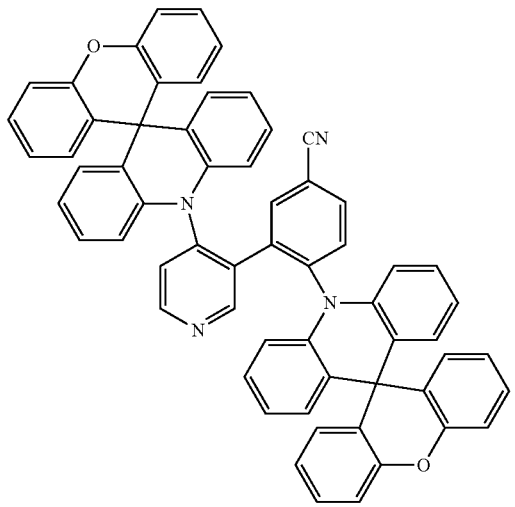
258
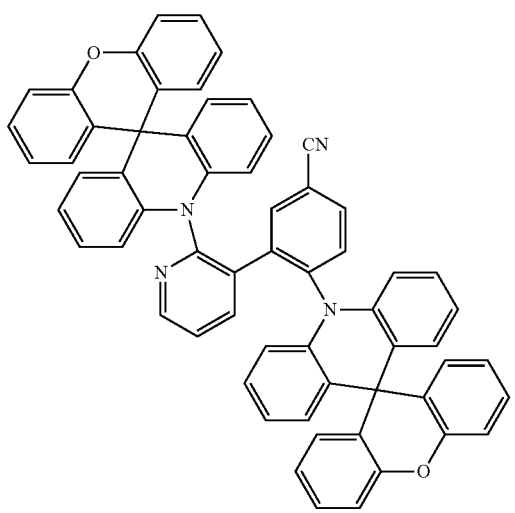
259
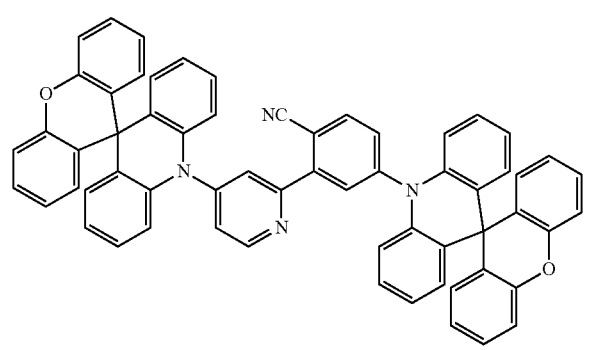
260
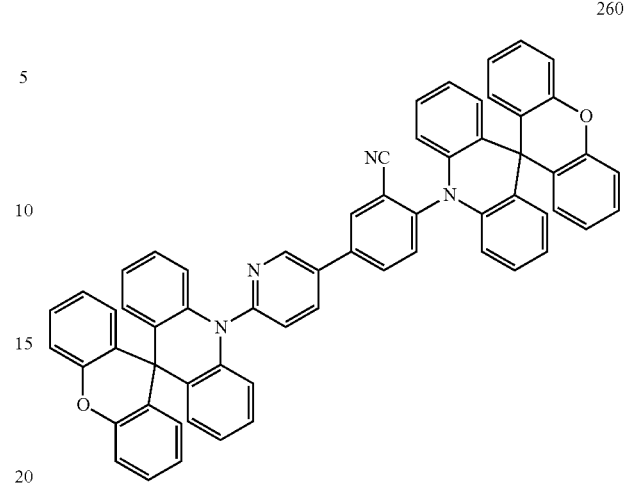
261
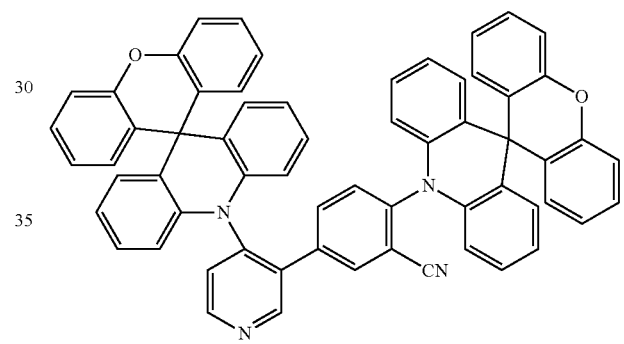
262
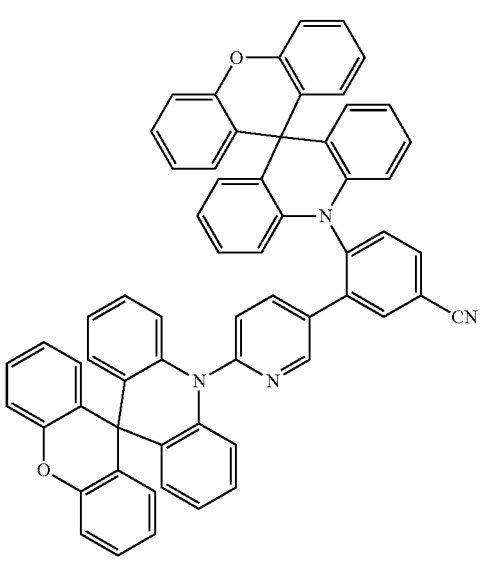

-continued

263

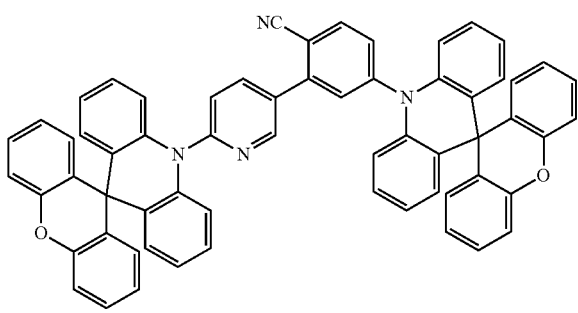

264

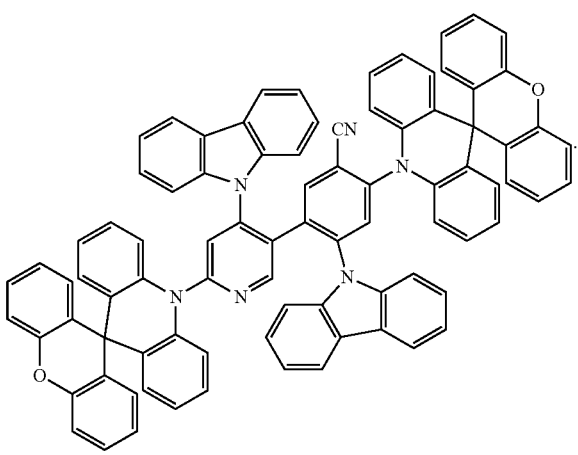

7. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a polycyclic compound represented by following Formula 1:

Formula 1

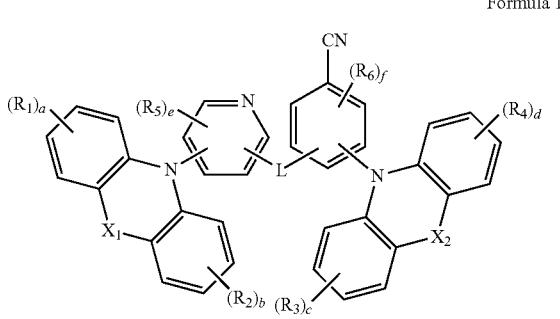

wherein in Formula 1,
$X_1$ and $X_2$ are each independently a direct linkage, $CR_7R_8$, $SiR_9R_{10}$, O, or S, L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring,
$R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;
$R_1$ to $R_4$ are each optionally independently combined with an adjacent group to form a ring,
a, b, c and d are each independently an integer of 0 to 4,
$R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;
$R_5$ to $R_{14}$ are each optionally independently combined with an adjacent group to form a ring, and
e and f are each independently an integer of 0 to 3,
wherein when L is a direct linkage, then:
1) the pyridine group of Formula 1 is at an ortho or a meta position to the cyano group of the benzonitrile group of Formula 1,
e and f are each 3,
at least one $R_5$ or $R_6$ is a substituted or unsubstituted carbazole group, a substituted pyridyl group, or a substituted benzonitrile group and a rest of $R_5$ and $R_6$ are each a hydrogen atom, and
the benzonitrile group of Formula 1 is at a meta position to the $X_1$ containing group of Formula 1; or
2) the pyridine group of Formula 1 is at an ortho or a meta position to the cyano group of the benzonitrile group of Formula 1, and $X_1$, and/or
$X_2$ is $CR_7R_8$, in which $R_7$ and $R_8$ are combined to form a 9H-xanthenyl or 9H-fluorenyl ring.

8. The organic electroluminescence device of claim 7, wherein the polycyclic compound represented by Formula 1 is represented by one of following Formula 1-1 to Formula 1-3:

Formula 1-1

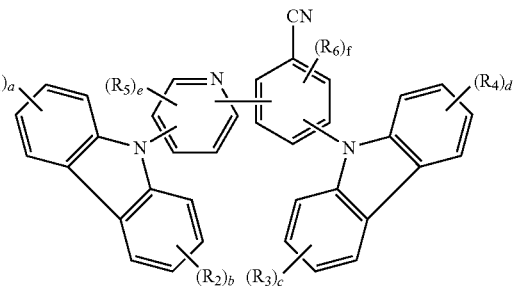

Formula 1-2

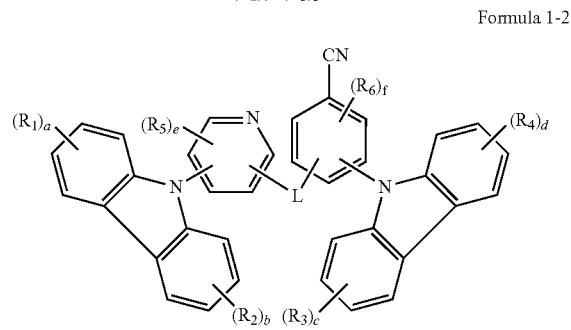

-continued

Formula 1-3

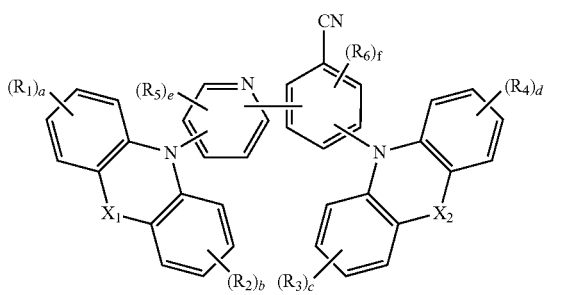

wherein in Formula 1-1 to Formula 1-3, $X_1$ and $X_2$, L, $R_1$ to $R_6$, and a to f are the same as respectively defined in association with Formula 1.

9. A polycyclic compound represented by following Formula 1:

Formula 1

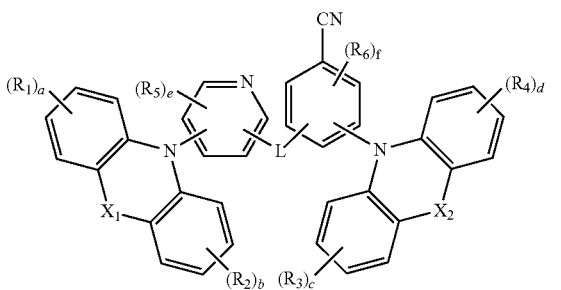

wherein in Formula 1, $X_1$ and $X_2$ are each independently a direct linkage, $CR_7R_8$, $SiR_9R_{10}$, O, or S, L is a direct linkage, CO, $SO_2$, $SiR_{11}R_{12}$, a substituted or unsubstituted arylene group having 6 to 30 carbon atoms for forming a ring, or a substituted or unsubstituted heteroarylene group having 2 to 30 carbon atoms for forming a ring, $R_1$ to $R_4$ are each independently a hydrogen atom, a deuterium atom, a halogen atom, $NR_{13}R_{14}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;

$R_1$ to $R_4$ are each optionally independently combined with an adjacent group to form a ring, a, b, c and d are each independently an integer of 0 to 4, $R_5$ to $R_{14}$ are each independently a hydrogen atom, a deuterium atom, a halogen atom, a cyano group, a substituted or unsubstituted amino group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring;

$R_5$ to $R_{14}$ are each optionally independently combined with an adjacent group to form a ring, and e and f are each independently an integer of 0 to 3, wherein when L is a direct linkage, then:
1) the pyridine group of Formula 1 is at an ortho or a meta position to the cyano group of the benzonitrile group of Formula 1,
e and f are each 3,
at least one $R_5$ or $R_6$ is a substituted or unsubstituted carbazole group, a substituted pyridyl group, or a substituted benzonitrile group and a rest of $R_5$ and $R_6$ are each a hydrogen atom, and
the benzonitrile group of Formula 1 is at a meta position to the $X_1$ containing group of Formula 1; or
2) the pyridine group of Formula 1 is at an ortho or a meta position to the cyano group of the benzonitrile group of Formula 1, and
$X_1$ and/or $X_2$ is $CR_7R_8$, in which $R_7$ and $R_8$ are combined to form a 9H-xanthenyl or 9H-fluorenyl ring.

10. The polycyclic compound of claim 9, wherein the polycyclic compound represented by Formula 1 is represented by one of following Formula 1-1 to Formula 1-3:

Formula 1-1

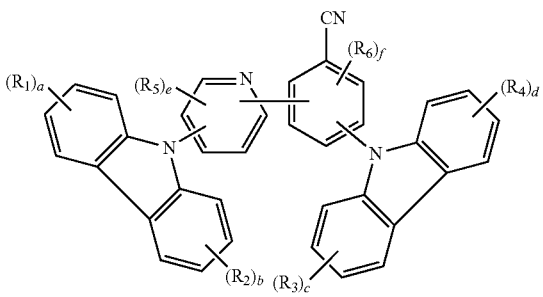

Formula 1-2

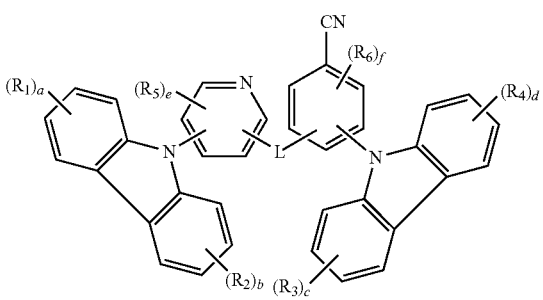

Formula 1-3

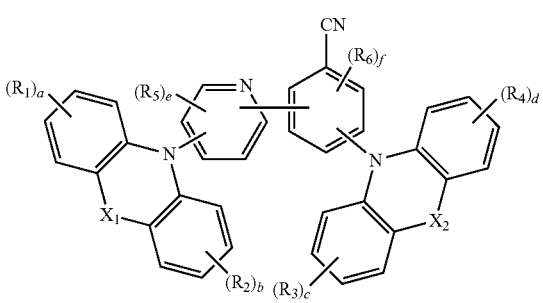

wherein in Formula 1-1 to Formula 1-3, $X_1$ and $X_2$, L, $R_1$ to $R_6$, and a to f are the same as respectively defined in association with Formula 1.

11. The polycyclic compound of claim 9, wherein the compound represented by Formula 1 is a material for emitting thermally activated delayed fluorescence.

12. The polycyclic compound of claim 9, wherein the compound represented by Formula 1 has an absolute value of a difference between a singlet energy level and a triplet energy level of about 0.2 eV or less.

13. The polycyclic compound of claim 9, wherein $X_1$ and $X_2$ of Formula 1 are the same.

14. The polycyclic compound of claim 9, wherein $R_5$ and $R_6$ of Formula 1 are each independently one of following Formula 2-1 to Formula 2-4:

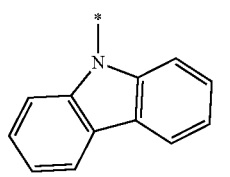

Formula 2-1

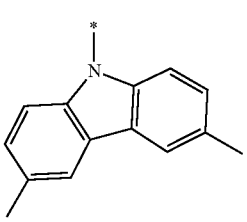

Formula 2-2

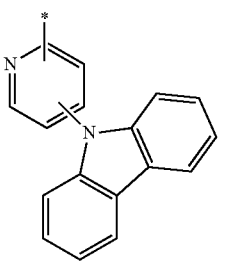

Formula 2-3

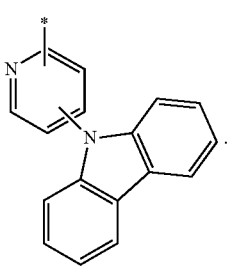

Formula 2-4

15. The polycyclic compound of claim 9, wherein $R_1$ to $R_4$ of Formula 1 are each independently one of following Formula 3-1 to Formula 3-3:

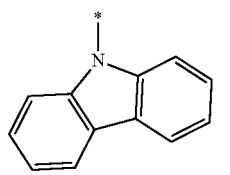

Formula 3-1

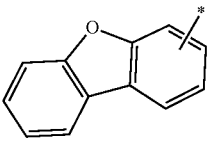

Formula 3-2

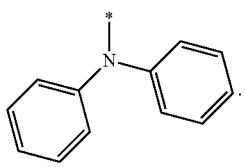

Formula 3-3

16. The polycyclic compound of claim 9, wherein the compound represented by Formula 1 is any one among compounds represented in following Compound Group 1:

[Compound Group 1]

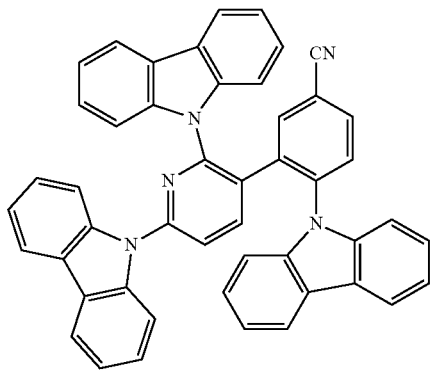

78

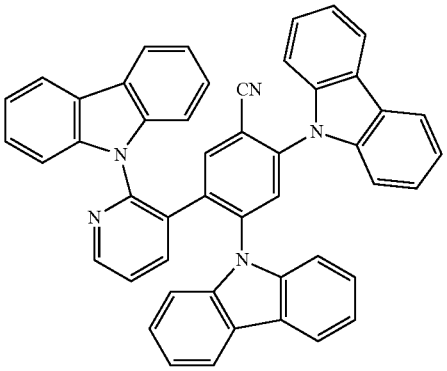

79

-continued
80
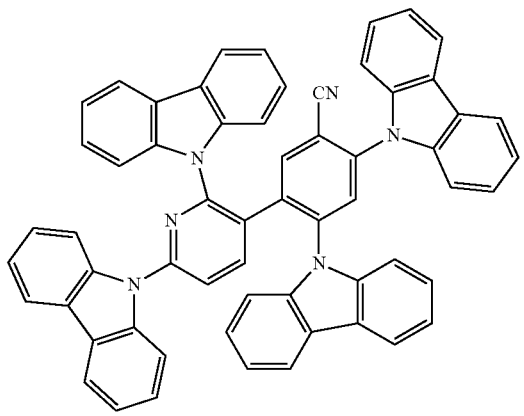
81
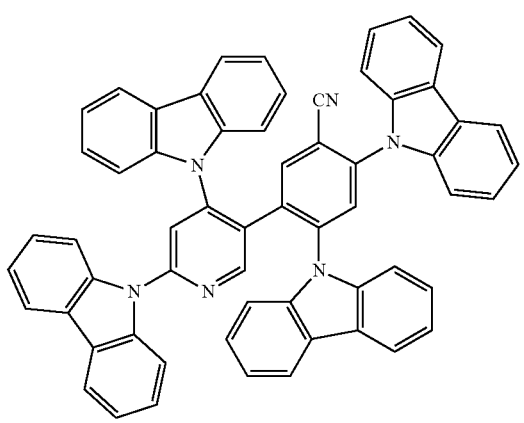
82
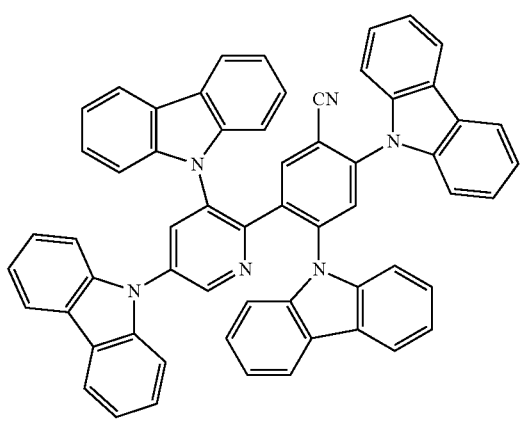
-continued
83
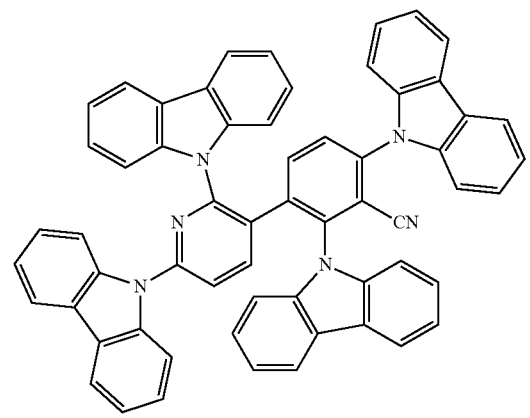
85
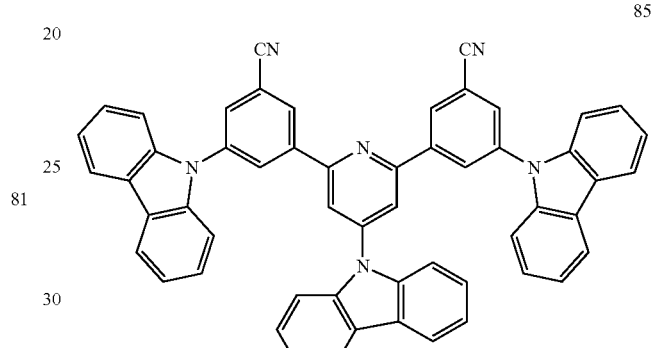
86
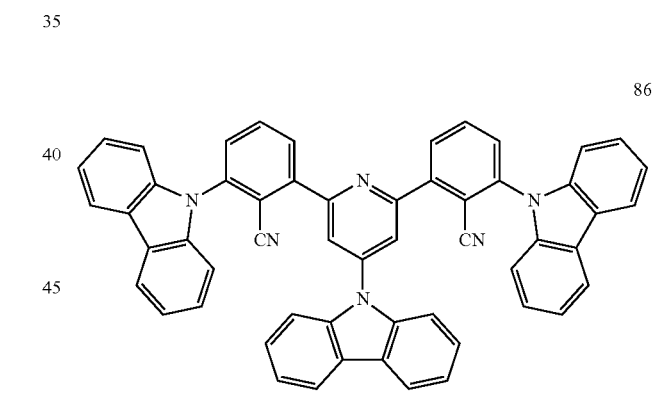
87
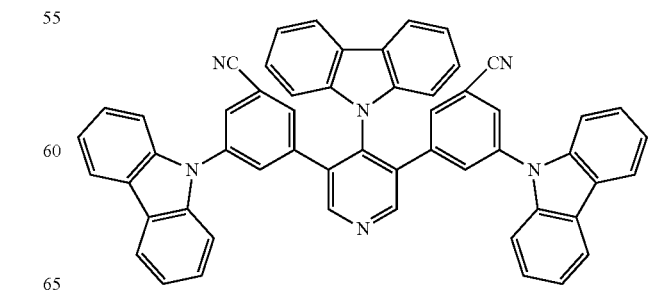

88
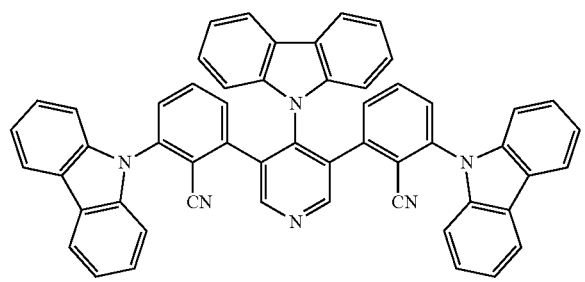
89
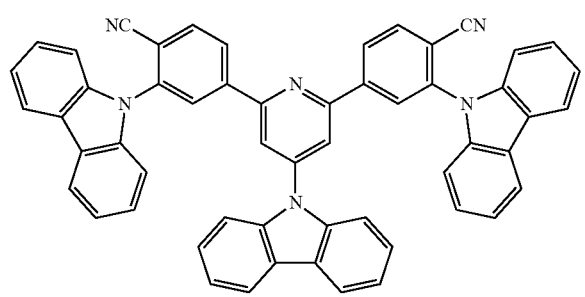
90
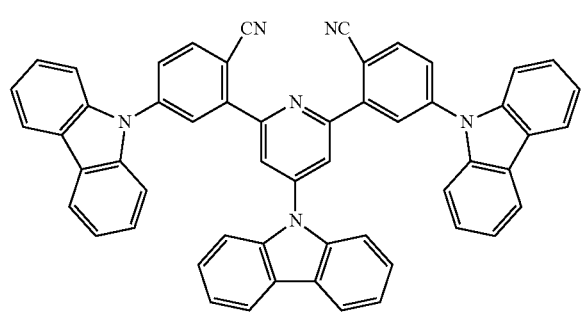
92
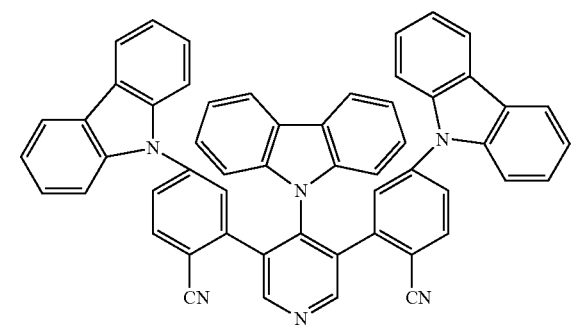
93
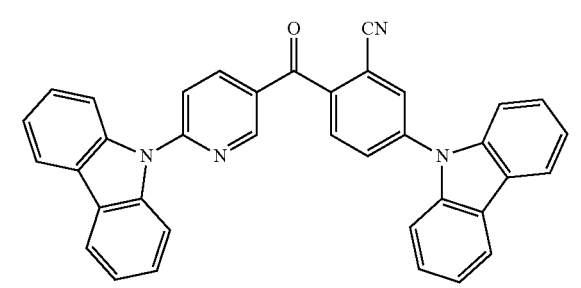
94
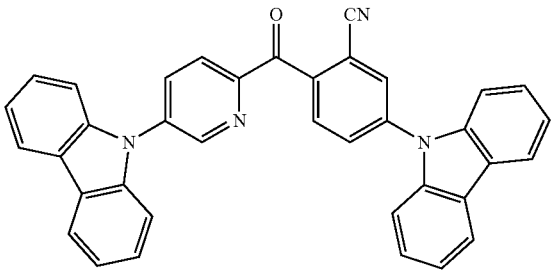
95
96
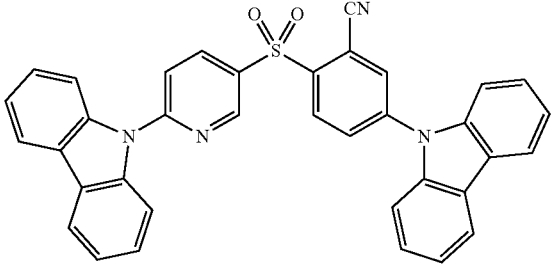
97
98
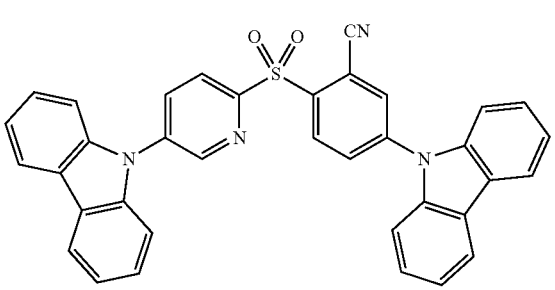

99
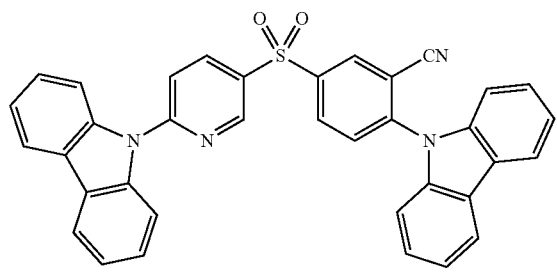
100
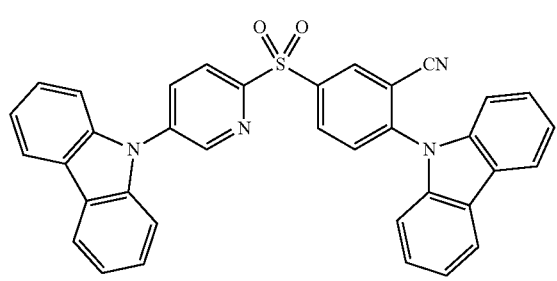
101
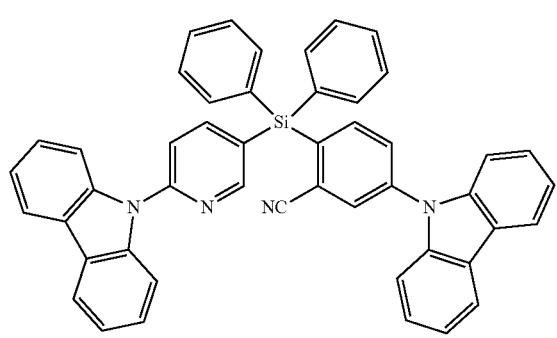
102
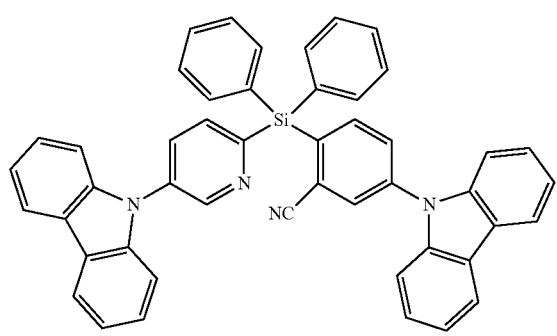
103
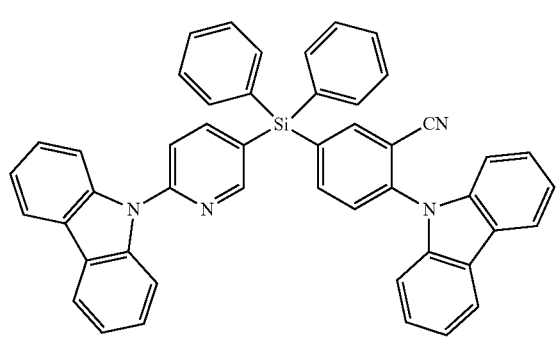
104
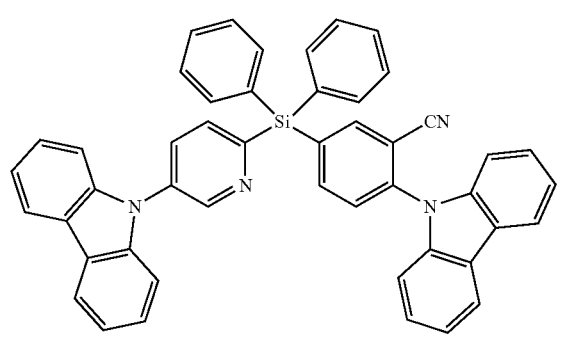
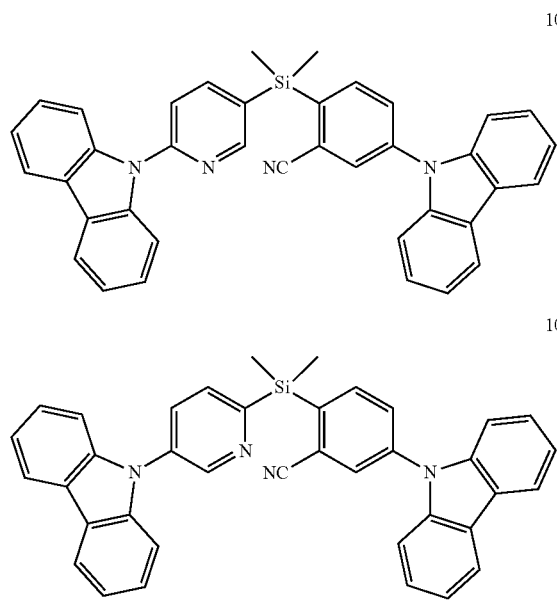

109
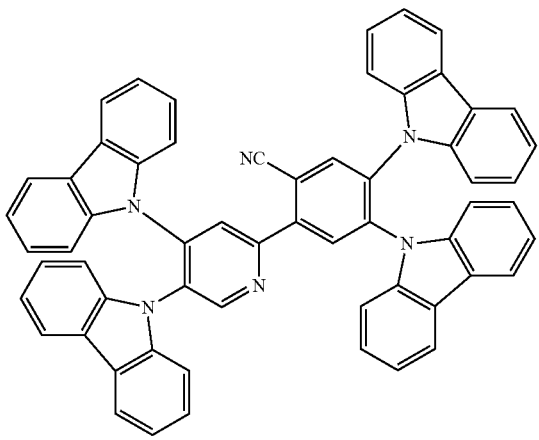
110
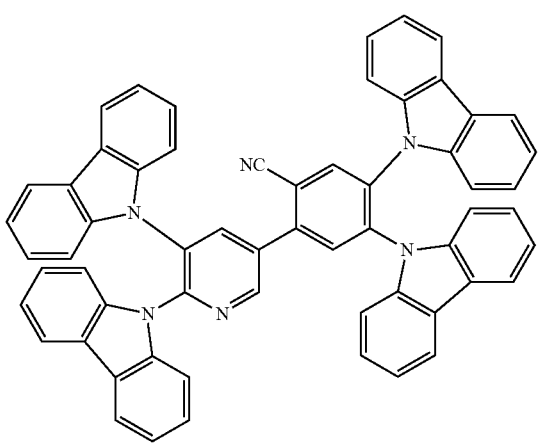
111
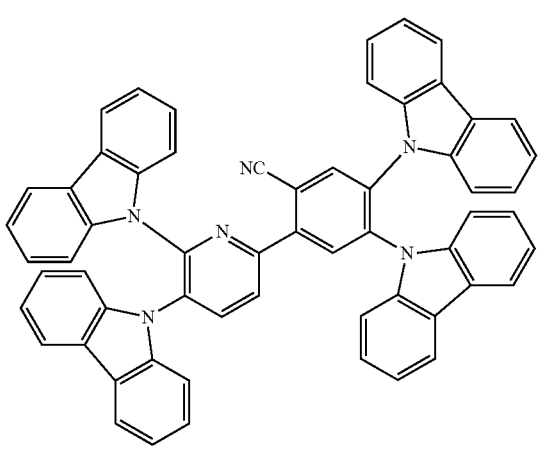
112
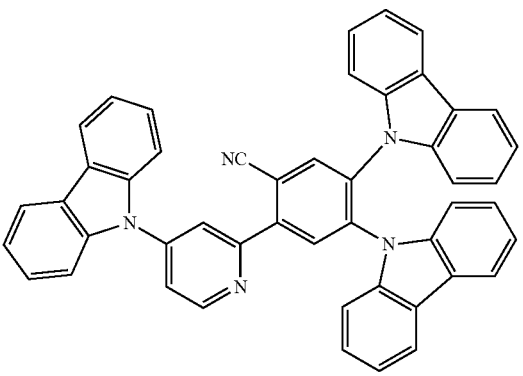
113
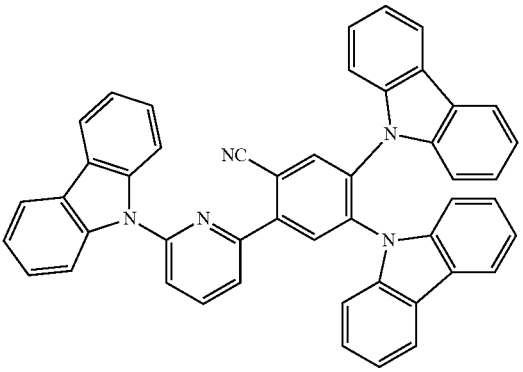
114
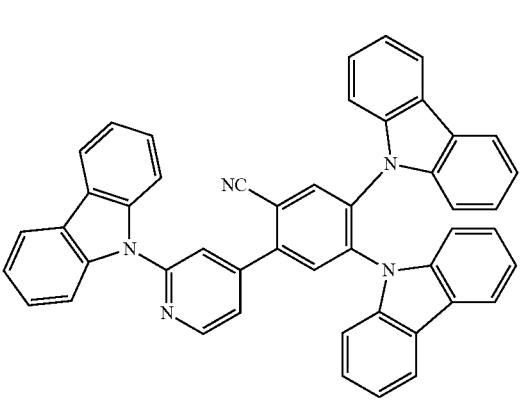
115
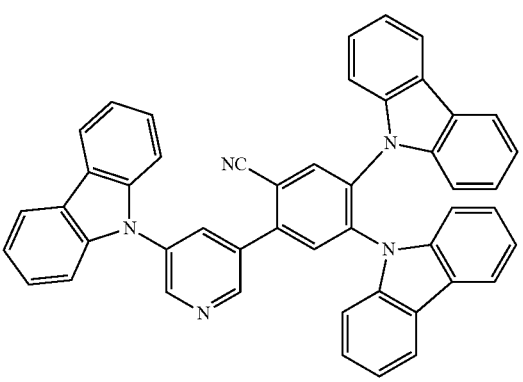

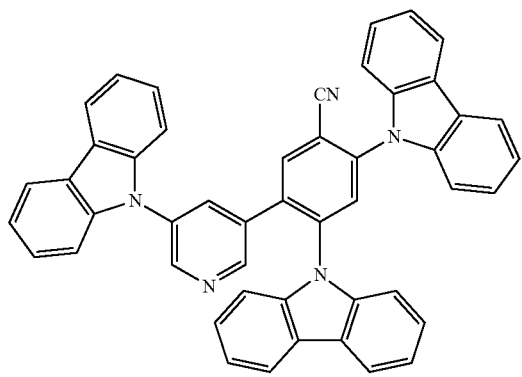
116
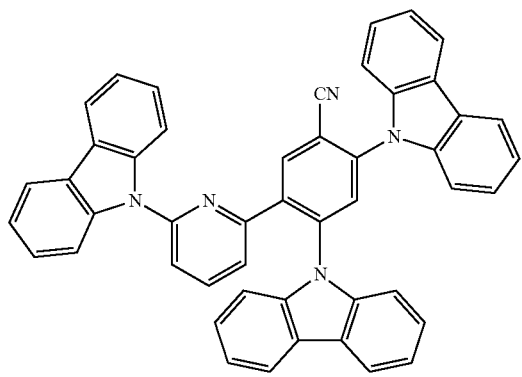
117
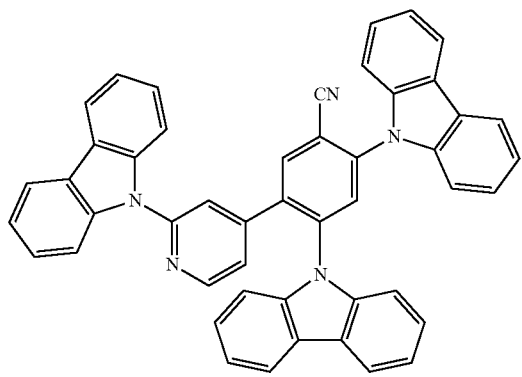
118
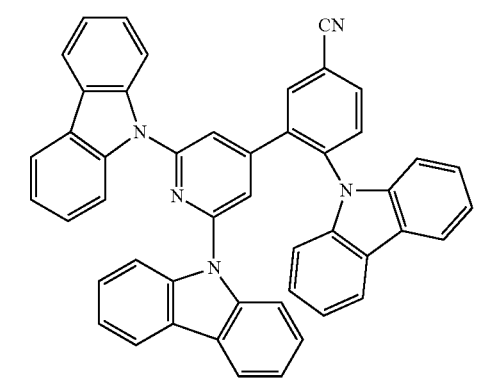
119
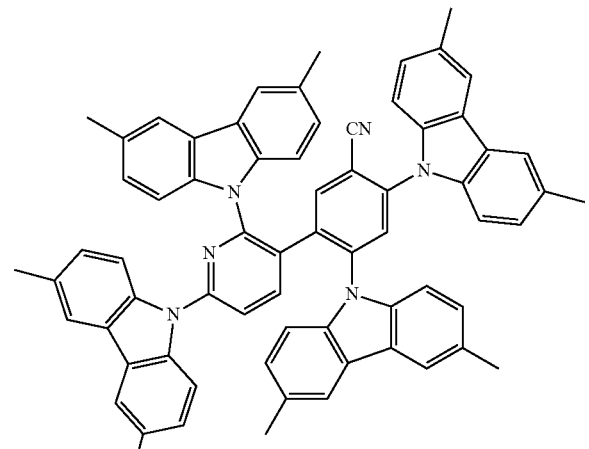
120
121
122
123
124

125
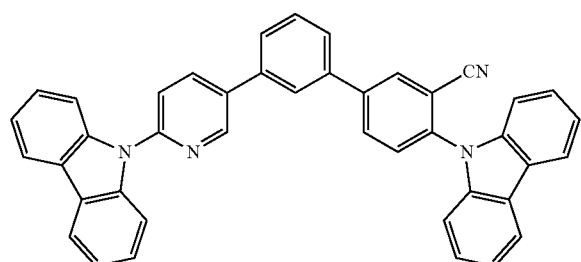
126
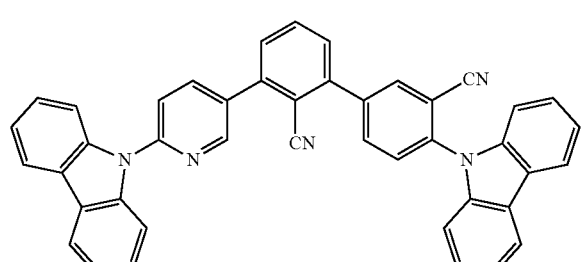
127
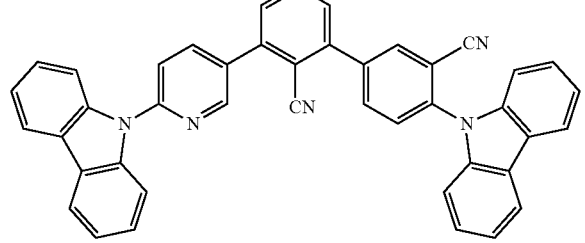
128
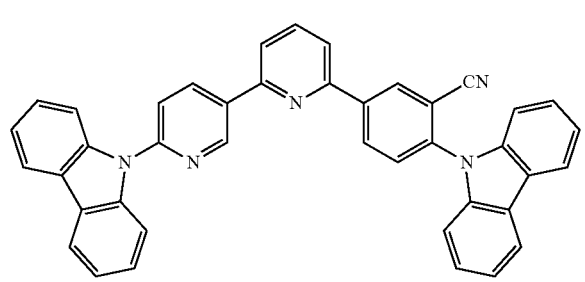
129
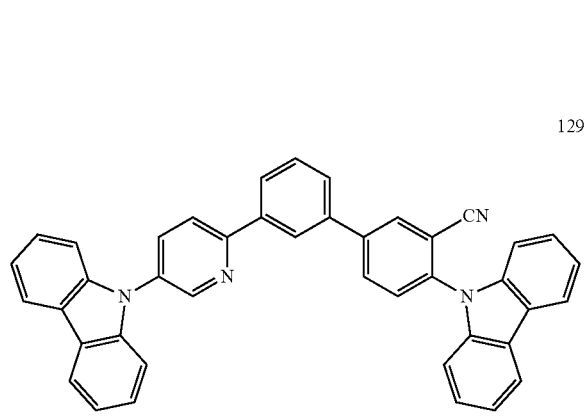
130
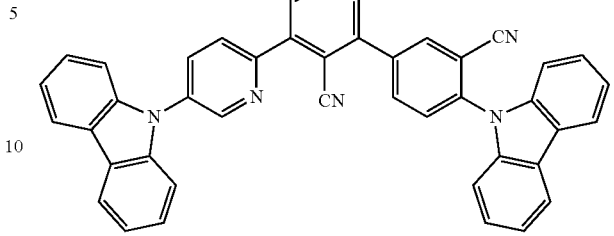
131
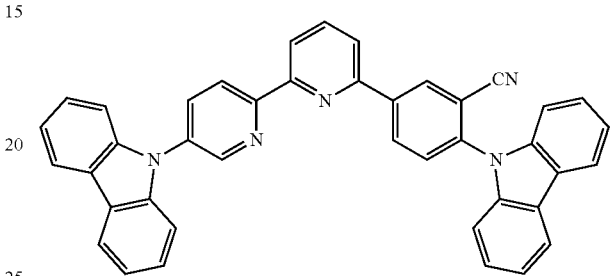
132
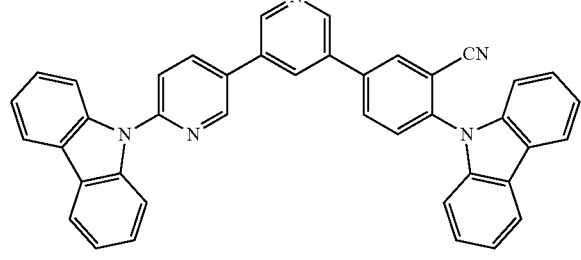
133
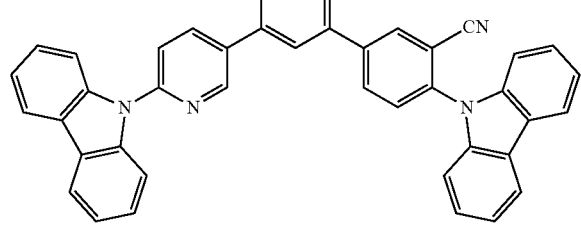
134
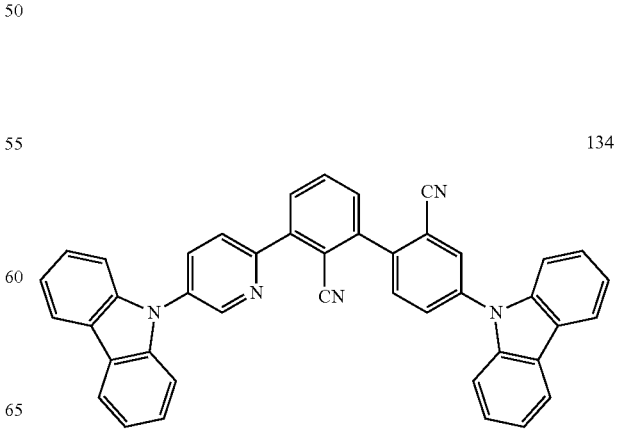

135
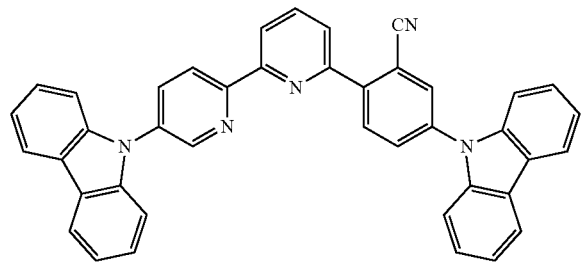
136
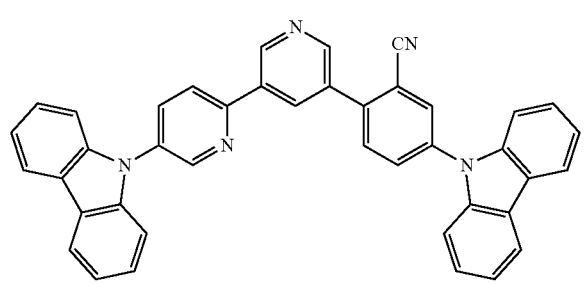
137
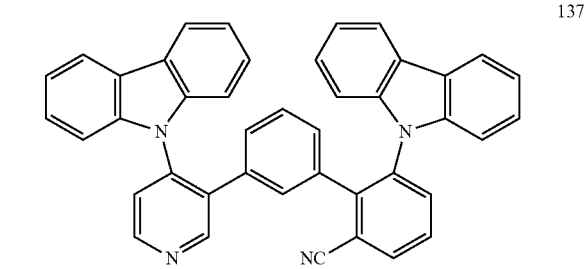
138
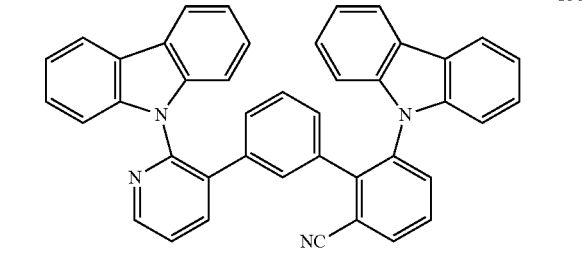
139
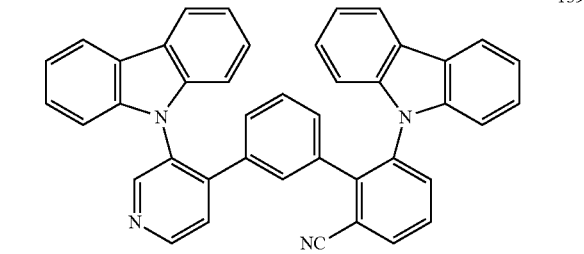
140
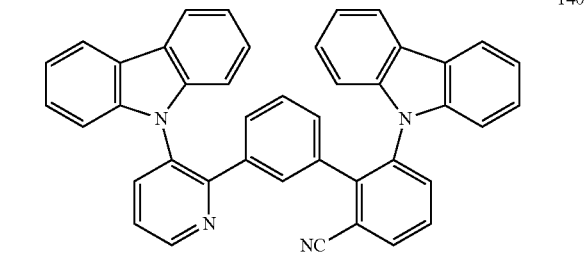
141
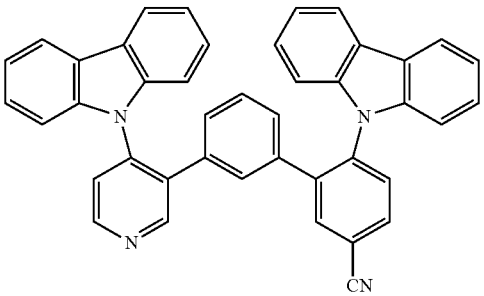
142
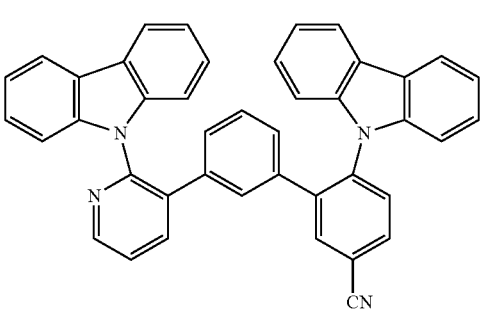
143
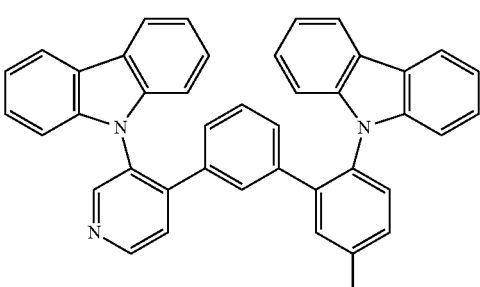
144
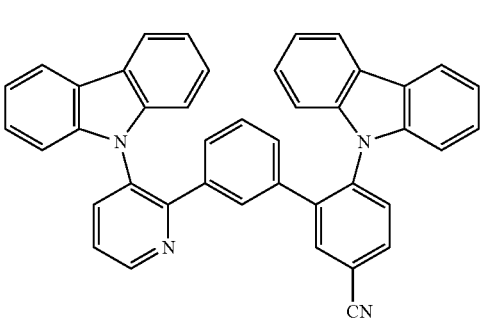
145
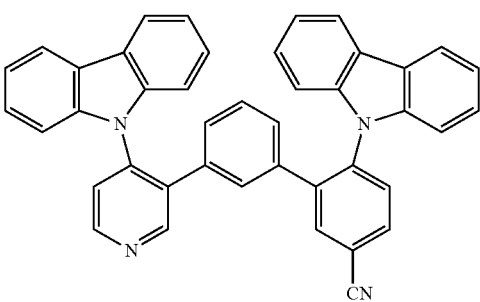

146
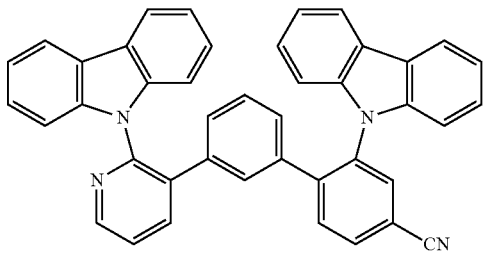
147
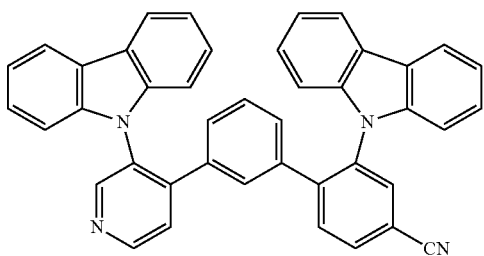
148
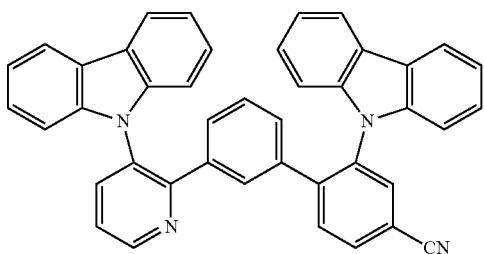
149
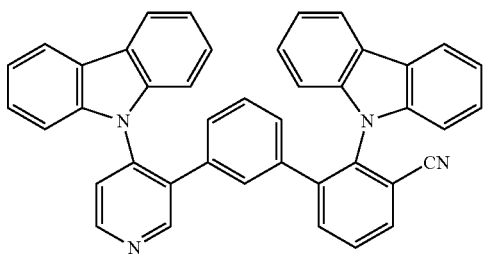
150
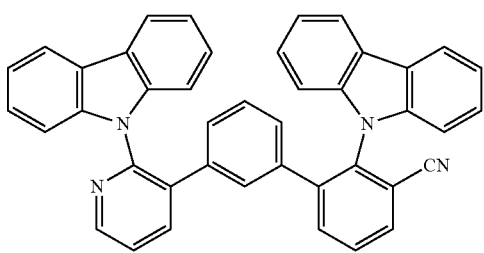
151
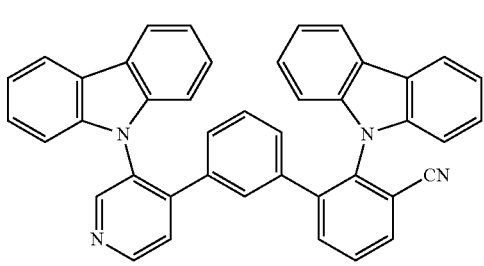
152
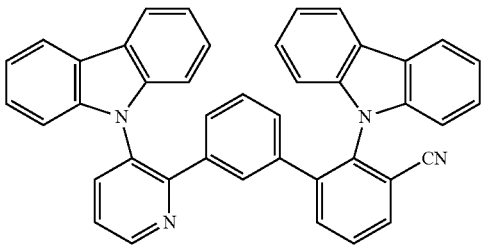
153
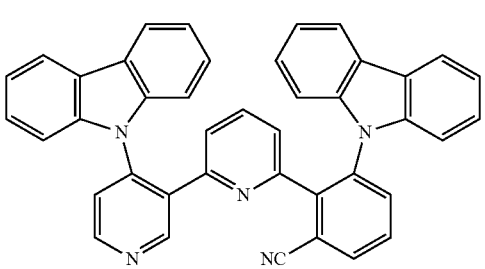
154
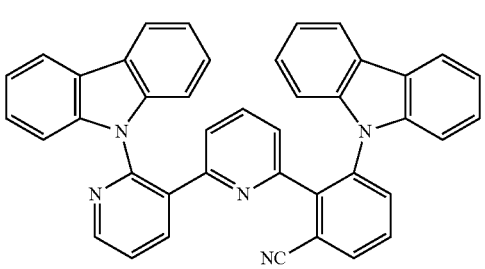
155
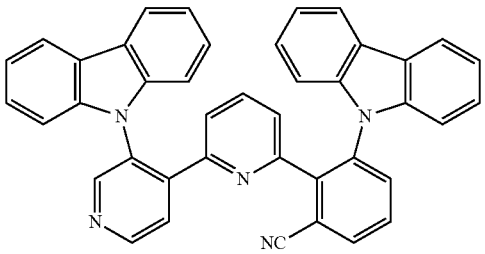
156
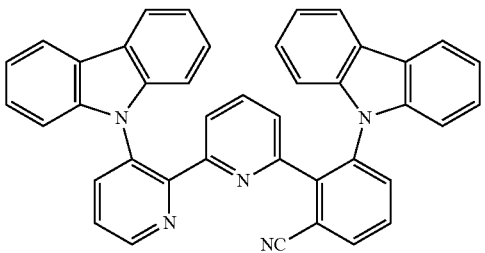

-continued
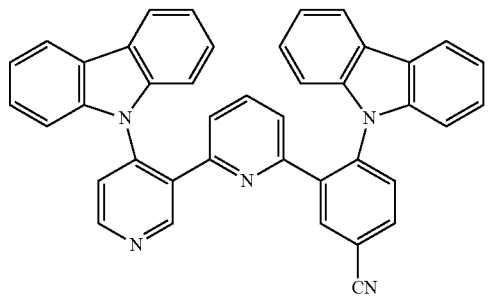
157
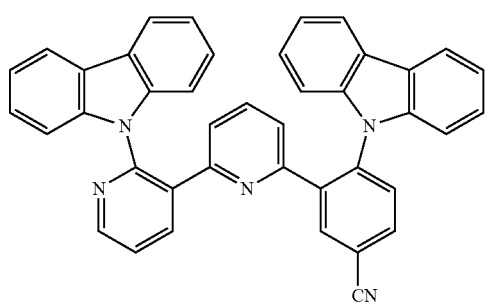
158
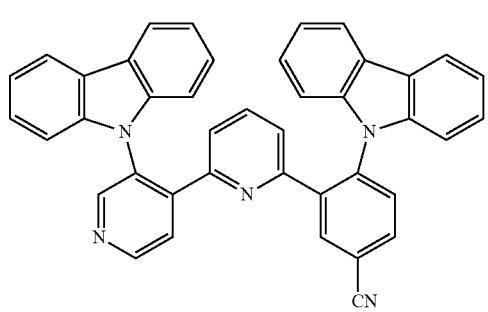
159
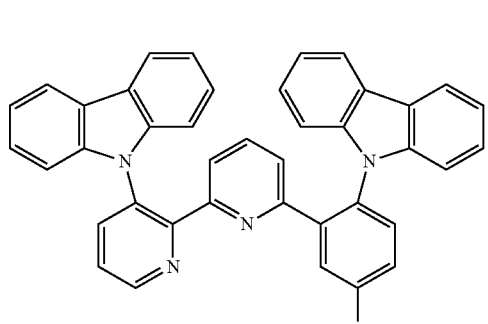
160
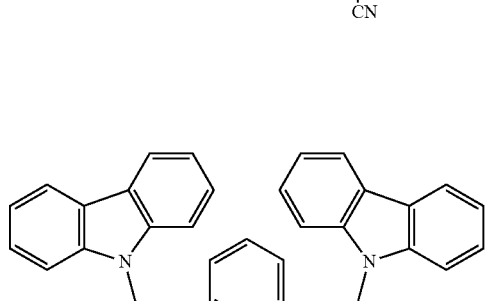
161
-continued
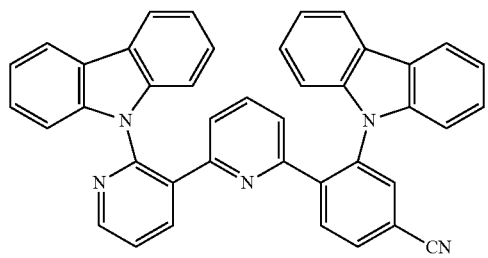
162
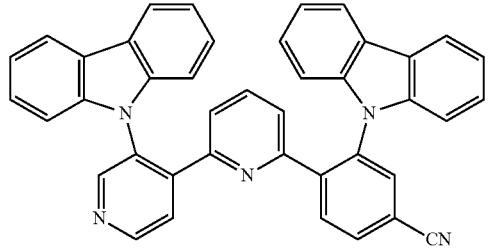
163
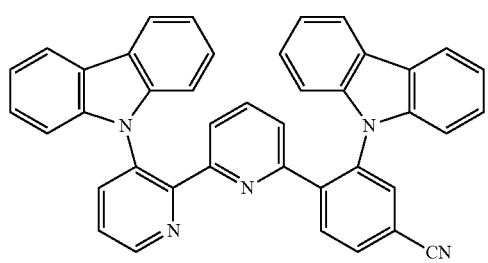
164
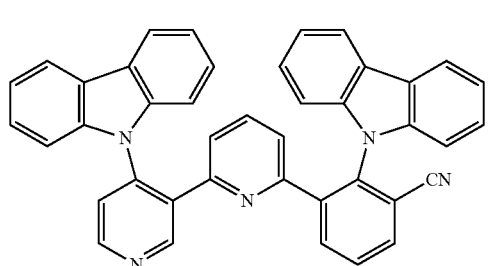
165
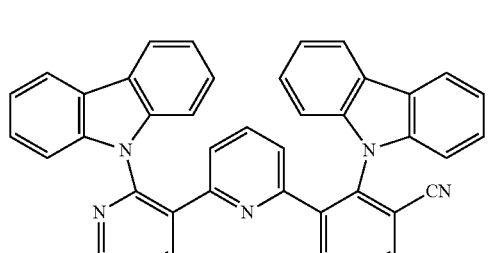
166
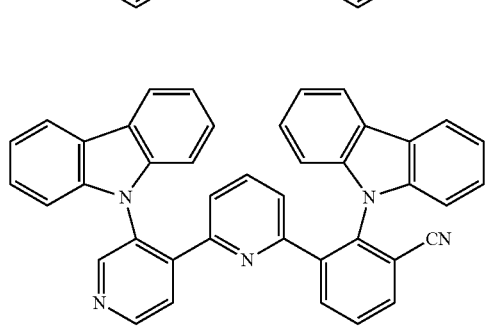
167

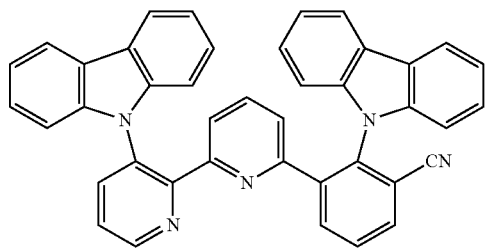
168
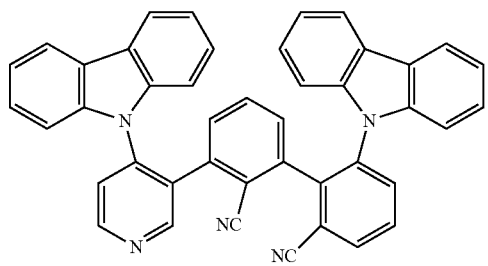
169
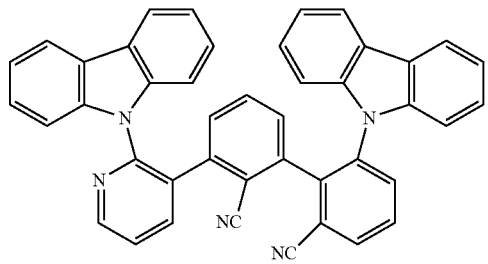
170
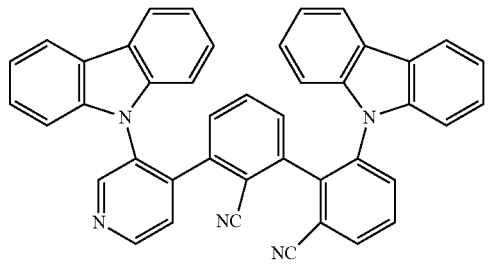
171
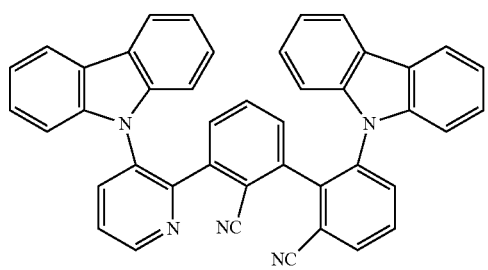
172
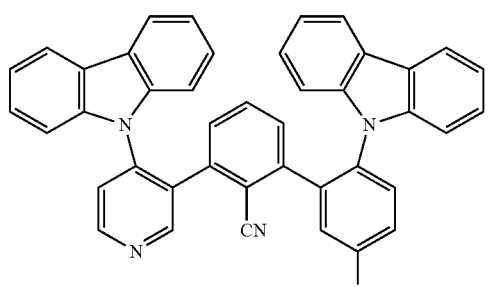
173
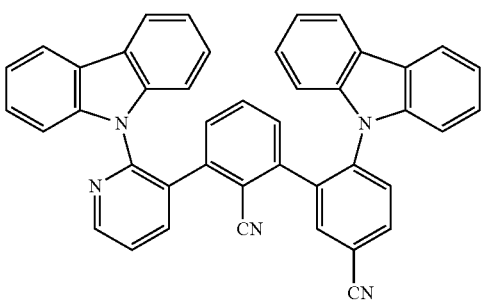
174
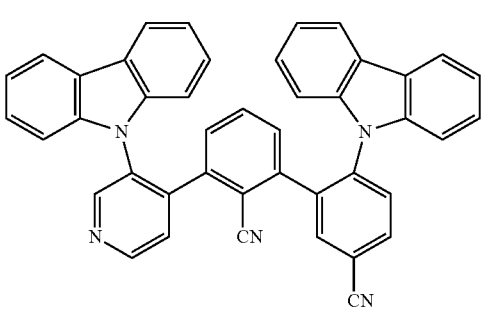
175
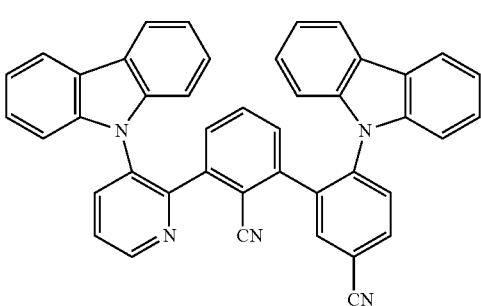
176
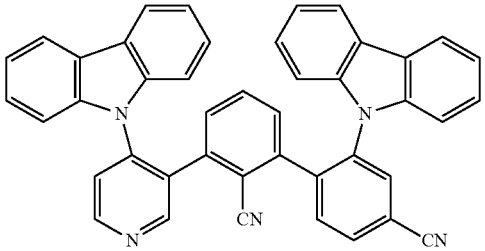
177
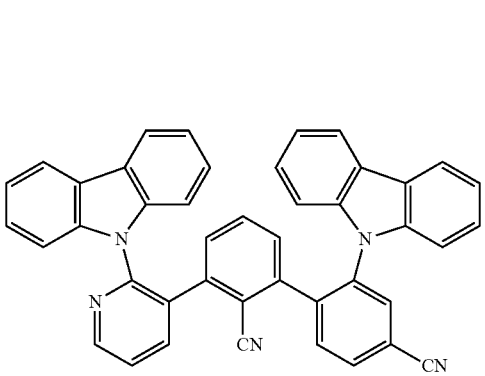
178

179
180
181
182
183
184
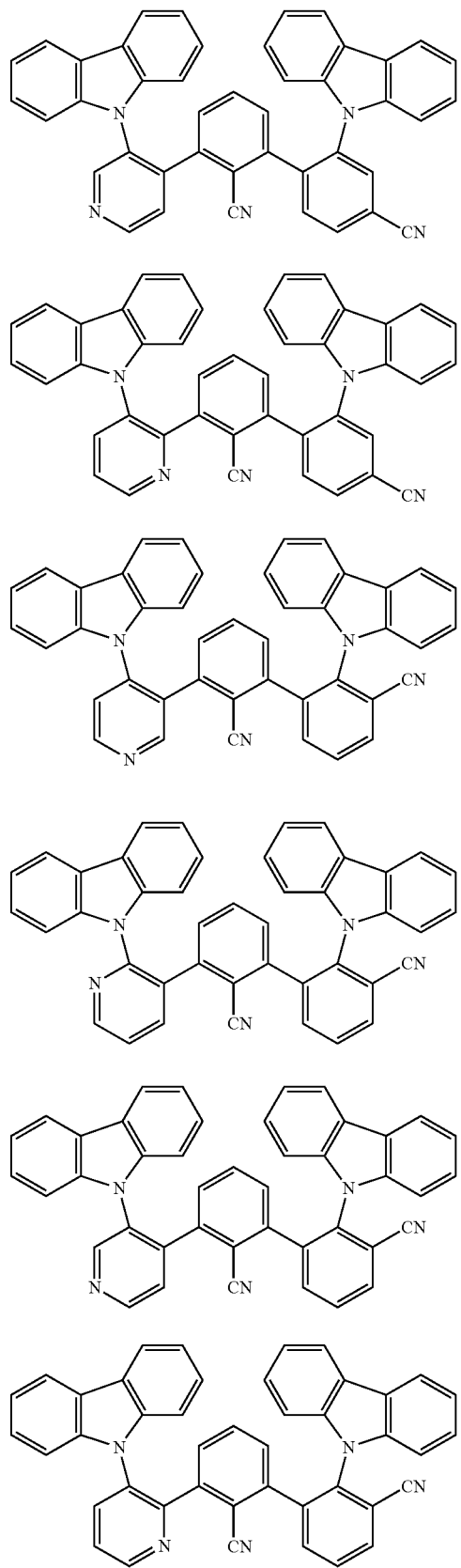
185
186
187
188
189
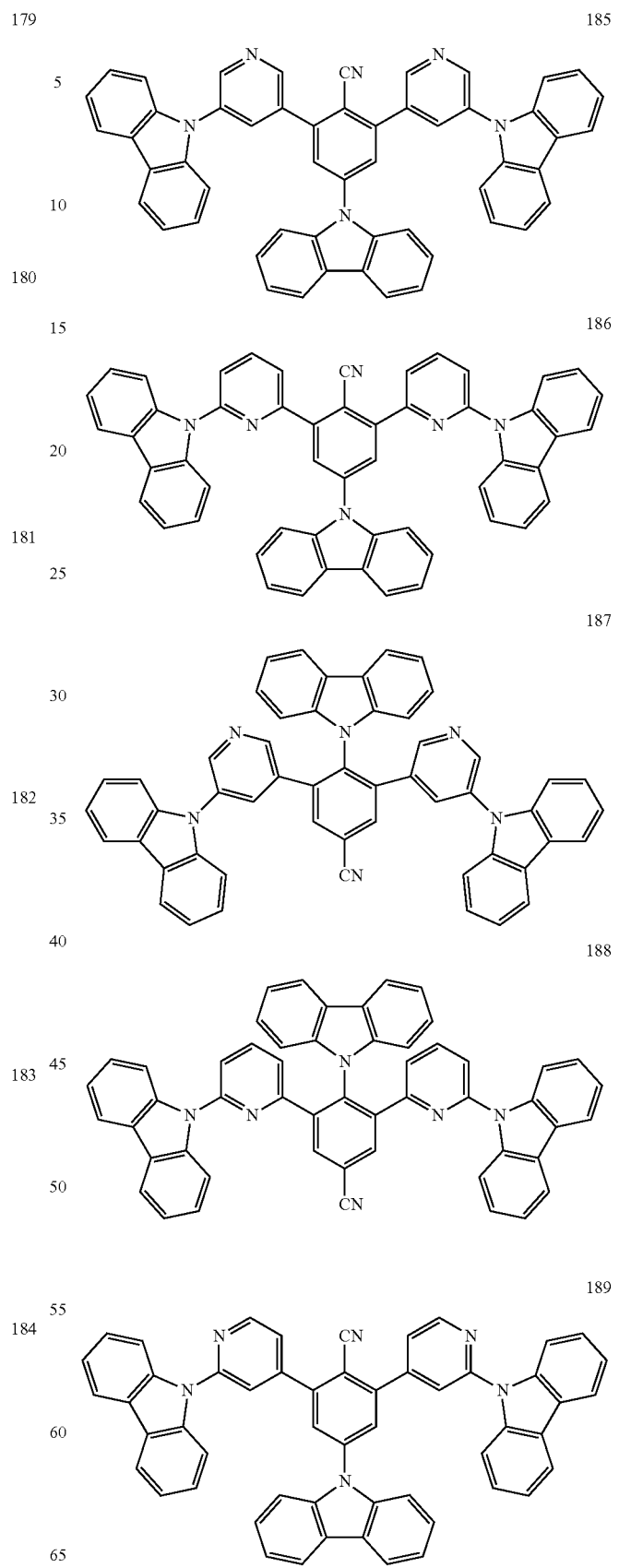

-continued
190
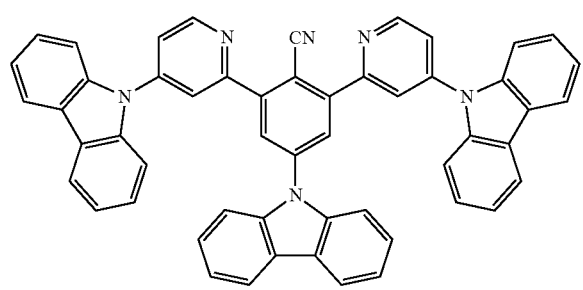
191
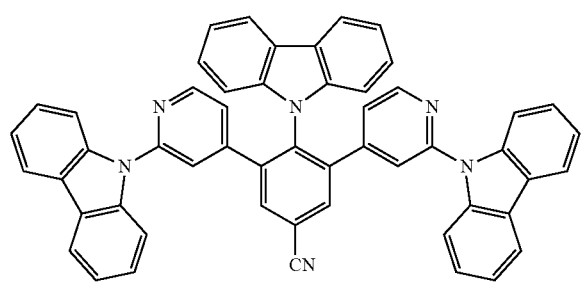
192
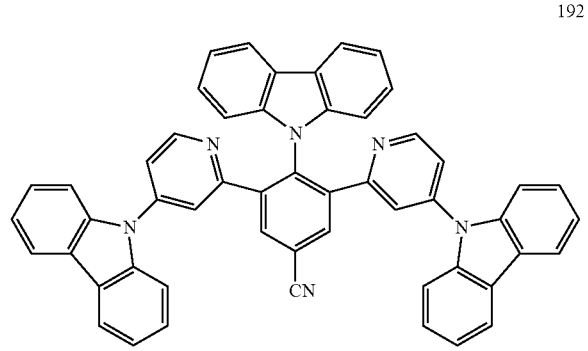
193
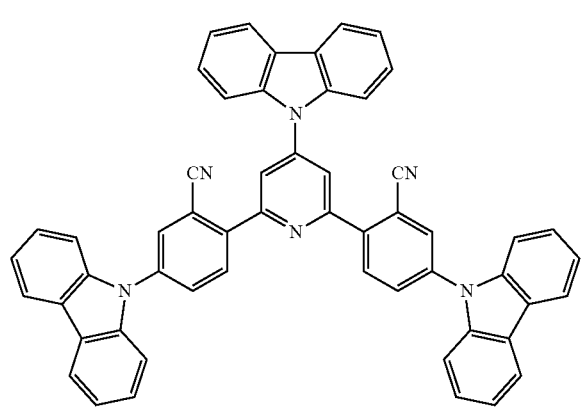
-continued
194
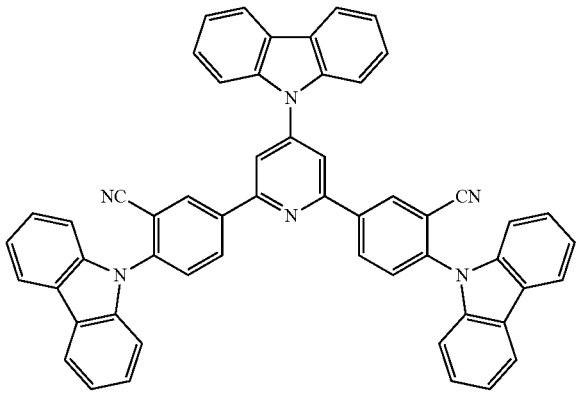
195
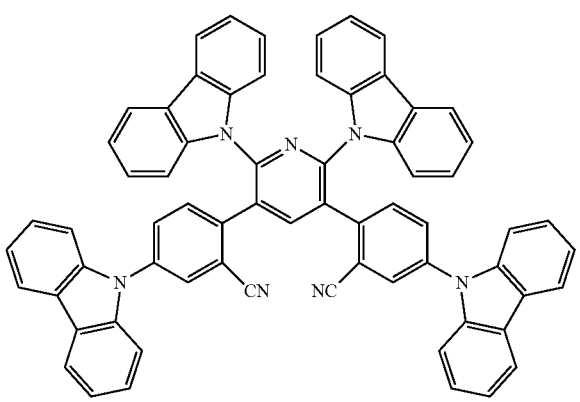
196
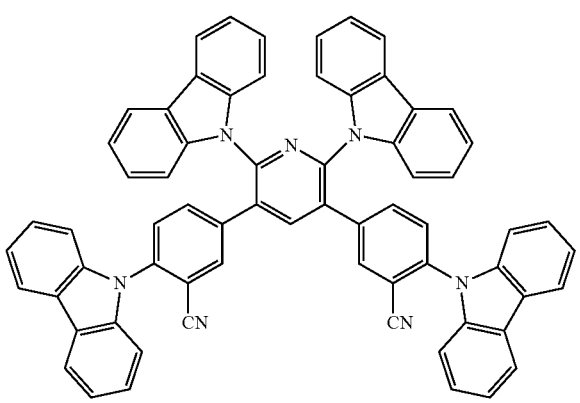
197
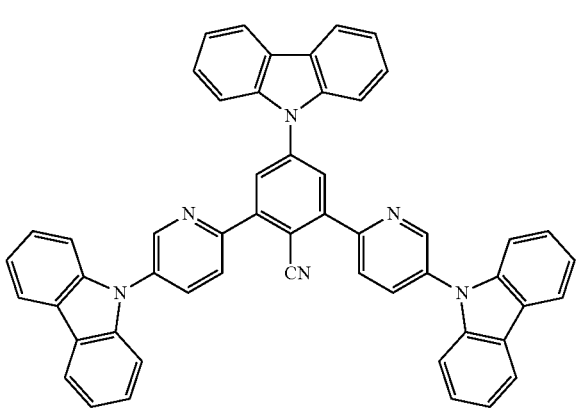

-continued
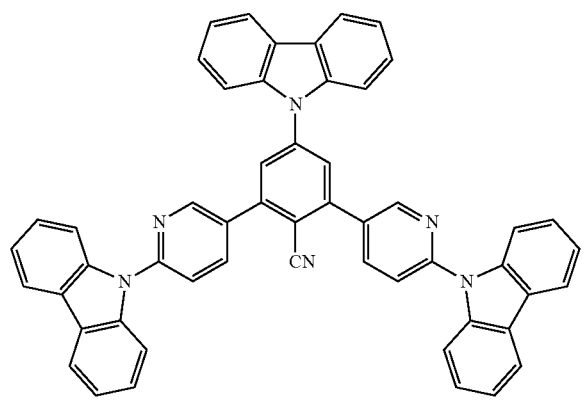
198
199
200
201
-continued
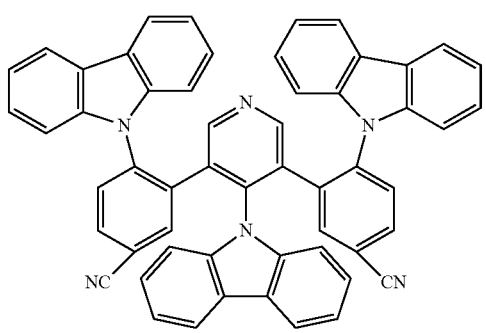
202
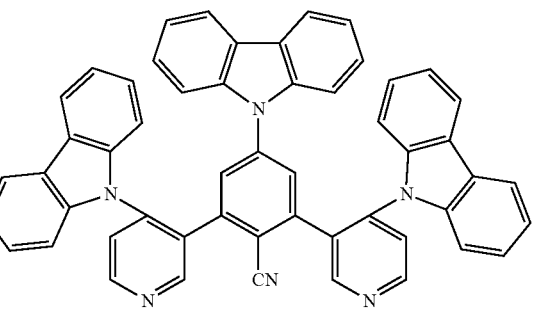
203
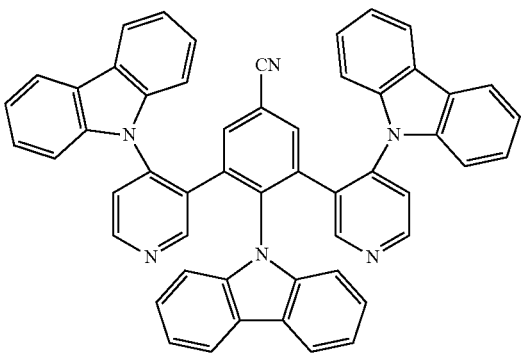
204
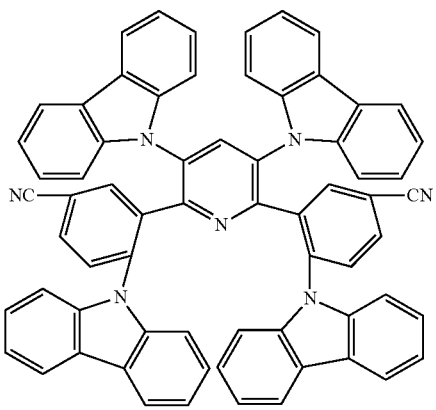
205

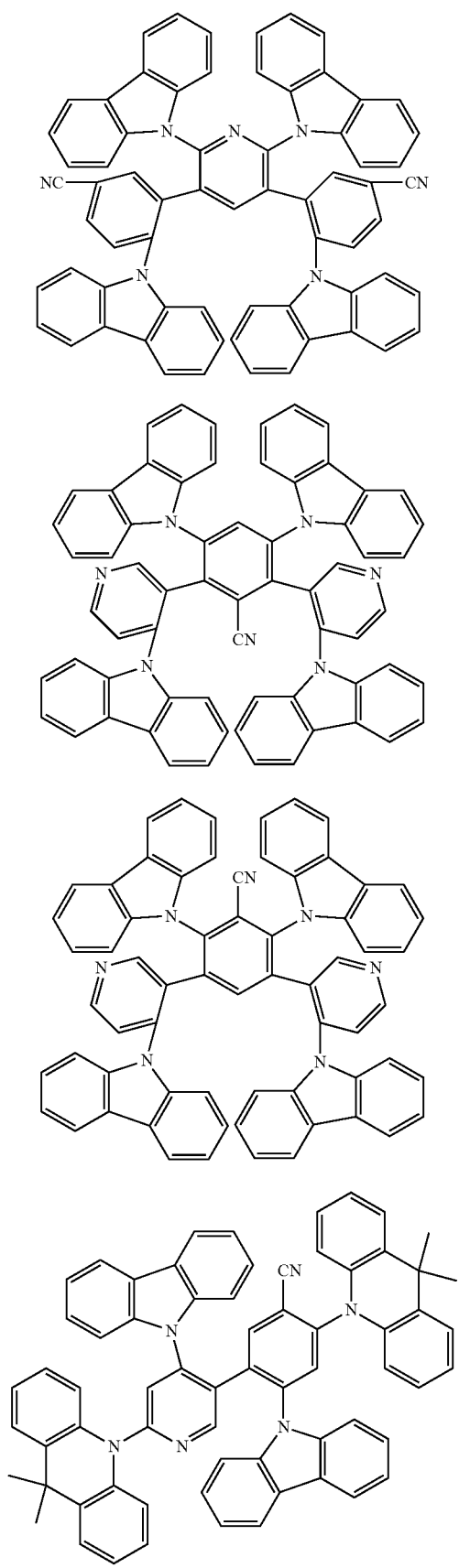
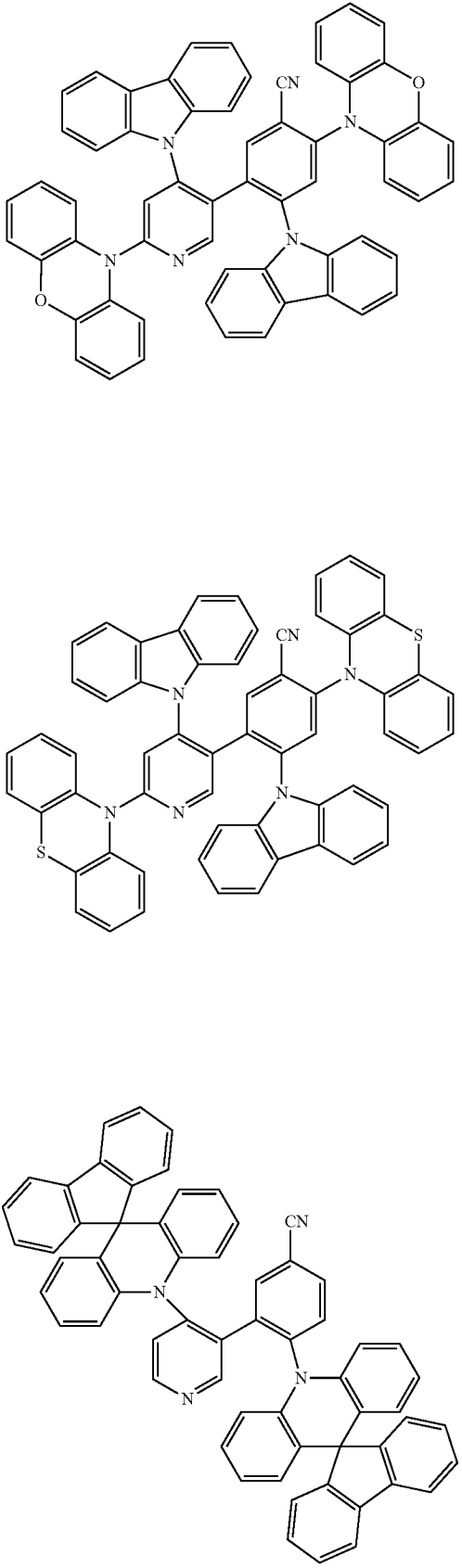

179
-continued
250
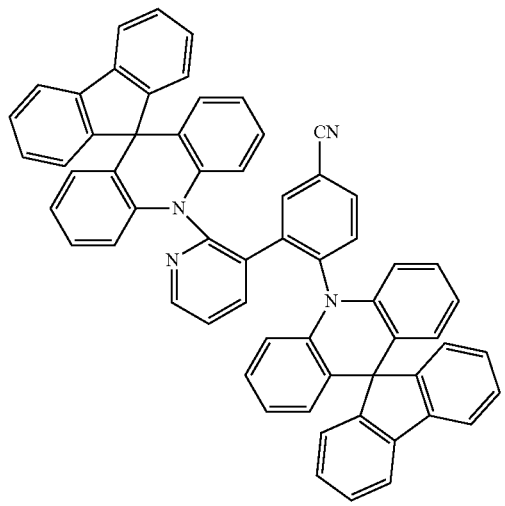
251
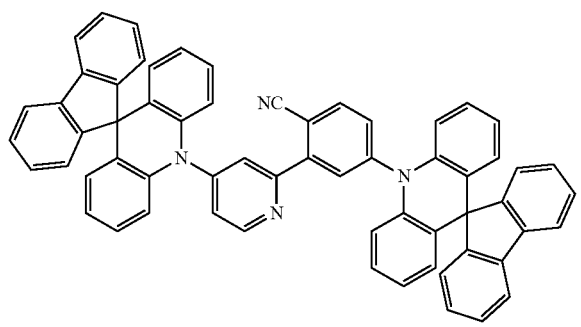
252
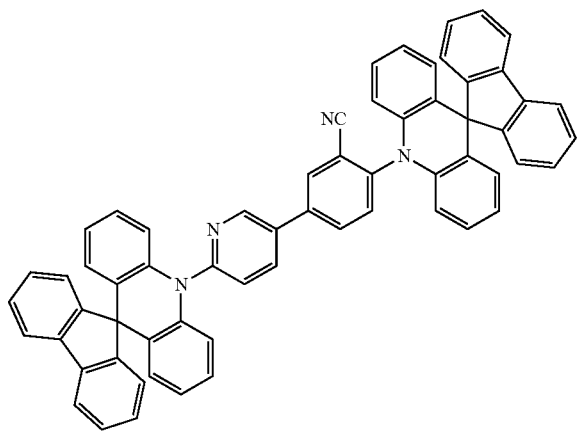
180
-continued
253
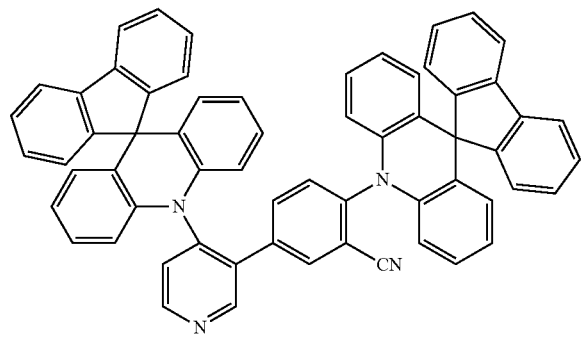
254
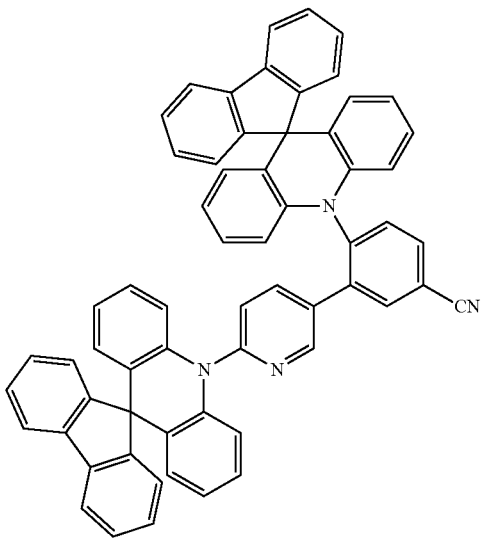
255
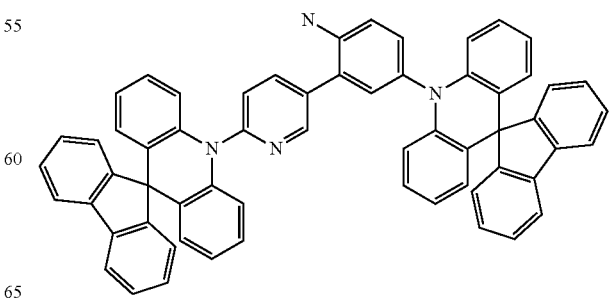

256
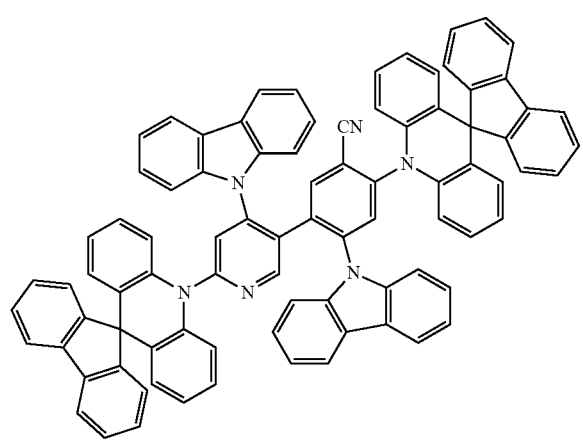
257
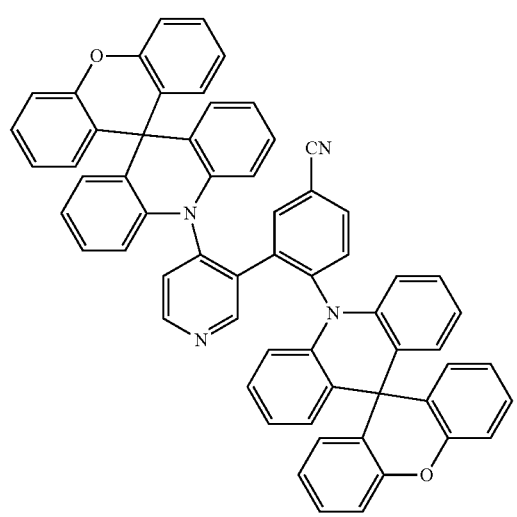
258
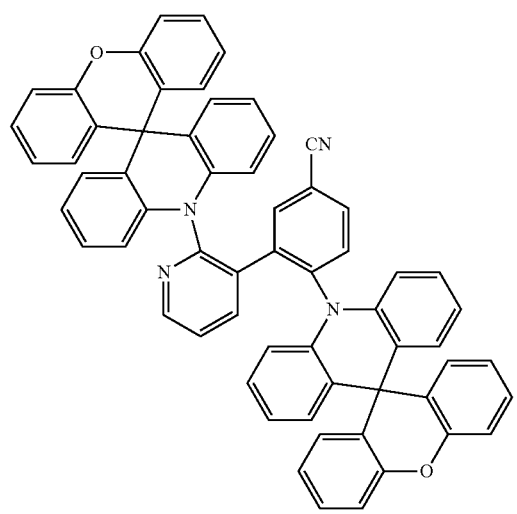
259
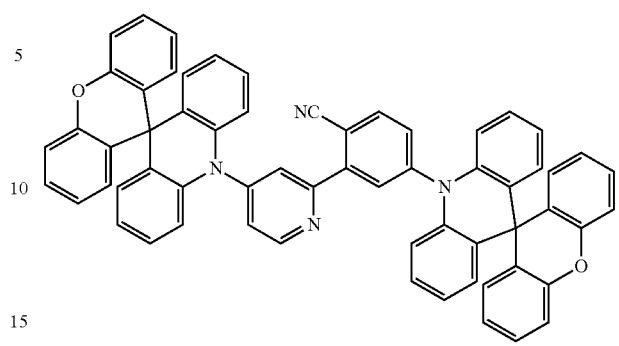
260
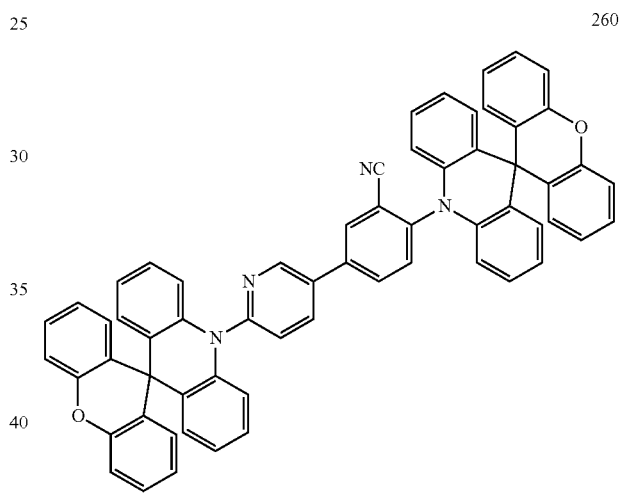
261
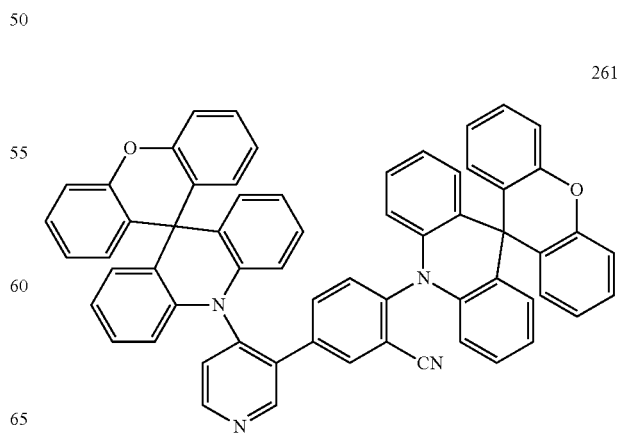

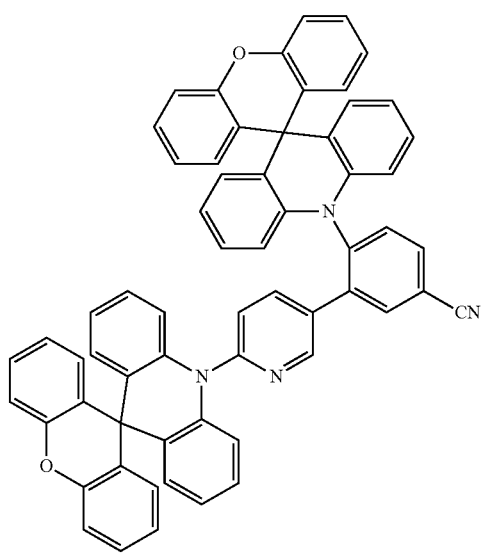

262

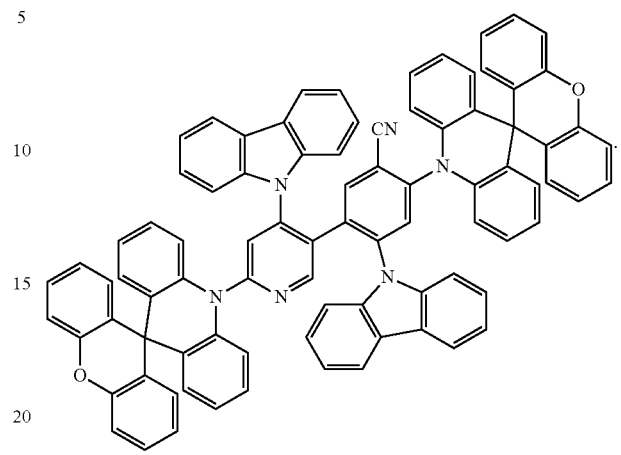

264

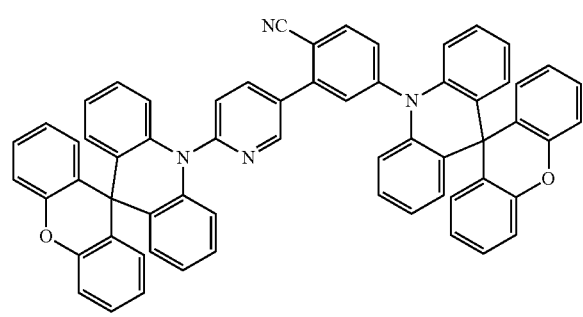

263

17. The organic electroluminescence device of claim 1, wherein the emission layer is configured to emit delayed fluorescence.

18. The organic electroluminescence device of claim 1, wherein the emission layer is a delayed fluorescence emission layer comprising a host and a dopant, and the dopant is the polycyclic compound.

19. The organic electroluminescence device of claim 1, wherein the emission layer is a thermally activated delayed fluorescence emission layer configured to emit blue light.

* * * * *